United States Patent

Nagase et al.

[11] Patent Number: 5,539,119
[45] Date of Patent: Jul. 23, 1996

[54] INDOLE DERIVATIVES

[75] Inventors: Hiroshi Nagase; Akira Mizusuna; Yoshihiro Onoda; Koji Kawai; Shu Matsumoto, all of Kamakura; Takashi Endo, Chigasaki, all of Japan

[73] Assignee: Toray Industries, Inc., Japan

[21] Appl. No.: 36,521

[22] Filed: Mar. 24, 1993

Related U.S. Application Data

[63] Continuation of Ser. No. 828,889, filed as PCT/JP91/00759 Jun. 5, 1991, Pat. No. 5,244,904.

[30] Foreign Application Priority Data

Jun. 5, 1990 [JP] Japan .................................. 2-148179
Nov. 29, 1990 [JP] Japan .................................. 2-335458

[51] Int. Cl.$^6$ .................................................. C07D 217/14
[52] U.S. Cl. ............................................................ 546/183
[58] Field of Search ............................................. 546/183

[56] References Cited

U.S. PATENT DOCUMENTS

| | | | |
|---|---|---|---|
| 3,933,827 | 1/1976 | Brossi et al. | 260/287 C |
| 4,189,583 | 2/1980 | Rapoport et al. | 546/141 |
| 4,310,667 | 1/1982 | Le Pecq et al. | 546/70 |
| 4,419,517 | 12/1983 | Brittelli et al. | 546/70 |
| 4,434,290 | 2/1984 | Bisagni et al. | 546/144 |

FOREIGN PATENT DOCUMENTS 49-85075  7/1973  Japan .

OTHER PUBLICATIONS

Morrison & Boyd p. 180 & p. 757, 3rd Ed. 1976.
"Reactions of Alcohols, Phenols, and Ethers," Norman L. Allinger et al, Organic Chemistry, Second Edition, pp. 438–440.

*Primary Examiner*—Gary Geist
*Assistant Examiner*—Catherine Kilby Scaizo
*Attorney, Agent, or Firm*—Austin R. Miller

[57] ABSTRACT

This invention is directed to a indole derivative represented by the general formula (1)

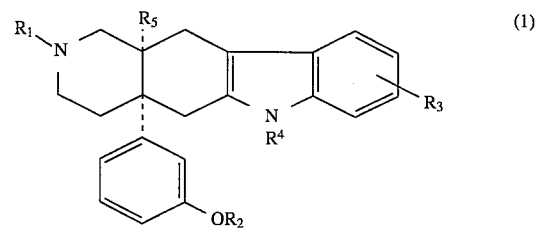

wherein $R_1$ stands for alkyl of 1 to 5 carbon atoms, cycloalkylalkyl of 4 to 7 carbon atoms, cycloalkenylalkyl of 5 to 7 carbon atoms, aralkyl of 7 to 14 carbon atoms, trans-alkenyl of 4 or 5 carbon atoms, allyl, furanyl-2-ylalkyl of 1 to 5 carbon atoms, thienyl-2-ylalkyl of 1 to 5 carbon atoms, vinyloxycarbonyl, trichloroethoxycarbonyl, benzyloxycarbonyl, alkanoyl of 1 to 5 carbon atoms, aralkylcarbonyl of 7 to 14 carbon atoms, 2-furoyl, thiophene-2-carbonyl, cycloalkylcarbonyl of 4 to 7 carbon atoms, alkenylcarbonyl of 3 to 8 carbon atoms, or anisoyl, providing that said general formula (1) embraces a (+) form, a (–) form, and a (±) form, or a pharmacologically acceptable salt thereof and to an immunorepressing agent having as an active component thereof the indole derivative or the pharmacologically acceptable salt thereof.

2 Claims, No Drawings

INDOLE DERIVATIVES

This application is a Divisional of application Ser. No. 07/828,889, filed as PCT/JP91/00759 Jun. 5, 1991 now U.S. Pat. No. 5,244,904.

TECHNICAL FIELD OF THE INVENTION

This invention relates to a compound having an affinity for the delta-opioid receptor. The delta-opioid receptor is concerned in the analgesic, immune, and circulatory (particularly blood pressure) systems. Ligands having high selectivity for the receptor are usable as medicines like analgesics, immunosuppressants, immunopotentiating agents, and antihypertensive agents.

BACKGROUND OF THE INVENTION

The delta opioid receptor is possessed of many pharmacological actions as described above. Compounds having high selectivity for this receptor promise adoption as analgesics, immunosuppressants, immunopotentiating agents, and antihypertensive agents. Except for peptide type compounds, no ligand of high selectivity for the delta receptor has been discovered until recent years. The peptide type compounds have not easily permitted their own development as the medicines mentioned above because they have the fault that they encounter difficulty in passing the blood-brain barrier and yield easily to in vivo decomposition with peptidase. Thus, agonists and antagonists possessed of high selectivity for the delta receptor are in demand. Recently, Portoghese et al have discovered an antagonist, NTI, possessed of high selectivity for the delta-opioid receptor (P. S. Portoghese et al., J. Med. Chem., Vol. 31, No. 2, 1988). This NTI is an alkaloid and, unlike peptides, is free from the problem of passage through the blood-brain barrier and the problem of decomposition with a peptidase. The NTI, however, is problematic in respect that the cost of its production is high because it is synthesized from naltrexone as a raw material and naltrexone is difficult to procure because it is synthesized from thebaine which is a narcotic. As regards delta receptor agonists, peptides such as DADLE and DPDPE have been known in the art. Alkaloids of high selectivity remain to be developed.

An object of this invention is to provide a ligand (agonist and antagonist) which has high affinity and selectivity for the delta receptor promising to manifest the aforementioned pharmacological actions, attains synthesis of its own through a route not using a narcotic as a raw material, passes through the blood-brain barrier, enjoys high stability in resisting a peptidase, and is not excessively expensive.

DISCLOSURE OF THE INVENTION

To accomplish the object described above, this invention is constructed as follows.

To be specific, this invention is directed to an indole derivative represented by the general formula (1):

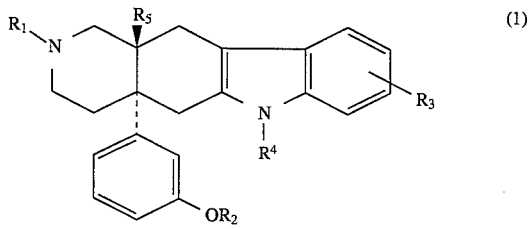

wherein $R_1$ stands for alkyl having 1 to 5 carbon atoms, cycloalkylalkyl having 4 to 7 carbon atoms, cycloalkenylalkyl having 5 to 7 carbon atoms, aralkyl having 7 to 14 carbon atoms, trans-alkenyl having 4 or 5 carbon atoms, allyl, furanyl-2-ylalkyl having 1 to 5 carbon atoms, thienyl-2-ylalkyl having 1 to 5 carbon atoms, vinyloxycarbonyl, trichloroethoxycarbonyl, benzyloxycarbonyl, alkanoyl having 1 to 5 carbon atoms, aralkylcarbonyl having 7 to 14 carbon atoms, 2-furoyl, thiophene-2-carbonyl, cycloalkylcarbonyl having 4 to 7 carbon atoms, alkenylcarbonyl having 3 to 8 carbon atoms, or anisoyl, $R_2$ stands for a hydrogen atom, alkyl having 1 to 3 carbon atoms, benzyl, or alkanoyl having 1 to 5 carbon atoms, $R_3$ stands for a hydrogen atom, a fluorine atom, a chlorine atom, a bromine atom, nitro, or alkyl having 1 to 5 carbon atoms, $R_4$ stands for a hydrogen atom, alkyl having 1 to 5 carbon atoms, benzyl, or phenyl, and $R_5$ stands for a hydrogen atom, hydroxy, or alkanoyloxy having 1 to 5 carbon atoms, or a pharmacologically acceptable salt thereof.

As pharmacologically desirable salts, inorganic salts such as hydrochloride, sulfate, hydrobromide, and phosphate, and organic salts such as acetate, lactate, methanesulfonate, p-toluenesulfonate, phthalate, fumarate, maleate, glutarate, and tartrate may be mentioned for example. Of course, these salts are not exclusive examples.

In the general formula (1), $R_1$ stands for methyl, ethyl, propyl, butyl, pentyl, cyclopropylmethyl, cyclobutylmethyl, cyclopentylmethyl, cyclohexylmethyl, cyclopentenylmethyl, cyclohexenylmethyl, allyl, 2-furanylmethyl, 2-thienylmethyl, trans-2butenyl, cyclopropylcarbonyl, 2,2,2-trichloroethoxycarbonyl, or vinyloxycarbonyl, $R_2$ stands for a hydrogen atom, methyl, ethyl, propyl, benzyl, acetyl, propanoyl, butanoyl, or pentanoyl, $R_3$ stands for a hydrogen atom, a fluorine atom, a chlorine atom, a bromine atom, nitro, methyl, ethyl, propyl, butyl, or pentyl, $R_4$ for a hydrogen atom, methyl, ethyl, propyl, butyl, pentyl, phenyl, or benzyl, and $R_5$ stands for a hydrogen atom, hydroxy, acetoxy, propanoyloxy, butanoyloxy, or pentanoyloxy, for example. Preferably, $R_1$ stands for methyl, cyclopropylmethyl, cyclobutylmethyl, allyl, 2-furanylmethyl, cyclopropylcarbonyl, 2,2,2-trichloroethoxycarbonyl, or vinyloxycarbonyl, $R_2$ stands for a hydrogen atom, methyl, acetyl, or benzyl, $R_3$ stands for a hydrogen atom, a fluorine atom, a chlorine atom, a bromine, or methyl, $R_4$ stands for a hydrogen atom, methyl, or benzyl, and $R_5$ stands for a hydrogen atom, hydroxy, or acetoxy, for example.

In the compounds of this invention represented by the general formula (1), the particular compound having methyl as $R_1$ and hydrogen atoms each for $R_2$, $R_3$, $R_4$, and $R_5$ (Formula 2) is named 2-methyl-4aα-(3-hydroxyphenyl)-1,2,3,4,4a5,11,11aβ-octahydro-6H-indolo[2,3-g]isoquinoline.

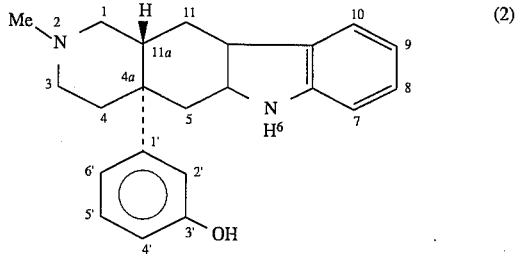

In accordance with the nomenclature exemplified above, as representative examples of the compound of the present invention, 2-methyl-4aα-(3-hydroxyphenyl)-1,2,3,4,4a,5,11,11aβ-octahydro-6H-indolo[2,3-g]isoquinoline, 2-methyl-4aα-(3-methoxyphenyl)-1,2,3,4,4a,5,11,11aβ-octahydro-6H-indolo[2,3-g]isoquinoline, 2-allyl-4aα-(3- hydroxyphenyl)-1,2,3,4,4a,5,11,11aβ-octahydro-6H-indolo[2,3-g]isoquinoline, 2-allyl-4aα-(3-methoxyphenyl)-1,2,3,4,4a,5,11,11aβ-octahydro-6H-indolo[2,3-g]isoquinoline, 2-cyclopropylmethyl-4aα-(3-hydroxyphenyl)-1,2,3,4,4a,5,11,11aβ-octahydro-6H-indolo[2,3-g]isoquinoline, 2-cyclopropylmethyl-4aα-(3-methoxyphenyl)-1,2,3,4,4a,5,11,11aβ-octahydro-6H-indolo[2,3-g]isoquinoline, 2-benzyl-4aα-(3-hydroxyphenyl)-1,2,3,4,4a,5,11,11aβ-octahydro-6H-indolo[2,3-g]isoquinoline, 2-benzyl-4aα-(3-methoxyphenyl)-1,2,3,4,4a,5,11,11aβ-octahydro-6H-indolo[2,3-g]isoquinoline, 2-phenethyl-4aα-(3-hydroxyphenyl)-1,2,3,4,4a,5,11,11aβ-octahydro-6H-indolo[2,3-g]isoquinoline, 2-phenethyl-4aα-(3-methoxyphenyl)-1,2,3,4,4a,5,11,11aβ-octahydro-6H-indolo[2,3-g]isoquinoline, 2-methyl-4aα-(3-hydroxyphenyl)-1,2,3,4,4a,5,11,11aβ-octahydro-6-methyl-indolo[2,3g]isoquinoline, 2-methyl-4aα-(3-methoxyphenyl)-1,2,3,4,4a,5,11,11aβ-octahydro-6-methyl-indolo[2,3-g]isoquinoline, 2-cyclopropylmethyl-4aα-(3-hydroxyphenyl)-1,2,3,4,4a,5,11,11aβ-octahydro-6-methyl-indolo[2,3-g]isoquinoline, 2-cyclopropylmethyl-4aα-(3-methoxyphenyl)-1,2,3,4,4a,5,11,11aβ-octahydro-6-methyl-indolo[2,3-g]isoquinoline, 2-benzyl-4aα-(3-hydroxyphenyl)-1,2,3,4,4a,5,11,11aβ-octahydro-6-methyl-indolo[2,3-g]isoquinoline, 2-benzyl-4aα-(3-methoxyphenyl)-1,2,3,4,4a,5,11,11aβ-octahydro-6-methyl-indolo[2,3-g]isoquinoline, 2-phenethyl-4aα-(3-hydroxyphenyl)-1,2,3,4,4a,5,11,11aβ-octahydro-6-methyl-indolo[2,3-g]isoquinoline, 2-phenethyl-4aα-(3-methoxyphenyl)-1,2,3,4,4a,5,11,11aβ-octahydro-6-methyl-indolo[2,3-g]isoquinoline, 2-allyl-4aα-(3-hydroxyphenyl)-1,2,3,4,4a,5,11,11aβ-octahydro-6-methyl-indolo[2,3-g]-isoquinoline, 2-allyl-4aα-(3-methoxyphenyl)-1,2,3,4,4a,5,11,11aβ-octahydro-6-methyl-indolo[2,3-g]isoquinoline, 2-methyl-4aα-(3-hydroxyphenyl)-9-methyl-1,2,3,4,4a,5,11,11aβ-octahydro-6H-indolo[2,3-g]isoquinoline, 2-methyl-4aα-(3-methoxyphenyl)-9-methyl-1,2,3,4,4a,5,11,11aβ-octahydro-6H-indolo[2,3-g]isoquinoline, 2-benzyl-4aβ-(3-hydroxyphenyl)-9-methyl-1,2,3,4,4a,5,11,11aβ-octahydro-6H-indro[2,3-g]isoquinoline, 2-benzyl-4aα-(3-methoxyphenyl)-9-methyl-1,2,3,4,4a,5,11,11aβ-octahydro-6H-indolo[2,3-g]isoquinoline, 2-phenethyl-4aα-(3-hydroxyphenyl)-9-methyl-1,2,3,4,4a,5,11,11aβ-octahydro-6H-indolo[2,3-g]isoquinoline, 2-phenethyl-4aα-(3-methoxyphenyl)-9-methyl-1,2,3,4,4a,5,11,11aβ-octahydro-6H-indolo[2,3-g]isoquinoline, 2-cyclopropylmethyl-4aα-(3-hydroxyphenyl)-9-methyl-1,2,3,4,4a,5,11,11aβ-octahydro-6H-indolo[2,3-g]isoquinoline, 2-cyclopropylmethyl-4aα-(3-methoxyphenyl)-9-methyl-1,2,3,4,4a,5,11,11a-octahydro-6H-indolo[2,3-g]isoquinoline, 2-allyl-4aα-(3-hydroxyphenyl)-9-methyl-1,2,3,4,4a,5,11,11aβ-octahydro-6H-indolo[2,3-g]isoquinoline, 2-allyl-4aα-(3-methoxyphenyl)-9-methyl-1,2,3,4,4a,5,11,11aβ-octahydro-6H-indolo[2,3-g]isoquinoline, 2-methyl-4aα-(3-hydroxyphenyl)-9-methyl -1,2,3,4,4a,5,11,11aβ-octahydro-6-methyl-indolo[2,3-g]isoquinoline, 2-methyl-4aα-(3-methoxyphenyl)-9-methyl-1,2,3,4,4a,5,11,11aβ-octahydro-6-methyl-indolo[2,3-g]isoquinoline, 2-allyl-4aα-(3-hydroxyphenyl)-9-methyl-1,2,3,4,4a,5,11,11aβ-octahydro-6-methyl-indolo[2,3-g]isoquinoline, 2-allyl-4aα-(3-methoxyphenyl)-9-methyl-1,2,3,4,4a,5,11,11aβ-octahydro-6-methyl-indolo[2,3-g]isoquinoline, 2-cyclopropylmethyl-4aα-(3-hydroxyphenyl)-9-methyl-1,2,3,4,4a,5,11,11aβ-octahydro-6-methyl-indolo[2,3-g]isoquinoline, 2-cyclopropylmethyl-4aα-(3-methoxyphenyl)-9-methyl-1,2,3,4,4a,5,11,11aβ-octahydro-6-methyl-indolo[2,3-g]isoquinoline, 2-benzyl-4aα-(3-hydroxyphenyl)-9-methyl-1,2,3,4,4a,5,11,11aβ-octahydro-6-methyl-indolo[2,3-g]isoquinoline, 2-benzyl-4aα-(3-methoxyphenyl)-9-methyl-1,2,3,4,4a,5,11,11aβ-octahydro-6-methyl-indolo[2,3-g]isoquinoline, 2-phenethyl-4aα-(3-hydrophenyl)-9-methyl-1,2,3,4,4a,5,11,11aβ-octahydro-6-methyl-indolo[2,3-g]isoquinoline, 2-phenethyl-4aα-(3-methoxyphenyl)-9-methyl-1,2,3,4,4a,5,11,11aβ-octahydro-6-methyl-indolo[2,3-g]isoquinoline, 2-methyl-4aα-(3-hydroxyphenyl)-9-bromo-1,2,3,4,4a,5,11,11aβ-octahydro-6H-indolo[2,3-g]isoquinoline, 2-methyl-4aα-(3-methoxyphenyl)-9-bromo-1,2,3,4,4a,5,11,11aβ-octahydro-6H-indolo[2,3-g]isoquinoline, 2-benzyl-4aα-(3-hydroxyphenyl)-9-bromo-1,2,3,4,4a,5,11,11aβ-octahydro-6H-indolo[2,3-g]isoquinoline, 2-benzyl-4aα-(3-methoxyphenyl)-9-bromo-1,2,3,4,4a,5,11,11aβ-octahydro-6H-indolo[2,3-g]isoquinoline, 2-phenethyl-4aα-(3-hydroxyphenyl)-9-bromo-1,2,3,4,4a,5,11,11aα-octahydro-6H-indolo[2,3-g]isoquinoline, 2-phenethyl-4aα-(3-methoxyphenyl)-9-bromo-1,2,3,4,4a,5,11,11aβ-octahydro-6H-indolo[2,3-g]isoquinoline, 2-cyclopropylmethyl-4aα-(3-hydroxyphenyl)-9-bromo-1,2,3,4,4a,5,11,11aβ-octahydro-6H-indolo[2,3-g]isoquinoline, 2-cyclopropylmethyl-4aα-(3-methoxyphenyl)-9-bromo-1,2,3,4,4a,5,11,11aβ-octahydro-6H-indolo[2,3-g]isoquinoline, 2-allyl-4aα-(3-hydroxyphenyl)-9-bromo-1,2,3,4,4a,5,11,11aβ-octahydro-6H-indolo[2,3-g]isoquinoline, 2-allyl-4aα-(3-methoxyphenyl)-9-bromo-1,2,3,4,4a,5,11,11aβ-octahydro-6H-indolo[2,3-g]isoquinoline, 2-methyl-4aα-(3-hydroxyphenyl)-9-bromo-1,2,3,4,4a,5,11,11aβ-octahydro-6-methyl-indolo[2,3-g]isoquinoline, 2-methyl-4aα-(3-methoxyphenyl)-9-bromo-1,2,3,4,4a,5,11,11aβ-octahydro-6-methyl-indolo[2,3-g]isoquinoline, 2-allyl-4aα-(3-hydroxyphenyl)-9-bromo-1,2,3,4,4,a5,11,11aβ-octahydro-6methyl-indolo[2,3-g]isoquinoline, 2-allyl-4aα-(3-methoxyphenyl)-9-bromo-1,2,3,4,4a,5,11,11aβ-octahydro-6-methyl-indolo[2,3-g]isoquinoline, 2-cyclopropylmethyl-4aα-(3-hydroxyphenyl)-9-bromo-1,2,3,4,4a,5,11,11aβ-octahydro-6-methyl-indolo[2,3-g]isoquinoline, 2-cyclopropylmethyl-4aα-(3-methoxyphenyl)-9-bromo-1,2,3,4,4a,5,11,11aβ-octahydro-6-methyl-indolo[2,3-g]isoquinoline, 2-benzyl-4aα-(3-hydroxyphenyl)-9-bromo-1,2,3,4,4a,5,11,11aβ-octahydro-6-methyl-indolo[2,3-g]isoquinoline, 2-benzyl-4aα-(3-methoxyphenyl)-9-bromo-1,2,3,4,4a,5,11,11β-octahydro-6-methyl-indolo[2,3-g]isoquinoline, 2-phenethyl-4aα-(3-hydroxyphenyl)-9-bromo-1,2,3,4,4a,5,11,11aβ-octahydro-6-methyl-indolo[2,3,-g]isoquinoline, 2-phenethyl-4aα-(3-methoxyphenyl)-9-bromo-1,2,3,4,4a,5,11,11aβ-octahydro-6-methyl-indolo[2,3-g]isoquinoline, 2-methyl-4aα-(3-hydroxyphenyl)-9-chloro-1,2,3,4,4a,5,11,11aβ-octahydro-6H-indolo[2,3-g]isoquinoline, 2-methyl-4aα(3-methoxyphenyl)-9-chloro-1,2,3,4,4a,5,11,11aβ-octahydro-6H-indolo[2,3-g]isoquinoline, 2-benzyl-4aα-(3-hydroxyphenyl)-9-chloro-1,2,3,4,4a,5,11,11aβ-octahydro-6H-indolo[2,3-g]isoquinoline, 2-benzyl-4aα-(3-methoxyphenyl)-9-chloro-1,2,3,4,4a,5,11,11aβ-octahydro-6H-indolo[2,3-g]isoquinoline, 2-phenethyl-4aα-(3-hydroxyphenyl)-9-chloro-1,2,3,4,4a,5,11,11aβ-octahydro-6H-indolo[2,3-g]isoquinoline, 2-phenethyl-4aα-(3-methoxyphenyl)-9-chloro-1,2,3,4,4a,5,11,11aβ-octahydro-6H-indolo[2,3-g]isoquinoline, 2-cyclopropylmethyl-4aα-(3-hydroxyphenyl)-9-chloro-1,2,3,4,4a,5,11,11aβ-octahydro-6H-indolo[2,3-g]isoquinoline, 2-cyclopropylmethyl-4aα-(3-methoxyphenyl)-9-chloro-1,2,3,4,4a,5,11,11sβ-octahydro-6H-indolo[2,3-g]isoquinoline, 2-allyl-4aα-(3-hydroxyphenyl)-9-chloro-1,2,3,4,4a,5,11,11aβ-octahydro-6H-indolo[2,3-g]isoquinoline, 2-allyl-4aα-(3-methoxyphenyl)-9-chloro-1,2,3,4,4a,5,11,11aβ-octahydro- 6H-indolo[2,3-g]isoquinoline, 2-methyl-4aα-(3-hydroxyphenyl)-9-chloro-1,2,3,4,4a,5,11,11aβ-octahydro-2,3-g]isoquinoline, 2-methyl-4aα-(3-methoxyphenyl)-9-chloro-1,2,3,4,4a,5,11,11aβ-octahydro-6-methyl-indolo[2,3-g]isoquinoline, 2-allyl-4aα-(3-hydroxyphenyl)-9-chloro-1,2,3,4,4a,5,11,11aβ-octahydro-6-methyl-indolo[2,3-g]isoquinoline, 2-allyl-4aα-(3-methoxyphenyl)-9-chloro-1,2,3,4,4a,5,11,11aβ-octahydro-6-methyl-indro[2,3-g]isoquinoline, 2-cyclopropylmethyl-4aα-(3-hydroxyphenyl)-9-chloro-1,2,3,4,4a,5,11,11aβ-octahydro-6-methyl-indolo[2,3-g]isoquinoline, 2-cyclopropylmethyl-4aα-(3-methoxyphenyl)-9-chloro-1,2,3,4,4a,5,11,11aβ-octahydro-6-methyl-indolo[2,3-g]isoquinoline, 2-benzyl-4aα-(3-hydroxyphenyl)-9-chloro-1,2,3,4,4a,5,11,11aβ-octahydro-6-methyl-indolo[2,3-g]isoquinoline, 2-benzyl-4aα-(3-methoxyphenyl)-9-chloro-1,2,3,4,4a,5,11,11aβoctahydro-6-methyl-indolo[2,3-g]isoquinoline, 2-phenethyl-4aα-(3-hydroxyphenyl)-9-chloro-1,2,3,4,4a,5,11,11aβ-octahydro-6-methyl-indolo[2,3-g]isoquinoline, 2-phenethyl-4aα-(3-methoxyphenyl)-9-chloro-1,2,3,4,4a,5,11,11aβ-octahydro-6-methyl-indolo[2,3-g]isoquinoline, 2-methyl-4aα-(3-hydroxyphenyl)-7-fluoro-1,2,3,4,4a,5,11,11aβ-octahydro-6H-indolo[2,3-g]isoquinoline, 2-methyl-4aα-(3-methoxyphenyl)-7-fluoro-1,2,3,4,4a,5,11,11aβ-octahydro-6H-indolo[2,3-]isoquinoline, 2-benzyl-4aα-(3-hydroxyphenyl)-7-fluoro-1,2,3,4,4a5,11,11aβ-octahydro-6H-indolo[2,3-g]isoquinoline, 2-benzyl-4aα-(3-methoxyphenyl)-7-fluoro-1,2,3,4,4a,5,11,11aβ-octahydro-6H-indolo[2,3-g]isoquinoline, 2-phenethyl-4aα-(3-hydroxyphenyl)-7-fluoro-1,2,3,4,4a,5,11,11aβ-octahydro-6H-indolo[2,3-g]isoquinoline, 2-phenethyl-4aα-(3-methoxyphenyl)-7-fluoro-1,2,3,4,4a,5,11,11aβ-octahydro-6H-indolo[2,3-g]isoquinoline, 2-cyclopropylmethyl-4aα-(3-hydroxyphenyl)-7-fluoro-1,2,3,4,4a,5,11,11aβ-octahydro-6H-indolo[2,3-g]isoquinoline, 2-cyclopropylmethyl-4aα-(3-methoxyphenyl)-7-fluoro-1,2,3,4,4a,5,11,11aβ-octahydro-6H-indolo[2,3-g]isoquinoline, 2-allyl-4aα-(3-hydroxyphenyl)-7-fluoro-1,2,3,4,4a,5,11,11aβ-octahydro-6H-indolo[2,3-g]isoquinoline, 2-allyl-4aα-(3-methoxyphenyl)-7-fluoro-1,2,3,4,4a,5,11,11aβ-octahydro-6H-indolo[2,3-g]isoquinoline, 2-methyl-4aα-(3-hydroxyphenyl)-7-fluoro-1,2,3,4,4a,5,11,11aβ-octahydro-6-methyl-indolo[2,3-g]isoquinoline, 2-methyl-4aα-(3-methoxyphenyl)-7-fluoro-1,2,3,4,4a,5,11,11aβ-octahydro-6-methyl-indolo[2,3-g]isoquinoline, 2-allyl-4aα-(3-hydroxyphenyl)-7-fluoro-1,2,3,4,4a,5,11,11aβ-octahydro-6-methyl-indolo[2,3-g]isoquinoline, 2-allyl-4aα-(3-methoxyphenyl)-7-fluoro-1,2,3,4,4a,5,11,11aβ-octahydro-6-methyl-indolo[2,3-g]isoquinoline, 2-cyclopropylmethyl-4aα-(3-hydroxyphenyl)-7-fluoro-1,2,3,4,4a,5,11,11aβ-octahydro-6-methyl-indolo[2,3-g]isoquinoline, 2-cyclopropylmethyl-4aα-(3-methoxyphenyl)-7-fluoro-1,2,3,4,4a,5,11,11aβ-octahydro-6-methyl-indolo[2,3-g]isoquinoline, 2-benzyl-4aα-(3-hydroxyphenyl)-7-fluoro-1,2,3,4,4a,5,11,11aβ-octahydro-6-methyl-indro[2,3-g]isoquinoline, 2-benzyl-4aα-(3-methoxyphenyl)-7-fluoro-1,2,3,4,4a,5,11,11aβ-octahydro-6-methyl-indolo[2,3-g]isoquinoline, 2-phenethyl-4aα-(3-hydroxyphenyl)-7-fluoro-1,2,3,4,4a,5,11,11aβ-octahydro-6-methyl-indolo[2,3-g]isoquinoline, 2-phenethyl-4aα-(3-methoxyphenyl)-7-fluoro-1,2,3,4,4a,5,11,11aβ-octahydro-6-methyl-indolo[2,3-g]isoquinoline, 2-methyl-4aα-(3-hydroxyphenyl)-9-fluoro-1,2,3,4,4a,5,11,11aβ-octahydro-6H-indolo[2,3-g]isoquinoline, 2-methyl-4aα-(3-methoxyphenyl)-9-fluoro-1,2,3,4,4a,5,11,11aβ-octahydro-6H-indolo[2,3-g]isoquinoline, 2-benzyl-4aα-(3-hydroxyphenyl)-9-fluoro-1,2,3,4,4a, 5,11,11aβ-octahydro-6H-indolo[2,3-g]isoquinoline, 2-benzyl-4aα-(3-methoxyphenyl)-9-fluoro-1,2,3,4,4a,5,11,11aβ-octahydro-6H-indolo[2,3-g]isoquinoline, 2-phenethyl-4aα-(3-hydroxyphenyl)-9-fluoro-1,2,3,4,4a,5,11,11aβ-octahydro-6H-indolo[2,3-g]isoquinoline, 2-phenethyl-4aα-(3-methoxyphenyl)-9-fluoro-1,2,3,4,4a,5,11,11aβ-octahydro-6H-indolo[2,3-g]isoquinoline, 2-cyclopropylmethyl-4aα-(3-hydroxyphenyl)-9-fluoro-1,2,3,4,4a,5,11,11aβ-octahydro-6H-indolo[2,3-g]isoquinoline, 2-cyclopropylmethyl-4aα-(3-methoxyphenyl)-9-fluoro-1,2,3,4,4a,5,11,11aβ-octahydro-6H-indolo[2,3-g]isoquinoline, 2-allyl-4aα-(3-hydroxyphenyl)-9-fluoro-1,2,3,4,4a,5,11,11aβ-octahydro-6H-indolo[2,3-g]isoquinoline, 2-allyl-4aα-(3-methoxyphenyl)-9-fluoro-1,2,3,4,4a,5,11,11aβ-octahydro-6H-indolo[2,3-g]isoquinoline, 2-methyl-4aα-(3-hydroxyphenyl)-9-fluoro-1,2,3,4,4a,5,11,11aβ-octahydro-6-methyl-indolo[2,3-g]isoquinoline, 2-methyl-4aα-(3-methoxyphenyl)-9-fluoro-1,2,3,4,4a,5,11,11aβ-octahydro-6-methyl-indolo[2,3-g]isoquinoline, 2-allyl-4aα-(3-hydroxyphenyl)-9-fluoro-1,2,3,4,4a,5,11,11aβ-octahydro-6-methyl-indolo[2,3-g]isoquinoline, 2-allyl-4aα-(3-methoxyphenyl)-9-fluoro-1,2,3,4,4a,5,11,11aβ-octahydro-6-methyl-indolo[2,3-g]isoquinoline, 2-cyclopropylmethyl-4aα-(3-hydroxyphenyl)-9-fluoro-1,2,3,4,4a,5,11,11aβ-octahydro-6-methyl-indolo[2,3-g]isoquinoline, 2-cyclopropylmethyl-4aα-(3-methoxyphenyl)-9-fluoro-1,2,3,4,4a,5,11,11aβ-octahydro-6-methyl-indolo[2,3-g]isoquinoline, 2-benzyl-4aα-(3-hydroxyphenyl)-9-fluoro-1,2,3,4,4a,5,11,11aβ-octahydro-6-methyl-indolo[2,3-g]isoquinoline, 2-benzyl-4aα-(3-methoxyphenyl)-9-fluoro-1,2,3,4,4a,5,11,11aβ-octahydro-6-methyl-indolo[2,3-g]isoquinoline, 2-phenethyl-4aα-(3-hydroxyphenyl)-9-fluoro-1,2,3,4,4a,5,11,11aβ-octahydro-6-methyl-indolo-[2,3-g]isoquinoline, 2-phenethyl-4aα-(3-methoxyphenyl)-9-fluoro-1,2,3,4,4a,5,11,11aβ-octahydro-6-methyl-indolo[2,3-g]isoquinoline, 2-methyl-4aα-(3-hydroxyphenyl)-8-methyl-1,2,3,4,4a,5,11,11aβ-octahydro-6H-indolo[2,3-g]isoquinoline, 2-methyl-4aα-(3-methoxyphenyl)-8-methyl-1,2,3,4,4a,5,11,11aβ-octahydro-6H-indolo[2,3-g]isoquinoline, 2-benzyl-4aα-(3-hydroxyphenyl)-8-methyl-1,2,3,4,4a,5,11,11aα-octahydro-6H-indolo[2,3-g]isoquinoline, 2-benzyl-4aα-(3-methoxyphenyl)-8-methyl-1,2,3,4,4a,5,11,11aβ-octahydro-6H-indolo[2,3-g]isoquinoline, 2-phenethyl-4aα-(3-hydroxyphenyl)-8-methyl-1,2,3,4,4a,5,11,11aβ-octahydro-6H-indolo[2,3-g]isoquinoline, 2-phenethyl-4aα-(3-methoxyphenyl)-8-methyl-1,2,3,4,4a,5,11,11aβ-octahydro-6H-indolo[2,3-g]isoquinoline, 2-cyclopropylmethyl-4aα-(3-hydroxyphenyl)-8-methyl-1,2,3,4,4a,5,11,11aβ-octahydro-6H-indolo[2,3-g]isoquinoline, 2-cyclopropylmethyl-4aα-(3-methoxyphenyl)-8-methyl-1,2,3,4,4a,5,11,11aβ-octahydro-6H-indolo[2,3-g]isoquinoline, 2-allyl-4aα-(3-hydroxyphenyl)-8-methyl-1,2,3,4,4a,5,11,11aβ-octahydro-6H-indolo[2,3-g]isoquinoline, 2-allyl-4aα-(3-methoxyphenyl)-8-methyl-1,2,3,4,4a,5,11,11aβ-octahydro-6H-indolo[2,3-g]isoquinoline, 2-methyl-4aα-(3-hydroxyphenyl)-8-methyl-1,2,3,4,4a,5,11,11aβ-octahydro-6-methyl-indolo[2,3-g]isoquinoline, 2-methyl-4aα-(3-methoxyphenyl)-8-methyl-1,2,3,4,4a,5,11,11aβ-octahydro-6-methyl-indolo[2,3-g]isoquinoline, 2-allyl-4aα-(3-hydroxyphenyl)-8-methyl-1,2,3,4,4a,5,11,11aβ-octahydro-6-methyl-indolo[2,3-g]isoquinoline, 2-allyl-4aα-(3-methoxyphenyl)-8-methyl-1,2,3,4,4a,5,11,11aβ-octahydro-6-methyl-indolo[2,3-g]isoquinoline, 2-cyclopropylmethyl-4aα-(3-hydroxyphenyl)-8-methyl-1,2,3,4,4a,5,11,11aβ-octahydro-6-methyl-indolo[2,3-g]isoquinoline, 2-cyclopropylmethyl-4aα-(3-methoxyphenyl)-8-methyl-1,2,3,4,4a,5,11,11aβ-octahydro-6-methyl-indolo[2,3-g]isoquinoline, 2-benzyl-4aα-(3-hydroxyphenyl)-8-methyl-1,2,3,4,4a,5,11,11aβ-octahydro-6-methyl-indolo[2,3-g]isoquinoline, 2-benzyl-4aα-(3-methoxyphenyl)-8-methyl-1,2,3,4,4a,5,11,11aβ-octahydro-6-methyl-indolo[2,3-g]isoquinoline, 2-phenethyl-4aα-(3-hydroxyphenyl)-8-methyl-1,2,3,4,4a,5,11,11aβ-octahydro-6-methyl-indolo[2,3-g]isoquinoline, 2-phenethyl-4aα-(3-methoxyphenyl)-8-methyl-1,2,3,4,4a,5,11,11aβ-octahydro-6-methyl-indolo[2,3-g]isoquinoline, 2-methyl-4aα-(3-hydroxyphenyl)-9-nitro-1,2,3,4,4a,5,11,11aβ-octahydro-6H-indolo[2,3-g]isoquinoline, 2-methyl-4aα-(3-methoxyphenyl)-9-nitro-1,2,3,4,4a,5,11,11aβ-octahydro-6H-indolo[2,3-g]isoquinoline, 2-benzyl-4aα(3-hydroxyphenyl)-9-nitro-1,2,3,4,4a,5,11,11aβ-octahydro-6H-indolo[2,3-g]isoquinoline, 2-benzyl-4aα-(3-methoxyphenyl)-9-nitro-1,2,3,4,4a,5,11,11aβ-octahydro-6H-indolo[2,3-g]isoquinoline, 2-phenethyl-4aα-(3-hydroxyphenyl)-9-nitro-1,2,3,4,4a,5,11,11aβ-octahydro-6H-indolo[2,3-g]isoquinoline, 2-phenethyl-4aα-(3-methoxyphenyl)-9-nitro-1,2,3,4,4a,5,11,11aβ-octahydro-6H-indolo[2,3-g]isoquinoline, 2-cyclopropylmethyl-4aα-(3-hydroxyphenyl)-9-nitro-1,2,3,4,4a,5,11,11aβ-octahydro-6H-indolo[2,3-g]isoquinoline, 2-cyclopropylmethyl-4aα-(3-methoxyphenyl)-9-nitro-1,2,3,4,4a,5,11,11aβ-octahydro-6H-indolo[2,3-g]isoquinoline, 2-allyl-4aα-(3-hydroxyphenyl)-9-nitro-1,2,3,4,4a,5,11,11aβ-octahydro-6H-indolo[2,3-g]isoquinoline, 2-allyl-4aα-(3-methoxyphenyl)-9-nitro-1,2,3,4,4a,5,11,11aβ-octahydro-6H-indolo[2,3-g]isoquinoline, 2-methyl-4aα-(3-hydroxyphenyl)-9-nitro-1,2,3,4,4a,5,11,11aβ-octahydro-6-methyl-indolo[2,3-g]isoquinoline, 2-methyl-4aα-(3-methoxyphenyl)-9-nitro-1,2,3,4,4a,5,11,11aβ-octahydro-6-methyl-indolo[2,3-g]isoquinoline, 2-allyl-4aα-(3-hydroxyphenyl)-9-nitro-1,2,3,4,4a,5,11,11aβ-octahydro-6-methyl-indolo[2,3-g]isoquinoline, 2-allyl-4aα-(3-methoxyphenyl)-9-nitro-1,2,3,4,4a,5,11,11aβ-octahydro-6-methyl-indolo[2,3-g]isoquinoline, 2-cyclopropylmethyl-4aα-(3-hydroxyphenyl)-9-nitro-1,2,3,4,4a,5,11,11aβ-octahydro-6-methyl-indolo[2,3-g]isoquinoline, 2-cyclopropylmethyl-4aα-(3-methoxyphenyl)-9-nitro-1,2,3,4,4a,5,11,11aβ-octahydro-6-methyl-indolo[2,3-g]isoquinoline, 2-benzyl-4aα-(3-hydroxyphenyl)-9-nitro-1,2,3,4,4a,5,11,11aβ-octahydro-6-methyl-indolo[2,3-g]isoquinoline, 2-benzyl-4aα-(3-methoxyphenyl)-9-nitro-1,2,3,4,4a,5,11,11aβ-octahydro-6-methyl-indolo[2,3-g]isoquinoline, 2-phenethyl-4aα-(3-hydroxyphenyl)-9-nitro-1,2,3,4,4a,5,11,11aβ-octahydro-6-methyl-indolo[2,3-g]isoquinoline, 2-phenethyl-4aα-(3-methoxyphenyl)-9-nitro-1,2,3,4,4a,11,11aβ-octahydro-6-methyl-indolo[2,3-g]isoquinoline, 2-methyl-4aα-(3-hydroxyphenyl)-7-bromo-1,2,3,4,4a,5,11,11aβ-octahydro-6H-indolo[2,3-g]isoquinoline, 2-methyl-4aα-(3-methoxyphenyl)-7-bromo-1,2,3,4,4a,5,11,11aβ-octahydro-6H-indolo[2,3-g]isoquinoline, 2-benzyl-4aα-(3-hydroxyphenyl)-7-bromo-1,2,3,4,4a,5,11,11aβ-octahydro-6H-indolo[2,3-g]isoquinoline, 2-benzyl-4aα-(3-methoxyphenyl)-7-bromo-1,2,3,4,4a,5,11,11aβ-octahydro-6H-indolo[2,3-g]isoquinoline, 2-phenethyl-4aα-(3-hydroxyphenyl)-7-bromo-1,2,3,4,4a,5,11,11aβ-octahydro-6H-indolo[2,3-g]isoquinoline, 2-phenethyl-4aα-(3-methoxyphenyl)-7-bromo-1,2,3,4,4a,5,11,11aβ-octahydro-6H-indolo[2,3-g]isoquinoline, 2-cyclopropylmethyl-4aα-(3-hydroxyphenyl)-7-bromo-1,2,3,4,4a,5,11,11aβ-octahydro-6H-indolo[2,3-g]isoquinoline, 2-cyclopropylmethyl-4aα-(3-methoxyphenyl)-7-bromo-1,2,3,4,4a,5,11,11aβ-octahydro-6H-indolo[2,3-g]isoquinoline, 2-allyl-4aα-(3-hydroxyphenyl)-7-bromo-1,2,3,4,4a,5,11,11aβ-octahydro-6H-indolo[2,3-g]isoquinoline, 2-allyl-4aα-(3-methoxyphenyl)-7-bromo-1,2,3,4,4a,5,11,11aβ-octahydro-6H-indolo[2,3-g]isoquinoline, 2-methyl-4aα-(3-hydroxyphenyl)-7-bromo-1,2,3,4,4a,5,11,11aβ-octahydro-6-methyl-indolo[2,3-g]isoquinoline, 2-methyl-4aα-(3-methoxyphenyl)-7-bromo-1,2,3,4,4a,5,11,11aβ-octahydro-6-methyl-indolo[2,3-g]isoquinoline, 2-allyl-4aα-(3-hydroxyphenyl)-7-bromo-1,2,3,4,4a,5,11,11aβ-octahydro-6-methyl-indolo[2,3-g]isoquinoline, 2-allyl-4aα-(3-methoxyphenyl)-7-bromo-1,2,3,4,4a,5,11,11aβ-octahydro-6-methyl-indolo[2,3-g]isoquinoline, 2-cyclopylmethyl-4aα-(3-hydroxyphenyl)-7-bromo-1,2,3,4,4a,5,11,11aβ-octahydro-6-methyl-indolo[2,3-g]isoquinoline, 2-cyclopropylmethyl-4aα-(3-methoxyphenyl)-7-bromo-1,2,3,4,4a,5,11,11a,β-octahydro-6-methyl-indolo[2,3-g]isoquinoline, 2-benzyl-4aα-(3-hydroxyphenyl)-7-bromo-1,2,3,4,4a,5,11,11a-β-octahydro-6-methyl-indolo[2,3-g]isoquinoline, 2-benzyl-4aα-(3-methoxyphenyl)-7-bromo-1,2,3,4,4a,5,11,11aβ-octahydro-6-methyl-indolo[2,3-g]isoquinoline, 2-phenethyl-4aα-(3-hydroxyphenyl)-7-bromo-1,2,3,4,4a,5,11,11aβ-octahydro-6-methyl-indolo[2,3-g]isoquinoline, 2-phenethyl-4aα-(3-methoxyphenyl)-7-bromo-1,2,3,4,4a,5,11,11aβ-octahydro-6-methyl-indolo[2,3-g]isoquinoline, 2-methyl-4aα-(3-hydroxyphenyl)-7-chloro-1,2,3,4,4a,5,11,11aβ-octahydro-6H-indolo[2,3-g]isoquinoline, 2-methyl-4aα-(3-methoxyphenyl)-7-chloro-1,2,3,4,4a,5,11,11aβ-octahydro-6H-indolo[2,3-g]isoquinoline, 2-benzyl-4aα-(3-hydroxyphenyl)-7-chloro-1,2,3,4,4a,5,11,11aβ-octahydro-6H-indolo[2,3-g]isoquinoline, 2-benzyl-4aα-(3-hydroxyphenyl)-7-chloro-1,2,3,4,4a,5,11,11aβ-octahydro-6H-indolo[2,3-g]isoquinoline, 2-benzyl-4aα-(3-methoxyphenyl)-7-chloro-1,2,3,4,4a,5,11,11aβ-octahydro-6H-indolo[2,3-g]isoquinoline, 2-phenethyl-4aα-(3-hydroxyphenyl)-7-chloro-1,2,3,4,4a,5,11,11aβ-octahydro-6H-indolo[2,3-g]isoquinoline, 2-phenethyl-4aα-(3-methoxyphenyl)-7-chloro-1,2,3,4,4a,5,11,11aβ-octahydro-6H-indolo[2,3-g]isoquinoline, 2-cyclopropylmethyl-4aα-(3-hydroxyphenyl)-7-chloro-1,2,3,4,4a,5,11,11aβ-octahydro-6H-indolo[2,3-g]isoquinoline, 2-cyclopropylmethyl-4aα-(3-methoxyphenyl)-7-chloro-1,2,3,4,4a,5,11,11aβ-octahydro-6H-indolo[2,3-g]isoquinoline, 2-allyl-4aα-(3-hydroxyphenyl)-7-chloro-1,2,3,4,4a,5,11,11aβ-octahydro-6H-indolo[2,3-g]isoquinoline, 2-allyl-4aα-(3-methoxyphenyl)-7-chloro-1,2,3,4,4a,5,11,11aβ-octahydro-6H-indolo[2,3-g]isoquinoline, 2-methyl-4aα-(3-hydroxyphenyl)-7-chloro-1,2,3,4,4a,5,11,11aβ-octahydro-6-methyl-indolo[2,3-g]isoquinoline, 2-methyl-4aα-(3-methoxyphenyl)-7-chloro-1,2,3,4,4a,5,11,11aβ-octahydro-6-methyl-indolo[2,3-g]isoquinoline, 2-allyl-4aα-(3-hydroxyphenyl)-7-chloro-1,2,3,4,4a,5,11,11aβ-octahydro-6-methyl-indolo[2,3-g]isoquinoline, 2-allyl-4aα-(3-methoxyphenyl)-7-chloro-1,2,3,4,4a,5,11,11aβ-octahydro-6-methyl-indolo[2,3-g]isoquinoline, 2-cyclopropylmethyl-4aα-(3-hydroxyphenyl)-7-chloro-1,2,3,4,4a,5,11,11aβ-octahydro-6-methyl-indolo[2,3-g]isoquinoline, 2-cyclopropylmethyl-4aα-(3-methoxyphenyl)-7-chloro-1,2,3,4,4a,5,11,11aβ-octahydro-6-methyl-indolo[2,3-g]isoquinoline, 2-benzyl-4aα-(3-hydroxyphenyl)-7-chloro-1,2,3,4,4a,5,11,11aβ-octahydro-6-methyl-indolo[2,3-g]isoquinoline, 2-benzyl-4aα-(3-methoxyphenyl)-7-chloro-1,2,3,4,4a,5,11,11aβ-octahydro-6-methyl-indolo[2,3-g]isoquinoline, 2-phenethyl-4aα-(3-hydroxyphenyl)-7-chloro-1,2,3,4,4a,5,11,11aβ-octahydro-6-methyl-indolo[2,3-g]isoquinoline, 2-phenethyl-4aα-(3-methoxyphenyl)-7-chloro-1,2,3,4,4a,5,11,11aβ-octahydro-6-methyl-indolo[2,3-g]isoquinoline, 2-methyl-4aα-(3-hydroxyphenyl)-7-methyl-1,2,3,4,4a,5,11,11aβ-octahydro-6H-indolo[2,3-g]isoquinoline, 2-methyl-4aα-(3-methoxyphenyl)-7-methyl-1, 2,3,4,4a,5,11,11aβ-octahydro-6H-indolo[2,3-g]isoquinoline, 2-cyclopropylmethyl-4aα-(3-hydroxyphenyl)-7-methyl-1,2,3,4,4a,5,11,11aβ-octahydro-6H-indolo[2,3-g]isoquinoline, 2-cyclopropylmethyl-4aα-(3-methoxyphenyl)-7-methyl-1,2,3,4,4a,5,11,11aβ-octahydro-6H-indolo[2,3-g]isoquinoline, 2-allyl-4aα-(3-hydroxyphenyl)-7-methyl-1,2,3,4,4a,5,11,11aβ-octahydro-6H-indolo[2,3-g]isoquinoline, 2-allyl-4aα-(3-methoxyphenyl)-7-methyl-1,2,3,4,4a,5,11,11aβ-octahydro-6H-indolo[2,3-g]isoquinoline, 2-benzyl-4aα-(3-hydroxyphenyl)-7-methyl-1,2,3,4,4a,5,11,11aβ-octahydro-6H-indolo[2,3-g]isoquinoline, 2-benzyl-4aα-(3-methoxyphenyl)-7-methyl-1,2,3,4,4a,5,11,11aβ-octahydro-6H-indolo[2,3-g]isoquinoline, 2-phenethyl-4aα-(3-hydroxyphenyl)-7-methyl-1,2,3,4,4a,5,11,11aβ-octahydro-6H-indolo[2,3-g]isoquinoline, 2-phenethyl-4aα-(3-methoxyphenyl)-7-methyl-1,2,3,4,4a,5,11,11aβ-octahydro-6H-indolo[2,3-g]isoquinoline, 2-methyl-4aα-(3-hydroxyphenyl)-10-methyl-1,2,3,4,4a,5,11,11aβ-octahydro-6H-indolo[2,3-g]isoquinoline, 2-methyl-4aα-(3-methoxyphenyl)-10-methyl-1,2,3,4,4a,5,11,11aβ-octahydro-6H-indolo[2,3-g]isoquinoline, 2-cyclopropylmethyl-4aα-(3-hydroxyphenyl)-10-methyl-1,2,3,4,4a,5,11,11aβ-octahydro-6H-indolo[2,3-g]isoquinoline, 2-cyclopropylmethyl-4aα-(3-methoxyphenyl)-10-methyl-1,2,3,4,4a,5,11,11aβ-octahydro-6H-indolo[2,3-g]isoquinoline, 2-allyl-4aα-(3-hydroxyphenyl)-10-methyl-1,2,3,4,4a,5,11,11aβ-octahydro-6H-indolo[2,3-g]isoquinoline, 2-allyl-4aα-(3-methoxyphenyl)-10-methyl-1,2,3,4,4a,5,11,11aβ-octahydro-6H-indolo[2,3-g]isoquinoline, 2-benzyl-4aα-(3-hydroxyphenyl)-10-methyl-1,2,3,4,4a,5,11,11aβ-octahydro-6H-indolo[2,3-g]isoquinoline, 2-benzyl-4aα-(3-methoxyphenyl)-10-methyl-1,2,3,4,4a,5,11,11aβ-octahydro-6H-indolo[2,3-g]isoquinoline, 2-phenethyl-4aα-(3-hydroxyphenyl)-10-methyl-1,2,3,4,4a,5,11,11aβ-octahydro-6H-indolo[2,3-g]isoquinoline, 2-phenethyl-4aα-(3-methoxyphenyl)-10-methyl-1,2,3,4,4a,5,11,11aβ-octahydro-6H-indolo[2,3-g]isoquinoline, 2-methyl-4aα-(3-hydroxyphenyl)-8-bromo-1,2,3,4,4a,5,11,11aβ-octahydro-6H-indolo[2,3-g]isoquinoline, 2-methyl-4aα-(3-methoxyphenyl)-8-bromo-1,2,3,4,4a,5,11,11aβ-octahydro-6H-indolo[2,3-g]isoquinoline, 2-cyclopropylmethyl-4aα-(3-hydroxyphenyl)-8-bromo-1,2,3,4,4a,5,11,11aβ-octahydro-6H-indolo[2,3-g]isoquinoline, 2-cyclopropylmethyl-4aα-(3-methoxyphenyl)-8-bromo-1,2,3,4,4a,5,11,11aβ-octahydro-6H-indolo[2,3-g]isoquinoline, 2-allyl-4aα-(3-hydroxyphenyl)-8-bromo-1,2,3,4,4a,5,11,11aβ-octahydro-6H-indolo[2,3-g]isoquinoline, 2-allyl-4aα-(3-methoxyphenyl)-8-bromo-1,2,3,4,4a,5,11,11aβ-octahydro-6H-indolo[2,3-g]isoquinoline, 2-benzyl-4aα-(3-hydroxyphenyl)-8-bromo-1,2,3,4,4a,5,11,11aβ-octahydro-6H-indolo[2,3-g]isoquinoline, 2-benzyl-4aα-(3-methoxyphenyl)-8-bromo-1,2,3,4,4a,5,11,11aβ-octahydro-6H-indolo[2,3-g]isoquinoline, 2-phenethyl-4aα-(3-hydroxyphenyl)-8-bromo-1,2,3,4,4a,5,11,11aβ-octahydro-6H-indolo[2,3-g]isoquinoline, 2-phenethyl-4aα-(3-methoxyphenyl)-8-bromo-1,2,3,4,4a,5,11,11aβ-octahydro-6H-indolo[2,3-g]isoquinoline, 2-methyl-4aα-(3-hydroxyphenyl)-10-bromo-1,2,3,4,4a,5,11,11aβ-octahydro-6H-indolo[2,3-g]isoquinoline, 2-methyl-4aα-(3-methoxyphenyl)-10-bromo-1,2,3,4,4a,5,11,11aβ-octahydro-6H-indolo[2,3-g]isoquinoline, 2-cyclopropylmethyl-4aα-(3-hydroxyphenyl)-10-bromo-1,2,3,4,4a,5,11,11aβ-octahydro-6H-indolo[2,3-g]isoquinoline, 2-cyclopropylmethyl-4aα-(3-methoxyphenyl)-10-bromo-1,2,3,4,4a,5,11,11aβ-octahydro-6H-indolo[2,3-g]isoquinoline, 2-allyl-4aα-(3-hydroxyphenyl)-10-bromo-1,2,3,4,4a,5,11,11aβ-octahydro-6H-indolo[2,3-g]isoquinoline, 2-allyl-4aα-(3-methoxyphenyl)-10-bromo-1,2,3,4,4a,5,11,11aβ-octahydro-6H-indolo[2,3-g]isoquinoline, 2-benzyl-4aα-(3-hydroxyphenyl)-10-bromo-1,2,3,4,4a,5,11,11aβ-octahydro-6H-indolo[2,3-g]isoquinoline, 2-benzyl-4aα-(3-methoxyphenyl)-10-bromo-1,2,3,4,4a,5,11,11aβ-octahydro-6H-indolo[2,3-g]isoquinoline, 2-phenethyl-4aα-(3-hydroxyphenyl)-10-bromo-1,2,3,4,4a,5,11,11aβ-octahydro-6H-indolo[2,3-g]isoquinoline, 2-phenethyl-4aα-(3-methoxyphenyl)-10-bromo-1,2,3,4,4a,5,11,11aβ-octahydro-6H-indolo[2,3-g]isoquinoline, 2-methyl-4aα-(3-hydroxyphenyl)-8-chloro-1,2,3,4,4a,5,11,11aβ-octahydro-6H-indolo[2,3-g]isoquinoline, 2-methyl-4aα-(3-methoxyphenyl)-8-chloro-1,2,3,4,4a,5,11,11aβ-octahydro-6H-indolo[2,3-g]isoquinoline, 2-cyclopropylmethyl-4aα-(3-hydroxyphenyl)-8-chloro-1,2,3,4,4a,5,11,11aβ-octahydro-6H-indolo[2,3-g]isoquinoline, 2-cyclopropylmethyl-4aα-(3-methoxyphenyl)-8-chloro-1,2,3,4,4a,5,11,11aβ-octahydro-6H-indolo[2,3-g]isoquinoline, 2-allyl-4aα-(3-hydroxyphenyl)-8-chloro-1,2,3,4,4a,5,11,11aβ-octahydro-6H-indolo[2,3-g]isoquinoline, 2-allyl-4aα-(3-methoxyphenyl)-8-chloro-1,2,3,4,4a,5,11,11aβ-octahydro-6H-indolo[2,3-g]isoquinoline, 2-benzyl-4aα-(3-hydroxyphenyl)-8-chloro-1,2,3,4,4a,5,11,11aβ-octahydro-6H-indolo[2,3-g]isoquinoline, 2-benzyl-4aα-(3-methoxyphenyl)-8-chloro-1,2,3,4,4a,5,11,11aβ-octahydro-6H-indolo[2,3-g]isoquinoline, 2-phenethyl-4aα-(3-hydroxyphenyl)-8-chloro-1,2,3,4,4a,5,11,11aβ-octahydro-6H-indolo[2,3-g]isoquinoline, 2-phenethyl-4aα-(3-methoxyphenyl)-8-chloro-1,2,3,4,4a,5,11,11aβ-octahydro-6H-indolo[2,3-g]isoquinoline, 2-methyl-4aα-(3-hydroxyphenyl)-10-chloro-1,2,3,4,4a,5,11,11aβ-octahydro-6H-indolo[2,3-g]isoquinoline, 2-methyl-4aα-(3-methoxyphenyl)-10-chloro-1,2,3,4,4a,5,11,11aβ-octahydro-6H-indolo[2,3-g]isoquinoline, 2-cyclopropylmethyl-4aα-(3-hydroxyphenyl)-10-chloro-1,2,3,4,4a,5,11,11aβ-octahydro-6H-indolo[2,3-g]isoquinoline, 2-cyclopropylmethyl-4aα-(3-methoxyphenyl)-10-chloro-1,2,3,4,4a,5,11,11aβ-octahydro-6H-indolo[2,3-g]isoquinoline, 2-allyl-4aα-(3-hydroxyphenyl)-10-chloro-1,2,3,4,4a,5,11,11aβ-octahydro-6H-indolo[2,3-g]isoquinoline, 2-allyl-4aα-(3-methoxyphenyl)-10-chloro-1,2,3,4,4a,5,11,11aβ-octahydro-6H-indolo[2,3-g]isoquinoline, 2-benzyl-4aα-(3-hydroxyphenyl)-10-chloro-1,2,3,4,4a,5,11,11aβ-octahydro-6H-indolo[2,3-g]isoquinoline, 2-benzyl-4aα-(3-methoxyphenyl)-10-chloro-1,2,3,4,4a,5,11,11aβ-octahydro-6H-indolo[2,3-g]isoquinoline, 2-phenethyl-4aα-(3-hydroxyphenyl)-10-chloro-1,2,3,4,4a,5,11,11aβ-octahydro-6H-indolo[2,3-g]isoquinoline, 2-phenethyl-4aα-(3-methoxyphenyl)-10-chloro-1,2,3,4,4a,5,11,11aβ-octahydro-6H-indolo[2,3-g]isoquinoline, 2-methyl-4aα-(3-hydroxyphenyl)-8-fluoro-1,2,3,4,4a,5,11,11aβ-octahydro-6H-indolo[2,3-g]isoquinoline, 2-methyl-4aα-(3-methoxyphenyl)-8-fluoro-1,2,3,4,4a,5,11,11aβ-octahydro-6H-indolo[2,3-g]isoquinoline, 2-cyclopropylmethyl-4aα-(3-hydroxyphenyl)-8-fluoro-1,2,3,4,4a,5,11,11aβ-octahydro-6H-indolo[2,3-g]isoquinoline, 2-cyclopropylmethyl-4aα-(3-methoxyphenyl)-8-fluoro-1,2,3,4,4a,5,11,11aβ-octahydro-6H-indolo[2,3-g]isoquinoline, 2-allyl-4aα-(3-hydroxyphenyl)-8-fluoro-1,2,3,4,4a,5,11,11aβ-octahydro-6H-indolo[2,3-g]isoquinoline, 2-allyl-4aα-(3-methoxyphenyl)-8-fluoro-1,2,3,4,4a,5,11,11aβ-octahydro-6H-indolo[2,3-g]isoquinoline, 2-benzyl-4aα-(3-hydroxyphenyl)-8-fluoro-1,2,3,4,4a,5,11,11aβ-octahydro-6H-indolo[2,3-g]isoquinoline, 2-benzyl-4aα-(3-methoxyphenyl)-8-fluoro-1,2,3,4,4a,5,11,11aβ-octahydro- 6H-indolo[2,3-g]isoquinoline, 2-phenethyl-4aα-(3-hydroxyphenyl)-8-fluoro-1,2,3,4,4a,5,11,11aβ-octahydro-6H-indolo[2,3-g]isoquinoline, 2-phenethyl-4aα-(3-methoxyphenyl)-8-fluoro-1,2,3,4,4a,5,11,11aβ-octahydro-6H-indolo[2,3-g]isoquinoline, 2-methyl-4aα-(3-hydroxyphenyl)-10-fluoro-1,2,3,4,4a,5,11,11aβ-octahydro-6H-indolo[2,3-g]isoquinoline, 2-methyl-4aα-(3-methoxyphenyl)-10-fluoro-1,2,3,4,4a,5,11,11aβ-octahydro-6H-indolo[2,3-g]isoquinoline, 2-cyclopropylmethyl-4aα-(3-hydroxyphenyl)-10-fluoro-1,2,3,4,4a,5,11,11aβ-octahydro-6H-indolo[2,3-g]isoquinoline, 2-cyclopropylmethyl-4aα-(3-methoxyphenyl)-10-fluoro-1,2,3,4,4a,5,11,11aβ-octahydro-6H-indolo[2,3-g]isoquinoline, 2-allyl-4aα-(3-hydroxyphenyl)-10-fluoro-1,2,3,4,4a,5,11,11aβ-octahydro-6H-indolo[2,3-g]isoquinoline, 2-allyl-4aα-(3-methoxyphenyl)-10-fluoro-1,2,3,4,4a,5,11,11aβ-octahydro-6H-indolo[2,3-g]isoquinoline, 2-benzyl-4aα-(3-hydroxyphenyl)-10-fluoro-1,2,3,4,4a,5,11,11aβ-octahydro-6H-indolo[2,3-g]isoquinoline, 2-benzyl-4aα-(3-methoxyphenyl)-10-fluoro-1,2,3,4,4a,5,11,11aβ-octahydro-6H-indolo[2,3-g]isoquinoline, 2-phenethyl-4aα-(3-hydroxyphenyl)-10-fluoro-1,2,3,4,4a,5,11,11aβ-octahydro-6H-indolo[2,3-g]isoquinoline, 2-phenethyl-4aα-(3-methoxyphenyl)-10-fluoro-1,2,3,4,4a,5,11,11aβ-octahydro-6H-indolo[2,3-g]isoquinoline, 2-methyl-4aα-(3-hydroxyphenyl)-7-nitro-1,2,3,4,4a,5,11,11aβ-octahydro-6H-indolo[2,3-g]isoquinoline, 2-methyl-4aα-(3-methoxyphenyl)-7-nitro-1,2,3,4,4a,5,11,11aβ-octahydro-6H-indolo[2,3-g]isoquinoline, 2-cyclopropylmethyl-4aα-(3-hydroxyphenyl)-7-nitro-1,2,3,4,4a,5,11,11aβ-octahydro-6H-indolo[2,3-g]isoquinoline, 2-cyclopropylmethyl-4aα-(3-methoxyphenyl)-7-nitro-1,2,3,4,4a,5,11,11aβ-octahydro-6H-indolo[2,3-g]isoquinoline, 2-allyl-4aα-(3-hydroxyphenyl)-7-nitro-1,2,3,4,4a,5,11,11aβ-octahydro-6H-indolo[2,3-g]isoquinoline, 2-allyl-4aα-(3-methoxyphenyl)-7-nitro-1,2,3,4,4a,5,11,11aβ-octahydro-6H-indolo[2,3-g]isoquinoline, 2-benzyl-4aα-(3-hydroxyphenyl)-7-nitro-1,2,3,4,4a,5,11,11aβ-octahydro-6H-indolo[2,3-g]isoquinoline, 2-benzyl-4aα-(3-methoxyphenyl)-7-nitro-1,2,3,4,4a,5,11,11aβ-octahydro-6H-indolo[2,3-g]isoquinoline, 2-phenethyl-4aα-(3-hydroxyphenyl)-7-nitro-1,2,3,4,4a,5,11,11aβ-octahydro-6H-indolo[2,3-g]isoquinoline, 2-phenethyl-4aα-(3-methoxphenyl)-7-nitro-1,2,3,4,4a,5,11,11aβ-octahydro-6H-indolo[2,3-g]isoquinoline, 2-methyl-4aα-(3-hydroxyphenyl)-8-nitro-1,2,3,4,4a,5,11,11aα-octahydro-6H-indolo[2,3-g]isoquinoline, 2-methyl-4aα-(3-methoxyphenyl)-8-nitro-1,2,3,4,4a,5,11,11aβ-octahydro-6H-indolo[2,3-g]isoquinoline, 2-cyclopropylmethyl-4aα-(3-hydroxyphenyl)-8-nitro-1,2,3,4,4a,5,11,11aα-octahydro-6H-indolo[2,3-g]isoquinoline, 2-cyclopropylmethyl-4aα-(3-methoxyphenyl)-8-nitro-1,2,3,4,4a,5,11,11aα-octahydro-6H-indolo[2,3-g]isoquinoline, 2-allyl-4aα-(3-hydroxyphenyl)-8-nitro-1,2,3,4,4a,5,11,11aβ-octahydro-6H-indolo[2,3-g]isoquinoline, 2-allyl-4aα-(3-methoxyphenyl)-8-nitro-1,2,3,4,4a,5,11,11aβ-octahydro-6H-indolo[2,3-g]isoquinoline, 2-benzyl-4aα-(3-hydroxyphenyl)-8-nitro-1,2,3,4,4a,5,11,11aβ-octahydro-6H-indolo[2,3-g]isoquinoline, 2-benzyl-4aα-(3-methoxyphenyl)-8nitro-1,2,3,4,4a,5,11,11aβ-octahydro-6H-indolo[2,3-g]isoquinoline, 2-phenethyl-4aα-(3-hydroxyphenyl-8-nitro-1,2,3,4,4a,5,11,11aβ-octahydro-6H-indolo[2,3-g]isoquinoline, 2-phenethyl-4aα-(3-methoxyphenyl)-8-nitro-1,2,3,4,4a,5,11,11aβ-octahydro-6H-indolo[2,3-g]isoquinoline, 2-methyl-4aα-(3-hydroxyphenyl)-10-nitro-1,2,3,4,4a,5,11,11aβ-octahydro-6H-indolo[2,3-g]isoquinoline, 2-methyl-4aα-(3-methoxyphenyl)-10-nitro-1,2,3,4,4a,5,11,11aβ-octahydro-6H-indolo[2,3-g]isoquinoline, 2-methyl-4aα-(3-hydroxyphenyl)-10-nitro-1,2,3,4,4a,5,11,11aβ-octahydro-3-methoxyphenyl)-10-nitro-1,2,3,4,4a,5,11,11aβ-octahydro-6H-indolo[2,3-g]isoquinoline, 2-cyclopropylmethyl-4aα-(3-hydroxyphenyl)-10-nitro-1,2,3,4,4a,5,11,11aβ-octahydro-6H-indolo[2,3-g]isoquinoline, 2-cyclopropylmethyl-4aα-(3-methoxyphenyl)-10-nitro-1,2,3,4,4a,5,11,11aβ-octahydro-6H-indolo[2,3-g]isoquinoline, 2-allyl-4aα-(3-hydroxyphenyl)-10-nitro-1,2,3,4,4a,5,11,11aβ-octahydro-6H-indolo[2,3-g]isoquinoline, 2-allyl-4aα-(3-methoxyphenyl)-10-nitro-1,2,3,4,4a,5,11,11aβ-octahydro-6H-indolo[2,3-g]isoquinoline, 2-benzyl-4aα-(3-hydroxyphenyl)-10-nitro-1,2,3,4,4a,5,11,11aβ-octahydro-6H-indolo[2,3-g]isoquinoline, 2-benzyl-4aα-(3-methoxyphenyl)-10-nitro-1,2,3,4,4a,5,11,11aβ-octahydro-6H-indolo[2,3-g]isoquinoline, 2-phenethyl-4aα-(3-hydroxyphenyl)-10-nitro-1,2,3,4,4a,5,11,11aβ-octahydro-6H-indolo[2,3-g]isoquinoline, 2-phenethyl-4aα-(3-methoxyphenyl)-10-nitro-1,2,3,4,4a,5,11,11aβ-octahydro-6H-indolo[2,3-g]isoquinoline, 2-methyl-4aα-(3-hydroxyphenyl)-11aβ-hydroxy-1,2,3,4,4a,5,11,11aβ-octahydro-6H-indolo[2,3-g]isoquinoline, 2-methyl-4aα-(3-methoxyphenyl)-11aβ-hydroxy-1,2,3,4,4a,5,11,11aβ-octahydro-6H-indolo[2,3-g]isoquinoline, 2-methyl-4aα-(3methoxyphenyl)-11aβ-hydroxy-1,2,3,4,4a,5,11,11aβ-octahydro-6H-indolo[2,3-g]isoquinoline, 2-cyclopropylmethyl-4aα-(3-hydroxyphenyl)-11aβ-hydroxy-1,2,3,4,4a,5,11,11aβ-octahydro-6H-indolo[2,3-g]isoquinoline, 2-cyclopropylmethyl-4aα-(3-methoxyphenyl)-11aβ-hydroxy-1,2,3,4,4a,5,11,11aβ-octahydro-6H-indolo-[2,3-g]isoquinoline, 2-allyl-4aα-(3hydroxyphenyl)-11aβhydroxy-1,2,3,4,4a,5,11,11aβ-octahydro-6H-indolo[2,3-g]isoquinoline, 2-allyl-4aα-(3-methoxyphenyl)-11aβ-hydroxy-1,2,3,4,4a,5,11,11aβ-octahydro-6H-indolo[2,3-g]isoquinoline, 2-benzyl-4aα-(3-hydroxyphenyl)-11aβ-hydroxy-1,2,3,4,4a,5,11,11aβ-octahydro-6H-indolo[2,3-g]isoquinoline, 2-benzyl-4aα-(3-methoxyphenyl)-11aα-hydroxy-1,2,3,4,4a,5,11,11aβ-octahydro-6H-indolo[2,3-g]isoquinoline, 2-phenethyl-4aα-(3-hydroxyphenyl)-11aβ-hydroxy-1,2,3,4,4a,5,11,11aβ-octahydro-6H-indolo[2,3-g]isoquinoline, 2-phenethyl-4aα-(3-methoxyphenyl)-11aβ-hydroxy-1,2,3,4,4a,5,11,11aβ-octahydro-6H-indolo[2,3-g]isoquinoline, 2-methyl-4aα-(3-hydroxyphenyl)-9-methyl-11aβ-hydroxy-1,2,3,4,4a,5,11,11aβ-octahydro-6H-indolo[2,3-g]isoquinoline, 2-methyl-4aα-(3-methoxphenyl)-9-methyl-11aβ-hydroxy-1,2,3,4,4a,5,11,11aβ-octahydro-6H-indolo[2,3-g]isoquinoline, 2-cyclopropylmethyl-4aα-(3-hydroxyphenyl)-9-bromo-11aβ-octahydro-6H-indolo[2,3-g]isoquinoline, 2-cyclopropylmethyl-4aα-(3-methoxyphenyl)-9-bromo-11aβ-hydroxy-1,2,3,4,4a,5,11,11aβ-octahydro-6H-indolo[2,3-g]isoquinoline, 2-allyl-4aα-(3-hydroxyphenyl)-9-chloro-11aβ-hydroxy-1,2,3,4,4a,5,11,11aβ-octahydro-6H-indolo[2,3-g]isoquinoline, 2-allyl-4aα-(3-methoxyphenyl)-9-chloro-11aβ-hydroxy-1,2,3,4,4a,5,11,11aβ-octahydro-6H-indolo[2,3-g]isoquinoline, 2-benzyl-4aα-(3-hydroxyphenyl)-7-fluoro-11aβ-hydroxy-1,2,3,4,4a,5,11,11aβ-octahydro-6H-indolo[2,3-g]isoquinoline, 2-benzyl-4aα-(3-methoxyphenyl)-7-fluoro-11aβ-hydroxy-1,2,3,4,4a,5,11,11aβ-octahydro-6H-indolo[2,3-g]isoquinoline, 2-phenethyl-4aα-(3-hydroxyphenyl)-9-fluoro-11aβ-hydroxy-1,2,3,4,4a,5,11,11aβ-octahydro-6H-indolo[2,3-g]isoquinoline, 2-phenethyl-4aα-(3-methoxyphenyl)-9-fluoro-11aβ-hydroxy-1,2,3,4,4a,5,11,11aβ-octahydro-6H-indolo[2,3-g]isoquinoline, 2-methyl-4aα-(3-hydroxyphenyl)-8-methyl-11aβ-hydroxy-1,2,3,4,4a,5,11,11aβ-octahydro-6H-indolo[2,3-g]isoquinoline, 2-methyl- 4aα-(3-methoxyphenyl)-8-methyl-11aβ-hydroxy-1,2,3,4,4a,5,11,11aβ-octahydro-6H-indolo[2,3-g]isoquinoline, 2-cyclopropylmethyl-4aα-(3-hydroxyphenyl)-9-nitro-11aβ-hydroxy-1,2,3,4,4a,5,11,11aβ-octahydro-6H-indolo[2,3-g]isoquinoline, 2-cyclopropylmethyl-4aα-(3-methoxyphenyl)-9-nitro-11aβ-hydroxy-1,2,3,4,4a,5,11,11aβ-octahydro-6H-indolo[2,3-g]isoquinoline, 2-allyl-4aα-(3-hydroxyphenyl)-7-bromo-11aβ-hydroxy-1,2,3,4,4a,5,11,11aβ-octahydro-6H-indolo[2,3-g]isoquinoline, 2-allyl-4aα-(3-methoxyphenyl)-7-bromo-11aβ-hydroxy-1,2,3,4,4a,5,11,11aβ-octahydro-6H-indolo[2,3-g]isoquinoline, 2-benzyl-4aα-(3-hydroxyphenyl)-7-fluoro-11aβ-hydroxy-1,2,3,4,4a,5,11,11aβ-octahydro-6H-indolo[2,3-g]isoquinoline, 2-benzyl-4aα-(3-methoxyphenyl)-7-fluoro-11aβ-hydroxy-1,2,3,4,4a,5,11,11aβ-octahydro-6H-indolo[2,3-g]isoquinoline, 2-phenethyl-4aα-(3-hydroxyphenyl)-7-chloro-11aβ-hydroxy-1,2,3,4,4a,5,11,11aβ-octahydro-6H-indolo[2,3-g]isoquinoline, 2-phenethyl-4aα-(3-methoxyphenyl)-7-chloro-11aβ-hydroxy-1,2,3,4,4a,5,11,11aβ-octahydro-6H-indolo[2,3-g]isoquinoline, 2-methyl-4aα-(3-hydroxyphenyl)-7-methyl-11aβ-hydroxy-1,2,3,4,4a,5,11,11aβ-octahydro-6H-indolo[2,3-g]isoquinoline, 2-methyl-4aα-(3-methoxyphenyl)-7-methyl-11aβ-hydroxy-1,2,3,4,4a,5,11,11aβ-octahydro-6H-indolo[2,3-g]isoquinoline, 2-cyclopropylmethyl-4aα-(3-hydroxyphenyl)-10-methyl-11aβ-hydroxy-1,2,3,4,4a,5,11,11aβ-octahydro-6H-indolo[2,3-g]isoquinoline, 2-cyclopropylmethyl-4aα-3-methoxyphenyl)-10-methyl-11aβ-hydroxy-1,2,3,4,4a,5,11,11aβ-octahydro-6H-indolo[2,3-g]isoquinoline, 2-allyl-4aα-(3-methoxyphenyl)-8-bromo-11aβ-hydroxy-1,2,3,4,4a,5,11,11aβ-octahydro-6H-indolo[2,3-g]isoquinoline, 2-benzyl-4aα-(3-hydroxyphenyl)-8-bromo-11aβ-hydroxy-1,2,3,4,4a,5,11,11aβ-octahydro-6H-indolo[2,3-g]isoquinoline, 2-benzyl-4aα-(3-hydroxyphenyl)-10-bromo-11aβ-hydroxy-1,2,3,4,4a,5,11,11aβ-octahydro-6H-indolo[2,3-g]isoquinoline, 2-benzyl-4aα-(3-methoxyphenyl)-10-bromo-11aβ-hydroxy-1,2,3,4,4a,5,11,11aβ-octahydro-6H-indolo[2,3-g]isoquinoline, 2-phenethyl-4aα-(3-hydroxyphenyl)-10-bromo-11aβ-hydroxy-1,2,3,4,4a,5,11,11aβ-octahydro-6H-indolo[2,3-g]isoquinoline, 2-phenethyl-4aα-(3-methoxyphenyl)-10-bromo-11aβ-hydroxy-1,2,3,4,4a,5,11,11aβ-octahydro-6H-indolo[2,3-g]isoquinoline, 2-methyl-4aα-(3-methoxyphenyl)-8-chloro-11aβ-hydroxy-1,2,3,4,4a,5,11,11aβ-octahydro-6H-indolo[2,3-g]isoquinoline, 2-methyl-4aα-(3-methoxyphenyl)-8-chloro-11aβ-hydroxy-1,2,3,4,4a,5,11,11aβ-octahydro-6H-indolo[2,3-g]isoquinoline, 2-cyclopropylmethyl-4aα-(3-hydroxyphenyl)-10-chloro-11aβ-hydroxy-1,2,3,4,4a,5,11,11aβ-octahydro-6H-indolo[2,3-g]isoquinoline, 2-cyclopropylmethyl-4aα-(3-methoxyphenyl)-10-chloro-11aβ-hydroxy-1,2,3,4,4a,5,11,11aβ-octahydro-6H-indolo[2,3-g]isoquinoline, 2-allyl-4aα-(3-hydroxyphenyl)-8-fluoro-11aβ-hydroxy-1,2,3,4,4a,5,11,11aβ-octahydro-6H-indolo[2,3-g]isoquinoline, 2-allyl-4aα-(3-methoxyphenyl)-8-fluoro-11aβ-hydroxy-1,2,3,4,4a,5,11,11aβ-octahydro-6H-indolo[2,3-g]isoquinoline, 2-benzyl-4aα-(3-hydroxyphenyl)-10-fluoro-11aβ-hydroxy-1,2,3,4,4a,5,11,11aβ-octahydro-6H-indolo[2,3-g]isoquinoline, 2-benzyl-4aα-(3-methoxyphenyl)-10-fluoro-11aβ-hydroxy-1,2,3,4,4a,5,11,11aβ-octahydro-6H-indolo[2,3-g]isoquinoline, 2-phenethyl-4aα-(3-hydroxyphenyl)-7-nitro-11aβ-hydroxy-1,2,3,4,4a,5,11,11aβ-octahydro-6H-indolo[2,3-g]isoquinoline, 2-phenethyl-4aα-(3-methoxyphenyl)-7-nitro-11aβ-hydroxy-1,2,3,4,4a,5,11,11aβ-octahydro-6H-indolo[2,3-g]isoquinoline, 2-methyl-4aα-(3-hydroxyphenyl)-8-nitro-11aβ-hydroxy-1,2,3,4,4a,5,11,11aβ-octahydro-6H-indolo[2,3-g]isoquinoline, 2-methyl-4aα-(3-methoxyphenyl)-8-nitro-11aβ-hydroxy-1,2,3,4,4a,5,11,11aβ-octahydro-6H-indolo[2,3-g]isoquinoline, 2-cyclopropylmethyl-4aα-(3-methoxyphenyl)-10-nitro-11aβ-hydroxy-1,2,3,4,4a,5,11,11aβ-octahydro-6H-indolo[2,3-g]isoquinoline, and 2-allyl-4aα-(3-hydroxyphenyl)-10-nitro-11aβ-hydroxy-1,2,3,4,4a,5,11,11aβ-octahydro-6H-indolo[2,3-g]isoquinoline, may be cited. Of course, these compounds are not exclusive examples.

This invention further provides an isoquinoline derivative, which is an intermediate for the production of the compound of this invention represented by the formula (1) and is represented by the formula (101):

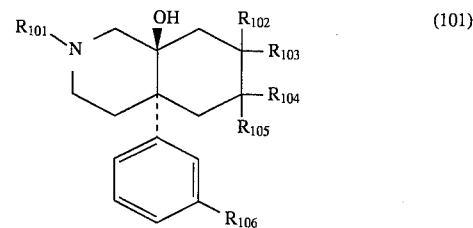

wherein $R_{101}$ stands for a hydrogen atom, alkyl having 1 to 5 carbon atoms, cycloalkylalkyl having 4 to 7 carbon atoms, cycloalkenylalkyl having 6 to 8 carbon atoms, aralkyl having 7 to 14 carbon atoms, trans-alkenyl having 4 or 5 carbon atoms, allyl, furanyl-2-alkyl, thienyl-2-alkyl, $R_{107}OCO$ (wherein $R_{107}$ stands for 2,2,2-trichloroethyl or benzyl), or $R_{108}CO$ (wherein $R_{108}$ stands for alkyl having 1 to 5 carbon atoms, cycloalkyl having 3 to 6 carbon atoms, cycloalkenyl having 5 to 7 carbon atoms, phenyl, aralkyl having 7 to 13 carbon atoms, trans-alkenyl having 4 or 5 carbon atoms, vinyl, 2-furanyl, or 2-thienyl), and $R_{102}$, $R_{103}$, $R_{104}$, and $R_{105}$ independently stand for a hydrogen atom, hydroxy, alkanoyloxy having 1 to 5 carbon atoms, or alkoxy having 1 to 5 carbon atoms, providing that $R_{102}$ and $R_{103}$ or $R_{103}$ and $R_{104}$ may form an oxo group and $R_{103}$ and $R_{104}$ may jointly form a 1,3-dioxolane ring, and $R_{106}$ stands for a hydrogen atom, hydroxy, alkoxy having 1 to 5 carbon atoms, or alkanoyloxy having 1 to 5 carbon atoms, or a pharmacologically acceptable salt thereof and a method for the production thereof.

The salts which are pharmacologically acceptable for use in this invention include salts with such inorganic acids as hydrochloric acid, hydrobromic acid, sulfuric acid, and phosphoric acid and salts with such organic acids as acetic acid, lactic acid, oxalic acid, succinic acid, methanesulfonic acid, benzene-sulfonic acid, toluenesulfonic acid, fumaric acid, maleic acid, and tartaric acid, for example.

Of the isoquinoline derivatives represented by the general formula (101), those which prove to be particularly desirable are such that $R_{101}$ stands for methyl, ethyl, propyl, cyclopropylmethyl, cyclobutylmethyl, cyclopentenylmethyl, cyclohexenylmethyl, benzyl, phenethyl, phenylpropyl, trans-butenyl, allyl, furanyl-2-ylmethyl, thienyl-2-ylmethyl, 2,2,2-trichloroethoxycarbonyl, benzyloxycarbonyl, acetyl, cyclopropanecarbonyl, cyclobutanecarbonyl, cyclopentenecarbonyl, benzoyl, phenylacetyl, trans-propenylcarbonyl, acryloyl, 2-furanylcarbonyl, or 2-thienylcarbonyl, $R_{102}$, $R_{103}$, $R_{104}$, and $R_{105}$ independently stand for hydrogen atom, hydroxy, acetoxy, or methoxy, providing that $R_{102}$ and $R_{103}$ as a pair, and/or $R_{104}$ and $R_{105}$ as a pair may form an oxo group or $R_{103}$ and $R_{104}$ may jointly form a 2,2-dimethyl-1,3-dioxolane ring, and $R_{106}$ represents for example, a hydrogen atom, hydroxy, methoxy, or acetoxy. These substituents are not exclusive examples.

Further, the isoquinoline derivatives which as represented by the following general formulas (101b) and (101c):

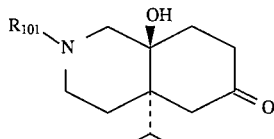
(101b)

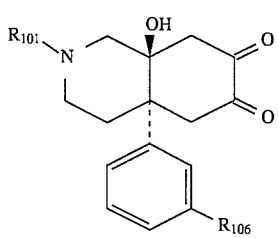
(101c)

wherein $R_{101}$ and $R_{106}$ have the same meanings as defined above having a ketone group at the 6 position and/or the 7 position prove to be particularly desirable.

In the compounds of this invention represented by the general formula (101), the particular compound (106) wherein $R_{101}$ is methyl, $R_{102}$ and $R_{103}$ are a hydrogen atom $R_{104}$ and $R_{105}$ are an oxygen atom, and $R_{106}$ is methoxy:

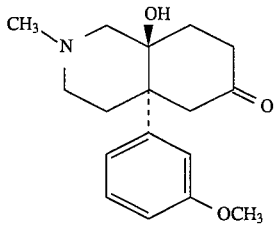
(106)

is named 2-methyl-4aα-(3-methoxyphenyl)-6-oxo-8aβ-hydroxy-1,2,3,4,4a,5,6,7,8,8a-decahydroisoquinoline. In accordance with the nomenclature exemplified above, as representative examples of the compound of this invention, 2-cyclopropylmethyl-4aα-(3-methoxyphenyl)-6-oxo-8aβ-hydroxy-1,2,3,4,4a,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-phenethyl-4aα-(3-methoxyphenyl)-6-oxo-8aβ-hydroxy-1,2,3,4,4a,5,6,7,8,8a-decahydroisoquinoline, 2-allyl-4aα-(3-methoxyphenyl)-6-oxo-8aβ-hydroxy-1,2,3,4,4a,5,6,7,8,8a-decahydroisoquinoline, 2-methyl-4aα-(3-methoxyphenyl)-6,7-dioxo-8aβ-hydroxy-1,2,3,4,4a,5,6,7,8,8a-decahydroisoquinoline, 2-cyclopropylmethyl-4aα-(3-methoxyphenyl)-6,7-dioxo-8aβ-hydroxy-1,2,3,4,4a,5,6,7,8,8a-decahydroisoquinoline, 2-benzyl-4aα-(3-methoxyphenyl)-6,7-dioxo-8aβ-hydroxy-1,2,3,4,4a,5,6,7,8,8a-decahydroisoquinoline, 2-phenethyl-4aα-(3-methoxyphenyl)-6,7-dioxo-8aβ-hydroxy-1,2,3,4,4a,5,6,7,8,8a-decahydroisoquinoline, 2-allyl-4aα-(3-methoxyphenyl)-6,7-dioxo-8aβ-hydroxy-1,2,3,4,4a,5,6,7,8,8a-decahydroisoquinoline, 2-methyl-4aα-(3-methoxyphenyl)-6,8aβ-dihydroxy-1,2,3,4,4a,5,6,7,8,8a-decahydroisoquinoline, 2-cyclopropylmethyl-4aα-(3-methoxyphenyl)-6,8aβ-dihydroxy-1,2,3,4,4a,5,6,7,8,8a-decahydroisoquinoline, 2-benzyl-4aα-(3-methoxyphenyl)-6,8aβ-dihydroxy)-1,2,3,4,4a,5,6,7,8,8a-decahydroisoquinoline, 2-phenethyl-4aα-(3-methoxyphenyl)-6,8aβ-dihydroxy-1,2,3,4,4a,5,6,7,8,8a-decahydroisoquinoline, 2-allyl-4aα-(3-methoxyphenyl)-6,8aβ-dihydroxy-1,2,3,4,4a,5,6,7,8,8a-decahydroisoquinoline, 2-methyl-4aβ-(3-methoxyphenyl)-6,7,8aβ-trihydroxy-1,2,3,4,4a,5,6,7,8,8a-decahydroisoquinoline, 2-cyclopropylmethyl-4aα-(3-methoxyphenyl)-6,7,8aβ-trihydroxy-1,2,3,4,4a,5,6,7,8,8a-decahydroisoquinoline, 2-benzyl-4aα-(3-methoxyphenyl)-6,7,8aβ-trihydroxy-1,2,3,4,4a,5,6,7,8,8a-decahydroisoquinoline, 2-phenethyl-4aα-(3-methoxyphenyl)-6,7,8aβ-trihydroxy-1,2,3,4,4a,5,6,7,8,8a-decahydroisoquinoline, 2-allyl-4aα-(3-methoxyphenyl)-6,7,8aβ-trihydroxy-1,2,3,4,4a,5,6,7,8,8a-decahydroisoquinoline, 2-(2,2,2-trichloroethoxycarbonyl)-4aα-(3-methoxyphenyl)-6-acetoxy-8aβ-hydroxy-1,2,3,4,4a,5,6,7,8,8a-decahydroisoquinoline, 2-benzyloxycarbonyl-4aα-(3-methoxyphenyl)-6-acetoxy-8aβ-hydroxy-1,2,3,4,4a,5,6,7,8,8a-decahydroisoquinoline, 2-cyclopropylcarbonyl-4aα-(3-methoxyphenyl)-6-acetoxy-8aβ-hydroxy-1,2,3,4,4a,5,6,7,8,8a-decahydroisoquinoline, 2-benzoyl-4aα-(3-methoxyphenyl)-6-acetoxy-8aβ-hydroxy-1,2,3,4,4a,5,6,7,8,8a-decahydroisoquinoline, 2-phenylacetyl-4aα-(3-methoxyphenyl)-6-acetoxy-8aβ-hydroxy-1,2,3,4,4a,5,6,7,8,8a-decahydroisoquinoline, 2-acryloyl-4aα-(3-methoxyphenyl)-6-acetoxy-8aβ-hydroxy-1,2,3,4,4a,5,6,7,8,8a-decahydroisoquinoline, 2-(2,2,2-trichloroethoxycarbonyl)-4aα-(3-methoxyphenyl)-8aβ-hydroxy-1,2,3,4,4a,5,6,7,8,8a-decahydro-2,2-dimethyl-1,3-dioxolo[4,5-g]isoquinoline, 2-benzyloxycarbonyl-4aα-(3-methoxyphenyl)-8aβ-hydroxy-1,2,3,4,4a,5,6,7,8,8a-decahydro-2,2-dimethyl-1,3-dioxolo[4,5-g]isoquinoline, 2-cyclopropylcarbonyl-4aα-(3-methoxyphenyl)-8aβ-hydroxy-1,2,3,4,4a,5,6,7,8,8a-decahydro-2,2-dimethyl-1,3-dioxolo[4,5-g]isoquinoline, 2-benzoyl-4aα-(3-methoxyphenyl)-8aβ-hydroxy-1,2,3,4,4a,5,6,7,8,8a-decahydro-2,2-dimethyl-1,3-dioxolo[4,5-g]isoquinoline, 2-phenylacetyl-4aβ-(3-methoxyphenyl)-hydroxy-1,2,3,4,4a,5,6,7,8,8a-decahydro-2,2-dimethyl-1,3-dioxolo[4,5-g]isoquinoline, and 2-acryloyl-4aα-(3-methoxyphenyl)-8aβ-hydroxy-1,2,3,4,4a,5,6,7,8,8a-decahydro-2,2-dimethyl-1,3-dioxolo[4,5-g] isoquinoline may be cited. Of course, these compounds are not exclusive examples.

The compounds of this invention embrace (+), (−), and (±) forms.

The compounds of this invention represented by the general formula (1) are produced easily by treating the corresponding compounds represented by the general formula (3) to react with amine derivatives represented by the general formula (4) in a solvent in the presence of an acid catalyst (Chart 1) [wherein $R_1$, $R_2$, $R_3$, $R_4$, and $R_5$ have the same meanings as defined above].

The solvents which are usable for the reaction include alcohols such as methanol and ethanol, fatty acid solvents such as acetic acid and propionic acid, and dipolar aprotic solvents such as DMF and DMSO, for example. Among other solvents mentioned above, alcohols prove to be desirable and ethanol is particularly desirable. As amine derivatives represented by the general formula (4), phenylhydrazine derivatives are cited. The acid catalysts which are usable effectively herein include inorganic acids such as hydrochloric acid, sulfuric acid, nitric acid, and phosphoric acid and organic acids such as methanesulfonic acid, p-toluenesulfonic acid, acetic acid, formic acid, and propionic acid, for example. Among other acids mentioned above hydrochloric acid, sulfuric acid, and methanesulfonic acid are desirably used. Of course, these acids are not exclusive examples. The reaction temperature is conceivable in the range of form 0° C. to 300° C. The reaction is practicable at temperatures in the range of from 25° C. to 150° C. Generally, the reaction is carried out favorably at temperatures in the range of from 60° C. to 120° C.

Of the compounds represented by the general formula (1), those of a general formula (1') having a hydrogen atom as $R_2$ are obtained by dissolving the corresponding compounds of the general formula (1) having methyl as $R_2$ in a solvent and causing the dissolved compounds to react with a base in the presence of mercaptan or to react with a trivalent boron compound (in the formulas, $R_1$, $R_3$, $R_4$, and $R_5$ have the same meanings as defined above). In the reaction using mercaptan and a base, such dipolar aprotic solvents as DMF, DMSO and HMPA are favorably usable and DMF is used particularly desirable. In the reaction using trivalent boron compound, halogenous solvents such as methylene chloride, chloroform, and carbon tetrachloride are favorably usable and methylene chloride is used particularly desirable. As mercaptans which are effectively usable in the reaction, those mercaptans possessed of a side chain having 1 to 10 carbon atoms may be cited. Generally, propyl mercaptan is desirably used. The bases which are effectively usable herein include alkali metal salts of alcohols such as potassium t-butoxide, potassium ethoxide, potassium methoxide, sodium t-butoxide, sodium ethoxide, and sodium methoxide, metal hydrides such as sodium hydride and potassium hydride, and metal salts of ammonia such as sodium amide, for example. Generally, the reaction using potassium t-butoxide yields fully satisfactory results. As trivalent boron compounds effectively usable herein, boron tribromide and boron trichloride may be cited. Boron tribromide proves to be particularly desirable. The reaction temperature when the reaction uses a mercaptan is conceivable in the range of from 0° C. to 300° C. and is desirable in the range of from 50° C. to 200° C. This reaction performed at temperatures in the range of from 100° C. to 160° C. yields fully satisfactory results. In the reaction using a trivalent boron compound, the reaction temperature is desired in the range of from –80° C. to 50° C., preferably from 0° C. to 30° C.

In the compounds of the general formula (3), the particular compound having methyl as $R_1$ and $R_2$ and a hydrogen atom as $R_5$ can be synthesized in accordance with the method reported by D. M. Zimmerman (J. Org. Chem., 1989, 54, 1442.).

Chart 1

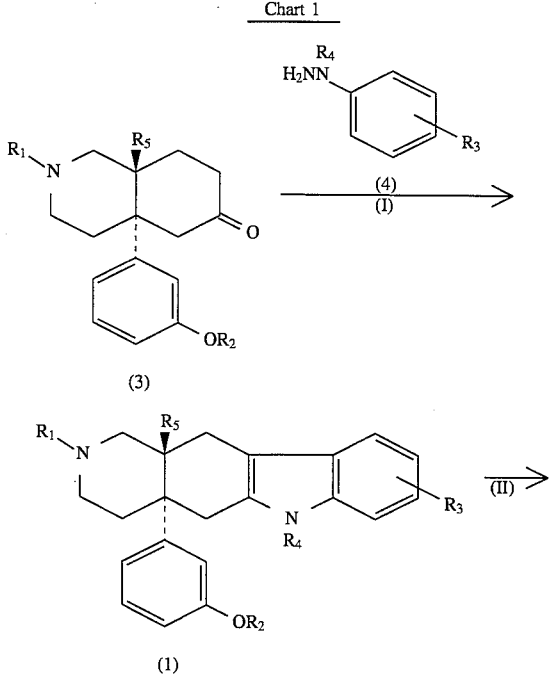

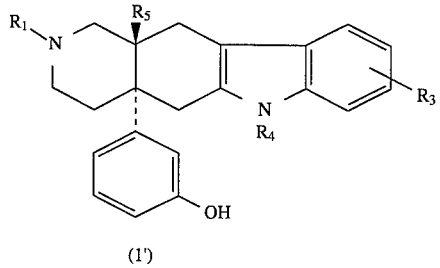

(1')

In the compounds of the general formula (1), those having alkyl of 2 to 5 carbon atoms, cycloalkylalkyl of 3 to 6 carbon atoms, cycloalkenylalkyl of 5 to 7 carbon atoms, aralkyl, trans-alkenyl of 4 to 5 carbon atoms, allyl or furanyl-2-ylalkyl as $R_1$, methyl as $R_2$, and a hydrogen atom as $R_4$ can be produced through a route indicated in Chart 2. The first step resides in converting the methyl group on the nitrogen atom of ketone (3) into a carbamate by the use of a chlorocarbonic ester represented by the general formula (5) in the presence of a base. In the formula (5), $R_6$ stands for a vinyl or trichloroethyl group. The base to be used in the conversion has a large enough steric hindrance to avoid reacting with an acid chloride. For example, such bases as proton sponge and Hünig base prove to be desirable. As regards the solvent, such halogenous solvents as methylene chloride, chloroform, carbon tetrachloride, and 1,2-dichloroethane are favorably usable. Generally, 1,2-dichloroethane is desirably used. The reaction temperature is practicable in the range of from –80° C. to 100° C. Generally, the reaction performed at temperatures in the range of from 0° C. to normal room temperature yields satisfactory results. The second step resides in producing a compound represented by the general formula (7) by the use of a reagent represented by the general formula (4) in the same manner as in Chart 1 (the reaction conditions and $R_4$ and $R_3$ are identical to those in Chart 1). The third step resides in deprotection nitrogen atom of a protective group on the nitrogen atom to afford a secondary amine. Where $R_6$ is a vinyl group, hydrolysis is easily effected by the use of hydrochloric acid-methanol. The reaction is generally executed at the reflux temperature of methanol. Where $R_6$ is a trichloroethyl group, the removal can be effected by virtue of reduction with zinc in the presence of an acid catalyst. The acids that are effectively usable in the reaction include acetic acid, hydrochloric acid, sulfuric acid, and nitric acid, for example. Generally, the reaction performed with acetic acid both as solvent and acid catalyst yields fully satisfactory results. The reaction can be generally carried out at room temperature. The fourth step resides in producing an amide (10) by the reaction of the compound represented by the general formula (8) with an acid chloride in the presence of a base ($R_7$ stands for alkyl having 1 to 4 carbon atoms, cycloalkyl having 3 to 6 carbon atoms, cycloalkenyl having 5 to 7 carbon atoms, aryl, trans-alkenyl having 3 or 4 carbon atoms, vinyl, or 2-furanyl and $R_3$ has the same meaning as defined above). The bases that are effectively usable in the reaction include tertiary amines such as triethylamine, diisopropylethylamine, and proton sponge, for example. Generally, the reaction using triethylamine yields fully satisfactory results. As respects the solvent, such halogenous solvents as dichloromethane, chloroform, and 1,2-dichloroethane are effectively usable. Among other solvents mentioned above, dichloromethane particularly is favorably used. The reaction can be carried out at temperatures in the range of from −80° C. to 100° C., preferably from 0° C. to 30° C. The fifth step resides in converting the amide, by reduction, into an amine. The reducing agents that are effectively usable in the conversion include sodium borohydride, lithium aluminum hydride, DIBAR, and lithium borohydride, for example. Among other reducing agents mentioned above, DIBAR and lithium aluminum hydride prove to be particularly desirable. As regards the solvent, such ethers as ether, THF, DME, and dioxane are desirably used. Among other solvents mentioned above, THF proves to be particularly desirable. The reaction can be carried out at temperatures in the range of from −40° C. to 100° C., preferably 0° C. to 30° C. The sixth step resides in the conversion into a hydroxide group by the removal of the methyl group. The conversion can be effected under the same conditions as those used in the production of the particular compound of the general formula (1) having a hydrogen atom as $R_2$.

Chart 2

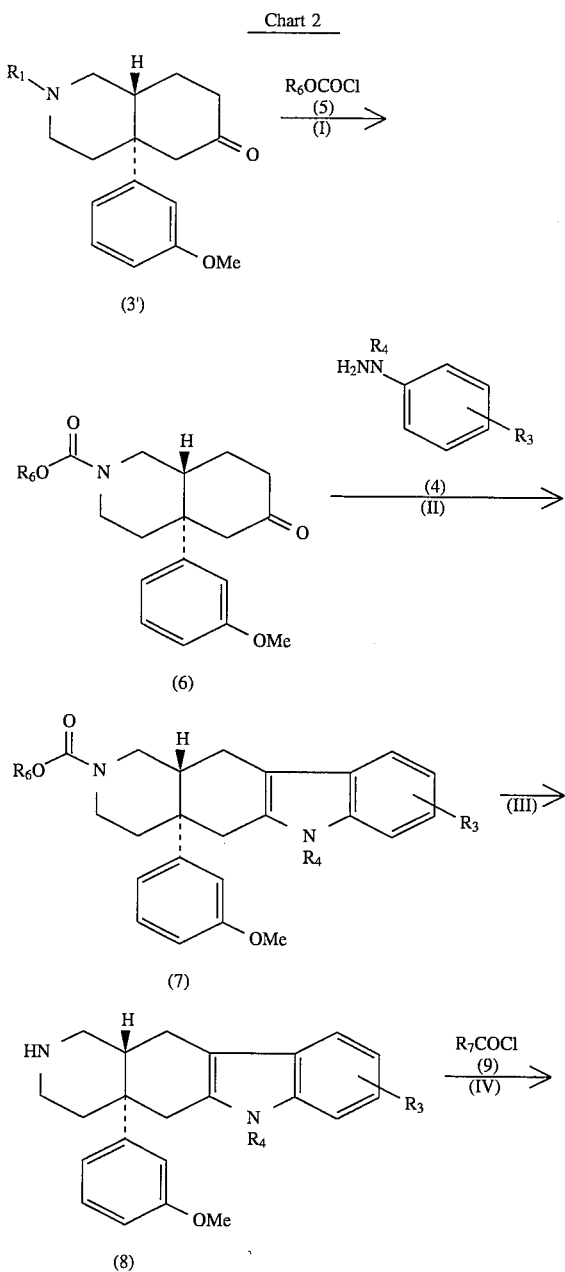

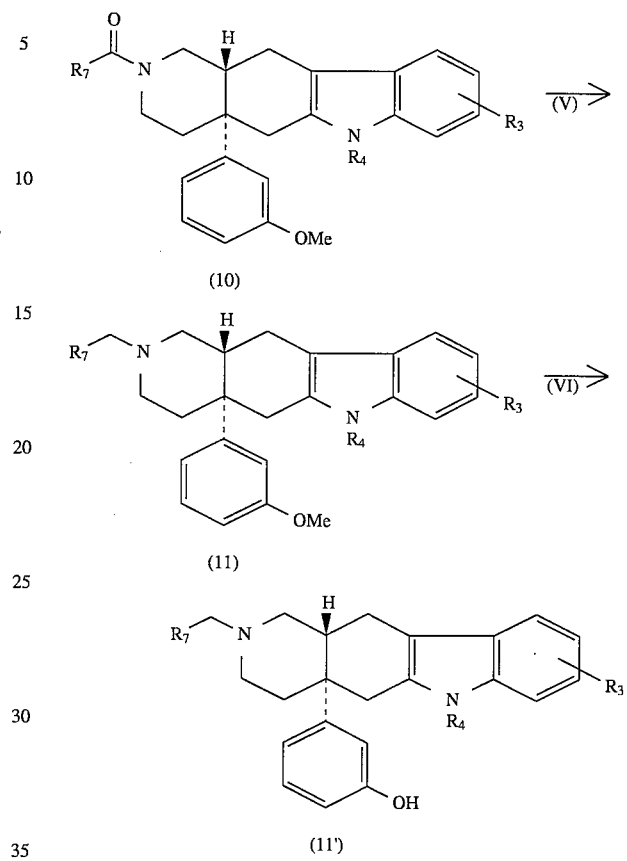

In the compounds represented by the general formula (1), those which have alkyl of 2 to 5 carbon atoms, cycloalkylalkyl of 3 to 6 carbon atoms, cycloalkenylalkyl of 5 to 7 carbon atoms, aralkyl, transalkenyl of 4 or 5 carbon atoms, allyl, or furanyl-2-ylalkyl as $R_1$ and a hydrogen atom as $R_2$ and $R_5$ can be also produced through a route shown in Chart 3.

The first step resides in producing a compound represented by the general formula (6) ($R_6$ and has the same meaning as defined above). The reaction conditions involved therein are the same as those of the first step in Chart 2. The second step resides in deprotection atom a protective group in the nitrogen and affording a secondary amine. Where $R_6$ is vinyl, the hydrolysis can be easily effected with hydrochloric acid-methanol. The reaction is generally carried out at the reflux temperature of methanol. Where $R_6$ is a trichloroethyl group, the removal of the protective group can be attained by reduction with zinc in the presence of an acid catalyst. The acids effectively usable for the catalysis include acetic acid, hydrochloric acid, sulfuric acid, and nitric acid, for example. Generally, the reaction using acetic acid both as solvent and catalyst yields fully satisfactory results. The third step resides in producing an amine (13) by the reaction of a secondary amine (12) with an acid chloride (9) in the presence of a base ($R_7$ has the same meaning as defined above). The bases which are effectively usable for the reaction include such tertiary amines as triethylamine, diisopropylethylamine, and proton sponge, for example. Generally, the reaction using triethylamine yields fully satisfactory results. The solvents which are effectively usable in the reaction include such halogenous solvents as dichloromethane, chloroform, and 1,2- dichloroethane, for example. Generally, dichloromethane is favorably used. The reaction can be carried out at temperatures in the range of form −80° C. to 100° C., preferably from 0° C. to 30° C. The fourth step resides in producing a compound represented by the general formula (10) by the use of a represented by the general formula (4) in the same manner as in Chart 1 ($R_3$ and $R_4$ have the same meanings as defined above). The reaction conditions involved herein are the same as those of the second step in Chart 2. The fifth step resides in converting the amide by reduction into an amine and the sixth step in converting the amine into a hydroxyl group by the removal of a methyl group. The reaction conditions involved in these steps are identical, respectively, to those of the fifth and sixth steps in Chart 2.

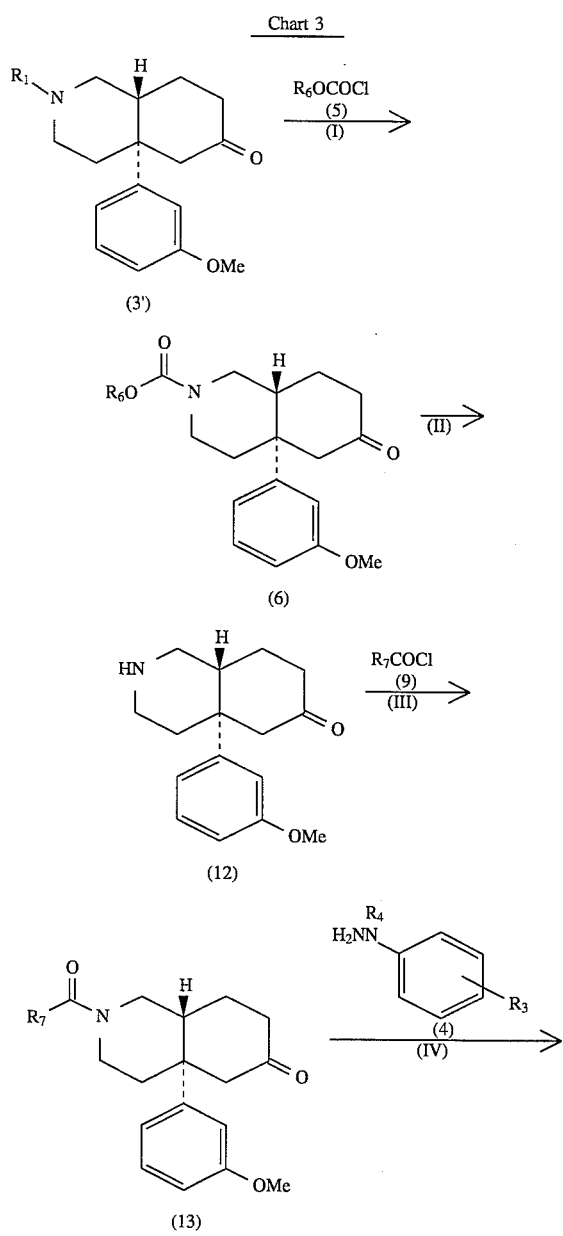

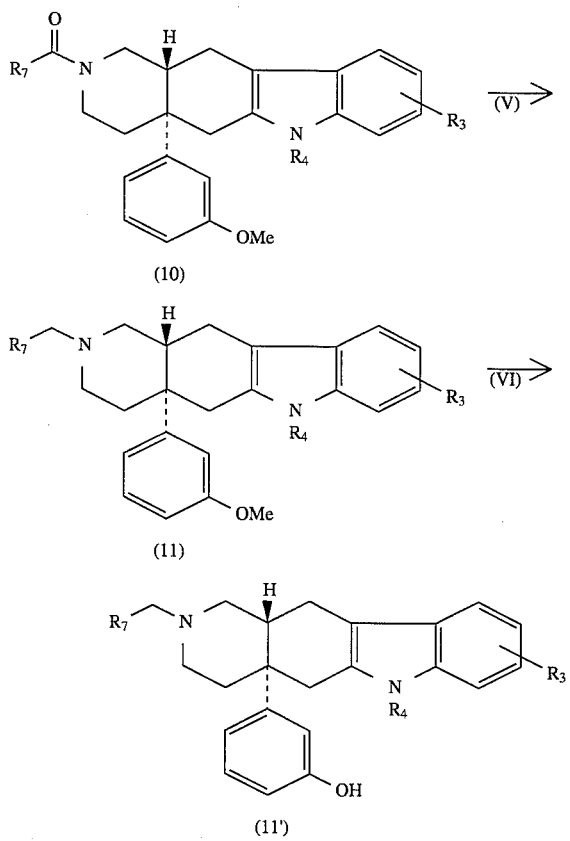

In the compounds represented by the general formula (3), those having alkyl of 2 of 5 carbon atoms, cycloalkylalkyl of 3 to 6 carbon atoms, cycloalkenylalkyl of 5 to 7 carbon atoms, aralkyl, trans-alkenyl of 4 or 5 carbon atoms, allyl, or furanyl-2-ylalkyl as $R_1$, methyl as $R_2$ and a hydrogen atom as $R_5$ can be produced through a route shown in Chart 4. The first step resides in converting the methyl group on the nitrogen atom of an acetate (14) into a carbamate by the use of a chlorocarbonic ester represented by the general formula (5) in the presence of a base. As $R_6$, vinyl and trichloroethyl are cited. Trichloroethyl is particularly desirable. The base to be used is possessed of steric hindrance large enough to avoid reacting with the acid chloride. Generally, a proton sponge and Hünig base are used as bases. The solvents usable herein include such halogenous solvents as methylene chloride, chloroform, carbon tetrachloride, and 1,2-dichloroethane. Especially, 1,2-dichloroethane is particularly desirable. The reaction can be carried out at temperature in the range of from −80° C. to 100° C. Generally, the reaction performed at temperature in the range of from 0° C. to normal room temperature yields satisfactory results. The second step resides in producing a secondary amine (16) by deprotection of a protective group in the nitrogen atom through reduction with zinc in the presence of an acid catalyst. The acids include acetic acid, hydrochloric acid, sulfuric acid, and nitric acid. Generally, the reaction using acetic acid both as solvent and catalyst yields fully satisfactory results. The reaction can be carried out generally at room temperature. The third step resides in producing an amide (17) by the reaction of an amine (16) with an acid chloride represented by the general formula (9) ($R_7$ has the same meaning as defined above). The reaction can be carried out under the same conditions as those of the third step in Chart 3. The fourth step resides in producing a compound represented by the general formula (18) by the conversion of an amide by reduction into an amine and an ester to an alcohol. The reducing agents include lithium aluminum hydride, DIBAR, and lithium borohydride, for example. Among other reducing agents, lithium aluminum hydride and DIBAR are particularly desirable. The solvents include such ethers as ether, THF, and DME. Among other solvents, THF is particularly desirable. The reaction can be carried out at temperatures in the range of from −40° C. to 100° C., preferably from 0° C. to 30° C. The fifth step resides in producing a ketone (19) by the oxidation of an alcohol (18). The oxidizing agents include chromic acid, potassium permanganate, DMSO-DCC, and DMSO-DCC, and DMSO-oxalyl chloride, for example. Among other oxidizing agents, DMSO-oxalyl chloride is particularly desirable. The solvents include such halogenous solvents as dichloromethane and chloroform. Among the solvents cited above, dichloromethane is particularly desirable. The reaction can be carried out at temperatures in the range of from −100° C. to 0° C., preferably from −80° C. to −50° C.

Chart 4

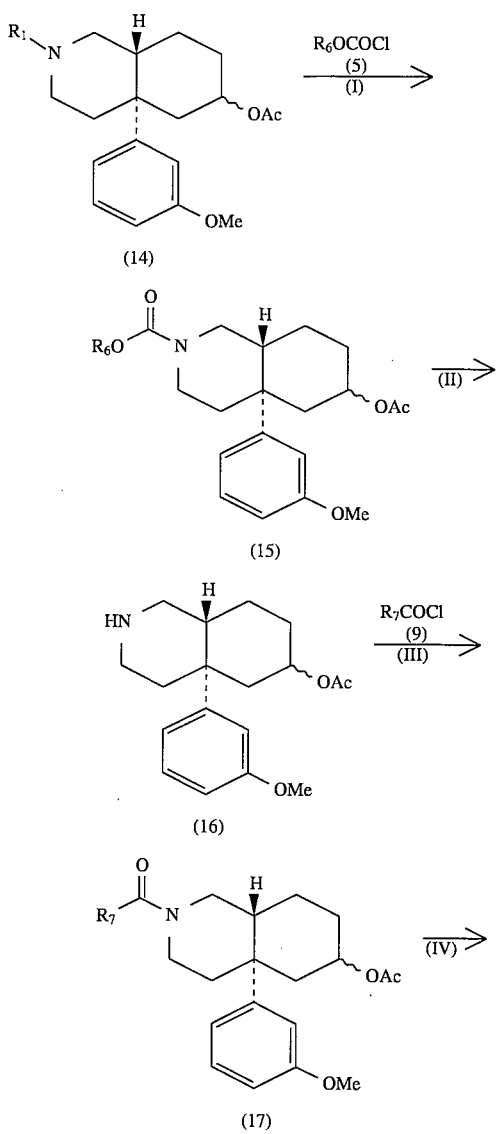

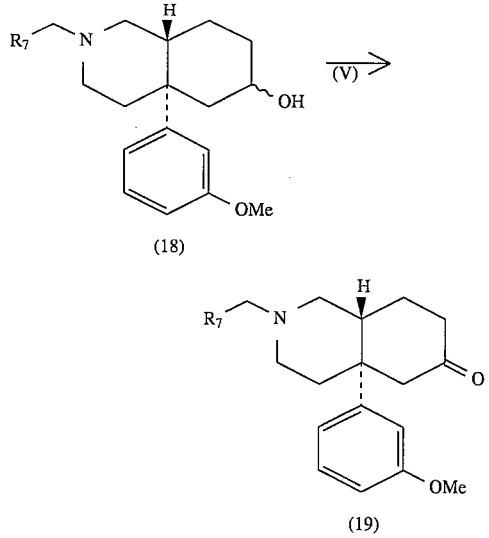

In the compounds of the general formula (1), those having a methyl group as $R_1$ and a hydroxyl group as $R_5$ are specifically produced under the following conditions (Chart 5). The first step resides in conversion of methyl group on the nitrogen atom in an enamine form (20) synthesizable in accordance with the method reported by D. M. Zimmerman et al (J. Org. Chem. 1989, 54, 1442) to a carbamate form by the use of a chlorocarbonic ester represented by the general formula (21) in the presence of a base. In the formula (21), $R_8$ stands for trichloroethyl or benzyl, the former being preferred over the latter. The base to be used in the reaction is possessed of steric hindrance large enough to avoid reacting with the acid chloride. The bases that are effectively usable herein are proton sponge and Hünigbase, for example. The solvents that are favorably usable herein include such halogenated hydrocarbons as methylene chloride, chloroform, carbon tetrachloride, and 1,2-dichloroethane, for example. Generally, 1,2-dichloroethane is desirably used. The reaction temperature is practicable in the range of from −180° C. to 100° C. Generally, the reaction performed at temperatures in the range of from 0° C. to normal room temperature yields satisfactory results. The second step resides in conversion of a carbamate form (22) into an epoxy form with a peracid. Generally, the reaction using m-chloroperbenzoic acid as the peracid yields fully satisfactory results. The solvents that are favorably usable herein include such halogen type solvents as methylene chloride, chloroform, and carbon tetrachloride, for example. Generally, methylene chloride is used. The reaction temperature is practicable in the range of from −80° C. to 50° C. Generally, the reaction carried out at temperatures in the range of from 0° C. to room temperature yields satisfactory results. The third step resides in converting the epoxy form (23) into a bridgehead-hydroxyl group form (24) through reducing ring cleavage. As the reducing agent, such metal hydride compounds as sodium borohydride and sodium cyanoborohydride are usable. The reaction performed under the acidic conditions using acetic acid, hydrochloric acid, or methanesulfonic acid yields desirable results. Particularly, the reduction is desirably effected with sodium borohydride by the use of acetic acid both as solvent and acid catalyst. The reaction temperature is practicable in the range of from −80° C. to 50° C. Particularly, the reaction performed at temperatures in the range of from 0° C. to room temperature yields satisfactory results. The fourth step resides in producing a dihydroxyamine (25) by the simultaneous reduction of the carbamate moiety and acetate moiety of the hydroxyl (24) in the bridgehead portion. The reducing agents that are effectively usable for the reaction include lithium aluminum hydride, aluminum diisobutyl hydride, and lithium borohydride, for example. Among other reducing agents mentioned above, lithium aluminum hydride proves to be particularly desirable. The solvents that are desirably usable herein include such ethers as ether, THF, DME, and dioxane, for example. Among other solvents mentioned above, THF proves to be particularly desirable. The reaction temperature is practicable in the range of from −40° C. to 100° C., preferably from 0° C. to room temperature. The fifth step resides in converting the secondary hydroxyl group of a dihydroxyamine from (25) into a hydroxyketone form (26) through oxidation. The oxidizing agents that are effectively usable in the conversion include chromic acid, potassium permanganate, DMSO-DCC, and DMSO-oxalyl chloride, for example. Among other oxidizing agents, DMSO-oxalyl chloride proves to be particularly desirable. The solvent to be used herein may be a halogenous solvent such as dichloromethane or chloroform. Among other solvents usable at all herein, dichloromethane proves to be particularly desirable. The reaction can be performed at temperatures in the range of from −100° C. to 0° C., preferably from −80° to −50° C. The sixth step for producing an indole form (27) and the seventh step for producing a compound represented by the general formula (27') having a hydrogen atom as $R_2$ can be carried out under the same conditions as those shown respectively in the first step and the second step in Chart 1.

In the compounds of the general formula (1), those compounds that have a hydroxyl group as $R_5$ and alkyl of 2 to 5 carbon atoms, cycloalkylalkyl of 3 to 6 carbon atoms, trans-alkenyl of 4 or 5 carbon atoms, allyl, or furanyl-2-ylalkyl as $R_1$ can be produced through the following route (Chart 6). The first and second steps jointly reside in causing an 8a-hydroxycarbamate form (24) obtained in consequence of the first, second, and third steps in Chart 5 to be converted into an amide form (29) via a secondary amine (28). These steps can be carried out in accordance with the respective procedures of the second and third steps of Chart 3. The third step resides in converting an amide acetate form (29) into a dihydroxyamine form (30). This step can be carried out by the same procedure as that of the fourth step of Chart 5. The fourth step, similarly to the fifth step of Chart 5, resides in oxidizing the secondary hydroxyl group of the dihydroxyamine form (30) into a ketone. Further, the fifth step for producing an indole form (32) and the sixth step for producing a compound represented by the general formula (32') having a hydrogen atom as $R_2$ can be produced under the same conditions as those, respectively, of the first and second steps of Chart 1.

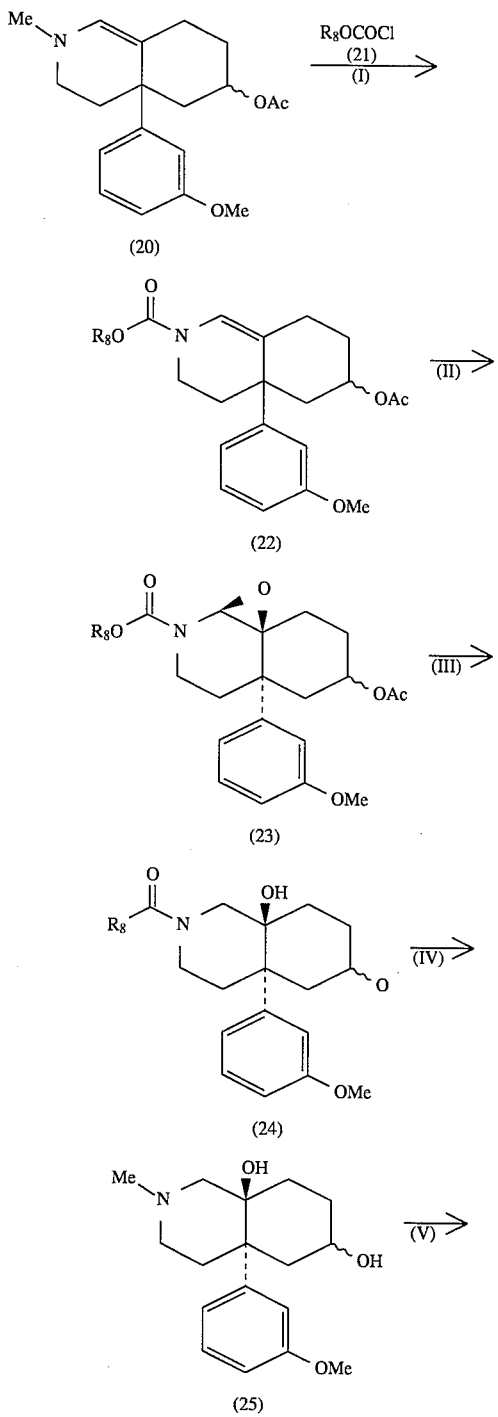

Chart 5

27
-continued
Chart 5
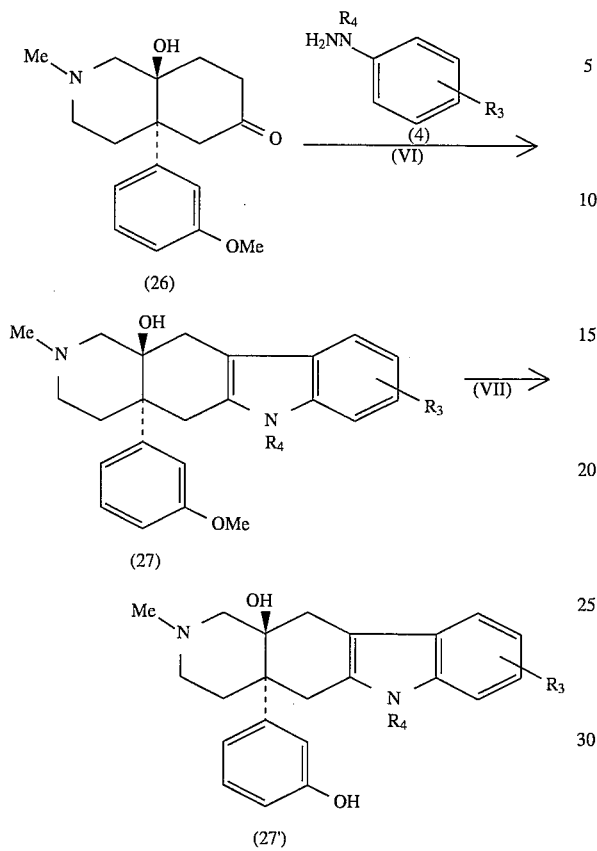
Chart 6
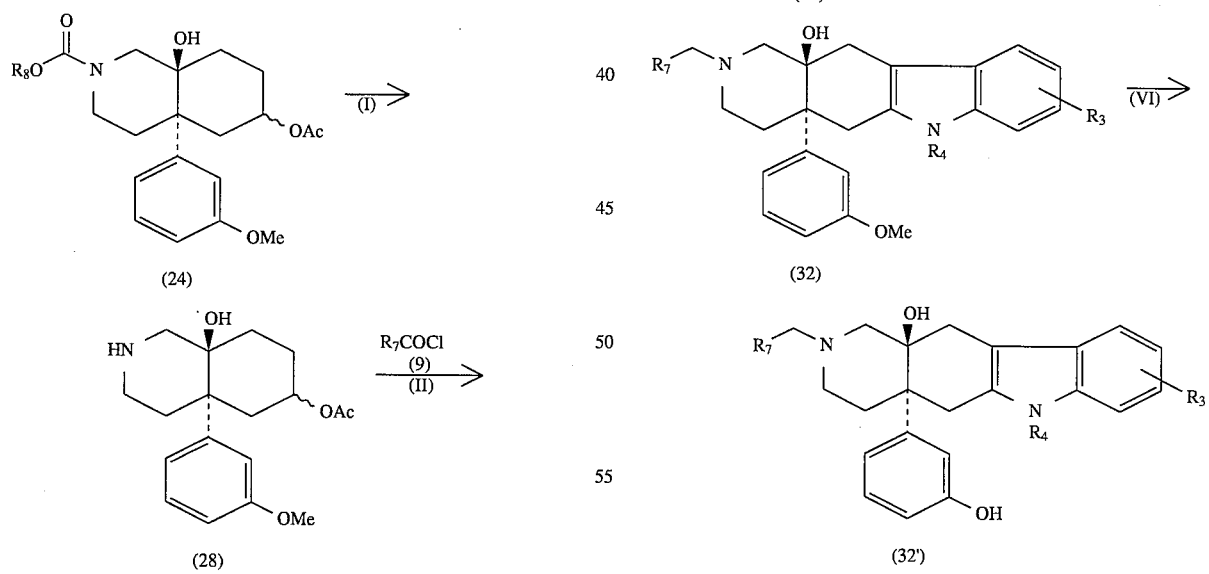
28
-continued
Chart 6
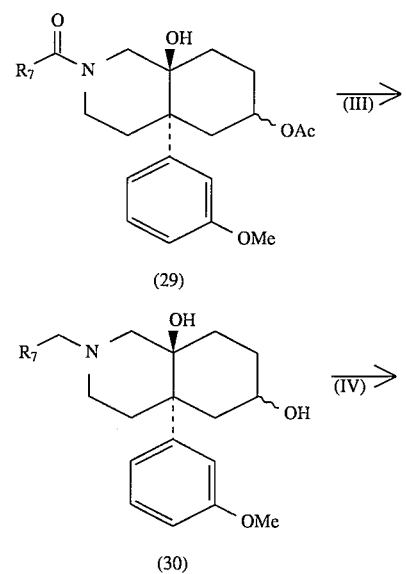
The isoquinoline derivatives represented by the general formula (101) can be produced by following the procedure consisting of the following steps.
To be specific, a compound represented by the general formula (101) is obtained by reaction of a chlorocarbonic ester with an enamine represented by the general formula (102):

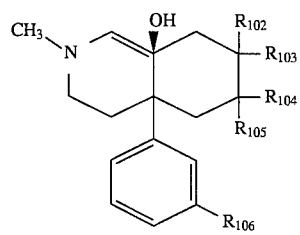 (102)

[wherein $R_{102}$, $R_{103}$, $R_{104}$, $R_{105}$, and $R_{106}$ have the same meanings as defined above] in the presence of a suitable base thereby forming a carbamate form represented by the general formula (103):

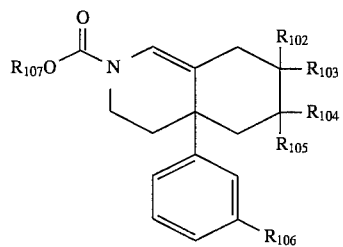 (103)

[wherein $R_{102}$, $R_{103}$, $R_{104}$, $R_{105}$, $R_{106}$, and $R_{107}$ have the same meanings as defined above], epoxidizing the olefin moiety of the carbamate form, thereby giving rise to an epoxy form represented by the general formula (104):

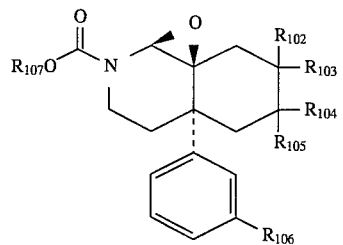 (104)

[wherein $R_{102}$, $R_{103}$, $R_{104}$, $R_{105}$, $R_{106}$, and $R_{107}$ have the same meanings as defined above], and then reducing the epoxy form under acidic conditions thereby obtaining a 4aα-aryl-8aβ-hydroxydecahydroisoquinoline represented by the general formula (101a):

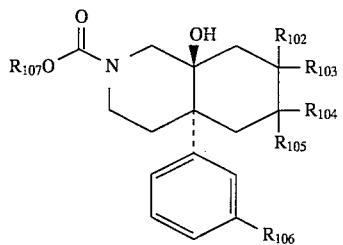 (101a)

[wherein $R_{102}$, $R_{103}$, $R_{104}$, $R_{105}$, $R_{106}$, and $R_{107}$ have the same meanings as defined above].

The production of the compound of this invention can be effected more specifically under the following conditions. Of the compounds of the general formula (101b), those compounds that have a methoxy group as $R_{106}$ are produced specifically under the following conditions (Chart 101).

Chart 101

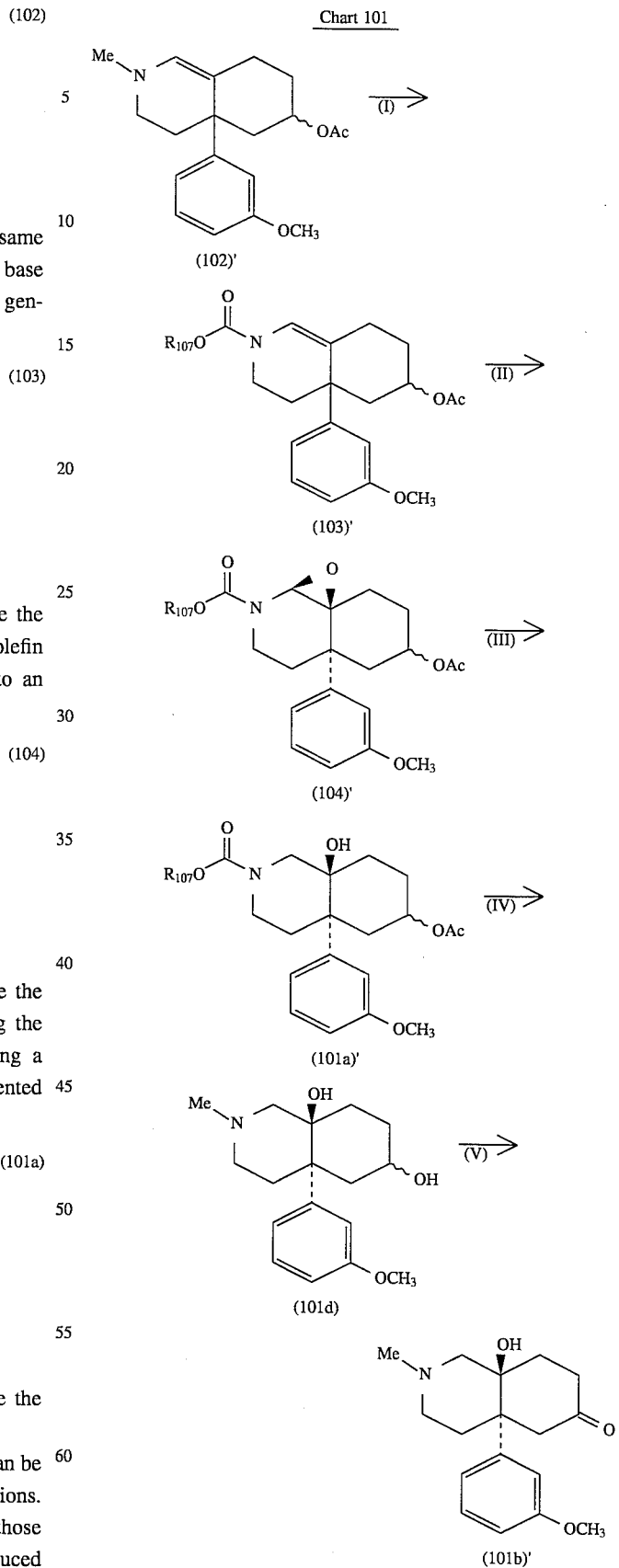

The first step resides in conversion of the methyl group on the nitrogen atom of an enamine form (102)' synthesizable in accordance with the method reported by Zimmerman et al [J. Org. Chem., 541442 (1989)] to a carbamate form (103)' by the use of a chlorocarbonic ester in the presence of a base. The bases that are effectively usable in the conversion include tertiary amines such as triethylamine, diisopropylethylamine, and proton sponge, and pyridine, and imidazole, for example. Among other bases cited above, proton sponge and diisopropylethylamine which are tertiary amines having steric hindrance are enough to avoid reacting with an acid chloride are particularly desirable. The solvents that are effectively usable herein are thought to include halogenous solvents such as methylene chloride, chloroform, carbon tetrachloride, and 1,2-dichloroethane and ethers such as THF, DME, and dioxane, for example. Generally, halogenous solvents, especially 1,2-dichloroethane, are favorable usable. The reaction temperature is practicable in the range of from –80° C. to 100° C. Generally, the reaction performed at temperatures in the range of from 0° C. to room temperature yields satisfactory results.

The second step resides in converting a carbamate form (103)' into an epoxy form. As regards the epoxidizing agent, all the reacting agents that are generally used for epoxidation are thought to be usable. Among other conceivable epoxidizing agents, peracids such as perbenzoic acid, m-chloroperbenzoic acid, peracetic acid, and trifluoroperacetic acid and hydrogen peroxide are favorably used. Particularly, m-chloroperbenzoic acid proves to be desirable. The solvents that are effectively usable herein are thought to include halogenous solvents such as methylene chloride, chloroform, and carbon tetrachloride and aromatic hydrocarbon type solvents such as benzene and toluene, for example. Generally, halogenous solvents, especially methylene chloride, are favorably used. The reaction temperature is practicable in the range of from –80° C. to 50° C. Generally, the reaction carried out at temperature in the range of from 0° C. to room temperature yields satisfactory results.

The third step resides in converting an epoxy form (104)' into a bridgehead hydroxyl group form (101a)' by reductive ring cleavage. As regards the reducing agent for this conversion, all the reducing agents that are generally used for reduction of an epoxy group are thought to be usable. The reducing agents that are inactive to the carbamate moiety and the acetate moiety and capable of selectively reducing the epoxy group such as, for example, metal hydride compounds like sodium borohydride, sodium cyanoborohydride, and zinc borohydride are favorably usable. In this case, the reaction yields desirable results when the solution used therefor is adjusted for acidity in advance of use. The acids that are effectively usable for this adjustment are thought to include inorganic acids such as hydrochloric acid, sulfuric acid, nitric acid, and phosphoric acid and organic acids such as acetic acid, propionic acid, oxalic acid, methanesulfonic acid, benzenesulfonic acid, and toluenesulfonic acid, for example. The solvents that are effectively usable herein are thought to include ethers such as THF, ether, and DME, halogenous solvents such as methylene chloride and chloroform, alcohols such as methanol and ethanol, and organic acids such as acetic acid, propionic acid, and butanoic acid, which are usable as solvents, for example. The reduction, with sodium borohydride in acetic acid both as solvent and acid catalyst, yields desirable results. The reaction temperature is practicable in the range of from –80° C. to 50° C. The reaction carried out at temperatures in the range of from 0° C. to room temperature yields satisfactory results.

The fourth step resides in producing a dihydroxyamine form (101d) by simultaneous reduction of the carbamate moiety and the acetate moiety of the bridgehead hydroxy group form (101a)'. As regards the reducing agent, all the metal hydrides that the generally used as a reducing agent are thought to be favorably usable. Such metal hydride compounds as lithium aluminum hydride, diisobutyl aluminum hydride, aluminum hydride, lithium borohydride, and diborane, which are possessed of strong reducing potential, may be cited as examples. Among other reducing agents mentioned above, lithium aluminum hydride proves to be particularly desirable. As regards the solvent, where lithium aluminum hydride, lithium borohydride, or diborane is used as a reducing agent, such ethers as ether, THF, DME, and dioxane are favorably used. Among other solvents cited above, THF proves to be particularly desirable. Where diisobutyl aluminum hydride or aluminum hydride is used as a reducing agent, such aromatic type hydrocarbons as benzene and toluene are favorably used as solvents. The reaction can be effected at temperatures in the range of from –40° C. to 100° C., preferably from 0° C. to normal room temperature.

The fifth step resides in converting the secondary hydroxyl group of the dihydroxyamine form (101d) into the hydroxyketone form (101b)' by oxidation. As regards the oxidizing agent, all the compounds that are generally used for the oxidation of a secondary hydroxyl group are thought to be usable. Specifically, chromic acid type oxidizing agents, permanganic acid type oxidizing agents, DMSO-DCC type oxidizing agents, and DMSO-oxalyl chloride type oxidizing agents may be cited as examples. The DMSO-oxalyl chloride type oxidizing agents are favorably used. As regards the solvent, such halogenous solvents as dichloromethane and chloroform, such ethers as ether, THF, and DME, and such aprotic dipolar solvents as DMSO and DMF are thought to be effectively usable. The halogenous solvents, particularly dichloromethane, prove to be particularly desirable. The reaction can be carried out at temperatures in the range of from –100° C. to 50° C. In the case of the DMSO-oxalyl chloride type oxidizing agents, the reaction carried out at temperatures in the range of from –80° C. to –50° C. yields desirable results.

The compounds of the general formula (101b)" having a substituent other than methyl as $R_1$ can be produced by using the following conditions (Chart 102).

Chart 102

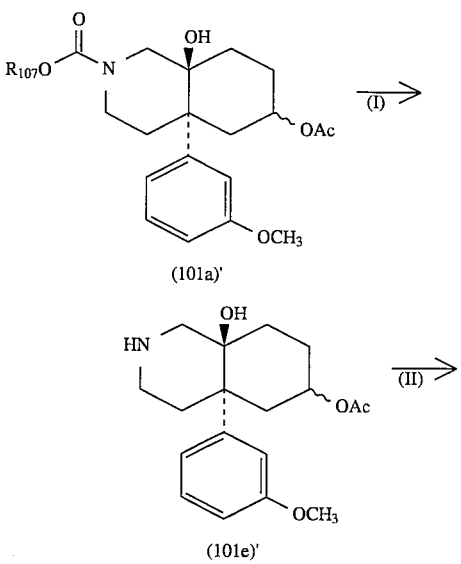

(101a)'

(101e)'

-continued
Chart 102

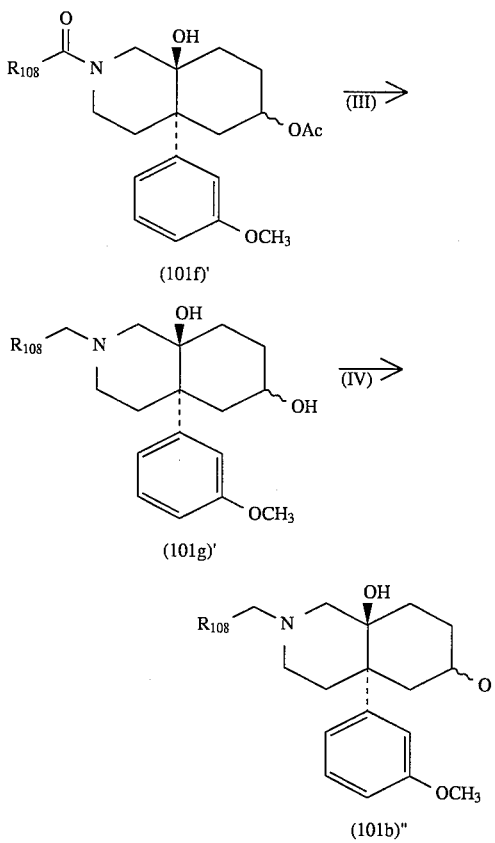

The first step resides in causing an 8aβ-hydroxycarbamate form (101a)' formed in consequence of the first, second, and third steps of Chart 1 to be converted into a secondary amine (101e)' by deprotection of protective group on the nitrogen atom. Where $R_{107}$ is 2,2,2-trichloroethyl, this step can be effected by the reduction with zinc in the presence of an acid catalyst. The acids that are effectively usable for the catalysis are thought to include inorganic acids such as hydrochloric acid, sulfuric acid, nitric acid, and phosphoric acid and organic acids such as acetic acid, propionic acid, oxalic acid, methanesulfonic acid, benzenesulfonic acid, and toluenesulfonic acid, for example. As regards the solvent, alcohols such as methanol and ethanol, ethers such as ether, THF, and DME, aprotic dipolar solvents such as DMSO and DMF, and such organic acids as acetic acid, propionic acid, and butanoic acid, which are usable as solvents may be cited as examples. Generally, the reaction using acetic acid both as catalyst and solvent yields desirable results. The reaction temperature is conceivable in the range of from −20° C. to 150° C., preferably from 0° C. to 50° C. Where $R_{107}$ is benzyl, the removal of the protective group can be attained under hydrolyzing conditions. As regards the catalyst, all the compounds generally used for hydrolysis are thought to be effectively usable. Among other catalysts available palladium/carbon and platinum catalyst are favorably used. The hydrogen pressure is conceivable in the range of from 1 to some tens of atmospheres. Generally, the reaction performed under 1 atmosphere yields fully satisfactory results. As regards the solvent for use in the reaction, alcoholic solvents such as methanol and ethanol, etherial solvents such as THF and DME, and aromatic hydrocarbon type solvents such as benzene and toluene are thought to be effectively usable.

The second step resides in producing an amide form (101f)' by the reaction of a secondary amine (101e)' with an acid chloride or acid anhydride in the presence of a base. The base that is effectively usable for this reaction include tertiary amines such as triethylamine, diisopropylethylamine, and proton sponge and pyridine, dimethylaminopyridine, and imidazole, for example. In the reaction performed in the presence of an acid chloride, the use of triethylamine or protone sponge as the base brings about fully satisfactory results. The solvents that are effectively usable in the reaction include halogenous solvents such as methylene chloride, chloroform, carbon tetrachloride, and 1,2-dichloroethane, ethers such as ether, THF, and DME, and pyridine, for example. Particularly in the reaction that is performed in the presence of an acid chloride, halogenous solvents are desirably used and methylene chloride is particularly favorably. In the reaction carried out in the presence of an acid anhydride, pyridine is used desirably both as base and solvent. The reaction is practicable at temperatures in the range of from −80° C. to 100° C. Particularly, the reaction performed at temperatures in the range of from 0° C. to room temperature.

The subsequent third step resides in converting an amide acetate form (101f)' to a dihydroxyamine form (101g)'. This step can be executed by following the procedure of the fourth step of Chart 1. The fourth step, similarly to the fifth step of Chart 1, resides in oxidizing a secondary hydroxyl group form (101g)' into a ketone form (101b)'.

Further, the compounds (101a)" having 2,2,2-trichloroethoxycarbonyl as $R_{101}$ and a hydrogen atom as $R_{102}$, $R_{103}$, $R_{104}$, and $R_{105}$ and the compounds (101g)' having $R_{108}CH_2$ as $R_{101}$ and a hydrogen atom as $R_{102}$, $R_{103}$, $R_{104}$, and $R_{105}$ can be produced from an N-methylenamine form (102)' obtained by the method reported by Evans et al. [D. A. Evans et al., J. Am. Chem. Soc., 102, 5955, (1980)]through the procedure consisting of the first, second, and third steps of chart 1 and the first, second, and third steps of Chart 102 as illustrated in Chart 103. By the same procedure, the compounds having varying substituents as $R_{102}$, $R_{103}$, $R_{104}$, and $R_{105}$ can be produced.

Chart 103

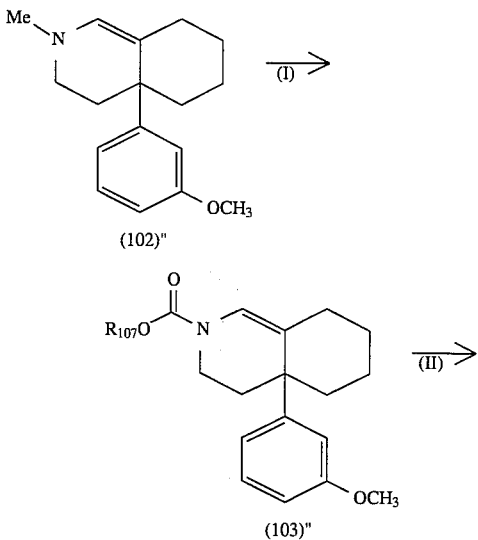

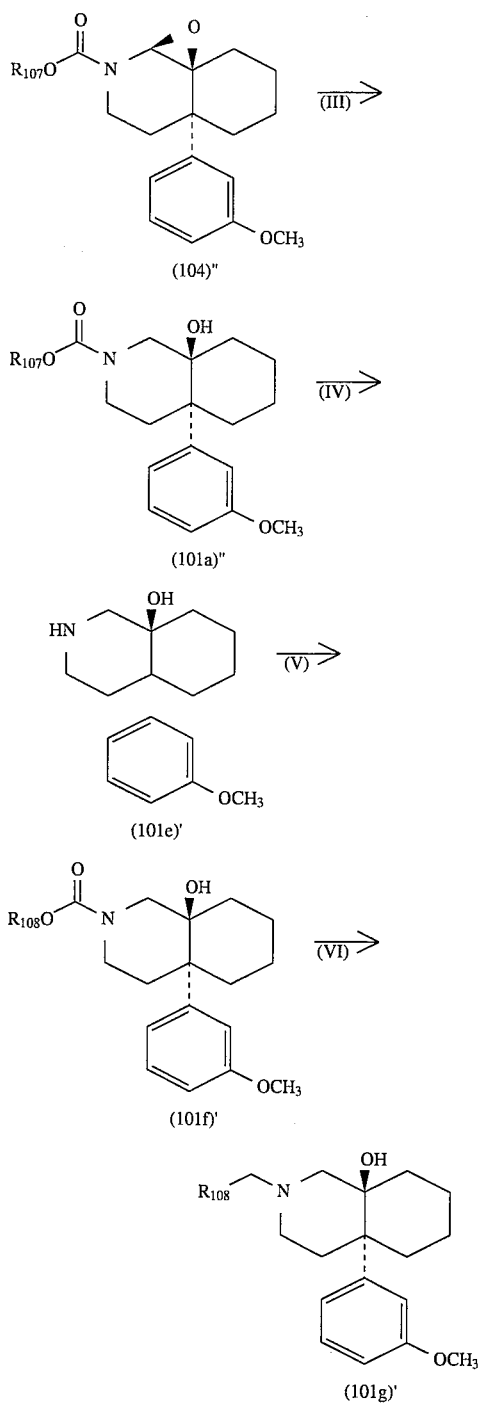

action. Thus, the elucidation of detailed pharmacological actions of the subtypes is desired. The compounds of this invention, which are possessed of very high selectively for the delta-receptors are expected to play a role in this elucidation. Further, the delta-opioid receptors relate to analgasia, immunity, and circulatory functions (particularly blood pressure). The ligands, which are highly selective for these receptors have the possibility of being utilized as such medicines as analgesics, immunorepressants [usable in transplantation of internal organs (kidney, liver, and heart), skin transplantations, and autoimmune diseases (sparingly tractable diseases such as rheumatism, various alergies, collagen disease, and oesteoporosis)], and antihypertensive agents. Since the compounds of this invention possesses selective δ-receptor antagonist, in particular, they are expected to serve as an outstanding immunorepressant among other diseases mentioned above.

When a compound of this invention is used clinically as an immunorepressive agent, it may be in the form of a free base or a salt thereof and may be suitably mixed with excipients such as stabilizers, buffers, diluents, isotonizers, and antiseptics. As regards the dosage form, the immunorepressive agent may be in injection, form capsules, suppository, or oral pills. The dosage is suitably determined by the subject of administration, the method of administration, and the symptom. When the medicine is used in the form of injection, the daily dose is selected in the range of from 0.0001 to 1 g. When it is administered orally, the daily dose is in the range of from 0.001 to 10 g. In a medicine using the compound of this invention, the proper content of this compound is thought to be in the range of from 0.05 to 99%. Generally, the content of this compound in injection form is in the range of from 0.5 to 20% and in pill form in the range of from 0.1 to 50%.

EXAMPLES

Now, the present invention will be described more specifically below with the reference to working examples. It should be noted, however, that this invention is not limited by these examples.

Example 1

2-methyl-4aα-(3-methoxyphenyl)-1,2,3,4,4a,5,11,11aβ-octahydro-6H-indolo[2,3-g]isoquinoline 1

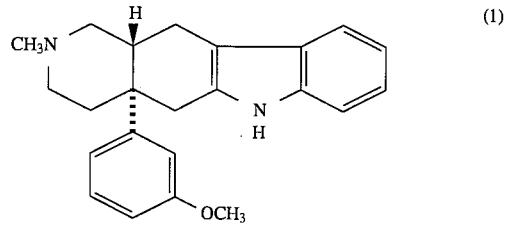

A solution of 161 mg of 2-methyl-4aα-(3-methoxyphenyl)-6-oxo-1,2,3,4,4a,5,6,7,8,8aβ-decahydroisoquinoline and 0.064 ml of phenyl hydrazine in 3 ml of ethanol was refluxed. The solution so refluxed and 0.383 ml of methanesulfonic acid added thereto meanwhile was stirred and continuously refluxed for one hour. The resultant reaction mixture was cooled to room temperature and 10 ml of a saturated aqueous solution of sodium hydrogen carbonate was added thereto and cooled with ice. The produced mixture was extracted three times from 10 ml of chloroform. The organic layers consequently separated were combined, The indole derivatives of the aforementioned general formula (1) can be obtained by using the isoquinoline derivatives of this invention as intermediates for synthesis.

Since the compounds of the present invention are antagonists possessed of very high selectivity for delta receptors, they become highly useful probes in the study of complicated opioid receptors (consisting of the three subtypes, μ, δ, and κ).

The opioid receptors have some bearing on complicated actions such as gastrointestinal tract transportation, renal function, appetite, memory, secretion of gastric juice, analgesia, circulatory function, respiration, and psychiatric washed with 5 ml of a saturated aqueous saline solution, dried, and concentrated, to obtain 250 mg of a powder. This powder, when it was separated and refined by column chromatography [silica gel:methanol:chloroform: 28% aqua ammonia=2.5:97.5:0.1–5.0:95.0:0.1], produced 150 mg of the captioned compound (yield 73.5%).

IR (KBr)cm$^{-1}$: 3400, 2936, 1609, 1448

NMR (CDCl$_3$) 500 MHz δ: 1.98 (1H, m), 2.10 (1H, m), 2.32 (3H, s), 2.39 (1H, m), 2.58 (1H, m) 2.65 (1H, t, J=11.6 Hz), 2.73 (1H, d, J=12.2 Hz), 2.87–3.06 (4H, m), 3.07 (1H, d, J=15.9 Hz), 3.67 (3H, s), 6.61 (1H, m), 7.01–7.10 (5H, m), 7.20 (1H, m), 7.43 (1H, m), 7.65 (1H, brs)

Mass (m/e): 346 (M$^+$)

Similarly, 2-methyl-4aα-(3-methoxyphenyl)-9-nitro-1,2, 3,4,4a,5,11,11aβ-octahydro-6H-indolo[2,3-g]isoquinoline is obtained by using 4-nitrophenylhydrazine instead of phenylhydrazine, 2-methyl-4aα-(3-methoxyphenyl)-8-nitro-1, 2,3,4,4a,5,11,11aβ-octahydro-6H-indolo[2,3-g]isoquinoline and 2-methyl-4aα-(3-methoxyphenyl)-10-nitro-1,2,3,4,4a, 5,11,11aβ-octahydro-6H-indolo[2,3-g]isoquinoline are obtained by using 3-nitrophenylhydrazine instead, and 2-methyl-4aα-(3-methoxyphenyl)-7-nitro-1,2,3,4,4a,5,11, 11aβ-octahydro-6H-indolo[2,3-g]isoquinoline is obtained by using 2-nitrophenylhydrazine instead.

Example 2

2-Methyl-4aα-(3-hydroxyphenyl)-1,2,3,4,4a,5,11, 11aβ-octahydro-6H-indolo[2,3-g]isoquinoline 2

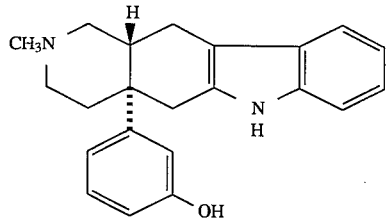

(2)

In an atmosphere of argon, 95.7 mg of 2-methyl-4aα-(3-methoxyphenyl)-1,2,3,4,4a,5,11,11aβ-octahydro-6H-indolo[2,3-g]isoquinoline and 93.1 mg of potassium-t-butoxide were dissolved in 3 ml of anhydrous DMF and the resultant solution and 0.08 ml of 1-propane thiol added thereto were stirred at 140° C. for 7.5 hours. The produced mixture and 10 ml of a saturated aqueous solution of sodium hydrogen carbonate added thereto was extracted three times from 30 ml of a chloroform:methanol (5:1) mixed solvent. The organic layers consequently separated were combined, washed with 5 ml of a saturated saline solution, dried, and concentrated, to afford 100 mg of a powder. This powder was suspended in 1 ml of methanol and converted by the addition of methanesulfonic acid into a methanesulfonate. When the methanesulfonate was separated and refined by column chromatography [Sephadex LH-20: methanol], it produced 51.6 mg of the methanesulfonate of the captioned compound (yield 43.5%).

IR (KBr) cm$^{-1}$: 3400, 1586, 1466

NMR (DMSO-d$_6$) 500 MHz δ: 2.00 (1H, m), 2.31 (3H, s), 2.44–2.64 (3H, m), 2.81 (3H, s), 2.81–2.90 (2H, m), 2.97 (1H, m), 3.10 (1H, d, J=16.5 Hz), 3.36–3.44 (2H, m), 3.61 (1H, m), 6.53 (1H, m), 6.90–6.99 (4H, m), 7.04 (1H, t, J=7.9 Hz), 7.18 (1H, d, J=7.9 Hz), 7.34 (1H, d, J=7.3 Hz), 9.24 (1H, s), 9.53 (1H, brs), 10.46 (1H, s)

Mass (FAB): 333 (M$^+$+1)

Elementary analyses: For C$_{22}$H$_{24}$N$_2$O.CH$_3$SO$_3$H

| | C | H | N | S |
|---|---|---|---|---|
| Calculated | 64.46 | 6.59 | 6.54 | 7.48 |
| Found | 64.12 | 6.31 | 6.25 | 7.33 |

Similarly, 2-methyl-4aα-(3-hydroxyphenyl)-10-nitro-1,2, 3,4,4a,5,11,11aβ-octahydro-6H-indolo[2,3-g]isoquinoline is obtained by using 2-methyl-4aα-(3-methoxyphenyl)-10-nitro-1,2,3,4,4a,5,11,11aβ-octahydro-6H-indolo[2,3-g]isoquinoline instead of 2-methyl-4aα-(3-methoxyphenyl)-1,2, 3,4,4a,5,11,11aβ-octahydro-6H-indolo[2,3-g]isoquinoline, 2-methyl-4aα-(3-hydroxyphenyl)-9-nitro-1,2,3,4,4a,5,11, 11aβ-octahydro-6H-indolo[2,3-g]isoquinoline is obtained by using 2-methyl-4aα-(3-methoxyphenyl)-9-nitro-1,2,3,4, 4a,5,11,11aβ-octahydro-6H-indolo[2,3-g]isoquinoline instead, 2-methyl-4aα-(3-hydroxyphenyl)-8-nitro-1,2,3,4, 4a,5,11,11aβ-octahydro-6H-indolo[2,3-g]isoquinoline is obtained by using 2-methyl-4aα-(3-methoxyphenyl)-8-nitro-1,2,3,4,4a,5,11,11aβ-octahydro-6H-indolo[2,3-g]isoquinoline instead, and 2-methyl-4aα-(3-hydroxyphenyl)-7-nitro-1,2,3,4,4a,5,11,11aβ-octahydro-6H-indolo[2,3-g] isoquinoline is obtained by using 2-methyl-4aα-(3-methoxyphenyl)-7-nitro-1,2,3,4,4a,5,11,11aβ-octahydro-6H-indolo[2,3-g]isoquinoline instead.

Example 3

2-Methyl-4aα-(3-methoxyphenyl)-9-methyl-1,2,3,4, 4a,5,11,11aβ-octahydro-6H-indolo[2,3-g]isoquinoline 3

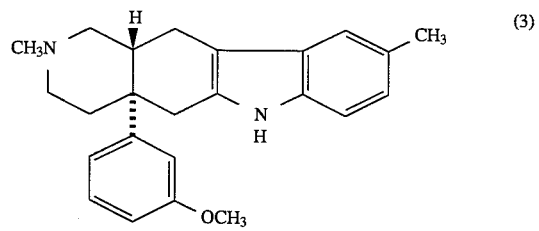

(3)

A solution of 250 mg of 2-methyl-4aα-(3-methoxyphenyl)-6-oxo-1,2,3,4,4a,5,6,7,8,8aβ-decahydro-isoquinoline and 260 mg of p-tollyl hydrazine hydrochloride in 3 ml of ethanol was refluxed. The solution thus refluxed and 0.58 ml of methanesulfonic acid added meantime thereto was stirred and continuously refluxed for one hour. The resultant mixture was cooled to room temperature. The cooled reaction mixture and 10 ml of a saturated aqueous solution of sodium hydrogen carbonate added thereto and cooled with ice was extracted three times from 10 ml of chloroform. The organic layers consequently separated were combined, washed with a saturated aqueous saline solution, dried, and concentrated, to obtain 400 mg of a powder. When this powder was separated and refined by column chromatography [silica gel:methanol:chloroform:aqueous 28% ammonia solution= 2.5:97.5":0.1–5.0":9.50:0.1], it produced 313 mg of the captioned compound (yield 94.9%).

IR (KRr) cm$^{-1}$: 3402, 2922, 1607, 1580

NMR (CDCl$_3$) 500 MHz δ: 2.12 (1H, m), 2.25 (1H, m), 2.40 (1H, m), 2.42 (3H, s), 2.43 (3H, s), 2.60 (1H, m), 2.71–2.79 (2H, m), 2.86–2.91 (3H, m), 3.03–3.08 (2H, m), 3.68 (3H, s), 6.62 (1H, m), 6.90 (1H, d, J=8.6 Hz), 6.97–6.98 (2H, m), 7.10 (2H, dd, J=18.3 Hz, 7.9 Hz), 7.18 (1H, s), 7.81 (1H, s)

Mass (m/e): 360 (M⁺)

Similarly, 2-methyl-4aα-(3-methoxyphenyl)-7-methyl-1,2,3,4,4a,5,11,11aβ-octahydro-6H-indolo[2,3-g]isoquinoline is produced by using o-tollyl hydrazine hydrochloride instead of p-tollylphenylhydrazine.

Example 4

2-Methyl-4aα-(3-hydroxyphenyl)-9-methyl-1,2,3,4,4a,5,11,11aβ-octahydro-6H-indolo[2,3-q]isoquinoline
4

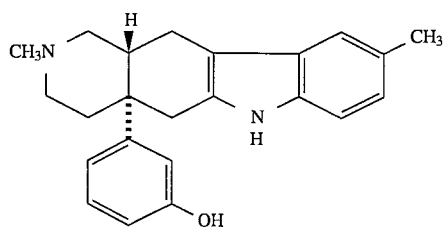

(4)

In an atmosphere of argon, 237 mg of 2-methyl-4aα-(3-methoxyphenyl)-9-methyl-1,2,3,4,4a,5,11,11aβ-octahydro-6H-indolo[2,3-g]isoquinoline and 333 mg of potassium-t-butoxide were dissolved in 8 ml of anhydrous DMF and 0.28 ml of 1-propane thiol was added thereto. The resultant mixture was stirred at 140° C. for 4.5 hours and then cooled to room temperature. The mixture was distilled under a vacuum to expel DMF. The distillate and 10 ml of a saturated aqueous solution of sodium hydrogen carbonate added thereto were extracted three times from 30 ml of a chloroform: methanol (5:1) mixed solvent. The organic layers consequently separated were combined, washed with a saturated aqueous saline solution, dried, and concentrated, to obtain 166 mg of a powder. This powder was suspended in 1 ml of methanol and converted by the addition of methanesulfonic acid into a methanesulfonate. When this methanesulfonate was refined by column chromatography [Sephadex, LH-20; methanol], it produced 134 mg of the methanesulfonate of the captioned compound (yield 46.1%).

IR (KBr) cm⁻¹: 3400, 2926, 2732, 1599

NMR (DMSO-$d_6$) 500 MHz δ: 2.00 (1H, s), 2.33 (3H, s), 2.37 (3H, s), 2.51–2.64 (3H, m), 2.81 (3H, s), 2.80–2.97 (3H, m), 3.06 (1H, d, J=16.5 Hz), 3.36 (2H, m), 3.61 (1H, d, J=11.66 Hz), 6.53 (1H, d, J=7.9 Hz), 6.80 (1H, d, J=8.6 Hz), 6.88 (1H, s), 6.92 (1H, d, J=7.9 Hz), 7.03 (1H, t, J=7.9 Hz), 7.06 (1H, d, J=8.6 Hz), 7.12 (1H, s), 9.24 (1H, s), 9.53 (1H, brs), 10.46 (1H, s)

Mass (FAB): 347 (M⁺+1)

Elementary analyses For $C_{23}H_{26}N_2O \cdot CH_3SO_3H \cdot 0.1H_2O$

|  | C | H | N | S |
|---|---|---|---|---|
| Calculated | 64.87 | 6.85 | 6.30 | 7.22 |
| Found | 64.62 | 7.04 | 6.16 | 7.53 |

Similarly, 2-methyl-4aα-(3-hydroxyphenyl)-7-methyl-1,2,3,4,4a,5,11,11aβ-octahydro-6H-indolo[2,3-g]isoquinoline is obtained by using 2-methyl-4aα-(3-methoxyphenyl)-7-methyl-1,2,3,4,4a,5,11, 11aβ-octahydro-6H-indolo[2,3-g]isoquinoline instead of 2-methyl-4aα-(3-methoxyphenyl)-9-methyl-1,2,3,4,4a,5,11,11aβ-octahydro-6H-indolo[2,3-g]isoquinoline.

Example 5

2-Methyl-4aα-(3-methoxyphenyl)-9-chloro-1,2,3,4,4a,5,11,11aβ-octahydro-6H-indolo[2,3-q]isoquinoline
5

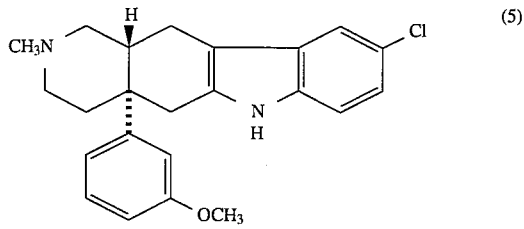

(5)

A solution of 250 mg of 2-methyl-4aα-(3-methoxyphenyl)-6-oxo-1,2,3,4,4a,5,6,7,8,8aβ-decahydroisoquinoline and 180 mg of 4-chlorophenylhydrazine in 3 ml of ethanol was refluxed. The solution thus refluxed and 0.6 ml of methanesulfonic acid added meantime thereto were stirred and continuously refluxed for one hour. The resultant reaction mixture was cooled to room temperature. The cooled reaction mixture and 10 ml of a saturated aqueous solution of sodium hydrogen carbonate added thereto and cooled with ice was extracted three times from 10 ml of chloroform. The organic layers consequently separated were combined, washed with a saturated aqueous saline solution, dried, and concentrated, to afford 420 mg of a powder. When this powder was separated and refined by column chromatography [silica gel:methanol:chloroform:28% aqua ammonia= 2.5:97.5:0.1–5.0:95.0:0.1], it produced 315 mg of the captioned compound (yield 90.4%).

IR (KBr) cm⁻¹: 3418, 2936, 1582, 1446

NMR (CDCl₃) 500 MHz δ: 2.09 (1H, m), 2.23 (1H, m), 2.40 (1H, m), 2.43 (3H, s), 2.51–2.02 (2H, m), 2.76 (1H, t, J=11.6 Hz), 2.82–2.91 (3H, m), 3.02 (1H, m), 3.09 (1H, d, J=15.3 Hz), 3.68 (3H, s), 6.63 (1H, dd, J=7.9 Hz, 2.4 Hz), 6.95 (2H, m), 7.02 (1H, dd, J=8.5 Hz, 1.8 Hz), 7.10 (1H, t, J=7.9 Hz), 7.15 (1H, d, J=7.9 Hz), 7.33 (1H, d, J=1.8 Hz), 8.13 (1H, brs)

Mass (m/e): 380 (M⁺)

Similarly, 2-methyl-4aα-(3-methoxyphenyl)-8-chloro-1,2,3,4,4a,5,11,11aβ-octahydro-6H-indolo[2,3-g]isoquinoline and 2-methyl-4aα-(3-methoxyphenyl)-10-chloro-1,2,3,4,4a,5,11,11aβ-octahydro-6H-indolo[2,3-g]isoquinoline are obtained by using 3-chlorophenylhydrazine instead of 4-chlorophenylhydrazine and 2-methyl-4aα-(3-methoxyphenyl)-7-chloro-1,2,3,4,4a,5,11,11aβ-octahydro-6H-indolo[2,3-g]isoquinoline is obtained by using 2-chlorophenylhydrazine instead.

Example 6

2-Methyl-4aα-(3-hydroxyphenyl)-9-chloro-1,2,3,4,4a,5,11,11aβ-octahydro-6H-indolo[2,3-q]isoquinoline6

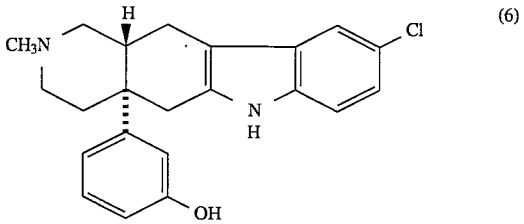

(6)

In an atmosphere of argon, 255 mg of 2-methyl-4aα-(3-methoxyphenyl)-9-chloro-1,2,3,4,4a,5,11,11aβ-octahydro-6H-indolo[2,3-g]isoquinoline and 452 mg of potassium-t-butoxide were dissolved in 6 ml of DMF and the resultant solution and 0.4 ml of 1-propane thiol added thereto were stirred at 140° C. for 5.5 hours. The resultant reaction mixture was cooled to room temperature, distilled under a vacuum to expel DMF, combined with 5 ml of a saturated aqueous solution of sodium hydrogen carbonate, and extracted three times from 30 ml of chloroform. The organic layers consequently separated were combined, washed with a saturated aqueous saline solution, dried, and concentrated, to afford 278 mg of a powder. When this powder was suspended in 1 ml of methanol, converted by the addition of methanesulfonic acid into a methanesulfonate, and separated and refined by column chromatography [Sephadex, LH-20; methanol], there was obtained 100 mg of the methanesulfonate of the captioned compound (yield 41.2%).

IR (KBr) cm$^{-1}$: 3240, 1601, 1586, 1450

NMR (DMSO-d$_6$) 500 MHz δ: 2.07 (1H, t, J=12.8 Hz), 2.32 (3H, s), 2.53 (1H, m), 2.64 (2H, m), 2.79 (3H, s), 2.84–2.97 (3H, m), 3.09 (1H, d, J=15.9 Hz), 3.35 (2H, m), 3.58 (1H, d, J=11.0 Hz), 6.54 (1H, dd, J=7.9 Hz, 1.8 Hz), 6.90 (2H, m), 6.97 (1H, dd, J= 8.6 Hz, 1.8 Hz), 7.04 (1H, t, J=7.9 Hz), 7.20 (1H, d, J=8.6 Hz), 7.37 (1H, d, J=1.9 Hz), 9.28 (1H, s), 10.03 (1H, brs), 10.86 (1H, s)

Mass (FAB): 367 (M$^+$+1)

Elementary analyses For C$_{22}$H$_{23}$N$_2$OCl·CH$_3$SO$_3$H

|  | C | H | N | Cl | S |
|---|---|---|---|---|---|
| Calculated | 59.67 | 5.88 | 6.05 | 7.66 | 6.93 |
| Found | 59.78 | 5.93 | 6.24 | 7.45 | 6.63 |

Similarly, 2-methyl-4aα-(3-hydroxyphenyl)-10-chloro-1,2,3,4,4a,5,11,11aβ-octahydro-6H-indolo[2,3-g]isoquinoline is obtained by using 2-methyl-4aα-(3-methoxyphenyl)-10-chloro-1,2,3,4,4a,5,11,11aβ-octahydro-6H-indolo[2,3-g]isoquinoline instead of 2-methyl-4aα-(3-methoxyphenyl)-9-chloro-1,2,3,4,5,11,11aβ-octahydro-6H-indolo[2,3-g]isoquinoline, 2-methyl-4aα-(3-hydroxyphenyl)-8-chloro-1,2,3,4,4a,5,11,11aβ-octahydro-6H-indolo[2,3-g]isoquinoline is produced by using 2-methyl-4aα-(3-methoxyphenyl)-8-chloro-1,2,3,4,4a,5,11,11aβ-octahydro-6H-indolo[2,3-g]isoquinoline instead, and 2-methyl-4aα-(3-hydroxyphenyl)-7-chloro-1,2,3,4,4a,5,11,11aβ-octahydro-6H-indolo[2,3-g]isoquinoline is obtained by using 2-methyl-4aα-(3-methoxyphenyl)-7-chloro-1,2,3,4,4a,5,11,11aβ-octahydro-6H-indolo[2,3-g]isoquinoline instead.

Example 7

2-Methyl-4aα-(3-methoxyphenyl)-7-fluoro-1,2,3,4,4a,5,11,11aβ-octahydro-6H-indolo[2,3-g]isoquinoline

7

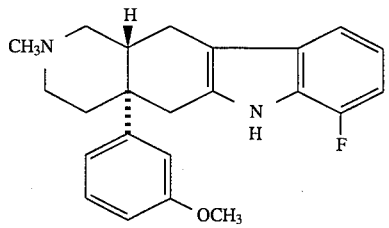
(7)

A solution of 250 mg of 2-methyl-4aα-(3-methoxyphenyl)-6-oxo-1,2,3,4,4a,5,6,7,8,8aβ-decahydroisoquinoline and 164 mg of hydrochloride-2-fluorophenylhydrazine in 3 ml of ethanol was refluxed. The solution thus refluxed and 0.6 ml of methanesulfonic acid added meantime thereto were stirred and continuously refluxed for one hour. The resultant reaction mixture was cooled to normal room temperature. The cooled reaction mixture and 10 ml of a saturated aqueous solution of sodium hydrogen carbonated added thereto and cooled with ice were extracted three times from 10 ml of chloroform. The organic layers consequently separated were combined, washed with 5 ml of a saturated aqueous saline solution, dried,and concentrated, to obtain 407 mg of a powder. When this powder was separated and refined by column chromatography [silica gel:methanol:chloroform: 28% aqua ammonia=2.5:97.5:0.1–5.0:95.0:0.1], it produced 120 mg of the captioned compound (yield 36.1%).

IR (KBr) cm$^{-1}$: 3412, 2938, 1607, 1491

NMR (CDCl$_3$) 500 MHz δ: 2.10 (1H, m), 2.20 (1H, m), 2.41 (3H, s), 2.43 (1H, s), 2.60 (1H, m), 2.76 (1H, t, J=11.6 Hz), 2.81–2.98 (4H, m), 3.05 (1H, m), 3.13 (1H, m), 3.69 (3H, s), 6.64 (1H, m), 6.79 (1H, m), 6.96 (3H, m), 7.11 (1H, t, J=7.9 Hz), 7.17 (1H, d, J=7.9 Hz), 8.04 (1H, brs)

Mass (m/e): 364 (M$^+$)

Similarly, 2-methyl-4aα-(3-methoxyphenyl)-8-fluoro-1,2,3,4,4a,5,11,11aβ-octahydro-6H-indolo[2,3g]isoquinoline and 2-methyl-4aα-(3-methoxyphenyl)-10-fluoro-1,2,3,4,4a,5,11,11aβ-octahydro-6H-indolo[2,3-g]isoquinoline are obtained by using 3-fluorophenylhydrazine instead of 2-fluorophenyl-hydrazine, and 2-methyl-4aα-(3-methoxyphenyl)-9-fluoro-1,2,3,4,4a,5,11,11aβ-octahydro-6H-indolo[2,3-g]isoquinoline is obtained by using 4-fluorophenylhydrazine instead.

Example 8

2-Methyl-4aα-(3-hydroxyphenyl)-7-fluoro-1,2,3,4,4a,5,11,11aβ-octahydro-6H-indolo[2,3-g]isoquinoline

8

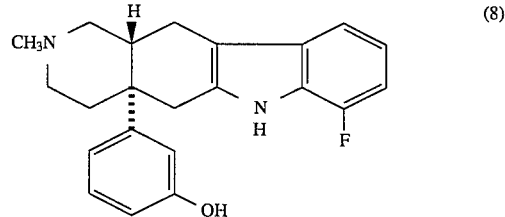
(8)

In an atmosphere of argon, 136 mg of 2-methyl-4aα-(3-methoxyphenyl)-7-fluoro-1,2,3,4,4a,5,11,11aβ-octahydro-6H-indolo[2,3-g]isoquinoline and 126 mg of potassium-t-butoxide were dissolved in 3 ml of anhydrous DMF and the resultant solution and 0.1 ml of 1-propane thiol added thereto were stirred at 140° C. for three hours. The resultant reaction mixture was cooled to room temperature, distilled under a vacuum to expel DMF, combined with a saturated aqueous solution of sodium hydrogen carbonate, and extracted three times from 30 ml of chloroform. The organic layers consequently separated were combined, washed with a saturated aqueous saline solution, dried, and concentrated, to afford 268 mg of a powder. This powder was separated and refined by column chromatography [silica gel:methanol:chloroform: 28% aqua ammonia=5:95:0.1–10:90:0.1]. The powder was suspended in 1 ml of methanol and converted by the addition of methanesulfonic acid into a methanesulfonate. When the methanesulfonate was refined by Sephadex column (LH-20: methanol), there was obtained 38.7 mg of the methanesulfonate of the captioned compound (yield 23.1%).

IR (KBr) cm$^{-1}$: 3400, 1599, 1400

NMR (DMSO-d$_6$) 500 MHz δ: 2.01 (1H, m), 2.32 (3H, s), 2.46–2.57 (3H, m), 2.82 (3H, s), 2.89 (2H, m), 2.97 (1H, m), 3.10 (1H, m), 3.35 (2H, m), 3.62 (1H, d, J=11.6 Hz), 6.55 (1H, m), 6.80 (1H, m), 6.89–6.99 (3H, m), 7.04 (1H, m), 7.18 (1H, m), 9.27 (1H, s), 9.54 (1H, brs), 11.09 (1H, s)

Mass (FAB): 351 (M$^+$1)

Elementary analyses For C$_{22}$H$_{23}$N$_2$OF·CH$_3$SO$_3$H

|  | C | H | N | S |
|---|---|---|---|---|
| Calculated | 61.86 | 6.09 | 6.27 | 7.18 |
| Found | 61.77 | 6.12 | 6.35 | 7.43 |

Similarly, 2-methyl-4aα-(3-hydroxyphenyl)-10-fluoro-1,2,3,4,4a,5,11,11aβ-octahydro-6H-indolo[2,3-g]isoquinoline is obtained by using 2-methyl-4aα-(3-methoxyphenyl)-10-fluoro-1,2,3,4,4a,5,11,11aβ-octahydro-6H-indolo[2,3-g]isoquinoline instead of 2-methyl-4aα-(3-methoxyphenyl)-7-fluoro-1,2,3,4,4a, 5,11,11aβ-octahydro-6H-indolo[2,3-g]isoquinoline, 2-methyl-4aα-(3-hydroxyphenyl)-9-fluoro-1,2,3,4,4a,5,11,11aβ-octahydro-6H-indolo[2,3-g]isoquinoline is obtained by using 2-methyl-4aα-(3-methoxyphenyl)-9-fluoro-1,2,3,4,4a,5,11,11aβ-octahydro-6H-indolo[2,3-g]isoquinoline instead, and 2-methyl-4aα-(3-hydroxyphenyl)-8-fluoro-1,2,3,4,4a,5,11,11aβ-octahydro-6H-indolo[2,3-g]isoquinoline is obtained by using 2-methyl-4aα-(3-methoxyphenyl)-8-fluoro-1,2,3,4,4a,5,11,11aβ-octahydro-6H-indolo[2,3-g]isoquinoline instead.

Example 9

2-Methyl-4aα-(3-methoxyphenyl)-9-bromo-1,2,3,4,4a,5,11,11aβ-octahydro-6H-indolo[2,3-g]isoquinoline
9

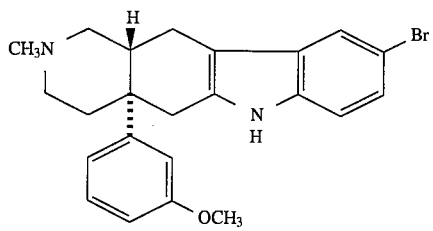

A solution of 250 mg of 2-methyl-4aα-(3-methoxyphenyl)-6-oxo-1,2,3,4,4a,5,6,7,8,8aβ-decahydroisoquinoline and 225 mg of p-bromophenylhydrazine hydrochloride is 3 ml of ethanol was refluxed. The solution thus refluxed and 0.594 ml of methanesulfonic acid added meantime thereto were stirred and continuously refluxed for one hour. The resultant reaction mixture was cooled to room temperature. The cooled reaction mixture and 10 ml of a saturated aqueous solution of sodium hydrogen carbonate added thereto and cooled with ice were extracted three times from 10 ml of chloroform. The organic layers consequently separated were combined, washed with 5 ml of a saturated aqueous saline solution, dried, and concentrated, to afford 474 mg of a powder. When this powder was separated and refined by column chromatography [silica gel:methanol:chloroform: 28% aqua ammonia= 2.5:97.5:0.1–5.0:95.0:0.1], it produced 348 mg of the captioned compound (yield 89.5%).

IR (KBr) cm$^{-1}$: 3412, 2938, 1580, 1466, 1446

NMR (CDCl$_3$) 500 MHz δ: 2.09 (1H, m), 2.23 (1H, m), 2.39 (1H, s), 2.43 (3H, s), 2.50–2.53 (2H, m), 2.73–2.89 (4H, m), 3.01 (1H, m), 3.09 (1H, d, J=15.3 Hz), 3.68 (3H, s), 6.63 (1H, dd, J=7.9 Hz, J=1.8 Hz), 6.93–6.95 (2H, m), 7.09–7.16 (3H, m), 7.49 (1H, d, J=1.8 Hz), 8.21 (1H, brs)

Mass (m/e): 424 (M$^+$)

Similarly, 2-methyl-4aα-(3-methoxyphenyl)-8-bromo-1,2,3,4,4a,5,11,11aβ-octahydro-6H-indolo[2,3-g]isoquinoline and 2-methyl-4aα-(3-methoxyphenyl)-10-bromo-1,2,3,4,4a,5,11,11aβ-octahydro-6H-indolo[2,3-g]isoquinoline are obtained by using 3-bromophenylhydrazine instead of 4-bromophenylhydrazine, and 2-methyl-4aα-(3-methoxyphenyl)-7-bromo-1,2,3,4,4,a,5,11,11aβ-octahydro-6H-indolo[2,3-g]isoquinoline is obtained by using 2-bromophenylhydrazine instead.

Example 10

2-Methyl-4aα-(3-hydroxyphenyl)-9-bromo-1,2,3,4,4a,5,11,11aβ-octahydro-6H-indolo[2,3-g]isoquinoline
10

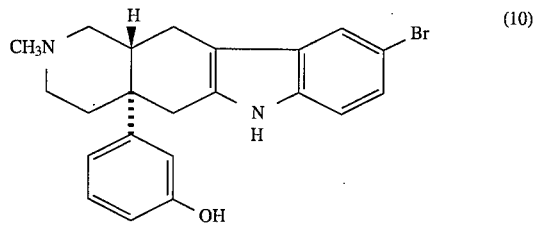

In an atmosphere of argon, 248.5 mg of 2-methyl-4aα-(3-methoxyphenyl)-9-bromo-1,2,3,4,4a,5,11,11aβ-octahydro-6H-indolo[2,3-g]isoquinoline and 296 mg of potassium-6-butoxide were dissolved in 5 ml of anhydrous DMF and the resultant solution and 0.248 ml of 1-propane thiol added thereto were stirred at 140° C. for 5.5 hours. The resultant reaction mixture was cooled to room temperature, distilled under a vacuum to expel DMF, combined with 10 ml of a saturated aqueous solution of sodium hydrogen carbonate, and extracted the times from 20 ml of a chloroform:methanol mixed solvent. The organic layers consequently separated are combined, washed with 10 ml of a saturated aqueous saline solution, dried, and concentrated, to afford 208 mg of a powder. This powder was suspended in 1 ml of methanol, converted by addition of methanesulfonic acid into a methanesulfonate, and separated and refined by column chromatography [Sephadex LH-20; methanol], to afford 96 mg of the methanesulfonate of the captioned compound (yield 32.4%).

IR (KBr) cm$^{-1}$: 3390, 1584, 1468

NMR (DMSO-d$_6$) 500 MHz δ: 2.00 (1H, m), 2.33 (3H, s), 2.54–2.68 (3H, m), 2.82 (3H, d, J=4.9 Hz), 2.84–2.98 (3H, m), 3.09 (1H, d, J=15.9 Hz), 3.33–3.44 (2H, m), 3.61 (1H, d, J=12.2 Hz), 6.54 (1H, dd, J=7.9 Hz, J=1.8 Hz), 6.87 (1H, s), 6.91 (1H, d, J=7.9 Hz), 7.04 (1H, t, J=7.9 Hz), 7.08 (1H, dd, J=8.5 Hz, J=1.8 Hz), 7.16 (1H, d, J=8.6 Hz), 7.52 (1H, d, J=1.8 Hz), 9.26 (1H, s), 9.51 (1H, brs), 10.87 (1H, s)

Mass (FAB): 411 (M$^+$+1)

Elementary analyses For $C_{22}H_{23}N_2OBr \cdot CH_3SO_3H$

|  | C | H | N | Br | S |
|---|---|---|---|---|---|
| Calculated | 54.44 | 5.36 | 5.52 | 15.75 | 6.32 |
| Found | 54.24 | 5.58 | 5.37 | 15.35 | 6.61 |

Similarly, 2-methyl-4aα-(3-hydroxyphenyl)-10-bromo-1,2,3,4,4a,5,11,11aβ-octahydro-6H-indolo[2,3-g]isoquinoline is obtained by using 2-methyl-4aα-(3-methoxyphenyl)-10-bromo-1,2,3,4,4a,5,11,11aβ-octahydro-6H-indolo[2,3-g]isoquinoline instead of 2-methyl-4aα-(3-methoxyphenyl)-9-bromo-1,2,3,4,4a,5,11,11aβ-octahydro-6H-indolo[2,3-g]isoquinoline, 2-methyl-4aα-(3-hydroxyphenyl)-8-bromo-1,2,3,4,4a,5,11,11aβ-octahydro-6H-indolo[2,3-g]isoquinoline is obtained by using 2-methyl-4aα-(3-methoxyphenyl)-8-bromo-1,2,3,4,4a,5,11,11aβ-octahydro-6H-indolo[2,3-g]isoquinoline instead, and 2-methyl-4aα-(3-hydroxyphenyl)-7-bromo-1,2,3,4,4a,5,11,11aβ-octahydro-6H-indolo[2,3-g]isoquinoline is obtained by using 2-methyl-4aα-(3-methoxyphenyl)-7-bromo-1,2,3,4,4a,5,11,11aβ-octahydro-6H-indolo[2,3-g]isoquinoline instead.

Example 11

2-Methyl-4aα-(3-methoxyphenyl)-1,2,3,4,4a,5,11,11aβ-octahydro-6-methyl-indolo[2,3-g]isoquinoline 11

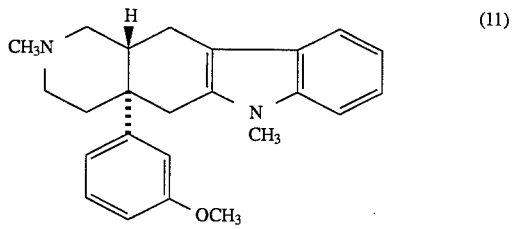

(11)

In an atmosphere of argon, 35 mg of sodium hydroxide (60% mineral oil dispersion) was washed with 2 ml of anhydrous THF and suspended in 2 ml of anhydrous hexamethylphosphoramide (HMPA). In the resultant suspension, a solution of 138 mg of 2-methyl-4aα-(3-methoxyphenyl)-1,2,3,4,4a,5,11,11aβ-octahydro-6H-indolo[2,3-g]isoquinoline in 3 ml of anhydrous HMPA added dropwise thereto was stirred at room temperature for five hours. The resultant reaction mixture and a solution of 0.2 ml of methyl iodide in 4.8 ml of anhydrous HMPA added dropwise thereto were stirred at room temperature for 16 hours. The produced reaction solution was combined with 5 ml of water and extracted two times from 10 ml of ethyl acetate. The organic layers consequently separated were combined, washed with a saturated aqueous saline solution, dried, and concentrated, to afford 1.85 g of an oily substance. When this only substance was separated and refined by column chromatography [silica gel:methanol:chloroform:28% aqua ammonia= 2.5:97.5:0.1–5.0:95.0:0.1], it produced 125 mg of the captioned compound (yield 87.0%).

IR (liquid film method) $cm^{-1}$: 2938, 1607, 1508, 1470

NMR (CDCl$_3$) 500 MHz δ: 2.23 (1H, m), 2.33 (1H, m), 2.47 (3H, s), 2.50 (1H, s), 2.74–2.87 (3H, m), 2.95–3.02 (3H, m), 3.14–3.17 (2H, m), 3.51 (3H, s), 3.69 (3H, s), 6.65 (1H, m), 7.01–7.07 (3H, m), 7.11 (2H, m), 7.19 (1H, d, J=7.9 Hz), 7.44 (1H, d, J=7.9 Hz)

Mass (m/e): 360 (M$^+$)

Similarly, 2-methyl-4aα-(3-methoxyphenyl)-9-methyl-1,2,3,4,4a,5,11,11aβ-octahydro-6-methyl-indolo[2,3-g]isoquinoline is obtained by using 2-methyl-4aα-(3-methoxyphenyl)-9-methyl-1,2,3,4,4a,5,11,11aβ-octahydro-6H-indolo[2,3-g]isoquinoline instead of 2-methyl-4aα-(3-methoxyphenyl)-1,2,3,4,4a,5,11,11aβ-octahydro-6H-indolo[2,3-g]isoquinoline, 2-methyl-4aα-(3-methoxyphenyl)-8-methyl-1,2,3,4,4a,5,11,11aβ-octahydro-6-methyl-indolo[2,3-g]isoquinoline is obtained by using 2-methyl-4aα-(3-methoxyphenyl)-8-methyl-1,2,3,4,4a,5,11,11aβ-octahydro-6H-indolo[2,3-g]isoquinoline instead, 2-methyl-4aα-(3-methoxyphenyl)-7-methyl-1,2,3,4,4a,5,11,11aβ-octahydro-6-methyl-indolo[2,3-g]isoquinoline is obtained by using 2-methyl-4aα-(3-methoxyphenyl)-7-methyl-1,2,3,4,4a,5,11,11aβ-octahydro-6H-indolo[2,3-g]isoquinoline instead, 2-methyl-4aα-(3-methoxyphenyl)-9-chloro-1,2,3,4,4a,5,11,11aβ-octahydro-6-methyl-indolo[2,3-g]isoquinoline is produced by using 2-methyl-4aα-(3-methoxyphenyl)-9-chloro-1,2,3,4,4a,5,11,11aβ-octahydro-6H-indolo[2,3-g]isoquinoline instead, 2-methyl-4aα-(3-methoxyphenyl)-8-chloro-1,2,3,4,4a,5,11,11aβ-octahydro-6-methyl-indolo[2,3-g]isoquinoline is obtained by using 2-methyl-4aα-(3-methoxyphenyl)-8-chloro-1,2,3,4,4a,5,11,11aβ-octahydro-6H-indolo[2,3-g]isoquinoline instead, 2-methyl-4aα-(3-methoxyphenyl)-7-chloro-1,2,3,4,4a,5,11,11aβ-octahydro-6-methyl-indolo[2,3-g]isoquinoline is obtained by using 2-methyl-4aα-(3-methoxyphenyl)-7-chloro-1,2,3,4,4a,5,11,11aβ-octahydro-6H-indolo[2,3-g]isoquinoline instead, 2-methyl-4aα-(3-methoxyphenyl)-9-bromo-1,2,3,4,4a,5,11,11aβ-octahydro-6-methyl-indolo[2,3-g]isoquinoline is obtained by using 2-methyl-4aα-(3-methoxyphenyl)-9-bromo-1,2,3,4,4a,5,11,11aβ-octahydro-6H-indolo[2,3-g]isoquinoline instead, 2-methyl-4aα-(3-methoxyphenyl)-8-bromo-1,2,3,4,4a,5,11,11aβ-octahydro-6-methyl-indolo[2,3-g]isoquinoline is obtained by using 2-methyl-4aα-(3-methoxyphenyl)-8-bromo-1,2,3,4,4a,5,11,11aβ-octahydro-6H-indolo[2,3-g]isoquinoline instead, 2-methyl-4aα-(3-methoxyphenyl)-7-bromo-1,2,3,4,4a,5,11,11aβ-octahydro-6-methyl-indolo[2,3-g]isoquinoline is obtained by using 2-methyl-4aα-(3-methoxyphenyl)-7-bromo-1,2,3,4,4a,5,11,11aβ-octahydro-6H-indolo[2,3-g]isoquinoline instead, 2-methyl-4aα-(3-methoxyphenyl)-9-fluoro-1,2,3,4,4a,5,11,11aβ-octahydro-6-methyl-indolo[2,3-g]isoquinoline is obtained by using 2-methyl-4aα-(3-methoxyphenyl)-9-fluoro-1,2,3,4,4a,5,11,11aβ-octahydro-6H-indolo[2,3-g]isoquinoline instead, 2-methyl-4aα-(3-methoxyphenyl)-8-fluoro-1,2,3,4,4a,5,11,11aβ-octahydro-6-methyl-indolo[2,3-g]isoquinoline is obtained by using 2-methyl-4aα-(3-methoxyphenyl)-8-fluoro-1,2,3,4,4a,5,11,11aβ-octahydro-6H-indolo[2,3-g]isoquinoline instead, and 2-methyl-4aα-(3-methoxyphenyl)-7-fluoro-1,2,3,4,4a,5,11,11aβ-octahydro-6-methyl-indolo[2,3-g]isoquinoline is obtained by using 2-methyl-4aα-(3-methoxyphenyl)-7-fluoro-1,2,3,4,4a,5,11,11aβ-octahydro-6H-indolo[2,3-g]isoquinoline instead. Similarly again, 2-cyclopropylmethyl-4aα-(3-methoxyphenyl)-1,2,3,4,4a,5,11,11aβ-octahydro-6-methyl-indolo[2,3-g]isoquinoline is obtained by using 2-cyclopropylmethyl-4aα-(3-methoxyphenyl)-1,2,3,4,4a,5,11,11aβ-octahydro-6H-indolo[2,3-g]isoquinoline instead, 2-cyclopropylmethyl-4aα-(3-methoxyphenyl)-9-methyl-1,2,3,4,4a,5,11,11aβ-octahydro-6-methyl-indolo[2,3-g]isoquinoline is obtained by using 2-cyclopropylmethyl-4aα-(3-methoxyphenyl)-9-methyl-1,2,3,4,4a,5,11,11aβ-octahydro-6H-indolo[2,3-g]isoquinoline instead, 2-cyclopropylmethyl-4aα-(3-methoxyphenyl)-8methyl-1,2,3,4,4a,5,11,11aβ-octahydro-6-methyl-indolo[2,3-g]isoquinoline is obtained by using 2-cyclopropylmethyl-4aα-(3-methoxyphenyl)-8-methyl-1, 2,3,4,4a,5,11,11aβ-octahydro-6H-indolo[2,3-g]isoquinoline instead, 2-cyclopropylmethy-4aα-(3-methoxyphenyl)-7-methyl-1,2,3,4,4a,5,11,11aβ-octahydro-6-methyl-indolo[2,3-g]isoquinoline is obtained by using 2-cyclopropylmethyl-4aα-(3-methoxyphenyl)-7-methyl-1,2,3,4,4a,5,11,11aβ-octahydro-6H-indolo[2,3-g]isoquinoline instead, 2-cyclopropylmethy-4aα-(3-methoxyphenyl)-9-chloro-1,2,3,4,4a,5,11,11aβ-octahydro-6-methyl-indolo[2,3-g]isoquinoline is obtained by using 2-cyclopropylmethy-4aα-(3-methoxyphenyl)-9-chloro-1,2,3,4,4a,5,11,11aβ-octahydro-6H-indolo[2,3-g]isoquinoline instead, 2-cyclopropylmethyl-4aα-(3-methoxyphenyl)-8-chloro-1,2,3,4,4a,5,11,11aβ-octahydro-6-methyl-indolo[2,3-g]isoquinoline is obtained by using 2-cyclopropylmethyl-4aα-(3-methoxyphenyl)-8-chloro-1,2,3,4,4a,5,11,11aβ-octahydro-6H-indolo[2,3-g]isoquinoline instead, 2-cyclopropylmethyl-4aα-(3-methoxyphenyl)-7-chloro-1,2,3,4,4a,5,11,11aβ-octahydro-6-methyl-indolo[2,3-g]isoquinoline is obtained by using 2-cyclopropylmethy-4aα-(3-methoxyphenyl)-7-chloro-1,2,3,4,4a,5,11,11aβ-octahydro-6H-indolo[2,3-g]isoquinoline instead, 2-cyclopropylmethyl-4aα-(3-methoxyphenyl)-9-bromo-1,2,3,4,4a,5,11,11aβ-octahydro-6-methyl-indolo[2,3-g]isoquinoline is obtained by using 2-cyclopropylmethyl-4aα-(3-methoxyphenyl)-9-bromo-1,2,3,4,4a,5,11,11aβ-octahydro-6H-indolo[2,3-g]isoquinoline instead, 2-cyclopropylmethyl-4aα-(3-methoxyphenyl)-8-bromo-1,2,3,4,4a,5,11,11aβ-octahydro-6-methyl-indolo[2,3-g]isoquinoline is obtained by using 2-cyclopropylmethyl-4aα-(3-methoxyphenyl)-8-bromo-1,2,3,4,4a,5,11,11aβ-octahydro-6H-indolo[2,3-g]isoquinoline instead, 2-cyclopropylmethyl-4aα-(3-methoxyphenyl)-7-bromo-1,2,4,4a,5,11,11aβ-octahydro-6-methyl-indolo[2,3-g]isoquinoline is obtained by using 2-cyclopropylmethyl-4aα-(3-methoxyphenyl)-7-bromo-1,2,3,4,4a,5,11,11aβ-octahydro-6H-indolo[2,3-g]isoquinoline instead, 2-cyclopropylmethyl-4aα-(3-methoxyphenyl)-9-fluoro-1,2,3,4,4a,5,11,11aβ-octahydro-6-methyl-indolo[2,3-g]isoquinoline is obtained by using 2-cyclopropylmethyl-4aα-(3-methoxyphenyl)-9-fluoro-1,2,3,4,4a,5,11,11aβ-octahydro-6H-indolo[2,3-g]isoquinoline instead, 2-cyclopropylmethyl-4aα-(3-methoxyphenyl)-8-fluoro-1,2,3,4,4a,5,11,11aβ-octahydro-6-methyl-indolo[2,3-g]isoquinoline is obtained by using 2-cyclopropylmethyl-4aα-(3-methoxyphenyl)-8-fluoro-1,2,3,4,4a,5,11,11aβ-octahydro-6H-indolo[2,3-g]isoquinoline instead, and 2-cyclopropylmethyl-4aα-(3-methoxyphenyl)-7-fluoro-1,2,3,4,4a,5,11,11aβ-octahydro-6-methyl-indolo[2,3-g]isoquinoline is obtained by using 2-cyclopropylmethyl-4aα-(3-methoxyphenyl)-7-fluoro-1,2,3,4,4a,5,11,11aβ-octahydro-6H-indolo[2,3-g]isoquinoline instead.

Example 12

2-Methyl-4aα-(3-hydroxyphenyl)-1,2,3,4,4a,5,11,11aβ-octahydro-6-methyl-indolo[2,3-g]isoquinoline
12

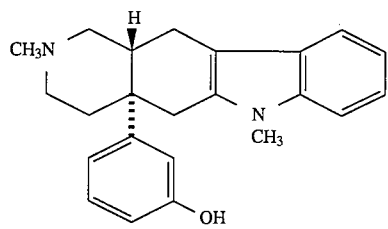

(12)

In an atmosphere of argon 118 mg of 2-methyl-4aα-(3-methoxyphenyl)-1,2,3,4,4a,5,11,11aβ-octahydro-6-methyl-indolo[2,3-g]isoquinoline and 110 mg of potassium-t-tutoxide were dissolved in 2 ml of anhydrous DMF and 0.1 ml of 1-propane thiol was added thereto. The produced mixture was stirred at 140° C. for 3.5 hours and then cooled to room temperature. The cooled mixture was distilled under a vacuum to expel DMF. The distillate and 10 ml of a saturated aqueous solution of sodium hydrogen carbonate added thereto were extracted two times from 20 ml of chloroform. The organic layers consequently separated were combined, washed with a saturated aqueous saline solution, dried, and concentrated, to afford 120 mg of a powder. This powder was suspended in 1 ml of methanol, converted by addition of methanesulfonic acid into a methanesulfonate, and thereafter refined by column chromatography [Sephadex LH-20; methanol], to produce 97.5 mg of the methanesulfonate of the captioned compound (yield 67.7%).

IR (KBr) cm$^{-1}$: 3386, 2936, 2718, 1601

NMR (DMSO-d$_6$) 500 MHz δ: 2.06 (1H, m), 2.32 (3H, m), 2.54–2.57 (2H, m), 2.65 (1H, m), 2.83 (3H, s), 2.85 (1H, m), 2.90 (1H, m), 3.00 (1H, m), 3.27–3.41 (3H, m), 3.52 (3H, s), 3.63 (1H, m), 6.55 (1H, dd, J=7.9 Hz, J=1.8 Hz), 6.94–6.99 (3H, m), 7.04–7.07 (2H, m), 7.30 (1H, d, J=8.6 Hz), 7.37 (1H, d, J=7.3 Hz), 9.28 (1H, s), 9.53 (1H, brs)

Mass (FAB): 347 (M$^+$+1)

Elementary analyses For $C_{23}H_{26}N_2O \cdot CH_3SO_3H \cdot 0.5H_2O$

|  | C | H | N | S |
| --- | --- | --- | --- | --- |
| Calculated | 63.83 | 6.92 | 6.20 | 7.10 |
| Found | 63.87 | 7.05 | 6.61 | 7.40 |

Similarly, 2-methyl-4aα-(3-hydroxyphenyl)-9-methyl-1,2,3,4,4a,5,11,11aβ-octahydro-6-methyl-indolo[2,3-g]isoquinoline is obtained by using 2-methyl-4aα-(3-methoxyphenyl)-9-methyl-1,2,3,4,4a,5,11,11a β-octahydro-6-methyl-indolo[2,3-g]isoquinoline instead of 2-methyl-4aα-(3-methoxyphenyl)-1,2,3,4,4a,5,11,11aβ-octahydro-6-methyl-indolo[2,3-g]isoquinoline, 2-methyl-4aα-(3-hydroxyphenyl)-8-methyl-1,2,3,4,4a,5,11,11aβ-octahydro-6-methyl-indolo[2,3-g]isoquinoline is obtained by using 2-methyl-4aα-(3-methyoxyphenyl)-8-methyl-1,2,3,4,4a,5,11,11aβ-octahydro-6-methyl-indolo[2,3-g]isoquinoline instead, 2-methyl-4aα-(3-hydroxyphenyl)-7-methyl-1,2,3,4,4a,5,11,11aβ-octahydro-6-methyl-indolo[2,3-g]isoquinoline is obtained by using 2-methyl-4aα-(3-methoxyphenyl]-7-methyl-1,2,3,4,4a,5,11,11aβ-octahydro-6-methyl-indolo[2,3-g]isoquinoline instead, 2-methyl-4aα-(3-hydroxyphenyl)-9-bromo-1,2,3,4,4a,5,11,11aβ-octahydro-6-methyl-indolo[2,3-g]isoquinoline is obtained by using 2-methyl-4aα-(3-hydroxyphenyl)-9-bromo-1,2,3,4,4a,5,11,11aβ-octahydro-6-methyl-indolo[2,3-g]isoquinoline instead, 2-methyl-4aα-(3-hydroxyphenyl]-8-bromo-1,2,3,4,4a,5,11,11aβ-octahydro-6-methyl-indolo[2,3-g]isoquinoline is obtained by using 2-methyl-4aα-(3-methoxyphenyl)-8-bromo-1,2,3,4,4a,5,11,11aβ-octahydro-6-methyl-indolo[2,3-g]isoquinoline instead, 2-methyl-4aα-(3-hydroxyphenyl)-7-bromo-1,2,3,4,4a,5,11,11aβ-octahydro-6-methyl-indolo[2,3-g] isoquinoline is obtained by using 2-methyl-4aα-(3-methoxyphenyl)-7-bromo-1,2,3,4,4a,5,11,11aβ-octahydro-6-methyl-indolo[2,3-g]isoquinoline instead, 2-methyl-4aα-(3-hydroxyphenyl)-9-chloro-1,2,3,4,4a,5,11,11aβ-octahydro-6-methyl-indolo[2,3-g]isoquinoline is obtained by using 2-methyl-4aα-(3-methoxyphenyl)-9-chloro-1,2,3,4,4a,5,11,11aβ-octahydro-6-methyl-indolo[2,3-g]isoquinoline instead, 2-methyl-4aα-(3-hydroxyphenyl)-8-chloro-1,2,3,4,4a,5,11,11aβ-octahydro-6-methyl-indolo[2,3-g]isoquinoline is obtained by using 2-methyl-4aα-(3-methoxyphenyl)-8-chloro-1,2,3,4,4a,5,11,11aβ-octahydro-6-methyl-indolo[2,3-g]isoquinoline instead, 2-methyl-4aα-(3-hydroxyphenyl)-7-chloro-1,2,3,4,4a,5,11,11aβ-octahydro-6-methyl-indolo[2,3-g]isoquinoline is obtained by using 2-methyl-4aα-(3-methoxyphenyl)-7-chloro-1,2,3,4,4a,5,11,11aβ-octahydro-6-methyl-indolo[2,3-g]isoquinoline instead, 2-methyl-4aα-(3-hydroxyphenyl)-9-fluoro-1,2,3,4,4a,5,11,11aβ-octahydro-6-methyl-indolo[2,3-g]isoquinoline is obtained by using 2-methyl-4aα-(3-methoxyphenyl)-9-fluoro-1,2,3,4,4a,5,11,11aβ-octahydro-6-methyl-indolo[2,3-g]isoquinoline instead, 2-methyl-4aα-(3-hydroxyphenyl)-8-fluoro-1,2,3,4,4a,5,11,11aβ-octahydro-6-methyl-indolo[2,3-g]isoquinoline is obtained by using 2-methyl-4aα-(3-methoxyphenyl)-8-fluoro-1,2,3,4,4a,5,11,11aβ-octahydro-6-methyl-indolo-[2,3-g]isoquinoline instead, and 2-methyl-4aα-(3-hydroxyphenyl)-7-fluoro-1,2,3,4,4a,5,11,11aβ-octahydro-6-methyl-indolo[2,3-g]isoquinoline is obtained by using 2-methyl-4aα-(3-methoxyphenyl)-7-fluoro-1,2,3,4,4a,5,11,11aβ-octahydro-6-methyl-indolo[2,3-g]isoquinoline instead. Similarly again, 2-cyclopropylmethyl-4aα-(3-hydroxyphenyl)-1,2,3,4,4a,5,11,11aβ-octahydro-6-methyl-indolo[2,3-g]isoquinoline is obtained by using 2-cyclopropylmethyl-4aα-(3-methoxyphenyl)-1,2,3,4,4a,5,11,11aβ-octahydro-6-methyl-indolo[2,3-g]isoquinoline instead, 2-cyclopropylmethyl-4aα-(3-hydroxyphenyl)-9-methyl-1,2,3,4,4a,5,11,11aβ-octahydro-6-methyl-indolo[2,3-g]isoquinoline is obtained by using 2-cyclopropylmethyl-4aα-(3-methoxyphenyl)-9-methyl-1,2,3,4,4a,5,11,11aβ-octahydro-6-methyl-indolo[2,3-g]isoquinoline instead, 2-cyclopropylmethyl-4aα-(3-hydroxyphenyl)-8-methyl-1,2,3,4,4a,5,11,11aβ-octahydro-6-methyl-indolo[2,3-g]isoquinoline is obtained by using 2-cyclopropylmethyl-4aα-(3-methoxyphenyl)-8-methyl-1,2,3,4,4a,5,11,11aβ-octahydro-6-methyl-indolo[2,3-g]isoquinoline instead, 2-cyclopropylmethyl-4aα-(3-hydroxyphenyl)-7-methyl-1,2,3,4,4a,5,11,11aβ-octahydro-6-methyl-indolo[2,3-g]isoquinoline is obtained by using 2-cyclopropylmethyl-4aα-(3-methoxyphenyl)-7-methyl-1,2,3,4,4a,5,11,11aβ-octahydro-6-methyl-indolo[2,3-g]isoquinoline instead, 2-cyclopropylmethyl-4aα-(3-hydryxyphenyl)-9-chloro-1,2,3,4,4a,5,11,11aβ-octahydro-6-methyl-indolo[2,3-g]isoquinoline is obtained by using 2-cyclopropylmethyl-4aα-(3-methoxyphenyl)-9-chloro-1,2,3,4,4a,5,11,11aβ-octahydro-6-methyl indolo[2,3-g]isoquinoline instead, 2-cyclopropylmethyl-4aα-(3-hydroxyphenyl)-8-chloro-1,2,3,4,4a,5,11,11aβ-octahydro-6-methyl-indolo[2,3-g]isoquinoline is obtained by using 2-cyclopropylmethyl-4aα-(3-methoxyphenyl)-8-chloro-1,2,3,4,4a,5,11,11aβ-octahydro-6-methyl-indolo[2,3-g]isoquinoline instead, 2-cyclopropylmethyl-4aα-(3-hydroxyphenyl)-7-chloro-1,2,3,4,4a,5,11,11aβ-octahydro-6-methyl-indolo[2,3-g]isoquinoline is obtained by using 2-cyclopropylmethyl-4aα-(3-methoxyphenyl)-7-chloro-1,2,3,4,4a,5,11,11aβ-octahydro-6-methyl-indolo[2,3-g]isoquinoline instead, 2-cyclopropylmethyl-4aα-(3-hydroxyphenyl)-9-bromo-1,2,3,4,4a,5,11,11aβ-octahydro-6-methyl-indolo[2,3-g]isoquinoline is obtained by using 2-cyclopropylmethyl-4aα-(3-methoxyphenyl)-9-bromo-1,2,3,4,4a,5,11,11aβ-octahydro-6-methyl-indolo[2,3-g]isoquinoline instead, 2-cyclopropylmethyl-4aα-(3-hydroxyphenyl)-8-bromo-1,2,3,4,4a,5,11,11aβ-octahydro-6-methyl-indolo[2,3-g]isoquinoline is obtained by using 2-cyclopropylmethyl-4aα-(3-methoxyphenyl)-8-bromo-1,2,3,4,4a,5,11,11aβ-octahydro-6-methyl-indolo[2,3-g]isoquinoline instead, 2-cyclopropylmethyl-4aα-(3-hydroxyphenyl)-7-bromo-1,2,3,4,4a,5,11,11aβ-octahydro-6-methyl-indolo[2,3-g]isoquinoline is obtained by using 2-cyclopropylmethyl-4aα-(3-methoxyphenyl)-7-bromo-1,2,3,4,4a,5,11,11aβ-octahydro-6-methyl-indolo[2,3-g]isoquinoline instead, 2-cyclopropylmethyl-4aα-(3-hydroxyphenyl)-9-fluoro-1,2,3,4,4a,5,11,11aβ-octahydro-6-methyl-indolo[2,3-g]isoquinoline is obtained by using 2-cyclopropylmethyl-4aα-(3-methoxyphenyl)-9-fluoro-1,2,3,4,4a,5,11,11aβ-octahydro-6-methyl-indolo[2,3-g]isoquinoline instead, 2-cyclopropylmethyl-4aα-(3-hydroxyphenyl)-8-fluoro-1,2,3,4,4a,5,11,11aβ-octahydro-6-methyl-indolo[2,3-g]isoquinoline is obtained by using 2-cyclopropylmethyl-4aα-(3-methoxyphenyl)-8-fluoro-1,2,3,4,4a,5,11,11aβ-octahydro-6-methyl-indolo[2,3-g]isoquinoline instead, and 2-cyclopropylmethyl-4aα-(3-hydroxyphenyl)-7-fluoro-1,2,3,4,4a,5,11,11aβ-octahydro-6-methyl-indolo[2,3-g]isoquinoline is obtained by using 2-cyclopropylmethyl-4aα-(3-methoxyphenyl)-7-fluoro-1,2,3,4,4a,5,11,11aβ-octahydro-6-methyl-indolo[2,3-g]isoquinoline instead.

Example 13

2-Methyl-4aα-(3-methoxyphenyl)-8-methyl-1,2,3,4,4a,5,11,11aβ-octahydro-6H-indolo[2,3-g]isoquinoline 13a and
2-methyl-4aα-(3-methoxyphenyl)-10-methyl-1,2,3,4,4a,5,11,11aβ-octahydro-6H-indolo[2,3-g]isoquinoline 13b

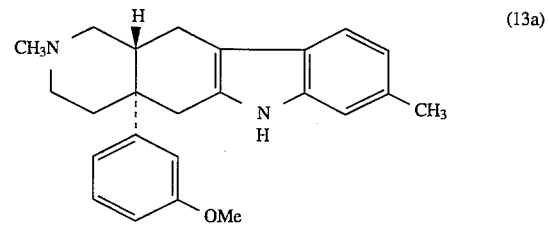

(13a)

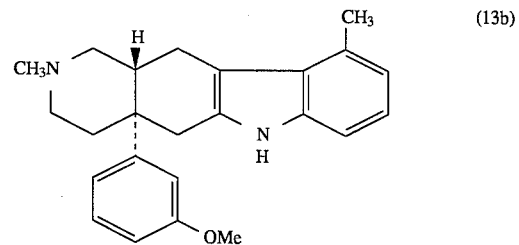

(13b)

A solution of 250 mg of 2-methyl-4aα-(3-methoxyphenyl)-6-oxo-1,2,3,4,4a,5,6,7,8,8a,βdecahydroisoquinoline and 160 mg of m-tolyl hydrazine hydrochloride in 3 ml of ethanol was refluxed. The solution thus refluxed and 0.594 ml of methanesulfonic acid added meantime thereto were stirred and continuously refluxed for one hour. The resultant reaction mixture was cooled to room temperature. The cooled reaction mixture and 10 ml of a saturated aqueous solution of sodium hydrogen carbonate added thereto and cooled with ice were extracted three times from 10 ml of chloroform. The organic layers consequently separated were combined, washed with 5 ml of a saturated aqueous saline solution, dried, and concentrated, to afford 365 mg of an oily substance. This only substance was separated and refined by column chromatography [silica gel:methanol:chloroform:

28% aqua ammonia=2.5:97.5:0.1–5.0:95.0:0.1], it produced 313 mg of a mixture of the captioned compounds (yield 94.9%).

IR (KBr) cm$^{-1}$: 3390, 2898, 1607, 1580, 1462

NMR (CDCl$_3$) 500 MHz δ: 1.98 (1H, m), 2,09 (1H, m), 2.32 (3H, sX2), 2.38 (1H, m), 2.40 (3H, sX2), 2.53–2.65 (3H, m), 2.73 (1H, m), 2.85–2.96 (3H, m), 3.03 (1H, m), 3.68 (3H, s), 6.61 (1H, m), 6.91 (1H, m), 6.99–7.10 (4H, m), 7.31 (1H, m), 7.47 (1H, brsX2).

Mass (m/e): 360 (M$^+$)

Example 14

2-Methyl-4aα-(3-hydroxyphenyl)-8-methyl-1,2,3,4,4a,5,11,11aβ-octahydro-6H-indolo[2,3-g]isoquinoline 14a and 2-methyl-4aα-(3-hydroxyphenyl)-10-methyl-1,2,3,4,4a,5,11,11aβ-octahydro-6H-indolo[2,3-g]isoquinoline 14b

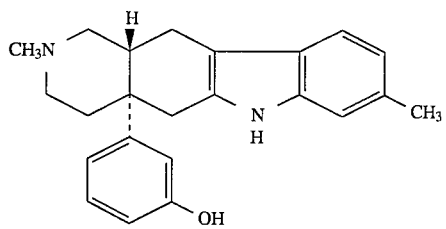

(14a)

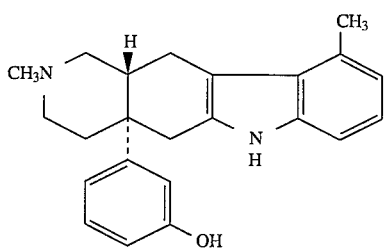

(14b)

In an atmosphere of argon, 255.3 mg of a mixture of 2-methyl-4aα-(3-methoxyphenyl)-8-methyl-1,2,3,4,4a,5,11,11aβ-octahydro-6H-indolo[2,3-g]isoquinoline and 2-methyl-4aα-(3-methoxyphenyl)-10-methyl-1,2,3,4,4a,5,11,11aβ-octahydro-6H-indolo[2,3-g]isoquinoline and 477 mg of potassium t-butoxide were dissolved in 6 ml of anhydrous DMF. The resultant solution and 0.4 ml of 1-propane thiol added thereto were stirred at 140° C. for 3.5 hours.

The produced mixture was cooled to room temperature, distilled to expel DMF, combined with 10 ml of a saturated aqueous solution of sodium hydrogen carbonate, and extracted three times from 20 ml of a mixed solvent of chloroform:methanol=5:1. The organic layers consequently separated were combined, washed with 10 ml of a saturated saline solution, dried, and concentrated, to obtain 401 mg of a powder. This powder was suspended in 1 ml of methanol, converted by the addition of methanesulfonic acid into a methanesulfonate, and then separated and refined by column chromatography [Sephadex LH-20; methanol], to produce 58 mg of a mixture of methanesulfonates of the captioned compounds (yield 18.5%).

IR (KBr) cm$^{-1}$: 3400, 1601, 1586, 1462

NMR (DMSO-d$_6$) 500 MHz δ: 201 (1H, m), 2.31 (3H, sX2), 2.33 (1H, m), 2.50 (3H, sX2), 2.57 (3H, sX2), 2.78–2.97 (5H, m), 3.05–3.08 (1H, m), 3.16–3.30 (2H, m), 3.60 (1H, m), 6.53 (1H, m), 6.79 (1H, m), 6.89–6.99 (3H, m), 7.01–7.06 (1H, m), 7.21 (1H, m), 9.25 (1H, sX2), 9.65 (1H, brsX2), 10.48 (1H, sX2)

Mass (FAB): 347 (M$^+$+1)

Elementary analyses For C$_{23}$H$_{26}$N$_2$O.0.9CH$_3$SO$_3$H.0.1H$_2$O

|  | C | H | N | S |
| --- | --- | --- | --- | --- |
| Calculated | 64.68 | 7.00 | 6.31 | 6.50 |
| Found | 64.50 | 6.93 | 6.62 | 6.47 |

Referential Example 1:

2-(2,2,2-Trichloroethoxycarbonyl)-4aα-(3-methoxyphenyl)-6-oxo-1,2,3,4,4a,5,6,7,8,8aβ-decahydroisoquinoline 15

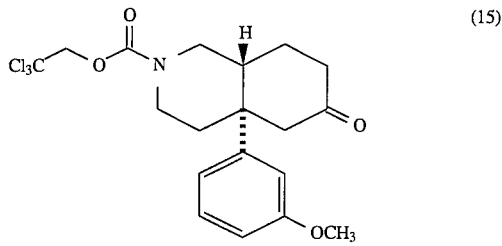

(15)

In an atmosphere of argon, 60 mg of proton sponge was dissolved in 2 ml of anhydrous dichloroethane. The resultant solution was cooled to 0° C. and 0.03 ml of 2,2,2-trichloroethyl chloroformate was added to the cooled solution. The produced mixture and a solution of 50 mg of 2-methyl-4aα-(3-methoxyphenyl)-6-oxo-1,2,3,4,4a,5,6,7,8,8aβ-decahydroisoquinoline in 0.5 ml anhydrous dichloroethane added dropwise thereto were stirred at room temperature for 30 minutes. The produced mixture was distilled under a vacuum to expel dichloroethane. The residue and 30 ml of ethyl acetate added thereto were washed with 1N hydrochloric acid and water, dried, and concentrated, to afford 90 mg of an oily substance. When this oily substance was refined by column chromatography [silica gel:hexane/ethyl acetate (3:1)], 73 mg of the captioned compound was produced (yield 91.8%).

IR (Liquid film method) cm$^{-1}$: 1715, 1431, 1243, 1125, 754, 717

NMR (CDCl$_3$) 400 MHz δ: 1.80 (1H, m), 2.03 (1H, m), 2.13 (1H, m), 2.26 (1H, m), 2.31–2.43 (4H, m), 2.85 (1H, m), 2.96 (1H, d, J=13.7 Hz), 3.54 (1H, m), 3.81 (3H, s), 4.02

(1H, m), 4.18 (1H, m), 4.71–4.81 (2H, m), 6.75 (1H, m), 6.95–6.98 (2H, m), 7.25 (1H, m)

Mass (EI): 433 (M⁺)

Example 15

2-(2-2,2-Trichloroethoxycarbonyl)-4aα-(3-methoxyphenyl)-1,2,3,4,4a,5,11,11aβ-octahydro-6H-indolo[2,3-g]isoquinoline 16

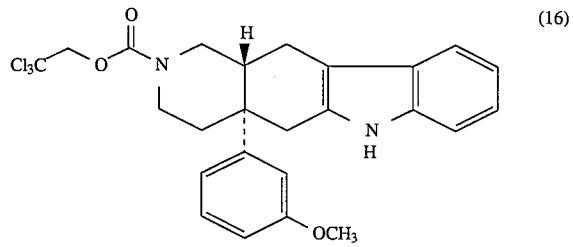

In an atmosphere of argon, 100 mg of 2-(2,2,2-trichloroethoxycarbonyl)-4aα-(3-methoxyphenyl)-6-oxo-1,2,3,4,4a,5,6,7,8,8aβ-decahydroisoquinoline and 25 μl of phenyl hydrazine were dissolved in 3 ml of ethanol and the resultant solution was heated to 80° C. The hot solution consequently obtained and 0.15 ml of methanesulfonic acid added thereto were stirred at 80° C. for 40 minutes and then cooled to room temperature. The produced mixture was distilled under a vacuum to expel ethanol. The residue of the distillation was combined with 5 ml of a saturated aqueous solution of sodium hydrogen carbonate and extracted three times with 20 ml of chloroform. The organic layers consequently separated were combined, washed with a saturated aqueous saline solution, dried, and concentrated, to afford 130 mg of an oily substance. When this oily substance was refined by column chromatography [silica gel:hexane/ethyl acetate (3:1)], 104 mg of crude crystals were obtained. The crude crystals, on being recrystallized from ethyl acetate, produced 60 mg of the captioned compound in a purified state (m.p. 197° to 198° C.) (yield 51.3%).

IR (KBr) cm⁻¹: 3410, 1707, 1441, 1245, 1127, 752

NMR (CDCl₃) 400 MHz δ: 1.84 (1H, td, J=13.2 Hz, 3.9 Hz), 2.38–2.46 (2H, m) 2.88–3.03 (4H, m), 3.11 (1H, d, J=14.7 Hz), 3.48 (1H, m), 3.68 (3H, s), 4.11 (1H, m), 4.28 (1H, m), 4.72–4.82 (2H, m), 6.65 (1H, m), 6.99–7.02 (2H, m), 7.05–7.14 (3H, m), 7.21 (1H, m), 7.44 (1H, m), 7.60 (1H, m)

Mass (EI): 506 (M⁺)

Elementary analyses For $C_{25}H_{25}Cl_3N_2O_3$

|  | C | H | N | S |
|---|---|---|---|---|
| Calculated | 59.13 | 4.96 | 5.52 | 20.94 |
| Found | 59.12 | 5.14 | 5.54 | 20.70 |

Similarly, 2-(2,2,2-trichloroethoxycarbonyl)-4aα-(3-methoxyphenyl)-9-methyl-1,2,3,4,4a5,11,11aβ-octahydro-6H-indolo[2,3-g]isoquinoline is produced by using p-tollyl hydrazine instead of phenylhydrazine, 2-(2,2,2-trichloroethoxycarbonyl)-4aα-(3-methoxyphenyl)-8-methyl-1,2,3,4,4a,5,11,11aβ-octahydro-6H-indolo[2,3-g]isoquinoline and 2-(2,2,2-trichloroethoxycarbonyl)-4aα-(3-methoxyphenyl)-10-methyl-1,2,3,4,4a,5,11,11aβ-octahydro-6H-indolo[2,3-g]isoquinoline are produced by using m-tollyl hydrazine instead, 2-(2,2,2-trichloroethoxycarbonyl)-4aα-(3-methoxyphenyl)-7-methyl-1,2,3,4,4a,5,11,11aβ-octahydro-6H-indolo[2,3-g]isoquinoline is produced by using o-tollyl hydrazine instead, 2-(2,2,2-trichloroethoxycarbonyl)-4aα-(3-methoxyphenyl)-9-chloro-1,2,3,4,4a,5,11,11aβ-octahydro-6H-indolo[2,3-g]isoquinoline is produced by using 4-chlorophenylhydrazine instead, 2-(2,2,2-trichloroethoxycarbonyl)-4aα-(3-methoxyphenyl)-8-chloro-1,2,3,4,4a,5,11,11aβ-octahydro-6H-indolo[2,3-g]isoquinoline and 2-(2,2,2-trichloroethoxyxcarbonyl)-4aα-(3-methoxyphenyl)-10-chloro-1,2,3,4,4a,5,11,11aβ-octahydro-6H-indolo[2,3-g]isoquinoline are produced by using 3-chlorophenylhydrazine instead, 2-(2,2,2-trichloroethoxycarbonyl)-4aα-(3-methoxyphenyl)-8-chloro-1,2,3,4,4a,5,11,11aβ-octahydro-6H-indolo[2,3-g]isoquinoline and 2-(2,2,2-trichloroethoxycarbonyl)-4aβ-(3-methoxyphenyl-10-chloro-1,2,3,4,4a,5,11,11aβ-octahydro-6H-indolo[2,3-g]isoquinoline are produced by using 3-chlorophenylhydrazine instead, 2-(2,2,2-trichloroethoxycarbonyl)-4aα-(3-methoxyphenyl)-9-bromo-1,2,3,4,4a,5,11,11aβ-octahydro-6H-indolo[2,3-g]isoquinoline is produced by using 4-bromophenylhydrazine instead, 2-(2,2,2-trichloroethoxycarbonyl)-4aα-(3-methoxyphenyl)-8-bromo-1,2,3,4,4a,5,11,11aβ-octahydro-6H-indolo[2,3-g]isoquinoline and 2-(2,2,2-trichloroethoxycarbonyl)-4aα-(3-methoxyphenyl)-10-bromo-1,2,3,4,4a,5,11,11aβ-octahydro-6H-indolo[2,3-g]isoquinoline are produced by using 3-bromophenyl hydrazine instead, 2-(2,2,2-trichloroethoxycarbonyl)-4aα-(3-methoxyphenyl)-7-bromo-1,2,3,4,4a,5,11,11aβ-octahydro-6H-indolo[2,3-g]isoquinoline is produced by using 2-bromophenylhydrazine instead, 2-(2,2,2-trichloroethoxycarbonyl)-4aα-(3-methoxyphenyl)-9-nitro-1,2,3,4,4a,5,11,11aβ-octahydro-6H-indolo[2,3-g]isoquinoline is produced by using 4-nitrophenylhydrazine instead, 2-(2,2,2-trichloroethoxycarbonyl)-4aα-(3-methoxyphenyl)-8-nitro-1,2,3,4,4a,5,11,11aβ-octahydro-6H-indolo[2,3-g]isoquinoline and 2-(2,2,2-trichloroethoxycarbonyl)-4aα-(3-methoxyphenyl)-10-nitro-1,2,3,4,4a,5,11,11aβ-octahydro-6H-indolo[2,3-g]isoquinoline are produced by using 3-nitrophenylhydrazine instead, 2-(2,2,2-trichloroethoxycarbonyl)-4aα-(3-methoxyphenyl)-7-nitro-1,2,3,4,4a,5,11,11aβ-octahydro-6H-indolo[2,3g]isoquinoline is produced by using 2-nitrophenylhydrazine instead, 2-(2,2,2-trichloroethoxycarbonyl)-4aα-(3-methoxyphenyl)-1,2,3,4,4a,5,11,11aβ-octahydro-6-methyl-indolo[2,3-g]isoquinoline is produced by using 1-methyl-1-phenylhydrazine instead, and 2-(2,2,2-trichloroethoxycarbonyl)-4aα-(3-methoxyphenyl)-1,2,3,4,4a,5,11,11aβ-octahydro-6-phenyl-indolo[2,3-g]isoquinoline is produced by using 1,1-diphenylhydrazine instead.

Example 16

2-Cyclopropylcarbonyl-4aα-(3-methoxyphenyl)-1,2,3,4,4a,5,11,11aβ-octahydro-6H-indolo[2,3-g]isoquinoline 17

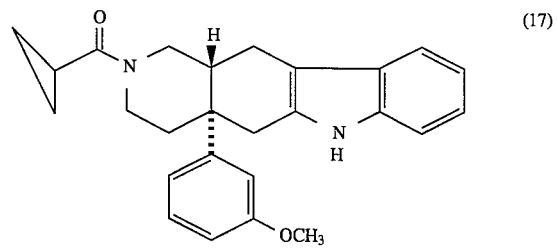

In an atmosphere of argon, 100 mg of 2-(2,2,2-trichloroethoxycarbonyl)-4aα-(3-methoxyphenyl)-1,2,3,4,4a,5,11,11aβ-octahydro-6H-indolo[2,3-g]isoquinoline was dissolved in 2 ml of acetic acid. The resultant solution and 130 mg of zinc dust added thereto were stirred at room temperature for 22 hours. The produced mixture was filtered to expel zinc, distilled under a vacuum to expel acetic acid, combined with 5 ml of a saturated aqueous solution of sodium hydrogen carbonate, and extracted three times from 20 ml of chloroform. The organic layers consequently separated were combined, washed with a saturated aqueous saline solution, dried, and concentrated, to afford a reaction mixture. In an atmosphere of argon, 50 mg of the reaction mixture was dissolved in 5 ml of anhydrous dichloromethane. The produced solution and 60 μl of triethylamine and 35 μl of cyclopropanecarbonyl chloride added thereto were stirred at room temperature for one hour. The resultant mixture was distilled under a vacuum to expel dichloromethane, combined with 5 ml of a saturated aqueous solution of sodium hydrogen carbonate, and extracted three times from 20 ml of chloroform. The organic layers consequently separated were combined, washed with a saturated aqueous saline solution, dried, and concentrated, to afford 65 mg of an oily substance. When this oily substance was refined by column chromatograph [silica gel; chloroform-chloroform/methanol(99/1)], 55 mg of crude crystals were obtained. The crude crystals, on being recrystallized from chloroform-hexane, produced 37 mg of the captioned compound in a purified form [m.p. 247° C. to 249° C. (decomposition)] (yield 46.9%).

IR (KBr) cm$^{-1}$: 3408, 3238, 1609, 1582, 1491, 1460, 1255, 1228

NMR (CDCl$_3$) 500 MHz δ: 0.75–0.78 (2H, m), 0.95–1.12 (2H, m), 1.75–1.87 (2H, m), 2.37–2.48 (2H, m), 2.85–3.30 (6H, m), 3.68 (3H, s), 4.05–4.72 (2H, br), 6.65 (1H, m), 7.01–7.14 (5H, m), 7.22 (1H, d, J=7.9 Hz), 7.44 (1H, d, J=6.7 Hz), 7.62 (1H. brs)

Mass (EI): 400 (M$^+$)

Elementary analyses For C$_{26}$H$_{28}$N$_2$O$_2$

|  | C | H | N |
| --- | --- | --- | --- |
| Calculated | 77.97 | 7.05 | 6.99 |
| Found | 77.77 | 7.34 | 6.64 |

Similarly, 2-acryloyl-4aα-(3-methoxyphenyl)-1,2,3,4,4a,5,11,11aβ-octahydro-6H-indolo[2,3-g]isoquinoline is produced by using acryloyl chloride instead of cyclopropane carbonyl chloride, 2-benzoyl-4aα-(3-methoxyphenyl)-1,2,3,4,4a,5,11,11aβ-octahydro-6H-indolo[2,3-g]isoquinoline is produced by using benzoyl chloride instead, 2-phenylacetyl-4aα-(3-methoxyphenyl)-1,2,3,4,4a,5,11,11aβ-octahydro-6H-indolo[2,3-g]isoquinoline is produced by using phenylacetyl chloride instead, 2-acetyl-4aα-(3-methoxyphenyl)-1,2,3,4,4a,5,11,11aβ-octahydro-6H-indolo[2,3-g]isoquinoline is produced by using acetyl chloride instead, 2-propionyl-4aα-(3-methoxyphenyl)-1,2,3,4,4a,5,11,11aβ-octahydro-6H-indolo[2,3g]isoquinoline is produced by using propionyl chloride instead, 2-butyryl-4aα-(3-methoxyphenyl)-1,2,3,4,4a,5,11,11aβ-octahydro-6H-indro[2,3-g]isoquinoline is produced by using butyryl chloride instead, 2-thiophenecarbonyl-4aα-(3-methoxyphenyl)-1,2,3,4,4a,5,11,11aβ-octahydro-6H-indolo]2,3-g]isoquinoline is produced by using 2-thiophenecarbonyl chloride instead, 2-valeryl-4aα-(3-methoxyphenyl)-1,2,3,4,4a,5,11,11aβ-octahydro-6H-indolo[2,3-g]isoquinoline is produced by using valeryl chloride instead, 2-furoyl-4aα-(3-methoxyphenyl)-1,2,3,4,4a,5,11,11aβ-octahydro-6H-indolo[2,3-g]isoquinoline is produced by using 2-furoyl chloride instead, 2-cyclobutylcarbonyl-4aα-(3-methoxyphenyl)-1,2,3,4,4a,5,11,11aβ-octahydro-6H-indolo[2,3-g]isoquinoline is produced by using cyclobutanecarbonyl chloride instead, 2-p-toluoyl-4aα-(3-methoxyphenyl)-1,2,3,4,4a,5,11,11aβ-octahydro-6H-indolo[2,3-g]isoquinoline is produced by using p-toluoyl chloride instead, 2-xyloyl-4aα-(3-methoxyphenyl)-1,2,3,4,4a,5,11,11aβ-octahydro-6H-indolo[2,3-g]isoquinoline is produced by using 2-xyloyl chloride instead, and 2-(p-anisoyl)-4aα-(3-methoxyphenyl)-1,2,3,4,4a,5,11,11aβ-octahydro-6H-indolo[2,3-g]isoquinoline is produced by using p-anisolyl chloride instead. Similarly, 2-cyclopropylcarbonyl-4aα-(3-methoxyphenyl)-7-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-chloro-1,2,3,4,4a,5,11,11aβ-octahydro-6H-indolo[2,3-g] isoquinoline instead of 2-(2,2,2-trichloroethoxycarbonyl)-4aα-(3-methoxyphenyl)-1,2,3,4,4a,5,11,11aβ-octahydro-6H-indolo[2,3-g]isoquinoline, 2-cyclopropylcarbonyl-4aα-(3-methoxyphenyl)-8-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-chloro-1,2,3,4,4a,5,11,11aβ-octahydro-6H-indolo[2,3-g]isoquinoline instead, 2-cyclopropylcarbonyl-4aα-(3-methoxyphenyl)-9-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-chloro-1,2,3,4,4a,5,11,11aβ-octahydro-6H-indolo[2,3-g]isoquinoline instead, 2-cyclopropylcarbonyl-4aα-(3-methoxyphenyl)-10-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-chloro-1,2,3,4,4a,5,11,11aβ-octahydro-6H-indolo[2,3-g]isoquinoline instead, 2-cyclopropylcarbonyl-4aα-(3-methoxyphenyl)-7-bromo-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-bromo-1,2,3,4,4a,5,11,11aβ-octahydro-6H-indolo[2,3-g]isoquinoline instead, 2-cyclopropylcarbonyl-4aα-(3-methoxyphenyl)-8-bromo-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-bromo-1,2,3,4,4a,5,11,11aβ-octahydro-6H-indolo[2,3-g]isoquinoline instead, 2-cyclopropylcarbonyl-4aα-(3-methoxyphenyl)-9-bromo-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-bromo-1,2,3,4,4a,5,11,11aβ-octahydro-6H-indolo[2,3-g]isoquinoline instead, 2-cyclopropylcarbonyl-4aα-(3-methoxyphednyl)-10-bromo-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-bromo-1,2,3,4,4a,5,11,11aβ-octahydro-6H-indolo[2,3-g]isoquinoline instead, 2-cyclopropylcarbonyl-4aα-(3-methoxyphenyl)-7-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-nitro-1,2,3,4,4a,5,11,11aβ-octahydro-6H-indolo[2,3-g]isoquinoline instead, 2-cyclopropylcarbonyl-4aα-(3-methoxyphenyl)-8-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-nitro-1,2,3,4,4a,5,11,11aβ-octahydro-6H-indolo[2,3-g] isoquinoline instead, 2-cyclopropylcarbonyl-4aα-(3-methoxyphenyl)-9-nitro-1,2,3,4,4a,5,11,11aβ-octahydro- 6H-indolo[2,3-g]isoquinoline is produced by using 2-(2,2, 2-trichloroethoxycarbonyl)-4aα-(3-methoxyphenyl)-9-nitro-1,2,3,4,4a,5,11,11aβ-octahydro-6H-indolo[2,3-g] isoquinoline instead, 2-cyclopropylcarbonyl-4aα-(3-methoxyphenyl)-10-nitro-1,2,3,4,4a,5,11,11aβ-octahydro-6H-indolo[2,3-g]isoquinoline is produced by using 2-(2,2, 2-trichloroethoxycarbonyl)-4aα-(3-methoxyphenyl)-10-nitro-1,2,3,4,4a5,11,11aβ-octahydro-6H-indolo[2,3-g] isoquinoline instead, and 2-cyclopropylcarbonyl-4aα-(3-methoxyphenyl)-7-nitro-1,2,3,4,4a,5,11,11aβ-octahydro-6H-indolo[2,3-g]isoquinoline is produced by using 2-(2,2, 2-trichloroethoxycarbonyl)-4aα-(3-methoxyphenyl)-1,2,3, 4,4a,5,11,11aβ-octahydro-6-methyl-indolo[2,3-g] isoquinoline instead. Similarly, 2-acryloyl-4aα-(3-methoxyphenyl)-7-methyl-1,2,3,4,4a,5,11,11aβ-octahydro-6H-indolo[2,3-g]isoquinoline is produced by using 2-(2,2, 2-trichloroethoxycarbonyl)-4aα-(3-methoxyphenyl)-7-methyl-1,2,3,4,4a,5,11,11aβ-octahydro-6H-indolo[2,3-g] isoquinoline and acryloyl chloride instead of 2-(2,2,2-trichloroethoxycarbonyl)-4aα-(3-methoxyphenyl)-1,2,3,4, 4a,5,11,11aβ-octahydro-6H-indolo[2,3-g]isoquinoline and cyclopropanecarbonyl chloride, 2-acryloyl-4aα-(3-methoxyphenyl)-8-methyl-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-methyl-1,2,3,4,4a,5,11,11aβ-octahydro-6H-indolo[2,3-g] isoquinoline and acryloyl chloride instead, 2-acryloyl-4aα-(3-methoxyphenyl)-9-methyl-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-methyl-1,2,3,4,4a,5,11,11aβ-octahydro-6H-indolo[2,3-g]isoquinoline and acryloyl chloride instead, 2-acryloyl-4aα-(3-methoxyphenyl)-10-methyl-1,2,3,4,4a,5, 11,11aβ-octahydro-6H-indolo[2,3-g]isoquinoline is produced by using 2-(2,2,2-trichloroethoxycarbonyl)-4aα-(3-methoxyphenyl)-10-methyl-1,2,3,4,4a,5,11,11aβ-octahydro-6H-indolo[2,3-g]isoquinoline and acryloyl chloride instead, 2-acryloyl-4aα-(3-methoxyphenyl)-7-chloro-1,2,3,4,4a,5,11,11aβ-octahydro-6H-indolo[2,3-g] isoquinoline is produced by using 2-(2,2,2-trichloroethoxycarbonyl)-4aα-(3-methoxyphenyl)-7-chloro-1,2,3,4,4a,5,11, 11aβ-octahydro-6H-indolo[2,3-g]isoquinoline and acryloyl chloride instead, 2-acryloyl-4aα-(3-methoxyphenyl)-8-chloro-1,2,3,4,4a,5,11,11aβ-octahydro-6H-indolo[2,3-g] isoquinoline is produced by using 2-(2,2,2-trichloroethoxycarbonyl)-4aα-(3-methoxyphenyl)-8-chloro-1,2,3,4,4a,5,11, 11aβ-octahydro-6H-indolo[2,3-g]isoquinoline and acryloyl chloride instead, 2-acryloyl-4aα-(3-methoxyphenyl)-9-chloro-1,2,3,4,4a,5,11,11aβ-octahydro-6H-indolo[2,3-g] isoquinoline is produced by using 2-(2,2,2-trichloroethoxycarbonyl)-4aα-(3-methoxyphenyl)-9-chloro-1,2,3,4,4a,5,11, 11aβ-octahydro-6H-indolo[2,3-g]isoquinoline and acryloyl chloride instead, 2-acryloyl-4aα-(3-methoxyphenyl)-10-bromo-1,2,3,4,4a,5,11,11aβ-octahydro-6H-indolo[2,3-g] isoquinoline is produced by using 2-(2,2,2-trichloroethoxycarbonyl)-4aα-(3-methoxyphenyl)-10-chloro-1,2,3,4,4a,5, 11,11aβ-octahydro-6H-indolo[2,3-g]isoquinoline and acryloyl chloride instead, 2-acryloyl-4aα-(3-methoxyphenyl)-7-bromo-1,2,3,4,4a,5,11,11aβ-octahydro-6H-indolo[2, 3-g]isoquinoline is produced by using 2-(2,2,2-trichloroethoxycarbonyl)-4aα-(3-methoxyphenyl)-7-bromo-1,2,3,4, 4a,5,11,11aβ-octahydro-6H-indolo[2,3-g]isoquinoline and acryloyl chloride instead, 2-acryloyl-4aα-(3-methoxyphenyl)-8-bromo-1,2,3,4,4a,5,11,11aβ-octahydro-6H-indolo[2, 3-g]isoquinoline is produced by using 2-(2,2,2-trichloroethoxycarbonyl)-4aα-(3-methoxyphenyl)-8-bromo-1,2,3,4, 4a,5,11,11aβ-octahydro-6H-indolo[2,3-g]isoquinoline and acryloyl chloride instead, 2-acryloyl-4aα-(3-methoxyphenyl)-9-bromo-1,2,3,4,4a,5,11,11aβ-octahydro-6H-indolo[2, 3-g]isoquinoline is produced by using 2-(2,2,2-trichloroethoxycarbonyl)-4aα-(3-methoxyphenyl)-9-bromo-1,2,3,4, 4a,5,11,11aβ-octahydro-6H-indolo[2,3-g]isoquinoline and acryloyl chloride instead, 2-acryloyl-4aα-(3-methoxyphenyl)-10-bromo-1,2,3,4,4a,5,11,11aβ-octahydro-6H-indolo [2,3-g]isoquinoline is produced by using 2-(2,2,2-trichloroethoxycarbonyl)-4aα-(3-methoxyphenyl)-10-bromo-1,2,3, 4,4a,5,11,11aβ-octahydro-6H-indolo[2,3-g]isoquinoline and acryloyl chloride instead, 2-acryloyl-4aα-(3-methoxyphenyl)-7-fluoro-1,2,3,4,4a,5,11,11aβ-octahydro-6H-indolo[2, 3-g]isoquinoline is produced by using 2-(2,2,2-trichloroethoxycarbonyl)-4aα-(3-methoxyphenyl)-7-fluoro-1,2,3,4,4a, 5,11,11aβ-octahydro-6H-indolo[2,3-g]isoquinoline and acryloyl chloride instead, 2-acryloyl-4aα-(3-methoxyphenyl)-8-fluoro-1,2,3,4,4a,5,11,11aβ-octahydro[2,3-g]isoquinoline is produced by using 2-(2,2,2-trichloroethoxycarbonyl)-4aα-(3-methoxyphenyl)-8-fluoro-1,2,3,4,4a,5,11, 11aβ-octahydro-6H-indolo[2,3-g]isoquinoline and acryl acryloyl chloride instead, 2-acryloyl-4aα-(3-methoxyphenyl)-9-fluoro-1,2,3,4,4a,5,11,11aβ-octahydro-6H-indolo[2, 3-g]isoquinoline is produced by using 2-(2,2,2-trichloroethoxycarbonyl)-4aα-(3-methoxyphenyl)-9-fluoro-1,2,3,4,4a, 5,11,11aβ-octahydro-6H-indolo[2,3-g]isoquinoline and acryloyl chloride instead, 2-acryloyl-4aα-(3-methoxyphenyl)-10-fluoro-1,2,3,4,4a,5,11,11aβ-octahydro[2,3-g]isoquinoline is produced by using 2-(2,2,2-trichloroethoxycarbonyl)-4aα-(3-methoxyphenyl)-10-fluoro-1,2,3,4,4a,5,11, 11aβ-octahydro-6H-indolo[2,3-g]isoquinoline and acryloyl chloride instead, 2-acryloyl-4aα-(3-methoxyphenyl)-7-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-nitro-1,2,3,4,4a,5,11, 11aβ-octahydro-6H-indolo[2,3-g]isoquinoline and acryloyl chloride instead, 2-acryloyl-4aα-(3-methoxyphenyl)-8-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-nitro-1,2,3,4,4a, 5,11, 11aβ-octahydro-6H-indolo[2,3-g]isoquinoline and acryloyl chloride instead, 2-acryloyl-4aα-(3-methoxyphenyl)-9-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-nitro-1,2,3,4,4a,5,11, 11aβ-octahydro-6H-indolo[2,3-g]isoquinoline and acryloyl chloride instead, 2-acryloyl-4aα-(3-methoxyphenyl)-10-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-nitro-1,2,3,4,4a,5,11, 11aβ-octahydro-6H-indolo[2,3-g]isoquinoline and acryloyl chloride instead, and 2-acryloyl-4aα-(3-methoxyphenyl)-1, 2,3,4,4a,5,11,11aβ-octahydro-6-methyl-indolo[2,3-g]isoquinoline is produced by using 2-(2,2,2-trichloroethoxycarbonyl)-4aα-(3-methoxyphenyl)-1,2,3,4,4a,5,11,11aβ-octahydro-6-methyl-indolo[2,3-g]isoquinoline and acryloyl chloride instead.

Similarly, 2-benzoyl-4aα-(3-methoxyphenyl)-7-methyl-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-methyl-1,2,3,4,4a, 5,11,11aβ-octahydro-6H-indolo[2,3-g]isoquinoline and benzoyl chloride, 2-benzoyl-4aα-(3-methoxyphenyl)-8-methyl-1,2, 3,4,4a,5,11,11aβ-octahydro-6H-indolo[2,3-g]isoquinoline is produced by using 2-(2,2,2-trichloroethoxycarbonyl)-4aα-(3-methoxyphenyl)-8-methyl-1,2,3,4,4a,5,11,11aβ-octahydro-6H-indolo[2,3-g]isoquinoline and benzoyl chloride instead, 2-benzoyl-4aα-(3-methoxyphenyl)-9-methyl-1,2,3, 4,4a,5,11,11aβ-octahydro-6H-indolo[2,3-g]isoquinoline is produced by using 2-(2,2,2-trichloroethoxycarbonyl)-4aα-(3-methoxyphenyl)-9-methyl-1,2,3,4,4a,5,11,11aβ-octahydro-6H-indolo[2,3-g]isoquinoline and benzoyl chloride instead, 2-benzoyl-4aα-(3-methoxyphenyl)-10-methyl-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-methyl-1,2,3,4,4a,5,11,11aβ-octahydro-6H-indolo[2,3-g]isoquinoline and benzoyl chloride instead, 2-benzoyl-4aα-(3-methoxyphenyl)-7-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-chloro-1,2,3,4,4a,5,11,11aβ-octahydro-6H-indolo[2,3-g]isoquinoline and benzoyl chloride instead, 2-benzoyl-4aα-(3-methoxyphenyl)-8-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-chloro-1,2,3,4,4a,5,11,11aβ-octahydro-6H-indolo[2,3-g]isoquinoline and benzoyl chloride instead, 2-benzoyl-4aα-(3-methoxyphenyl)-9-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-chloro-1,2,3,4,4a,5,11,11aβ-octahydro-6H-indolo[2,3-g]isoquinoline and benzoyl chloride instead, 2-benzoyl-4aα-(3-methoxyphenyl)-10-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-chloro-1,2,3,4,4a,5,11,11aβ-octahydro-6H-indolo[2,3-g]isoquinoline and benzoyl chloride instead, 2-benzoyl-4aα-(3-methoxyphenyl)-7-bromo-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-bromo-1,2,3,4,4a,5,11,11aβ-octahydro-6H-indolo[2,3-g]isoquinoline and benzoyl chloride instead, 2-benzoyl-4aα-(3-methoxyphenyl)-8-bromo-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-bromo-1,2,3,4,4a,5,11,11aβ-octahydro-6H-indolo[2,3-g]isoquinoline and benzoyl chloride instead, 2-benzoyl-4aα-(3-methoxyphenyl)-9-bromo-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-bromo-1,2,3,4,4a,5,11,11aβ-octahydro-6H-indolo[2,3-g]isoquinoline and benzoyl chloride instead, 2-benzoyl-4aα-(3-methoxyphenyl)-10-bromo-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-bromo-1,2,3,4,4a,5,11,11aβ-octahydro-6H-indolo[2,3-g]isoquinoline and benzoyl chloride instead, 2-benzoyl 4aα-(3-methoxyphenyl)-7-fluoro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-fluoro-1,2,3,4,4a,5,11,11aβ-octahydro-6H-indolo[2,3-g]isoquinoline and benzoyl chloride instead, 2-benzoyl-4aα-(3-methoxyphenyl)-8-fluoro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-fluoro-1,2,3,4,4a,5,11,11aβ-octahydro-6H-indolo[2,3-g]isoquinoline and benzoyl chloride instead, 2-benzoyl-4aα-(3-methoxyphenyl)-9-fluoro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-fluoro-1,2,3,4,4a,5,11,11aβ-octahydro-6H-indolo[2,3-g]isoquinoline and benzoyl chloride instead, 2-benzoyl-4aα-(3-methoxyphenyl)-10-fluoro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-fluoro-1,2,3,4,4a,5,11,11aβ-octahydro-6H-indolo[2,3-g]isoquinoline and benzoyl chloride, 2-benzoyl-4aα-(3-methoxyphenyl)-7-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-nitro-1,2,3,4,4a,5,11,11aβ-octahydro-6H-indolo[2,3-g]isoquinoline and benzoyl chloride instead, 2-benzoyl-4aα-(3-methoxyphenyl)-8-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-nitro-1,2,3,4,4a,5,11,11aβ-octahydro-6H-indolo[2,3-g]isoquinoline and benzoyl chloride instead, 2-benzoyl-4aα-(3-methoxyphenyl)-9-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-nitro-1,2,3,4,4a,5,11,11aβ-octahydro-6H-indolo[2,3-g]isoquinoline and benzoyl chloride instead, 2-benzoyl-4aα-(3-methoxyphenyl)-10-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-nitro-1,2,3,4,4a,5,11,11aβ-octahydro-6H-indolo[2,3-g]isoquinoline and benzoyl chloride instead, 2-benzoyl-4aα-(3-methoxyphenyl)-1,2,3,4,4a,5,11,11aβ-octahydro-6-methyl-indolo[2,3-g]isoquinoline is produced by using 2-(2,2,2-trichloroethoxycarbonyl)-4aα-(3-methoxyphenyl)-1,2,3,4,4a,5,11,11aβ-octahydro-6-methyl-indolo[2,3-g]isoquinoline and benzoyl chloride instead, 2-phenylacetyl-4aα-(3-methoxyphenyl)-7-methyl-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-methyl-1,2,3,4,4a,5,11,11aβ-octahydro-6H-indolo[2,3-g]isoquinoline and phenylacetyl chloride instead, 2-phenylacetyl-4aα-(3-methoxyphenyl)-8-methyl-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-methyl-1,2,3,4,4a,5,11,11aβ-octahydro-6H-indolo[2,3-g]isoquinoline and phenylacetyl chloride instead, 2-phenylacetyl-4aα-(3-methoxyphenyl)-9-methyl-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-methyl-1,2,3,4,4a,5,11,11aβ-octahydro-6H-indolo[2,3-g]isoquinoline and phenylacetyl chloride instead, 2-phenylacetyl-4aα-(3-methoxyphenyl)-10-methyl-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-methyl-1,2,3,4,4a,5,11,11aβ-octahydro-6H-indolo[2,3-g]isoquinoline and phenylacetyl chloride instead, 2-phenylacetyl-4aα-(3-methoxyphenyl)-7-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-chloro-1,2,3,4,4a,5,11,11aβ-octahydro-6H-indolo[2,3-g]isoquinoline and phenylacetyl chloride instead, 2-phenylacetyl-4aα-(3-methoxyphenyl)-8-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-chloro-1,2,3,4,4a,5,11,11aβ-octahydro-6H-indolo[2,3-g]isoquinoline and phenylacetyl chloride instead, 2-phenylacetyl-4aα-(3-methoxyphenyl)-9-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-chloro-1,2,3,4,4a,5,11,11aβ-octahydro-6H-indolo[2,3-g]isoquinoline and phenylacetyl chloride instead, 2-phenylacetyl-4aα-(3-methoxyphenyl)-10-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-chloro-1,2,3,4,4a,5, 11,11aβ-octahydro-6H-indolo[2,3-g]isoquinoline and phenylacetyl chloride instead, 2-phenylacetyl-4aα-(3-methoxyphenyl)-7-bromo-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-bromo-1,2,3,4,4a,5,11,11aβ-octahydro-6H-indolo[2,3-g]isoquinoline and phenylacetyl chloride instead, 2-phenylacetyl-4aα-(3-methoxyphenyl)-8-bromo-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-bromo-1,2,3,4,4a,5,11,11aβ-octahydro-6H-indolo[2,3-g]isoquinoline and phenylacetyl chloride instead, 2-phenylacetyl-4aα-(3-methoxyphenyl)-9-bromo-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-bromo-1,2,3,4,4a,5,11,11aβ-octahydro-6H-indolo[2,3-g]isoquinoline and phenylacetyl chloride instead, 2-phenylacetyl-4aα-(3-methoxyphenyl)-10-bromo-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-1,2,3,4,4a,5,11,11aβ-octahydro-6H-indolo[2,3-g]isoquinoline and phenylacetyl chloride instead, 2-phenylacetyl-4aα-(3-methoxyphenyl)-7-fluoro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-fluoro-1,2,3,4,4a,5,11,11aβ-octahydro-6H-indolo[2,3-g]isoquinoline and phenylacetyl chloride instead, 2-phenylacetyl-4aα-(3-methoxyphenyl)-8-fluoro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-fluoro-1,2,3,4,4a,5,11,11aβ-octahydro-6H-indolo[2,3-g]isoquinoline and phenylacetyl chloride instead, 2-phenylacetyl-4aα-(3-methoxyphenyl)-9-fluoro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-fluoro-1,2,3,4,4a,5,11,11aβ-octahydro-6H-indolo[2,3-g]isoquinoline and phenylacetyl chloride instead, 2-phenylacetyl-4aα-(3-methoxyphenyl)-10-fluoro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-fluoro-1,2,3,4,4a,5,11,11aβ-octahydro-6H-indolo[2,3-g]isoquinoline and phenylacetyl chloride instead, 2-phenylacetyl-4aα-(3-methoxyphenyl)-7-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-nitro-1,2,3,4,4a5,11,11aβ-octahydro-6H-indolo[2,3-g]isoquinoline and phenylacetyl chloride instead, 2-phenylacetyl-4aα-(3-methoxyphenyl)-8-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-nitro-1,2,3,4,4a,5,11,11aβ-octahydro-6H-indolo[2,3-g]isoquinoline and phenylacetyl chloride instead, 2-phenylacetyl-4aα-(3-methoxyphenyl)-9-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-nitro-1,2,3,4,4a,5,11,11aβ-octahydro-6H-indolo[2,3-g]isoquinoline and phenylacetyl chloride instead, and 2-phenylacetyl-4aα-(3-methoxyphenyl)-10-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-nitro-1,2,3,4,4a,5,11,11aβ-octahydro-6H-indolo[2,3-g]isoquinoline and phenylacetyl chloride instead, and 2-phenylacetyl-4aα-(3-methoxyphenyl)-1,2,3,4,4a,5,11,11aβ-octahydro-6-methyl-indolo[2,3-g]isoquinoline is produced by using 2-(2,2,2-trichloroethoxycarbonyl)-4aα-(3-methoxyphenyl)-1,2,3,4,4a,5,11,11aβ-octahydro-6-methyl-indolo[2,3-g]isoquinoline and phenylacetyl chloride instead.

Example 17

2-Cyclopropylmethyl-4aα-(3-methoxyphenyl)-1,2,3,4,4a,5,11,11aβ-octahydro-6H-indolo[2,3-g]isoquinoline 18

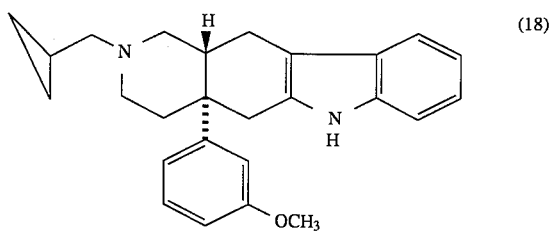

(18)

In an atmosphere of argon, 6 mg of lithium aluminum hydride was suspended in 1 ml of anhydrous THF, the produced suspension was cooled to 0° C., and combined with 20 mg of 2-cyclopropylcarbonyl-4aα-(3-methoxyphenyl)-1,2,3,4,4a,5,11,11aβ-octahydro-6H-indolo[2,3-g]isoquinoline. The resultant mixture was heated to room temperature, stirred at this temperature for one hour, cooled to 0° C., and combined with ethyl acetate and a saturated aqueous solution of potassium sodium tartrate. The mixture was filtered to expel impurities and distilled under a vacuum to expel ethyl acetate by vaporization, to obtain 20 mg of an oily substance. When this oily substance was refined by column chromatography [silica gel; chloroform-methanol/28% aqua ammonia/chloroform (3:0.1:97)], it produced 18 mg of the captioned compound (yield 93.2%). When this compound was recrystallized from chloroform-hexane, 10 mg of the compound in a purified form (m.p. 163.5° to 165.5° C.) was obtained.

IR (KBr) cm$^{-1}$: 2928, 2900, 2842, 1607, 1580

NMR (CDCl$_3$) 400 MHz δ: 0.11 (2H, m), 0.52 (2H, m), 0.91 (1H, m), 1.99–2.10 (2H, m), 2.24–2.35 (2H, m), 2.38–2.41 (1H, m), 2.58–2.67 (2H, m), 2.88–3.03 (4H, m), 3.07 (1H, d, J=15.6 Hz), 3.19 (1H, m), 3.67 (3H, s), 6.61 (1H, m), 7.01–7.10 (5H, m), 7.20 (1H, m), 7.43 (1H, m), 7.66 (1H, brs)

Mass (m/e): 386 (M$^+$)

Elementary analyses For $C_{26}H_{30}N_2O$

|  | C | H | N |
|---|---|---|---|
| Calculated | 80.79 | 7.82 | 7.25 |
| Found | 80.11 | 7.76 | 7.19 |

Similarly, 2-allyl-4aα-(3-methoxyphenyl)-1,2,3,4,4a,5,11,11aβ-octahydro-6H-indolo[2,3-g]isoquinoline is produced by using 2-acryloyl-4aα-(3-methoxyphenyl)-1,2,3,4,4a,5,11,11aβ-octahydro-6H-indolo[2,3-g]isoquinoline instead of 2-cyclopropylcarbonyl-4aα-(3-methoxyphenyl)-1,2,3,4,4a,5,11,11aβ-octahydro-6H-indolo[2,3-g]isoquinoline, 2-benzyl-4aα-(3-methoxyphenyl)-1,2,3,4,4a,5,11,11aβ-octahydro-6H-indolo[2,3-g]isoquinoline is produced by using 2-benzoyl-4aα-(3-methoxyphenyl)-1,2,3,4,4a,5,11,11aβ-octahydro-6H-indolo[2,3-g]isoquinoline instead, 2-phenethyl-4aα-(3-methoxyphenyl)-1,2,3,4,4a,5,11,11aβ-octahydro-6H-indolo[2,3-g]isoquinoline is produced by using 2-phenylacetyl-4aα-(3-methoxyphenyl)-1,2,3,4,4a,5,11,11aβ-octahydro-6H-indolo[2,3-g]isoquinoline instead, 2-ethyl-4aα-(3-methoxyphenyl)-1,2,3,4,4 5,11,11aβ-octhydro-6H-indolo[2,3-g]isoquinoline is produced by using 2-acetyl-4aα-(3-methoxyphenyl)-1,2,3,4,4a,5,11,11aβ-octahydro-6H-indolo[2,3-g]isoquinoline instead, 2-propyl-4aα-(3-methoxyphenyl)-1,2,3,4,4a,5,11,11aβ-octahydro-6H-indolo[2,3-g]isoquinoline is produced by using 2-propionyl-4aα-(3-methoxyphenyl)-1,2,3,4,4a,5,11,11aβ-octahydro-6H-indolo[2,3-g]isoquinoline instead, 2-butyl-4aα-(3-methoxyphenyl)-1,2,3,4,4a,5,11,11aβ-octahydro-6H-indolo[2,3-g]isoquinoline is produced by using 2-butyryl-4aα-(3-methoxyphenyl)-1,2,3,4,4a,5,11,11aβ-octahydro-6H-indolo[2,3-g]isoquinoline instead, 2-thienylmethyl-4aα-(3-methoxyphenyl)-1,2,3,4,4a,5,11,11aβ-octahydro-6H-indolo[2,3-g]isoquinoline is produced by using 2-thiopenecarbonyl-4aα-(3-methoxyphenyl)-1,2,3,4,4a,5,11,11aβ-octahydro-6H-indolo[2,3-g]isoquinoline instead, 2-pentyl-4aα-(3-methoxyphenyl)-1,2,3,4,4a,5,11,11aβ-octahydro-6H-indolo[2,3-g]isoquinoline is produced by using 2-valeryl-4aα-(3-methoxyphenyl)-1,2,3,4,4a,5,11,11aβ-octahydro-6H-indolo[2,3-g]isoquinoline instead, 2-furylmethyl-4aα-(3-methoxyphenyl)-1,2,3,4,4a,5,11,11aβ-octahydro-6H-indolo[2,3-g]isoquinoline is produced by using 2-furoyl-4aα-(3-methoxyphenyl)-1,2,3,4,4a,5,11,11aβ-octahydro-6H-indolo[2,3-g]isoquinoline instead, 2-cyclobutylmethyl-4aα-(3-methoxyphenyl)-1,2,3,4,4a,5,11,11aβ-octahydro-6H-indolo[2,3-g]isoquinoline is produced by using 2-cyclobutylcarbonyl-4aα-(3-methoxyphenyl)-1,2,3,4,4a,5,11,11aβ-octahydro-6H-indolo[2,3-g]isoquinoline instead, 2-(p-methylbenzyl)-4aα-(3-methoxyphenyl)-1,2,3,4,4a,5,11,11aβ-octahydro-6H-indolo[2,3-g]isoquinoline is produced by using 2-(p-toluoyl)-4aα-(3-methoxyphenyl)-1,2,3,4,4a,5,11,11aβ-octahydro-6H-indolo[2,3-g]isoquinoline instead, 2-(4-methoxybenzyl)-4aα-(3-methoxyphenyl)-1,2,3,4,4a,5,11,11aβ-octahydro-6H-indolo[2,3-g]isoquinoline is produced by using 2-(p-anisoyl)-4aα-(3-methoxyphenyl)-1,2,3,4,4a,5,11,11aβ-octahydro-6H-indolo[2,3-g]isoquinoline instead, 2-(3-methoxybenzyl)4aα-(3-methoxyphenyl)-1,2,3,4,4a,5,11,11aβ-octahydro-6H-indolo[2,3-g]isoquinoline is produced by using 2-(m-anisoyl)-4aα-(3-methoxyphenyl)-1,2,3,4,4a,5,11,11aβ-octahydro-6H-indolo[2,3-g]isoquinoline, 2-cyclopropylmethyl-4aα-(3-methoxyphenyl)-7-bromo-1,2,3,4,4a,5,11,11aβ-octahydro-6H-indolo[2,3-g]isoquinoline is produced by using 2-cyclopropylcarbonyl-4aα-(3-methoxyphenyl)-7-bromo-1,2,3,4,4a,5,11,11aβ-octahydro-6H-indolo[2,3-g]isoquinoline instead, 2-cyclopropylmethyl-4aα-(3-methoxyphenyl)-8-bromo-1,2,3,4,4a,5,11,11aβ-octahydro-6H-indolo[2,3-g]isoquinoline is produced by using 2-cyclopropylcarbonyl-4aα-(3-methoxyphenyl)-8-bromo-1,2,3,4,4a,5,11,11aβ-octahydro-6H-indolo[2,3-g]isoquinoline instead, 2-cyclopropylmethyl-4aα-(3-methoxyphenyl)-9-bromo-1,2,3,4,4a,5,11,11aβ-octahydro-6H-indolo[2,3-g]isoquinoline is produced by using 2-cyclopropylcarbonyl-4aα-(3-methoxyphenyl)-9-bromo-1,2,3,4,4a,5,11,11aβ-octahydro-6H-indolo[2,3-g]isoquinoline instead, and 2-cyclopropylmethyl-4aα-(3-methoxyphenyl)-10-bromo-1,2,3,4,4a,5,11,11aβ-octahydro-6H-indolo[2,3-g]isoquinoline is produced by using 2-cyclopropylcarbonyl-4aα-(3-methoxyphenyl)-10-bromo-1,2,3,4,4a,5,11,11aβ-octahydro-6H-indolo[2,3-g]isoquinoline instead. Similarly, 2-allyl-4aα-(3-methoxyphenyl)-7-methyl-1,2,3,4,4a,5,11,11aβ-octahydro-6H-indolo[2,3-g]isoquinoline is produced by using a-acryloyl-4aα-(3-methoxyphenyl)-7-methyl-1,2,3,4,4a,5,11,11aβ-octahydro-6H-indolo[2,3-g]isoquinoline instead, 2-allyl-4aα-(3-methoxyphenyl)-8-methyl-1,2,3,4,4a,5,11,11aβ-octahydro-6H-indolo[2,3-g]isoquinoline is produced by using 2-acryloyl-4aα-(3-methoxyphenyl)-8-methyl-1,2,3,4,4a,5,11,11aβ-octahydro-6H-indolo[2,3-g]isoquinoline instead, 2-allyl-4aα-(3-methoxyphenyl)-9-methyl-1,2,3,4,4a,5,11,11aβ-octahydro-6H-indolo[2,3-g]isoquinoline is produced by using 2-acryloyl-4aα-(3-methoxyphenyl)-9-methyl-1,2,3,4,4a,5,11,11aβ-octahydro-6H-indolo[2,3-g]isoquinoline instead, 2-allyl-4aα-(3-methoxyphenyl)-10-methyl-1,2,3,4,4a,5,11,11aβ-octahydro-6H-indolo[2,3-g]isoquinoline is produced by using 2-acryloyl-4aα-(3-methoxyphenyl)-10-methyl-1,2,3,4,4a,5,11,11aβ-octahydro-6H-indolo[2,3-g]isoquinoline instead, 2-allyl-4aα-(3-methoxyphenyl)-7-chloro-1,2,3,4,4a,5,11,11aβ-octahydro-6H-indolo[2,3-g]isoquinoline is produced by using 2-acryloyl-4aα-(3-methoxyphenyl)-7-chloro-1,2,3,4,4a,5,11,11aβ-octahydro-6H-indolo[2,3-g]isoquinoline instead, 2-allyl-4aα-(3-methoxyphenyl)-8-chloro-1,2,3,4,4a,5,11,11aβ-octahydro-6H-indolo[2,3-g]isoquinoline is produced by using 2-acryloyl-4aα-(3-methoxyphenyl)-8-chloro-1,2,3,4,4a,5,11,11aβ-octahydro-6H-indolo[2,3-g]isoquinoline instead, 2-allyl-4aα(3-methoxyphenyl)-9-chloro-1,2,3,4,4a,5,11,11aβ-octahydro-6H-indolo[2,3-g]isoquinoline is produced by using 2-acryloyl-4aα-(3-methoxyphenyl)-9-chloro-1,2,3,4,4a,5,11,11aβ-octahydro-6H-indolo[2,3-g]isoquinoline instead, 2-allyl-4aα-(3-methoxyphenyl)-10-chloro-1,2,3,4,4a,5,11,11aβ-octahydro-6H-indolo[2,3-g]isoquinoline is produced by using 2-acryloyl-4aα-(3-methoxyphenyl)-10-chloro-1,2,3,4,4a,5,11,11aβ-octahydro-6H-indolo[2,3-g]isoquinoline instead, 2-allyl-4aα-(3-methoxyphenyl)-7-bromo-1,2,3,4,4a,5,11,11aβ-octahydro-6H-indolo[2,3-g]isoquinoline is produced by using 2-acryloyl-4aα-(3-methoxyphenyl)-7-bromo-1,2,3,4,4a,5,11,11aβ-octahydro-6H-indolo[2,3-g]isoquinoline instead, 2-allyl-4aα-(3-methoxyphenyl)-8-bromo-1,2,3,4,4a,5,11,11aβ-octahydro-6H-indolo[2,3-g]isoquinoline is produced by using 2-acryloyl-4aα-(3-methoxyphenyl)-8-bromo-1,2,3,4,4a,5,11,11aβ-octahydro-6H-indolo[2,3-g]isoquinoline instead, 2-allyl-4aα-(3-methoxyphenyl)-9-bromo-1,2,3,4,4a,5,11,11aβ-octahydro-6H-indolo[2,3-g]isoquinoline is produced by using 2-acryloyl-4aα-(3-methoxyphenyl)-9-bromo-1,2,3,4,4a,5,11,11aβ-octahydro-6H-indolo]2,3-g]isoquinoline instead, 2-allyl-4aα-(3-methoxyphenyl)-10-bromo-1,2,3,4,4a,5,11,11aβ-octahydro-6H-indolo[2,3-g]isoquinoline is produced by using 2-acryloyl-4aα-(3-methoxyphenyl)-10-bromo-1,2,3,4,4a,5,11,11aβ-octahydro-6H-indolo[2,3-g]isoquinoline instead, 2-allyl-4aα-(3-methoxyphenyl)-7-fluoro-1,2,3,4,4a,5,11,11aβ-octahydro-6H-indolo-[2,3-g]isoquinoline is produced by using 2-acryloyl-4aα-(3-methoxyphenyl)-7-fluoro-1,2,3,4,4a,5,11,11aβ-octahydro-6H-indolo[2,3-g]isoquinoline instead, 2-allyl-4aα-(3-methoxyphenyl)-8-fluoro-1,2,3,4,4a,5,11,11aβ-octahydro-6H-indolo[2,3-g]isoquinoline is produced by using 2-acryloyl-4aα-(3-methoxyphenyl)-8-fluoro-1,2,3,4,4a,5,11,11aβ-octahydro-6H-indolo[2,3-g]isoquinoline instead, 2-allyl-4aα-(3-methoxyphenyl)-9-fluoro-1,2,3,4,4a,5,11,11aβ-octahydro-6H-indolo[2,3-g]isoquinoline is produced by using 2-acryloyl-4aα-(3-methoxyphenyl)-9-fluoro-1,2,3,4,4a,5,11,11aβ-octahydro-6H-indolo[2,3-g]isoquinoline instead, and 2-allyl-4aα-(3-methoxyphenyl)-10-fluoro-1,2,3,4,4a,5,11,11aβ-octahydro-6H-indolo[2,3-g]isoquinoline is produced by using 2-acryloyl-4aα-a methoxyphenyl)-10-fluoro-1,2,3,4,4a,5,11,11aβ-octahydro-6H-indolo[2,3-g]isoquinoline instead.

Similarly, 2-benzyl-4aα-(3-methoxyphenyl)-7-methyl-1,2,3,4,4a,5,11,11aβ-octahydro-6H-indolo[2,3-g]isoquinoline is produced by using 2-benzoyl-4aα-(3-methoxyphenyl)-7-methyl-1,2,3,4,4a,5,11,11aβ-octahydro-6H-indolo[2,3-g]isoquinoline instead, 2-benzyl-4aα-3-methoxyphenyl)-8-methyl-1,2,3,4,4a,5,11,11aβ-octahydro-6H-indolo[2,3-g]

isoquinoline is produced by using 2-benzoyl-4aα-(3-methoxyphenyl)-8-methyl-1,2,3,4,4a,5,11,11aβ-octahydro-6H-indolo[2,3-g]isoquinoline instead, 2-benzyl-4aα-(3-methoxyphenyl)-9-methyl-1,2,3,4,4a,5,11,11aβ-octahydro-6H-indolo[2,3-g]isoquinoline is produced by using 2-benzoyl-4aα-(3-methoxyphenyl)-9-methyl-1,2,3,4,4a,5,11,11aβ-octahydro-6H-indolo[2,3-g]isoquinoline instead, 2-benzyl-4aα-(3-methoxyphenyl)-10-methyl-1,2,3,4,4a,5,11,11aβ-octahydro-6H-indolo[2,3-g]isoquinoline is produced by using 2-benzoyl-4aα-(3-methoxyphenyl)-10-methyl-1,2,3,4,4a,5,11,11aβ-octahydro-6H-indolo[2,3-g]isoquinoline instead, 2-benzyl-4aα-(3-methoxyphenyl)-7-chloro-1,2,3,4,4a,5,11,11aβ-octahydro-6H-indolo[2,3-g]isoquinoline is produced by using 2-benzoyl-4aα-(3-methoxyphenyl)-7-chloro-1,2,3,4,4a,5,11,11aβ-octahydro-6H-indolo[2,3-g]isoquinoline instead, 2-benzyl-4aα-(3-methoxyphenyl)-8-chloro-1,2,3,4,4a,5,11,11aβ-octahydro-6H-indolo[2,3-g]isoquinoline is produced by using 2-benzoyl-4aα-(3-methoxyphenyl)-8-chloro-1,2,3,4,4a,5,11,11aβ-octahydro-6H-indolo[2,3-g]isoquinoline instead, 2-benzyl-4aα-(3-methoxyphenyl)-9-chloro-1,2,3,4,4a,5,11,11aβ-octahydro-6H-indolo[2,3-g]isoquinoline is produced by using 2-benzoyl-4aα-(3-methoxyphenyl)-9-chloro-1,2,3,4,4a,5,11,11aβ-octahydro-6H-indolo[2,3-g]isoquinoline instead, 2-benzyl-4aα-(3-methoxyphenyl)-10-chloro-1,2,3,4,4a,5,11,11aβ-octahydro-6H-indolo[2,3-g]isoquinoline is produced by using 2-benzoyl-4aα-(3-methoxyphenyl)-10-chloro-1,2,3,4,4a,5,11,11aβ-octahydro-6H-indolo]2,3-g]isoquinoline instead, 2-benzyl-4aα-(3-methoxyphenyl)-7-bromo-1,2,3,4,4a,5,11,11aβ-octahydro-6H-indolo[2,3-g]isoquinoline is produced by using 2-benzoyl-4aα-(3-methoxyphenyl)-7-bromo-1,2,3,4,4a,5,11,11aβ-octahydro-6H-indolo[2,3g-]isoquinoline instead, 2-benzyl-4aα-(3-methoxyphenyl)-8-bromo-1,2,3,4,4a,5,11,11aβ-octahydro-6H-indolo[2,3-g]isoquinoline is produced by using 2-benzoyl-4aα-(3-methoxyphenyl)-8-bromo-1,2,3,4,4a,5,11,11aβ-octahydro-6H-indolo[2,3-g]isoquinoline instead, 2-benzyl-4aα-(3-methoxyphenyl)-9-bromo-1,2,3,4,4a,5,11,11aβ-octahydro-6H-indolo[2,3-g]isoquinoline is produced by using 2-benzoyl-4aα-(3-methoxyphenyl)-9-bromo-1,2,3,4,4a,5,11,11aβ-octahydro-6H-indolo[2,3-g]isoquinoline instead, 2-benzyl-4aα-(3-methoxyphenyl)-10-bromo-1,2,3,4,4a,5,11,11aβ-octahydro-6H-indolo[2,3g-]isoquinoline is produced by using 2-benzoyl-4aα-(3-methoxyphenyl)-10-bromo-1,2,3,4,4a,5,11,11aβ-octahydro-6H-indolo[2,3-g] isoquinoline instead, 2-benzyl-4aα-(3-methoxyphenyl)-7-fluoro-1,2,3,4,4a,5,11,11aβ-octahydro-6H-indolo[2,3-g]isoquinoline is produced by using 2-benzoyl-4aα-(3-methoxyphenyl)-7-fluoro-1,2,3,4,4a,5,11,11aβ-octahydro-6H-indolo[2,3-g]isoquinoline instead, 2-benzyl-4aα-(3-methoxyphenyl)-8-fluoro-1,2,3,4,4a,5,11,11aβ-octahydro-6H-indolo[2,3-g]isoquinoline is produced by using 2-benzoyl-4aα-(3-methoxyphenyl)-8-fluoro-1,2,3,4,4a,5,11,11aβ-octahydro-6H-indolo[2,3-g]isoquinoline instead, 2-benzyl-4aα-(3-methoxyphenyl)-9-fluoro-1,2,3,4,4a,5,11,11aβ-octahydro-6H-indolo[2,3-g]isoquinoline is produced by using 2-benzoyl-4aα-(3-methoxyphenyl)-9-fluoro-1,2,3,4,4a,5,11,11aβ-octahydro-6H-indolo[2,3-g]isoquinoline instead, and 2-benzyl-4aα-(3-methoxyphenyl)-10-fluoro-1,2,3,4,4a,5,11,11aβ-octahydro-6H-indolo[2,3-g]isoquinoline is produced by using 2-benzoyl-4aα-(3-methoxyphenyl)-10-fluoro-1,2,3,4,4a,5,11,11aβ-octahydro-6H-indolo[2,3-g]isoquinoline instead.

Similarly, 2-phenethyl-4aα-(3-methoxyphenyl)-7-methyl-1,2,3,4,4a,5,11,11aβ-octahydro-6H-indolo[2,3-g]isoquinoline is produced by using 2-phenylacetyl-4aα-3-methoxyphenyl)7-methyl-1,2,3,4,4a,5,11,11aβ-octahydro-6H-indolo[2,3-g]isoquinoline instead, 2-phenethyl-4aα-(3-methoxyphenyl)-8-methyl-1,2,3,4,4a,5,11,11aβ-octahydro-6H-indolo[2,3-g]isoquinoline is produced by using 2-phenylacetyl-4aα-(3-methoxyphenyl)-8-methyl-1,2,3,4,4a,5,11,11aβ-octahydro-6H-indolo[2,3-g]isoquinoline instead, 2-phenethyl-4aα-(3-methoxyphenyl)-9-methyl-1,2,3,4,4a,5,11,11aβ-octahydro-6H-indolo[2,3-g]isoquinoline is produced by using 2-phenylacetyl-4aα-(3-methoxyphenyl)-9-methyl-1,2,3,4,4a,5,11,11aβ-octahydro-6H-indolo[2,3-g]isoquinoline instead, 2-phenethyl-4aα-(3-methoxyphenyl)-10-methyl-1,2,3,4,4a,5,11,11aβ-octahydro-6H-indolo[2,3-g]isoquinoline is produced by using 2-phenylacetyl-4aα-(3-methoxyphenyl)-10-methyl-1,2,3,4,4a,5,11,11aβ-octahydro-6H-indolo[2,3-g]isoquinoline instead, 2-phenethyl-4aα-(3-methoxyphenyl)-7-chloro-1,2,3,4,4a,5,11,11aβ-octahydro-6H-indolo[2,3-g]isoquinoline is produced by using 2-phenylacetyl-4aα-(3-methoxyphenyl)-7-chloro-1,2,3,4,4a,5,11,11aβ-octahydro-6H-indolo[2,3-g]isoquinoline instead, 2-phenethyl-4aα-(3-methoxyphenyl)-8-chloro-1,2,3,4,4a,5,11,11aβ-octahydro-6H-indolo[2,3-g]isoquinoline is produced by using 2-phenylacetyl-4aα-(3-methoxyphenyl)-8-chloro-1,2,3,4,4a,5,11,11aβ-octahydro-6H-indolo[2,3-g]isoquinoline instead, 2-phenethyl-4aα-(3-methoxyphenyl)-9-chloro-1,2,3,4,4a,5,11,11aβ-octahydro-6H-indolo[2,3-g]isoquinoline is produced by using 2-phenylacetyl-4aα-(3-methoxyphenyl)-9-chloro-1,2,3,4,4a,5,11,11aβ-octahydro-6H-indolo[2,3-g]isoquinoline instead, 2-phenethyl-4aα-(3-methoxyphenyl)-10-chloro-1,2,3,4,4a,5,11,11aβ-octahydro-6H-indolo[2,3-g]isoquinoline is produced by using 2-phenylacetyl-4aα-(3-methoxyphenyl)-10-chloro-1,2,3,4,4a,5,11,11aβ-octahydro-6H-indolo[2,3-g]isoquinoline instead, 2-phenethyl-4aα-(3-methoxyphenyl)-7-bromo-1,2,3,4,4a,5,11,11aβ-octahydro-6H-indolo[2,3-g]isoquinoline is produced by using 2-phenylacetyl-4aα-(3-methoxyphenyl)-7-bromo-1,2,3,4,4a,5,11,11aβ-octahydro-6H-indolo[2,3-g]isoquinoline instead, 2-phenethyl-4aα-(3-methoxyphenyl)-8-bromo-1,2,3,4,4a,5,11,11aβ-octahydro-6H-indolo[2,3-g]isoquinoline is produced by using 2-phenylacetyl-4aα-(3-methoxyphenyl)-8-bromo-1,2,3,4,4a,5,11,11aβ-octahydro-6H-indolo[2,3-g]isoquinoline instead, 2-phenethyl-4aα-(3-methoxyphenyl)-9-bromo-1,2,3,4,4a,5,11,11aβ-octahydro-6H-indolo[2,3-g]isoquinoline is produced by using 2-phenylacetyl-4aα-(3-methoxyphenyl)-9-bromo-1,2,3,4,4a,5,11,11aβ-octahydro-6H-indolo[2,3-g]isoquinoline instead, 2-phenethyl-4aα-(3-methoxyphenyl)-10-bromo-1,2,3,4,4a,5,11,11aβ-octahydro-6H-indolo[2,3-g]isoquinoline is produced by using 2-phenylacetyl-4aα-(3-methoxyphenyl)-10-bromo-1,2,3,4,4a,5,11,11aβ-octahydro-6H-indolo[2,3-g]isoquinoline instead, 2-phenethyl-4aα-(3-methoxyphenyl)-7-fluoro-1,2,3,4,4a,5,11,11aβ-octahydro-6H-indolo[2,3-g]isoquinoline is produced by using 2-phenylacetyl-4aα-(3-methoxyphenyl)-7-fluoro-1,2,3,4,4a,5,11,11aβ-octahydro-6H-indolo[2,3-g]isoquinoline instead, 2-phenethyl-4aα-(3-methoxyphenyl)-8-fluoro-1,2,3,4,4a,5,11,11aβ-octahydro-6H-indolo[2,3-g]isoquinoline is produced by using 2-phenylacetyl-4aα-(3-methoxyphenyl)-8-fluoro-1,2,3,4,4a,5,11,11aβ-octahydro-6H-indolo[2,3-g]isoquinoline instead, 2-phenethyl-4aα-(3-methoxyphenyl)-9-fluoro-1,2,3,4,4a,5,11,11aβ-octahydro-6H-indolo[2,3-g]isoquinoline is produced by using 2-phenylacetyl-4aα-(3-methoxyphenyl)-9-fluoro-1,2,3,4,4a,5,11,11aβ-octahydro-6H-indolo[2,3-g]isoquinoline instead, and 2-phenethyl-4 aα-(3-methoxyphenyl)-10-fluoro-1,2,3,4,4a,5,11,11aβ-octahydro-6H-indolo[2,3-g]isoquinoline is produced by using 2-phenylacetyl-4aα-(3-methoxyphenyl)-10-fluoro-1,2,3,4,4a,5,11,11aβ-octahydro-6H-indolo[2,3-g]isoquinoline instead.

Example 18

2-Cyclopropylmethyl-4aα-(3-hydroxyphenyl)-1,2,3,4,4a,5,11,11β-octahydro-6H-indolo[2,3-g]isoquinoline19

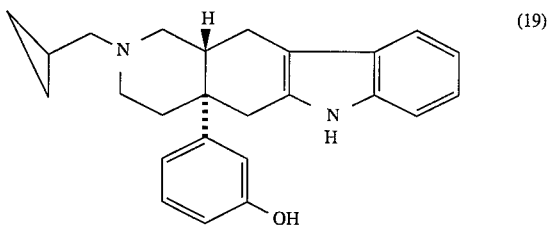

A solution of 128 mg (0.33 mmol) of 2-cyclopropylmethyl-4aα-(3-methoxyphenyl)-1,2,3,4,4a,5,11,11aβ-octahydro-6H-indolo[2,3-g]isoquinoline, 0.2 ml (2.20 mmol) of n-propanethiol, 225 mg (2.0 mmol) of potassium-t-butoxide in DMF was heated and stirred at 125° C. Four hours thereafter, the solution and 0.2 ml (2.2 mmol) of n-propanethiol and 225 mg (2.0 mmol) of potassium-t-butoxide added thereto were stirred at 125° C. for four hours. The resultant reaction mixture was cooled to room temperature and then concentrated. The concentrate was combined with a saturated aqueous solution of sodium hydrogen carbonate and extracted form a chloroform-methanol (3:1) mixture. When the organic layers consequently formed were combined, washed with a saturated aqueous saline solution, dried, and concentrated, it produced a powder. When this powder was separated and refined by column chromatography (silica gel:chloroform:methanol: 28% aqua ammonia= 95:5:0.1–90:10:0.1), 84 mg of the captioned compound was obtained. This compound was suspended in methanol, converted by addition of methanesulfonic acid into a methanesulfonate, and recrystallized from methanol-chloroform. Consequently, 59 mg of the methanesulfonate of the captioned compound in a purified form (m.p.<250° C.) was obtained.

IR (KBr) cm$^{-1}$: 3390, 1586, 1046

NMR (DMSO-d$_6$) 400 MHz δ: 0.38 (2H, br), 0.63 (2H, br), 1.07 (1H, m), 2.07 (1H, m), 2.31 (3H, s), 2.54–2.65 (3H, m), 2.88–3.05 (5H, m), 3.11 (1H, d, J=16.5 Hz), 3.37 (1H, m), 3.51 (1H, m), 3.74 (1H, m), 6.54 (1H, m), 6.90–6.99 (4H, m), 7.04 (1H, t, J=7.9 Hz), 7.19 (1H, d, J=7.9 Hz), 7.34 (1H, d, J=7.3 Hz), 9.26 (1H, s), 9.38 (1H, br), 10.62 (1H, s)

Mass (FAB): 373 (M$^+$+1)

Elementary analyses For $C_{25}H_{28}N_2O \cdot CH_3SO_3H$

|  | C | H | N | S |
|---|---|---|---|---|
| Calculated | 66.64 | 6.88 | 5.98 | 6.84 |
| Found | 66.32 | 6.93 | 6.05 | 6.76 |

Similarly, 2-benzyl-4aα-(3-hydroxyphenyl)-1,2,3,4,4a,5,11,11aβ-octahydro-6H-indolo[2,3-g]isoquinoline is produced by using 2-benzyl-4aα-(3-methoxyphenyl)-1,2,3,4,4a,5,11,11aβ-octahydro-6H-indolo_[2,3,-g]isoquinoline instead of 2-cyclopropylmethyl-4aα-(3-methoxyphenyl)1,2,3,4,4a,5,11,11aβ-octahydro-6H-indolo[2,3-g]isoquinoline, 2-phenethyl-4aα-(3-hydroxyphenyl)-1,2,3,4,4a,5,11,11aβ-octahydro-6H-indolo[2,3-g]isoquinoline is produced by using 2-phenethyl-4aα-(3-methoxyphenyl)-1,2,3,4,4a,5,11,11aβ-octahydro6H-indolo[2,3-g]isoquinoline, 2-ethyl-4aα-(3-hydroxyphenyl)-1,2,3,4,4a,5,11,11aβ-octahydro-6H-indolo[2,3-g]isoquinoline is produced by using 2-ethyl-4aα-(3-methoxyphenyl)-1,2,3,4,4a,5,11,11aβ-octahydro-6H-indolo[2,3-g]isoquinoline instead, 2-propyl-4aα-(3-hydroxyphenyl)-1,2,3,4,4a,5,11,11aβ-octahydro-6H-indolo[2,3-g]isoquinoline is produced by using 2-propyl-4aα-(3-methoxyphenyl)-1,2,3,4,4a,5,11,11aβ-octahydro-6H-indolo[2,3-g]isoquinoline instead, 2-butyl-4aα-(3-hydroxyphenyl)-1,2,3,4,4a,5,11,11aβ-octahydro-6H-indolo[2,3-g]isoquinoline is produced by using 2-butyl-4aα-(3-methoxyphenyl)-1,2,3,4,4a,5,11,11aβ-octahydro-6H-indolo[2,3-g]isoquinoline instead, 2-thienylmethyl-4aα-(4aα-(3-hydroxyphenyl)-1,2,3,4,4a,5,11,11aβ-octahydro-6H-indolo[2,3-g]isoquinoline is produced by using 2-thienylmethyl-4aα-(3-methoxyphenyl)-1,2,3,4,4a,5,11,11aβ-octahydro-6H-indolo[2,3-g]isoquinoline instead, 2-pentyl-4aα-(3-hydroxyphenyl)-1,2,3,4,4a,5,11,11aβ-octahydro-6H-indolo[2,3g]isoquinoline is produced by using 2-pentyl-4aα-(3-methoxyphenyl)-1,2,3,4,4a,5,11,11aβ-octahydro-6H-indolo[2,3-g]isoquinoline instead, 2-furylmethyl-4aα-(3-hydroxyphenyl)-1,2,3,4,4a,5,11,11aβ-octahydro-6H-indolo[2,3-g]isoquinoline is produced by using 2-furylmethyl-4aα0(3-methoxyphenyl)-1,2,3,4,4a,5,11,11aβ-octahydro-6H-indolo[2,3-g]isoquinoline instead, 2-cyclobutylmethyl-4aα-(3-hydroxyphenyl)-1,2,3,4,4a,5,11,11aβ-octahydro-6H-indolo[2,3-g]isoquinoline is produced by using 2-cyclobutylmethyl-4aα-(3-methoxyphenyl)-1,2,3,4,4a,5,11,11aβ-octahydro-6H,indolo[2,3-g]isoquinoline instead, 2-(4-tollylmethyl)-4aα-(3-hydroxyphenyl)-1,2,3,4,4a,5,11,11aβ-octahydro-6H-indolo[2,3-g]isoquinoline is produced by using 2-(4-tollylmethyl)-4aα-(3-methoxyphenyl)-1,2,3,4,4a,5,11,11aβ-octahydro-6H-indolo[2,3-g]isoquinoline instead, 2-cyclopropylmethyl-4aα-(3-hydroxyphenyl)-7-bromo-1,2,3,4,4a,5,11,11aβ-octahydro-6H-indolo[2,3-g]isoquinoline is produced by using 2-cyclopropylmethyl)-4aα-(3-methoxyphenyl)-7-bromo-1,2,3,4,4a,5,11,11aβ-octahydro-6H-indolo[2,3-g]isoquinoline instead, 2-cyclopropylmethyl-4aα-(3-hydroxyphenyl)-8-bromo-1,2,3,4,4a,5,11,11aβ-octahydro-6H-indolo[2,3-g]isoquinoline is produced by using 2-cyclopropylmethyl-4aα-(3-methoxyphenyl)-8-bromo-1,2,3,4,4a,5,11,11aβ-octahydro-6H-indolo[2,3-g]isoquinoline instead, 2-cyclopropylmethyl-4aα-(3-hydroxyphenyl)-9-bromo-1,2,3,4,4a,5,11,11aβ-octahydro-6H-indolo[2,3-g]isoquinoline is produced by using 2-cyclopropylmethyl-4aα-(3-methoxyphenyl)-9-bromo-1,2,3,4,4a,5,11,11aβ-octahydro-6H-indolo[2,3-g]isoquinoline instead, 2-cyclopropylmethyl-4α-(3-hydroxyphenyl)-10-bromo-1,2,3,4,4a,5,11,11aβ-octahydro-6H-indolo[2,3-g]isoquinoline is produced by using 2-cyclopropylmethyl-4aα-(3-methoxyphenyl)-10-bromo-1,2,3,4,4a,5,11,11aβ-octahydro-6H-indolo[2,3-g]isoquinoline instead, 2-cyclopropylmethyl-4aα-(3-hydroxyphenyl)-7-nitro-1,2,3,4,4a,5,11,11aβ-octahydro-6H-indolo[2,3-g]isoquinoline is produced by using 2-cyclopropylmethyl-4aα-(3-methoxyphenyl)-7-nitro-1,2,3,4,4a,5,11,11aβ-octahydro-6H-indolo[2,3-g]isoquinoline instead, 2cyclopropylmethyl-4aα-(3-hydroxyphenyl)-8-nitro-1,2,3,4,4a,5,11,11aβ-octahydro-6H-indolo[2,3-g]isoquinoline is produced by using 2-cyclopropylmethyl-4aα-(3-methoxyphenyl)-8-nitro-1,2,3,4,4a,5,11,11aβ-octahydro-6H-indolo[2,3-g]isoquinoline instead, 2-cyclopropylmethyl-4aα-(3-hydroxyphenyl)-9-nitro-1,2,3,4,4a,5,11,11aβ-octahydro-6H-indolo[2,3-g]isoquinoline is produced by using 2-cyclopropylmethyl-4aα-(3-methoxyphenyl)-9-nitro-1,2,3,4,4a,5,11,11aβ-octahydro-6H-indolo[2,3-g]isoquinoline instead, and 2-cyclopropylmethyl-4aα-(3-hydroxyphenyl)-10-nitro-1,2,3,4,4a,5,11,11aβ-octahydro-6H-indolo[2,3-g]isoquinoline is produced by using 2-cyclopropylmethyl- 4aα-(3-methoxyphenyl)-10-nitro-1,2,3,4,4a,5,11,11aβ-octahydro-6H-indolo[2,3-g]isoquinoline instead.

Similarly, 2benzyl-4aα-(hydroxyphenyl)-7-methyl-1,2,3,4,4a,5,11,11aβ-octahydro-6H-indolo[2,3-g]isoquinoline is produced by using 2-benzyl-4aα-(3-methoxyphenyl)-7-methyl-1,2,3,4,4a,5,11,11aβ-octahydro-6H-indolo[2,3-g]isoquinoline instead, 2-benzyl-4aα-(3-hydroxyphenyl)-8-methyl-1,2,3,4,4a,5,11,11aβ-octahydro-6H-indolo[2,3-g]isoquinoline is produced by using 2-benzyl-4aα-(3-methoxyphenyl)-8-methyl-1,2,3,4,4a,5,11,11aβ-octahydro-6H-indolo[2,3-g]isoquinoline instead, 2-benzyl-4aα-(3-hydroxyphenyl)-9-methyl-1,2,3,4,4a,5,11,11aβ-octahydro-6H-indolo[2,3-g]isoquinoline is produced by using 2-benzyl-4aα-(3-methoxyphenyl)-9-methyl-1,2,3,4,4a,5,11,11aβ-octahydro-6H-indolo[2,3-g]isoquinoline instead, 2-benzyl-4aα-(3-hydroxyphenyl)-10-methyl-1,2,3,4,4a,5,11,11aβ-octahydro-6H-indolo[2,3-g]-isoquinoline is produced by using 2-benzyl-4aα-(3-methoxyphenyl)-10-methyl-1,2,3,4,4a,5,11,11aβ-octahydro-6H-indolo[2,3-g]isoquinoline instead, 2-benzyl-4aα-(3-hydroxyphenyl)-7-chloro-1,2,3,4,4a,5,11,11aβ-octahydro-6H-indolo[2,3-g]isoquinoline is produced by using 2-benzyl-4aα-(3-methoxyphenyl)-7-chloro-1,2,3,4,4a,5,11,11aβ-octahydro-6H-indolo[2,3-g]isoquinoline instead, 2-benzyl-4aα-(3-hydroxyphenyl)-8-chloro-1,2,3,4,4a,5,11,11aβ-octahydro-6-H-indolo[2,3-g]isoquinoline is produced by using 2-benzyl-4aα-(3-hydroxyphenyl)-8-chloro-1,2,3,4,4a,5,11,11aβ-octahydro-6H-indolo[2,3-g]isoquinoline instead, 2-benzyl-4aα-(3-hydroxyphenyl)-9-chloro-1,2,3,4,4a,5,11,11aβ-octahydro-6H-indolo[2,3-g]isoquinoline is produced by using 2-benzyl-4aα-(3-methoxyphenyl)-9-chloro-1,2,3,4,4a,5,11,11aβ-octahydro-6H-indolo[2,3-g]isoquinoline instead, 2-benzyl-4aα-(3-hydroxyphenyl)-10-chloro-1,2,3,4,4a,5,11,11aβ-octahydro-6H-indolo[2,3-g]isoquinoline is produced by using 2-benzyl-4aα-(3-methoxyphenyl)-10-chloro-1,2,3,4,4a,5,11,11aβ-octahydro-6H-indolo[2,3-g]isoquinoline instead, 2-benzyl-4aα-(3-hydroxyphenyl)-7-bromo-1,2,3,4,4a,5,11,11aβ-octahydro-6H-indolo[2,3-g]isoquinoline is produced by using 2-benzyl-4aα-(3-methoxyphenyl)-7-bromo-1,2,3,4,4a,5,11,11aβ-octahydro-6H-indolo[2,3-g]isoquinoline instead, 2-benzyl-4aα-(3-hydroxyphenyl)-8-bromo-1,2,3,4,4a,5,11,11aβ-octahydro-6H-indolo[2,3-g]isoquinoline is produced by using 2-benzyl-4aα-(3-methoxyphenyl)-8-bromo-1,2,3,4,4a,5,11,11aβ-octahydro-6H-indolo[2,3-g]isoquinoline instead, 2-benzyl-4aα-(3-hydroxyphenyl)-9-bromo-1,2,3,4,4a,5,11,11aβ-octahydro-6H-indolo[2,3-g]isoquinoline is produced by using 2-benzyl-4aα-(3-methoxyphenyl)-9-bromo-1,2,3,4,4a,5,11,11aβ-octahydro-6H-indolo[2,3-g]isoquinoline instead, 2-benzyl-4aα-(3-hydroxyphenyl)-10-bromo-1,2,3,4,4a,5,11,11aβ-octahydro-6H-indolo[2,3-g]isoquinoline is produced by using 2-benzyl-4aα-(3-methoxyphenyl)-10-bromo-1,2,3,4,4a,5,11,11aβ-octahydro-6H-indolo[2,3-g]isoquinoline instead, 2-benzyl-4aα-(3-hydroxyphenyl)-7-fluoro-1,2,3,4,4a,5,11,11aβ-octahydro-6H-indolo[2,3-g]isoquinoline is produced by using 2-benzyl-4aα-(3-methoxyphenyl)-7-fluoro-1,2,3,4,4a,5,11,11aβ-octahydro-6H-indolo[2,3-g]isoquinoline instead, 2-benzyl-4aα-(3-hydroxyphenyl)-8-fluoro-1,2,3,4,4a,5,11,11aβ-octahydro-6H-indolo[2,3-g]isoquinoline is produced by using 2-benzyl-4aα-(3-methoxyphenyl)-8-fluoro-1,2,3,4,4a,5,11,11aβ-octahydro-6H-indolo[2,3-g]isoquinoline instead, 2-benzyl-4aα-(3-hydroxyphenyl)-9-fluoro-1,2,3,4,4a,5,11,11aβ-octahydro-6H-indolo[2,3-g]isoquinoline is produced by using 2-benzyl-4aα-(3-methoxyphenyl)-9-fluoro-1,2,3,4,4a,5,11,11aβ-octahydro-6H-indolo[2,3-g]isoquinoline instead, 2-benzyl-4aα-(3-hydroxyphenyl)-10-fluoro-1,2,3,4,4a,5,11,11aβ-octahydro-6H-indolo[2,3-g]isoquinoline is produced by using 2-benzyl-4aα-(3-methoxyphenyl)-10-fluoro-1,2,3,4,4a,5,11,11aβ-octahydro-6H-indolo[2,3-g]isoquinoline instead, 2-benzyl-4aα-(3-hydroxyphenyl)-7-nitro-1,2,3,4,4a,5,11,11aβ-octahydro-6H-indolo[2,3-g]isoquinoline is produced by using 2-benzyl-4aα-(3-methoxyphenyl)-7-nitro-1,2,3,4,4a,5,11,11aβ-octahydro-6H-indolo[2,3-g]isoquinoline instead, 2-benzyl-4aα-(3-hydroxyphenyl)-8-nitro-1,2,3,4,4a,5,11,11aβ-octahydro-6H-indolo[2,3-g]isoquinoline is produced by using 2-benzyl-4aα-(3-hydroxyphenyl)-8-nitro-1,2,3,4,4a,5,11,11aβ-octahydro-6H-indolo[2,3-g]isoquinoline instead, 2-benzyl-4aα-(3-hydroxyphenyl)-9-nitro-1,2,3,4,4a,5,11,11aβ-octahydro-6H-indolo[2,3-g]isoquinoline is produced by using 2-benzyl-4aα-(3-methoxyphenyl)-9-nitro-1,2,3,4,4a,5,11,11aβ-octahydro-6H-indolo[2,3-g]isoquinoline instead, and 2-benzyl-4aα-(3-hydroxyphenyl)-10-nitro-1,2,3,4,4a,5,11,11aβ-octahydro-6H-indolo[2,3-g]isoquinoline is produced by using 2-benzyl-4aα-(3-methoxyphenyl)-10-nitro-1,2,3,4,4a,5,11,11aβ-octahydro-6H-indolo[2,3-g]isoquinoline instead.

Similarly, 2-phenethyl-4aα-(3-hydroxyphenyl)-7-methyl-1,2,3,4,4a,5,11,11aβ-octahydro-6H-indolo[2,3-g]isoquinoline is produced by using 2-phenethyl-4aα-(3-methoxyphenyl)-7-methyl-1,2,3,4,4a,5,11,11aβ-octahydro-6H-indolo[2,3-g]isoquinoline instead, 2-phenethyl-4aα-(3-hydroxyphenyl)-8-methyl-1,2,3,4,4a,5,11,11aβ-octahydro-6H-indolo[2,3-g]isoquinoline is produced by using 2-phenethyl-4aα-(3-methoxyphenyl)-8-methyl-1,2,3,4,4a,5,11,11aβ-octahydro-6H-indolo[2,3-g]isoquinoline instead, 2-phenethyl-4aα-(3-hydroxyphenyl)-9-methyl-1,2,3,4,4a,5,11,11aβ-octahydro-6H-indolo[2,3-g]isoquinoline is produced by using 2-phenethyl-4aα-(3-methoxyphenyl)-9-methyl-1,2,3,4,4a,5,11,11aβ-octahydro-6H-indolo[2,3-g]isoquinoline instead, 2-phenethyl-4aα-(3-hydroxyphenyl)-10-methyl-1,2,3,4,4a,5,11,11aβ-octahydro-6H-indolo[2,3-g]isoquinoline is produced by using 2-phenethyl-4aα-(3-methoxyphenyl)-10-methyl-1,2,3,4,4a,5,11,11aβ-octahydro-6H-indolo[2,3-g]isoquinoline instead, 2-phenethyl-4aα-(3-hydroxyphenyl)-7-chloro-1,2,3,4,4a,5,11,11aβ-octahydro-6H-indolo[2,3-g]isoquinoline is produced by using 2-phenethyl-4aα-(3-methoxyphenyl)-7-chloro-1,2,3,4,4a,5,11,11aβ-octahydro-6H-indolo[2,3-g]isoquinoline instead, 2-phenethyl-4aα-(3-hydroxyphenyl)-8-chloro-1,2,3,4,4a,5,11,11aβ-octahydro-6H-indolo[2,3-g]isoquinoline is produced by using 2-phenethyl-4aα-(3-methoxyphenyl)-8-chloro-1,2,3,4,4a,5,11,11aβ-octahydro-6H-indolo[2,3-g]isoquinoline instead, 2-phenethyl-4aα-(3-hydroxyphenyl)-9-chloro-1,2,3,4,4a,5,11,11aβ-octahydro-6H-indolo [2,3-g]isoquinoline is produced by using 2-phenethyl-4aα-(3-methoxyphenyl)-9-chloro-1,2,3,4,4a,5,11,11aβ-octahydro-6H-indolo[2,3-g]isoquinoline instead, 2-phenethyl-4aα-(3-hydroxyphenyl)-10-chloro-1,2,3,4,4a,5,11,11aβ-octahydro-6H-indolo[2,3-g]isoquinoline is produced by using 2-phenethyl-4aα-(3-methoxyphenyl)-10-chloro-1,2,3,4,4a,5,11,11aβ-octahydro-6H-indolo[2,3-g]isoquinoline instead, 2-phenethyl-4aα-(3-hydroxyphenyl)-7-bromo-1,2,3,4,4a,5,11,11aβ-octahydro-6H-indolo[2,3-g]isoquinoline is produced by using 2-phenethyl-4aα-(3-methoxyphenyl)-7-bromo-1,2,3,4,4a,5,11,11aβ-octahydro-6H-indolo[2,3-g]isoquinoline instead, 2-phenethyl-4aα-(3-hydroxyphenyl)-8-bromo-1,2,3,4,4a,5,11,11aβ-octahydro-6H-indolo[2,3-g]isoquinoline is produced by using 2-phenethyl-4aα-(3-methoxyphenyl)-8-bromo-1,2,3,4,4a,5,11,11aβ-octahydro-6H-indro[2,3-g]isoquinoline, instead, 2-phenethyl-4aα-(3-hydroxyphenyl)-9-bromo-1,2,3,4,4a,5,11,11aβ-octahydro-6H-indolo[2,3-g]isoquinoline is produced by using 2-phenethyl-4aα-(3-methoxyphenyl)-9-bromo-1,2,3,4,4a,5,11,11aβ-octahydro-6H-indolo[2,3-g]isoquinoline instead, 2-phenethyl-4aα-(3-hydroxyphenyl)-10-bromo-1,2,3,4,4a,5,11,11aβ-octahydro-6H-indolo[2,3-g]isoquinoline is produced by using 2-phenethyl-4aα-(3-methoxyphenyl)-10-bromo-1,2,3,4,4a,5,11,11aβ-octahydro-6H-indolo[2,3-g]isoquinoline instead, 2-phenethyl-4aα-(3-hydroxyphenyl)-7-fluoro-1,2,3,4,4a,5,11,11aβ-octahydro-6H-indolo[2,3-g]isoquinoline is produced by using 2-phenethyl-4aα-(3-methoxyphenyl)-7-fluoro-1,2,3,4,4a,5,11,11aβ-octahydro-6H-indolo[2,3-g]isoquinoline instead, 2-phenethyl-4aα-(3-hydroxyphenyl)-8-fluoro-1,2,3,4,4a,5,11,11aβ-octahydro-6H-indolo[2,3-g]isoquinoline is produced by using 2-phenethyl-4aα-(3-methoxyphenyl)-8-fluoro-1,2,3,4,4a,5,11,11aβ-octahydro-6H-indolo[2,3-g]isoquinoline instead, 2-phenethyl-4aα-(3-hydroxyphenyl)-9-fluoro-1,2,3,4,4a,5,11,11aβ-octahydro-6H-indolo[2,3-g]isoquinoline is produced by using 2-phenethyl-4aα-(3-methoxyphenyl)-9-fluoro-1,2,3,4,4a,5,11,11aβ-octahydro-6H-indolo[2,3-g]isoquinoline instead, 2-phenethyl-4aα-(3-hydroxyphenyl)-10-fluoro-1,2,3,4,4a,5,11,11aβ-octahydro-6H-indolo[2,3-g]isoquinoline is produced by using 2-phenethyl-4aα-(3-methoxyphenyl)-10-fluoro-1,2,3,4,4a,5,11,11aβ-octahydro-6H-indolo[2,3-g]isoquinoline instead, 2-phenethyl-4aα-(3-hydroxyphenyl)-7-nitro-1,2,3,4,4a,5,11,11aβ-octahydro-6H-indolo[2,3-g]isoquinoline is produced by using 2-phenethyl-4aα-(3-methoxyphenyl)-7-nitro-1,2,3,4,4a,5,11,11aβ-octahydro-6H-indolo[2,3-g]isoquinoline instead, 2-phenethyl-4aα-(3-hydroxyphenyl)-8-nitro-1,2,3,4,4a,5,11,11aβ-octahydro-6H-indolo[2,3-g]isoquinoline is produced by using 2-phenethyl-4aα-(3-methoxyphenyl)-8-nitro-1,2,3,4,4a,5,11,11aβ-octahydro-6H-indolo[2,3-g]isoquinoline instead, 2-phenethyl-4aα-(3-hydroxyphenyl)-9-nitro-1,2,3,4,4a,5,11,11aβ-octahydro-6H-indolo[2,3-g]isoquinoline is produced by using 2-phenethyl-4aα-(3-methoxyphenyl)-9-nitro-1,2,3,4,4a,5,11,11aβ-octahydro-6H-indolo[2,3-g]isoquinoline instead, and 2-phenethyl-4aα-(3-hydroxyphenyl)-10-nitro-1,2,3,4,4a,5,11,11aβ-octahydro-6H-indolo[2,3-g]isoquinoline is produced by using 2-phenethyl-4aα-(3-methoxyphenyl)-1,2,3,4,4a,5,11,11aβ-octahydro-6H-indolo[2,3-g]isoquinoline instead.

Example 19

2-Cyclopropylmethyl-4aα-(3-methoxyphenyl)-9-methyl-1,2,3,4,4a,5,11,11aβ-6H-indolo[2,3-g]isoquinoline 20

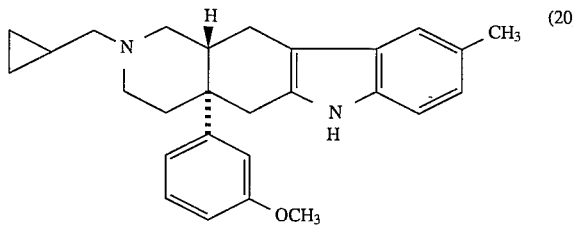

By subjecting 300 mg of 2-(2,2,2-trichloroethoxycarbonyl)-4aα-(3-methoxyphenyl)-6-oxo-1,2,3,4,4a,5,6,7,8,8aβ-decahydroisoquinoline and 168 mg of p-tollyl hydrazine hydrochloride to the procedure of Examples 15 to 17, 60 mg of the captioned compound was produced.

IR (KBr) cm$^{-1}$: 2922, 1605, 1580, 1464

NMR (CDCl$_3$) 400 MHz δ: 0.10–0.16 (2H, m), 0.13 (1H, m), 0.51–0.57 (2H, m), 2.02–2.13 (2H, m), 2.27–2.40 (3H, m), 2.42 (3H, s), 2.55–2.67 (2H, m), 2.83–3.06 (5H, m), 3.18 (1H, m), 3.67 (3H, s), 6.60 (1H, m), 6.89 (1H, dd, J=8.6 Hz, 1.2 Hz), 7.00–7.02 (2H, m), 7.06–7.10 (2H, m), 7.26 (1H, s), 7.62 (1H, brs)

Mass (m/e): 400 (M$^+$)

Similarly, 2-cyclopropylmethyl-4aα-(3-methoxyphenyl)-8-methyl-1,2,3,4,4a,5,11,11aβ-octahydro-6H-indolo[2,3-g]isoquinoline and 2-cyclopropylmethyl-4aα-(3-methoxyphenyl)-10-methyl-1,2,3,4,4a,5,11,11aβ-octahydro-6H-indolo[2,3-g]isoquinoline are produced by using 3-methylphenyl hydrazine instead of 4-methylphenyl hydrazine and 2-cyclopropylmethyl-4aα-(3-methoxyphenyl)-7-methyl-1,2,3,4,4a,5,11,11aβ-octahydro-6H-indolo[2,3-g]isoquinoline is produced by using 2-methylphenyl hydrazine instead.

Example 20

2-Cyclopropylmethyl-4aα-(3-hydroxyphenyl)-9-methyl-1,2,3,4,4a,5,11,11aβ-6H-indolo[2,3-g]isoquinoline 21

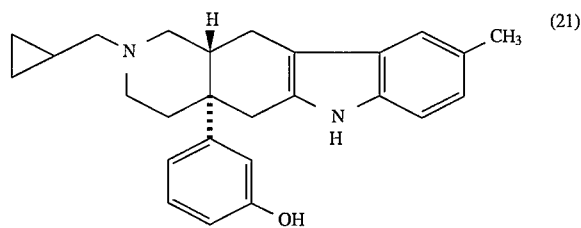

A solution of 105 mg (0.26 mmol) of 2-cyclopropylmethyl-4aα-(3-methoxyphenyl)-9-methyl-1,2,3,4,4a,5,11,11aβ-6H-indolo[2,3-g]isoquinoline, 0.27 ml (2.98 mmol) of n-propane thiol, and 300 mg (2.67 mmol) of potassium-t-butoxide in 5 ml of DMF was heated and stirred at 125° C. for four hours. The resultant reaction mixture was cooled to room temperature and concentrated. The residue was combined with a saturated aqueous solution of sodium hydrogen carbonate and extracted three times from chloroform-methanol (3:1). The organic layers consequently separated were combined, washed with a saturated aqueous saline solution, dried, and concentrated, to afford a powder. This powder was dissolved in methanol, combined with methanesulfonic acid, concentrated, and separated and refined by column chromatography [Sephadex, LH-20; methanol], to obtain 85 mg of the methanesulfonate of the captioned compound in a purified form (yield 67.2%).

IR (KBr) cm$^{-1}$: 3270, 1657, 1586, 1460

Mass (FAB): 387 (M$^+$+1)

Similarly, 2-cyclopropylmethyl-4aα-(3-hydroxyphenyl)-7-methyl-1,2,3,4,4a,5,11,11aβ-octahydro-6H-indolo[2,3-g]isoquinoline is produced by using 2-cyclopropylmethyl-4aα-(3-methoxyphenyl)-7-methyl-1,2,3,4,4a,5,11,11aβ-octahydro-6H-indolo[2,3-g]isoquinoline instead of 2-cyclopropylmethyl-4aα-(3-methoxyphenyl)-9-methyl-1,2,3,4,4a,5,11,11aβ-octahydro-6H-indolo[2,3-g]isoquinoline, 2-cyclopropylmethyl-4aα-(3-hydroxyphenyl)-8-methyl-1,2,3,4,4a,5,11,11aβ-octahydro-6H-indolo[2,3-g]isoquinoline is produced by using 2-cyclopropylmethyl-4aα-(3-methoxyphenyl)-8-methyl-1,2,3,4,4a,5,11,11aβ-octahydro-6H-indolo[2,3-g]isoquinoline instead, and 2-cyclopropylmethyl-4aα-(3-hydroxyphenyl)-10-methyl-1,2,3,4,4a,5,11,11aβ-octahydro-6H-indolo[2,3-g]isoquinoline is produced by using 2-cyclopropylmethyl-4aα-(3-methoxyphenyl)-10-methyl-1,2,3,4,4a,5,11,11aβ-octahydro-6H-indolo[2,3-g]isoquinoline instead.

Referential Example 2

2-Cyclopropylcarbonyl-4aα-(3-methoxyphenyl)-6-oxo-1,2,3,4,4a,5,6,7,8,8aβ-decahydroisoquinoline 22

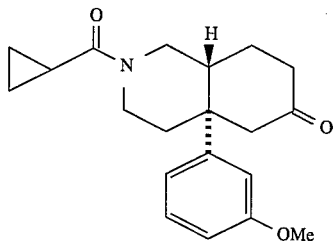
(22)

In an atmosphere of argon, 3.28 g of 2-(2,2,2-trichloroethoxycarbonyl)-4aα-(3-methoxyphenyl)-6-oxo-1,2,3,4,4a,5,6,7,8,8aβ-decahydroisoquinoline was dissolved in 50 ml of acetic acid. The produced solution and 4.90 g of zinc dust added thereto were stirred at room temperature for four hours. The resultant mixture was filtered to remove zinc, distilled under a vacuum to expel acetic acid, combined with 30 ml of an aqueous 1N sodium hydroxide solution, and extracted four times from 50 ml of chloroform. The organic layers consequently separated were combined, washed with a saturated aqueous saline solution, dried, and concentrated, to obtain 1.98 g of the reaction mixture. In an atmosphere of argon, this reaction mixture was dissolved in 50 ml of anhydrous dichloromethane. The produced solution and 2.1 ml of triethylamine and 0.9 ml of cyclopropanecarbonyl chloride added thereto were stirred at room temperature for three hours. The resultant mixture was washed with 1N hydrochloric acid and water, dried, and concentrated, to produce 2.86 g of an oily substance. This oily substance was refined by column chromatography [silica gel:chloroform/ethyl acetate (9/1)], to afford 1.77 g of the captioned compound (Yield 75.3%).

IR (Liquid film method) cm$^{-1}$: 2948, 1713, 1632, 1582, 1450, 1245

EI-MS (m/z): 327 (M$^+$)

NMR (CDCl$_3$) 400 MHz δ: 0.72–0.81 (2H, m), 0.96–1.03 (2H, m), 1.72–2.47 (9H, m), 2.76 (0.5H, m), 2.97 (1H, d, J=14.2 Hz), 3.07 (0.5H, m), 3.27 (0.5H, m), 3.75 (0.5H, m), 3.79 (3H, s), 4.01 (0.5H, m), 4.12 (0.5H, m), 4.33 (0.5H, m), 4.60 (0.5H, m), 6.75 (1H, dd, J=8.3 Hz, 2.0 Hz), 6.95–7.01 (2H, m), 7.25 (1H, J=8.3 Hz)

Similarly, 2-acryloyl-4aα-(3-methoxyphenyl)-6-oxo-1,2,3,4,4a,5,6,7,8,8aβ-decahydroisoquinoline is produced by using acryloyl chloride instead of cyclopropane carbonyl chloride, 2-benzoyl-4aα-(3-methoxyphenyl)-6-oxo-1,2,3,4,4a,5,6,7,8,8aβ-decahydroisoquinoline is produced by using benzoyl chloride instead, 2-phenylacetyl-4aα-(3-methoxyphenyl)-6-oxo-1,2,3,4,4a,5,6,7,8,8aβ-decahydroisoquinoline is produced by using phenylacetyl chloride instead, 2-acetyl-4aα-(3-methoxyphenyl)-6-oxo-1,2,3,4,4a,5,6,7,8,8aβ-decahydroisoquinoline is produced by using acetyl chloride, 2-propionyl-4aα-(3-methoxyphenyl)-6-oxo-1,2,3,4,4a,5,6,7,8,8aβ-decahydroisoquinoline is produce by using propionyl chloride instead, 2-butyryl-4aα-(3-methoxyphenyl)-6-oxo-1,2,3,4,4a,5,6,7,8,8aβ-decahydroisoquinoline is produced by using butyryl chloride instead, 2-thiophene carbonyl-4aα-(3-methoxyphenyl)-6-oxo-1,2,3,4,4a,5,6,7,8,8aβ-decahydroisoquinoline is produced by using 2-thiophene carbonyl chloride instead, 2-valeryl-4aα-(3-methoxyphenyl)-6-oxo-1,2,3,4,4a,5,6,7,8,8aβ-decahydroisoquinoline is produced by using valeryl chloride instead, 2-furoyl-4aα-(3-methoxyphenyl)-6-oxo-1,2,3,4,4a,5,6,7,8,8aβ-decahydroisoquinoline is produced by using 2-furoyl chloride instead, 2-cyclobutyl carbonyl-4aα-(3-methoxyphenyl)-6-oxo-1,2,3,4,4a,5,6,7,8,8aβ-decahydroisoquinoline is produced by using cyclobutane carbonyl chloride instead, 2-(p-toluoyl)-4aα-(3-methoxyphenyl)-6-oxo-1,2,3,4,4a,5,6,7,8,8aβ-decahydroisoquinoline is produced by using p-toluoyl chloride instead, 2-xyloyl-4aα-(3-methoxyphenyl)-6-oxo-1,2,3,4,4a,5,6,7,8,8aβ-decahydroisoquinoline is produced by using xyloyl chloride instead, and 2-(p-anisoyl)-4aα-(3-methoxyphenyl)-6-oxo-1,2,3,4,4a,5,6,7,8,8aβ-decahydroisoquinoline is produced by using p-anisoyl chloride instead.

Example 21

2-Cyclopropylcarbonyl-4aα-(3-methoxyphenyl)-1,2,3,4,4a,5,11,11aβ-octahydoro-6-methyl-indolo[2,3-g]isoquinoline 23

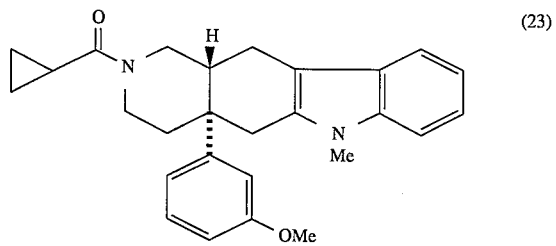
(23)

In an atmosphere of argon, 185 mg of 2-cyclopropylcarbonyl-4aα-(3-methoxyphenyl)-6-oxo-1,2,3,4,4a,5,6,7,8,8aβ-decahydroisoquinoline and 75 μl of 1-methyl-1-phenyl hydrazine were dissolved in 3 ml of ethanol and the produced solution was heated to 80° C. The hot solution and 0.37 ml of methanesulfonic acid added thereto were stirred at 80° C. for 15 minutes and then cooled to room temperature. The resultant mixture was distilled under a vacuum to expel ethanol, combined with 10 ml of a saturated aqueous solution of sodium hydrogen carbonate, and extracted three times from 20 ml of chloroform. The organic layers consequently separated were combined, washed with a saturated aqueous saline solution, dried, and concentrated, to obtain 330 mg of an oily substance. When this oily substance was refined by column chromatography [silica gel; dichloromethane/ether (19/1)], 162 mg of crude crystals were obtained. When the crude crystals were recrystallized from ethyl acetate-hexane, 141 mg of the captioned compound in a purified form having a m.p. of 131° to 132.5° C. (yield 60.2%) was obtained.

IR (KBr) cm$^{-1}$: 1634, 1470, 1441, 1261, 1245, 1228, 735

EI-MS (m/z): 414 (M$^+$), 157

NMR (CDCl$_3$) 400 MHz δ: 0.75–0.79 (2H, m), 0.95–1.03 (2H, m), 1.76–1.89 (2H, m), 2.38 (1H, m), 2.50 (1H, m), 2.80 (1H, m), 2.95–3.06 (3H, m), 3.22 (1H, d, J=15.6 Hz), 3.40–3.49 (1H, brm), 3.55 (3H, s), 3.69 (3H, s), 4.24–4.31 (1H, brm), 4.39–4.48 (1H, brm), 6.66 (1H, m), 7.03–7.08 (3H, m), 7.11–7.15 (2H, m), 7.21 (1H, d, J=7.9 Hz), 7.45 (1H, d, J=7.6 Hz)

Similarly, 2-cyclopropylcarbonyl-4aα-(3-methoxyphenyl)1,2,3,4,4a,5,11,11aβ-octahydro-6-phenyl-indolo[2,3-g]isoquinoline is produced by using 1,1-diphenyl hydrazine instead of 1-methyl-1-phenyl hydrazine, 2-acryloyl-4aα-(3-methoxyphenyl)-1,2,3,4,4a,5,11,11aβ-octahydro-6-methyl-indolo[2,3-g]isoquinoline is produced by using 2-acryloyl-4aα-(3-methoxyphenyl)-6-oxo-1,2,3,4,4a,5,6,7,8,8aβ- decahydroisoquinoline instead of 2-cyclopropyl carbonyl-4aα-(3-methoxyphenyl)-6-oxo-1,2,3,4,4a,5,6,7,8,8aβ-decahydroisoquinoline, 2-benzoyl-4aα-(3-methoxyphenyl)-1,2,3,4,4a,5,11,11aβ-octahydro-6-methyl-indolo[2,3-g]isoquinoline is produced by using 2-benzoyl-4aα-(3-methoxyphenyl)-6-oxo-1,2,3,4,4a,5,6,7,8,8aβ-decahydroisoquinoline instead, and 2-phenylacetyl-4aα-(3-methoxyphenyl)-1,2,3,4,4a,5,11,11aβ-octahydro-6-methyl-indolo[2,3-g]isoquinoline is produced by using 2-phenylacetyl-4aα-(3-methoxyphenyl)-6-oxo-1,2,3,4,4a,5,6,7,8,8aβ-decahydroisoquinoline instead.

Example 22

2-Cyclopropylmethyl-4aα-(3-methoxyphenyl)-1,2,3,4,4a,5,11,11aβ-octahydro-6-methyl-indolo[2,3-g]isoquinoline 24

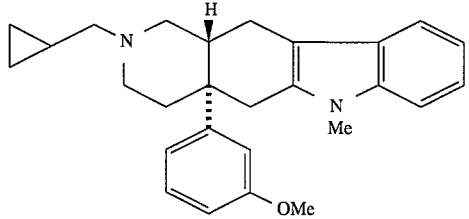

(24)

In an atmosphere of argon, 35 mg of lithium aluminum hydride was suspended in 5 ml of anhydrous THF and cooled to 0° C. and a solution of 150 mg of 2-cyclopropylcarbonyl-4aα-(3-methoxyphenyl)-1,2,3,4,4a,5,11,11aβ-octahydro-6-methyl-indolo[2,3-g]isoquinoline in 2 ml of anhydrous THF was dropped into the cooled suspension. The produced mixture was heated to room temperature, stirred for two hours, cooled to 0° C., and combined with ethyl acetate and a saturated aqueous solution of potassium sodium tartrate. When the resultant mixture was filtered to remove the insolubles and then distilled under a vacuum to expel ethyl acetate, 140 mg of an oily substance was obtained. When this oily substance was refined by column chromatography [silica gel; chloroform-chloroform/methanol (99/1)], 131 mg of the captioned compound was obtained. When this compound was recrystallized from ethyl acetate, 110 mg of the compound in a purified form (m.p. 133° to 134° C.) (yield 75.9%) was obtained.

IR (KBr) cm$^{-1}$: 3420, 1601, 1475, 1386, 1251, 764

EI-MS (m/z): 400 (M$^+$), 157

NMR (CDCl$_3$) 400 MHz δ: 0.16–0.21 (2H, m), 0.56–0.61 (2H, m), 1.02 (1H, m), 2.20–2.27 (2H, m), 2.40–2.50 (3H, m), 2.70–2.78 (2H, m), 2.85 (1H, brd, J=16.1 Hz), 3.00–3.04 (2H, m), 3.13–3.18 (2H, m), 3.31 (1H, m), 3.51 (3H, s), 3.68 (3H, s), 6.63 (1H, m), 7.02–7.14 (5H, m), 7.19 (1H, d, J=8.3 Hz), 7.44 (1H, d, J=7.3 Hz)

Similarly, 2-allyl-4aα-(3-methoxyphenyl)-1,2,3,4,4a,5,11,11aβ-octahydro-6-methyl-indolo[2,3-g]isoquinoline is produced by using 2-acryloyl-4aα0(3-methoxyphenyl)-1,2,3,4,4a,5,11,11aβ-octahydro-6-methyl-indolo[2,3-g]isoquinoline instead of 2-cyclopropyl carbonyl-4aα-(3-methoxyphenyl)-1,2,3,4,4a,5,11,11aβ-octahydro-6-methyl-indolo[2,3-g]isoquinoline, 2-benzyl-4aα-(3-methoxyphenyl)-1,2,3,4,4a,5,11,11aβ-octahydro-6-methyl-indolo[2,3-g]isoquinoline is produced by using 2-benzoyl-4aα-(3-methoxyphenyl)-1,2,3,4,4a,5,11,11aβ-octahydro-6-methyl-indolo[2,3-g]isoquinoline instead, and 2-phenethyl-4aα-(3-methoxyphenyl)-1,2,3,4,4a,5,11,11aβ-octahydro-6-methyl-indolo[2,3-g]isoquinoline is produced by using 2-phenylacetyl-4aα-(3-methoxyphenyl)-1,2,3,4,4a,5,11,11aβ-octahydro-6-methyl-indolo[2,3-g]isoquinoline instead.

Example 23

2-Cyclopropylmethyl-4aα-(3-hydroxyphenyl)-1,2,3,4,4a,5,11,11aβ-octahydro-6-methyl-indolo[2,3-g]isoquinoline 25

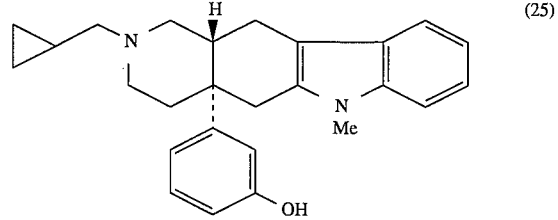

(25)

In an atmosphere of argon, 120 mg of 2-cyclopropylmethyl-4aα-(3-methoxyphenyl)-1,2,3,4,4a,5,11,11aβ-octahydro-6-methyl-indolo[2,3-g]isoquinoline, 0.2 ml of n-propane thiol, and 230 mg of potassium-t-butoxide were dissolved in 3 ml of anhydrous DMF and the produced solution was stirred at 130° C. Four hours thereafter, the resultant mixture and 0.2 ml of n-propane thiol and 230 mg of potassium-t-butoxide added thereto by way of replenishment were stirred at 130° C. for two hours and subsequently cooled to room temperature. The produced mixture was distilled under a vacuum to expel DMF, combined with 5 ml of water, and extracted three times from 20 ml of chloroform. The organic layers consequently separated were combined, washed with a saturated aqueous saline solution, dried, and concentrated, to produce 120 mg of a powder. This powder was suspended in 3 ml of methanol, combined with 20 μl of methanesulfonic acid, and dissolved by addition of DMF. The resultant mixture was distilled under a vacuum to expel DMF, combined with ethyl acetate, and filtered to separate a solid content. When this solid was recrystallized from methanol, 74 mg of the methanesulfonate of the captioned compound (decomposed at 250° C.) (yield 51.4%) was obtained.

IR (KBr) cm$^{-1}$: 3410, 1601, 1474, 1212, 1170, 1042, 784, 555

FAB-MS (m/z): 387 (M$^+$+1)

NMR (DMSO-d$_6$) 500 MHz: 0.36–0.41 (2H, m), 0.62–0.66 (2H, m), 1.07 (1H, m), 2.10 (1H, m), 2.30 (3H, s), 2.56–2.67 (3H, m), 2.85 (1H, m) 2.92 (1H, m), 2.98–3.08 (3H, m), 3.29–3.38 (2H, m), 3.53 (3H, s), 3.51–3.55 (1H, m), 3.75 (1H, m), 6.55 (1H, m), 6.94–6.99 (3H, m) 7.03–7.07 (2H, m), 7.31 (1H, d, J=7.9 Hz), 7.37 (1H, d, J=7.9 Hz), 9.25 (1H, s), 9.37 (1H, br)

Elementary analyses For $C_{26}H_{30}N_2O \cdot CH_3SO_3H \cdot 0.37H_2O$

|  | C | H | N | S |
| --- | --- | --- | --- | --- |
| Calculated | 66.28 | 7.16 | 5.73 | 6.55 |
| Found | 66.27 | 7.18 | 5.69 | 6.65 |

Similarly, 2-benzyl-4aα-(3-hydroxyphenyl)-1,2,3,4,4a,5,11,11aβ-octahydro-6-methyl-indolo[2,3-g]isoquinoline is produced by using 2-benzyl-4aα-(3-methoxyphenyl)-1,2,3,4,4a,5,11,11aβ-octahydro-6-methyl-indolo[2,3-g]isoquinoline instead of 2-cyclopropylmethyl-4aα-(3-methoxyphenyl)-1,2,3,4,4a,5,11,11aβ-octahydro-6-methyl-indolo[2,3-g]

77 isoquinoline, and 2-phenethyl-4aα-(3-hydroxyphenyl)-1,2,3,4,4a,5,11,11aβ-octahydro-6-methyl-indolo[2,3-g]isoquinoline is produced by using 2-phenethyl-4aα-(3-methoxyphenyl)-1,2,3,4,4a,5,11,11aβ-octahydro-6-methyl-indolo[2,3-g]isoquinoline instead.

Example 24

2-Cyclopropylcarbon-4aα-(3-methoxyphenyl)-7-fluoro-1,2,3,4,4a,5,11,11aβ-octahydro-6H-indolo[2,3-g]isoquinoline 26

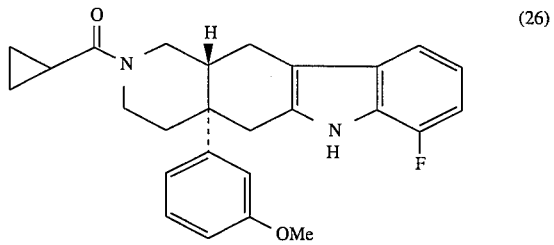

(26)

In an atmosphere of argon, 406 mg of 2-cyclopropylcarbonyl-4aα-(3-methoxyphenyl)-6-oxo-1,2,3,4,4a,5,6,7,8,8aβ-dicahydroisoquinoline and 267 mg of 2-fluorophenyl hydrazine hydrochloride were dissolved in 5 ml of ethanol and the produced solution was heated to 80° C. The resultant mixture and 0.94 ml of methanesulfonic acid added thereto were stirred at 80° C. for 30 minutes and then cooled to room temperature. The cooled mixture was alkalinized by addition of a saturated aqueous solution of sodium hydrogen carbonate and extracted three times from 50 ml of chloroform. The organic layers consequently separated were combined, washed with a saturated aqueous saline solution, dried, and concentrated, to afford 684 mg of an oily substance. When this oily substance was separated and refined by column chromatography [silica gel; cyclohexane/ethyl acetate (2/1–1/1)], 291 mg of crude crystals was obtained. When the crude crystals were recrystallized from chloroform-cyclohexane, 254 mg of the captioned compound having a m.p. of 275°–277° C. (colored in the neighborhood of 260° C.) (yield 48.9%) was obtained.

IR (KBr) cm$^{-1}$: 3252, 1619, 1581, 1460, 1249, 1228

EI-Ms (m/z): 418 (M$^+$), 161

NMR (CDCl$_3$) 400 MHz δ: 0.76–0.79 (2H, m), 0.95–0.14 (2H, m), 1.75–1.90 (2H, m), 2.35–2.49 (2H, m), 2.77–3.01 (4H, m), 3.08–3.25 (2H, m), 3.69 (3H, s), 3.97–4.74 (2H, brm), 6.67 (1H, m), 6.80 (1H, dd, J=10.7 Hz, 7.8 Hz), 6.96 (1H, td, J=7.8 Hz, 4.9 Hz), 7.00–7.19 (2H, m), 7.14 (1H, t, 7.8 Hz), 7.19 (1H, d, J=7.8 (1H, brs)

Similarly, 2-cyclopropylcarbonyl-4a α-(3-methoxyphenyl)-8-fluoro-1,2,3,4,4a,5,11, 11aβ-octahydro-6H-indolo[2,3-g]isoquinoline and 2-cyclopropylcarbonyl-4aα-(3-methoxyphenyl)-10-fluoro-1,2,3,4,4a,5,11,11aβ-octahydro-6H-indolo[2,3-g]isoquinoline are produced by using 3-fluorophenyl hydrazine instead of 2-fluorophenyl hydrazine, and 2-cyclopropylcarbonyl-4aα-(3-methoxyphenyl)-9-fluoro-1,2,3,4,4a,5,11,11a β-octahydro-6H-indolo[2,3-g]isoquinoline is produced by using 4-fluorophenyl hydrazine instead.

78

Example 25

2-(2,2,2-Trichloroethoxycarbonyl)4a α-(3-methoxyphenyl)-7-fluoro-1,2,3,4,4a,5,11,11aβ-octahydro-6H-indolo [2,3-g]isoquinoline 27

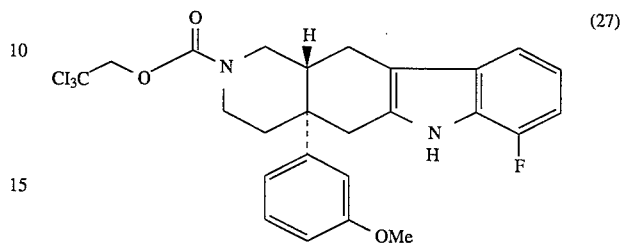

(27)

In an atmosphere of argon, 3.10 g of 2-(2,2,2-trichloroethoxycarbonyl)-4aα-(3-methoxyphenyl)-6-oxo-1,2,3,4,4a,5,6,7,8,8a β-decahydroisoquinoline and 1.39 g of 2-fluorophenyl hydrazine were dissolved in 40 ml of ethanol and the produced solution was heated to 80° C. The resultant mixture and 4.6 ml of methanesulfonic acid added thereto were stirred at 80° C. for 15 minutes and then cooled to room temperature. The mixture was distilled under a vacuum to expel ethanol, alkalinized by addition of an aqueous 1N sodium hydroxide solution, and extracted four times from 50 ml of chloroform. The organic layers consequently separated were combined, washed with a saturated aqueous saline solution, dried, and concentrated to afford 4.11 g of an oily substance. When this oily substance was separated and refined by column chromatography [silica gel; dichloromethane/cyclohexane (1/1)-dichloromethane], 3.00 g of crude crystals was obtained. When these crude crystals were recrystallized from ethyl acetate, 2.08 g of the captioned compound having a m.p. of 235° to 237° C. (yield 55.5%) was obtained.

IR (KBr) cm$^{-1}$: 3332, 1694, 1460, 1435, 1259, 1226, 1149, 1131, 1046, 777, 717

EI-MS (m/z): 524 (M$^+$), 526, 161

NMR (CDCl$_3$) 500 MHz δ: 1.85 (1H, m), 2.39–2.46 (2H, m), 2.88–2.99 (4H, m), 3.14 (1H, m), 3.49 (1H, m), 3.69 (3H, s), 4.10 (1H, m), 4.28 (1H, brd, J=13.4 Hz), 4.72–4.82 (2H, m), 6.66 (1H, m), 6.80 (1H, dd, J=11.0 Hz, 7.9 Hz), 6.94–7.01 (3H, m), 7.14 (1H, t, J=7.9 Hz), 7.20 (1H, m), 7.77 (1H, brd, J=7.3 Hz)

Similarly, 2-(2,2,2-trichloroethoxycarbonyl)-4aα-(3-methoxyphenyl)-8-fluoro-1,2,3,4,4a,5,11,11a β-octahydro-6H-indolo[2,3-]isoquinoline and 2-(2,2,2-trichloroethoxycarbonyl)-4a α-(3-methoxyphenyl)-10-fluoro-1,2,3,4,4a,5,11,11aβ-octahydro-6H-indolo[2,3-g]isoquinoline are produced by using 3-fluorophenyl hydrazine instead of 2-fluorophenyl hydrazine, and 2-(2,2,2-trichloroethoxycarbonyl)-4a α-(3-methoxyphenyl)-9-fluoro-1,2,3,4,4a,5,11,11a β-octahydro-6H-indolo[2,3-g]isoquinoline is produced by using 4-fluorophenyl hydrazine instead.

Example 26

2-Cyclopropylcarbonyl-4a α-(3-methoxyphenyl)-7-fluoro-1,2,3,4,4a,5,11,11a β-octahydro-6H-indolo[2,3-g]isoquinoline 26

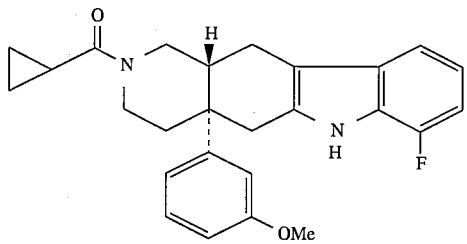

In an atmosphere of argon, 2.22 g of 2-(2,2,2-trichloroethoxycarbonyl)-4a α-(3-methoxyphenyl)-7-fluoro-1,2,3,4, 4a, 5,11,11aβ-octahydro-6H-indolo [2,3-g]isoquinoline was suspended in 40 ml of acetic acid and the produced suspension and 2.75 g of zinc dust added thereto were stirred at room temperature for three hours. The resultant mixture was filtered to remove zinc and distilled under a vacuum to expel acetic acid, alkalinized by addition of an aqueous 1N sodium hydroxide solution, and extracted three times from 50 ml of chloroform. The organic layers consequently separated were combined, washed with a saturated aqueous saline solution, dried, and concentrated, to prepare 1.70 g of a reaction mixture. This reaction mixture was suspended in 40 ml of and 1.20 ml of triethylamine and 0.57 ml of cyclopropanecarbonyl chloride added thereto were stirred at room temperature for two hours. The resultant mixture was distilled under a vacuum to expel dichloromethane. The distillate was combined with 20 ml of ethyl acetate and 20 ml of an aqueous 1N sodium hydroxide solution to induce precipitation of a solid substance. By separating this solid substance from the reaction mixture by means of filtration, 1.51 g of the captioned compound was obtained. In the meantime, the filtrate was divided into two layers and extracted three times from 20 ml of chloroform. The organic layers consequently separated were combined, washed with a saturated aqueous saline solution, dried, and concentrated, to obtain 550 mg of an oily substance. When this oily substance was separated and refined by column chromatography [silica gel; chloroform], 180 mg of the captioned compound (yield 95.6%) was obtained. Various spectral data obtained from the compound support identity of this compound compares with the compound obtained in Example 24.

Similarly, 2-cyclopropylcarbonyl-4aα-(3-methoxyphenyl)-8-fluoro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-fluoro-1,2,3,4,4a,5,11,11aβ-octahydro-6H-indolo[2,3-g]isoquinoline instead of 2-(2,2,2-trichloroethoxycarbonyl)-4aα-(3-methoxyphenyl)-7-fluoro-1,2,3,4,4a,5,11,11aβ-octahydro-6H-indolo[2,3-g]isoquinoline, 2-cyclopropylcarbonyl-4aα-(3-methoxyphenyl)-9-fluoro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-fluoro-1,2,3,4,4a,5,11,11aβ-octahydro-6H-indolo[2,3-g]isoquinoline instead, and 2-cyclopropylcarbonyl-4aα-(3-methoxyphenyl)-10-fluoro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-fluoro-1,2,3,4,4a,5,11,11aβ-octahydro-6H-indolo[ 2,3-g]isoquinoline instead.

Example 27

2-Cyclopropylmethyl-4aα-(3-methoxyphenyl)-7-fluoro-1,2,3,4,4a,5,11,11aβ-octahydro-6H-indolo [2,3-g]isoquinoline 28

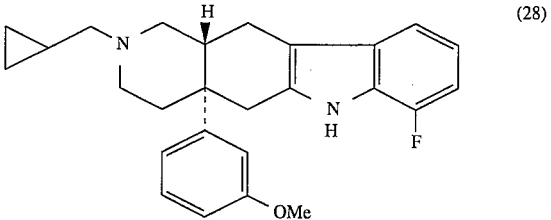

In an atmosphere of argon, 215 g of 2-cyclopropylcarbonyl-4aα-(3-methoxyphenyl)-7-fluoro-1,2,3,4,4a,5,11,11aβ-octahydro-6H-indolo[2,3-g]isoquinoline was suspended in 20 ml of anhydrous THF, cooled to 0° C., and combined with 60 mg of lithium aluminum hydride. The resultant mixture was heated to room temperature, stirred for one hour, cooled to 0° C., and combined with ethyl acetate and a saturated aqueous solution of potassium sodium tartrate. The mixture was filtered to remove insolubles and distilled under a vacuum to expel ethyl acetate and produce 210 mg of crude crystals. When these crude crystals were recrystallized from chloroform-ether, 170 mg of the captioned compound having a m.p. of 137° to 139° C. (yield 81.8%) was obtained.

IR (KBr) cm$^{-1}$: 2836, 1578, 1241, 1228, 1050, 779

EI - MS (m/z): 404 (M$^+$), 242

NMR (CDCl$_3$) 500 MHz δ: 0.07–0.12 (2H, m), 0.48–0.54 (2H, m), 0.88 (1H, m), 1.97–2.07 (2H, m), 2.23–2.32 (2H, m), 2.40 (1H, m), 2.54–2.65 (2H, m), 2.89–3.02 (4H, m) 3.10 (1H, d, J=15.9 Hz), 3.16 (1H, m) 3.68 (3H, s), 6.62 (1H, m), 6.78 (1H, dd, J=7.9 Hz, 11.0 Hz), 6.94 (1H, td, J=7.9 Hz, 4.9 Hz), 7.02–7.04 (2H, m), 7.09 (1H, t, J=7.9 Hz), 7.19 (1H, d, J=7.3 Hz), 7.80 (1H, brs)

Similarly, 2-cyclopropylmethyl-4aα-(3-methoxyphenyl)-8-fluoro-1,2,3,4,4a,5,11,11aβ-octahydro-6H-indolo]2,3-g]isoquinoline is produced by using 2-cyclopropylcarbonyl-4aα-(3-methoxyphenyl)-8fluoro-1,2,3,4,4a,5,11,11aβ-octahydro-6H-indolo[2,3-g]isoquinoline instead of 2-cyclopropylcarbonyl-4aα-(3-methoxyphenyl)-7-fluoro-1,2,3,4,4a,5,11,11aβ-octahydro-6H-indolo[2,3-g]isoquinoline, 2-cyclopropylmethyl-4aα-(3-methoxyphenyl)-9-fluoro-1,2,3,4,4a,5,11,11aβ-octahydro-6H-indolo[2,3-g]isoquinoline is produced by using -2-cyclopropylcarbonyl-4aα-(3-methoxyphenyl)-9-fluoro-1,2,3,4,4a,5,11,11aβ-octahydro-6H-indolo[2,3-g]isoquinoline instead, and 2-cyclopropylcarbonyl-4aα-(3-methoxyphenyl)-10-fluoro-1,2,3,4,4a,5,11,11aβ-octahydro-6H-indolo[2,3-g]isoquinoline is produced by using 2-cyclopropylcarbonyl-4aα-(3-methoxyphenyl)--10-fluoro-1,2,3,4,4a,5,11,11aβ-octahydro-6H-indolo[2,3,-g]isoquinoline instead.

Example 28

2-Cyclopropylmethyl-4aα-(3-hydroxyphenyl)-7-fluoro-1,2,3,4,4a,5,11,11aβ-octahydro-6H-indolo[2,3-g]isoquinoline 29

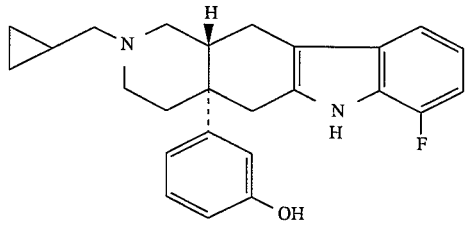
(29)

In an atmosphere of argon, 164 mg of 2-cyclopropylmethyl-4aα-(3-methoxyphenyl)-7-fluoro-1,2,3,4,4a,5,11,11aβ-octahydro-6H-indolo[2,3-g]isoquinoline, 0.31 ml of n-propane thiol, and 350 mg of potassium-t-butoxide were dissolved in 5 ml of anhydrous DMF and stirred at 230° C. for 4.5 hours. The produced solution was cooled to room temperature, then distilled under a vacuum to expel DMF, combined with 5 ml of water, and extracted three times from 15 ml of chloroform. The organic layers consequently separated were combined, washed with a saturated aqueous saline solution, dried, and concentrated, to produce 155 mg of a powder. This powder was suspended in 2 ml of methanol, converted into a methanesulfonated by addition of 25 μl of methanesulfonic acid, and separated and refined by column chromatography [Sephadex, LH-20; methanol], to afford 125 mg of crude crystals. When these crude crystals were recrystallized from ethanol, 51 mg of the methanesulfonate of the captioned compound (decomposed at 240° C.) (yield 25.9%) was obtained.

IR (KBr) cm$^{-1}$: 3180, 1601, 1460, 1330, 1210, 1046, 785

FAB-MS (m/z): 391 (M$^+$+1)

NMR (DMSO-d$_6$) 500 MHz δ: 0.35–0.40 (2H, m), 0.62–0.67 (2H, m), 1.06 (1H, m), 2.07 (1H, m), 2.31 (3H, s), 2.55–2.67 (3H, m), 2.89–3.07 (5H, m), 3.14 (1H, d, J=15.8 Hz), 3.38 (1H, m), 3.51 (1H, m), 3.73 (1H, m), 6.54 (1H, m), 6.81 (1H, dd, J=11.6 Hz, 7.9 Hz), 6.88–6.94 (3H, m), 7.04 (1H, t, J=7.9 Hz), 7.17 (1H, d, J=7.9 Hz), 9.26 (1H, s), 9.39 (1H, br), 11.09 (1H, s)

Elementary analyses For $C_{25}H_{27}N_2OF·CH_3SO_3H$

|  | C | H | N | F | S |
|---|---|---|---|---|---|
| Calculated | 64.18 | 6.42 | 5.76 | 3.90 | 6.59 |
| Found | 64.25 | 6.46 | 5.79 | 3.79 | 6.73 |

Similarly, 2-cyclopropylmethyl-4aα-(3-hydroxyphenyl)-8-fluoro-1,2,3,4,4a,5,11,11aβ-octahydro-6H-indolo[2,3-g]isoquinoline is produced by using 2-cyclopropylmethyl-4aα-(3-methoxyphenyl)-8-fluoro-1,2,3,4,4a,5,11,11aβ-octahydro-6H-indolo[2,3-g]isoquinoline instead of 2-cyclopropylmethyl-4α-(3-methoxyphenyl)-7-fluoro-1,2,3,4,4a,5,11,11aβ-octahydro-6H-indolo[2,3-g]isoquinoline, and 2-cyclopropylmethyl-4aα-(3-hydroxyphenyl)-10-fluoro-1,2,3,4,4a,5,11,11aβ-octahydro-6H-indolo[2,3-g]isoquinoline is produced by using 2-cyclopropylmethyl-4aα-(3-methoxyphenyl)-10-fluoro-1,2,3,4,4a,5,11,11aβ-octahydro-6H-indolo[2,3-g]isoquinoline instead.

Example 29

2-Allyl-4aα-(3-methoxyphenyl)-1,2,3,4,4a,5,11,11aβ-octahydro-6H-indolo[2,3-g]isoquinoline 30

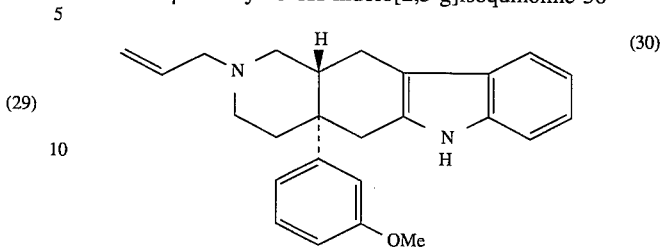
(30)

In an atmosphere of argon, 130 mg of 2-(2,2,2-trichloroethoxycarbonyl)-4aα-(3-methoxyphenyl)-1,2,3,4,4a,5,11,11aβ-octahydro-6H-indolo[2,3-g]isoquinoline was dissolved in 5 ml of acetic acid and the produced solution and 170 mg of zinc dust added thereto were stirred at room temperature for two hours. The resultant mixture was filtered to remove zinc, distilled under a vacuum to expel acetic acid, then combined with 10 ml of a saturated aqueous solution of sodium hydrogen carbonate, and extracted three times from 30 ml of chloroform/methanol (3/1). The organic layers consequently separated were combined, washed with a saturated aqueous saline solution, dried, and concentrated, to produce a reaction mixture. In an atmosphere of argon, 100 mg of the reaction mixture was dissolved in 5 ml of anhydrous DMF and the produced solution and 35 mg of sodium hydrogen carbonate and 23 μl of allyl bromide added thereto were thermally refluxed for 30 minutes. The resultant reaction solution was cooled to room temperature, combined with 10 ml of water, and extracted three times from 30 ml of chloroform. The organic layers consequently separated were combined, washed with a saturated aqueous saline solution, dried, and concentrated, to afford 120 mg of an oily substance. When this oily substance was separated and refined by column chromatography [silica gel; chromoform/methanol (97/3)], 77 mg of crude crystals was produced. When these crude crystals were recrystallized from ethyl acetate, 54 mg of the captioned compound having a m.p. of 188° to 189° C. (yield 56.6%) was obtained.

IR (KBr) cm$^{-1}$: 2930, 2838, 1609, 1578, 1460, 1294, 1238, 1042, 741

EI-MS (m/z): 372 (M$^+$), 143

NMR (CDCl$_3$) 500 MHz δ: 1.94–2.09 (2H, m), 2.39 (1H, m), 2.55–2.64 (2H, m), 2.80 (1H, m), 2.88–3.09 (7H, m), 3.68 (3H, s), 5.13–5.20 (2H, m), 5.91 (1H, m), 6.61 (1H, m), 7.01–7.11 (5H, m), 7.21 (1H, m), 7.43 (1H, m), 7.58 (1H, brs)

Similarly, 2-allyl-4aα-(3-methoxyphenyl)-7-methyl-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-methyl-1,2,3,4,4a,5,11,11aβ-octahydro-6H-indolo[2,3-g]isoquinoline instead of 2-(2,2,2-trichloroethoxycarbonyl)-4aα-(3-methoxyphenyl)-1,2,3,4,4a,5,11,11aβ-octahydro-6H-indolo[2,3-g]isoquinoline, 2-allyl-4aα-(3-methoxyphenyl)-8-methyl-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-methyl-1,2,3,4,4a,5,11,11aβ-octahydro-6H-indolo[2,3-g]isoquinoline instead, 2-allyl-4aα-(3-methoxyphenyl)-9-methyl-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-methyl-1,2,3,4,4a,5,11,11aβ-octahydro-6H-indolo[2,3-g]

isoquinoline instead, 2-allyl-4aα-(3-methoxyphenyl)-10-methyl-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-methyl-1,2,3,4,4a,5,11,11aβ-octahydro-6H-indolo[2,3-g]isoquinoline instead, 2-allyl-4aα-(3-methoxyphenyl)-7-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-chloro-1,2,3,4,4a,5,11,11aβ-octahydro-6H-indolo[2,3-g]isoquinoline instead, 2-allyl-4aα-(3-methoxyphenyl)-8-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-chloro-1,2,3,4,4a,5,11,11aβ-octahydro-6H-indolo[2,3-g]isoquinoline instead, 2-allyl-4aα-(3-methoxyphenyl)-9-chloro-1,2,3,4,4a,5,11,11aβ-octahydro-6H-indolo[[2,3-g]isoquinoline is produced by using 2-(2,2,2-trichloroethoxycarbonyl)-4aα-(3-methoxyphenyl)-9-chloro-1,2,3,4,4a,5,11,11aβ-octahydro-6H-indolo[2,3-g]isoquinoline instead, 2-allyl-4aα-(3-methoxyphenyl)-10-chloro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-10-chloro-1,2,3,4,4a,5,11,11aβ-octahydro-6H-indolo[2,3-g]isoquinoline instead, 2-allyl-4aα-(3-methoxyphenyl)-7-bromo-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-bromo-1,2,3,4,4a,5,11,11aβ-octahydro-6H-indolo[2,3-g]isoquinoline instead, 2-allyl-4aα-(3-methoxyphenyl)-8-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-bromo-1,2,3,4,4a,5,11,11a,β-octahydro-6H-indolo[2,3-g]isoquinoline instead, 2-allyl-4aα-(3-methoxyphenyl)-9-bromo-1,2,3,4,4a,5,11,11aβ-octahydro-6H-indolo[2,3-g]isoquinoline is produced by using 2-(2,2-trichloroethoxycarbonyl)-4aα-(3-methoxyphenyl)-9-bromo-1,2,3,4,4a,5,11,11aβ-octahydro-6H-indolo[2,3-g]isoquinoline instead, 2-allyl-4aα-(3-methoxyphenyl)-10-bromo-1,2,3,4a,5,11,11aβ-octahydro-6H-indolo[2,3-g]isoquinoline is produced by using 2-(2,2,2-trichloroethoxycarbonyl)-4aα-(3-methoxyphenyl)-10-bromo-1,2,3,4,4a,5,11,11aβ-octahydro-6H-indolo[2,3-g]isoquinoline instead, 2-allyl-4aα-(3-methoxyphenyl)-7-fluoro-1,2,3,4,4a,5,11,11aβ-octahydro-6H-indolo[2,30]isoquinoline is produced by using 2(2,2,2-trichloroethoxycarbonyl)-4aα-(3-methoxyphenyl)-7-fluoro-1,2,3,4,4a,5,11,11aβ-octahydro-6H-indolo[2,2-g]isoquinoline instead, 2-allyl-4aα-(3-methoxyphenyl)-8-fluoro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-fluoro-1,2,3,4,4a,5,11,11aβ-octahydro-6H-indolo[2,3-g]isoquinoline instead, 2-allyl-4aα-(3-methoxyphenyl)-9-fluoro-1,2,3,4,4a,5,11,11aβ-octahydro-6H-indolo[2,3,-g]isoquinoline is produced by using 2-(2,2,2-trichloroethoxycarbonyl)-4aα-(3-methoxyphenyl)-9-fluoro-1,2,3,4,4a,5,11,11aβ-octahydro-6H-indolo[2,3-g]isoquinoline instead, 2-allyl-4aα-(3-methoxyphenyl)-10-fluoro-1,2,3,4,4a,5,11,11aβ-octahydro-6H-indolo[2,3-g]isoquinoline is produced by using 2-(2,2,2-trichloroethoxycarbonyl)-4aβ-(3-methoxyphenyl)-10-fluoro-1,2,3,4,4a,5,11,11aβ-octahydro-6H-indolo[2,3-g]isoquinoline instead, 2-allyl-4aα-(3-methoxyphenyl)-7-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)_7-nitro-1,2,3,4,4a,5,11,11aβ-octahydro-6H-indolo[2,3-g]isoquinoline instead, 2-allyl-4aα-(3-methoxyphenyl)-7-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-7-nitro-1,2,3,4,4a,5,11,11aβ-octahydro-6H-indolo[2,3-g]isoquinoline instead, 2-allyl-4aα-(3-methoxyphenyl)-8-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-8-nitro-1,2,3,4,4a,5,11,11aβ-octahydro-6H-indolo[2,3-g]isoquinoline instead, 2-allyl-4aα-(3-methoxyphenyl)-9-nitro-1,2,3,4,4a,5,11,11aβ-octahydro-6H-indolo[2,3-g]isoquinoline is produced by using 2-(2,2,2-trichloroethoxycarbonyl)-4aα-(3-methoxyphenyl)-9-nitro-1,2,3,4,4a,5,11,11aβ-octahydro-6H-indolo[2,3-g]isoquinoline instead, and 2-allyl-4aα-(3-methoxyphenyl)-10-nitro-1,2,3,4,4a, 5,11,11aβ-octahydro-6H-indolo[2,3,-g]isoquinoline is produced by using 2-(2,2,2-trichloroethoxycarbonyl)-4aα-(3-methoxyphenyl)-10-nitro-1,2,3,4,4a,5,11,11aβ-octahydro-6H-indolo[2,3,-g]isoquinoline instead, and 2-allyl-4aα-(3-methoxyphenyl)-1,2,3,4,4a,5,11,11aβ-octahydro-6-methyl-indolo[2,3-g]isoquinoline is produced by using 2-(2,2,2-trichloroethoxycarbonyl)-4aα-(3-methoxyphenyl)-1,2,3,4,4a,5,11,11aβ-octahydro-6-methyl-indolo[2,3-g]isoquinoline instead.

Example 30

2-Allyl-4aα-(3-hydroxyphenyl)-1,2,3,4,4a,5,11,11aβ-octahydro-6H-indolo[2,3-g]isoquinoline 31

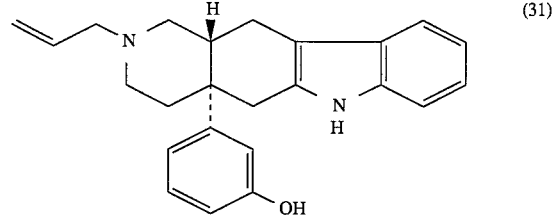

(31)

In an atmosphere of argon, 130 mg of 2-allyl-4aα-(3-methoxyphenyl)-1,2,3,4,4a,5,11,11aβ-octahydro-6H-indolo[2,3-g]isoquinoline was dissolved in 5 ml of anhydrous DMF and the produced solution and 0.35 ml of n-propane thiol, and 390 mg of potassium-t-butoxide added thereto were stirred at 130° C. for six hours. The resultant mixture was cooled to room temperature, distilled under a vacuum to expel DMF, combined with 5 ml of water and extracted three times from 20 ml of chloroform. The organic layers consequently separated were combined, washed with a saturated aqueous saline solution, dried, and concentrated, to afford 130 mg of an oily substance. When this oily substance was separated and refined by column chromatography [silica gel; chloroform/methanol/28% aqua ammonia (95/5/0.2)], 110 mg of a power was obtained. When this powder was suspended in 1 ml of methanol, converted into a methanesulfonate by addition of 22 μl of methanesulfonic acid, and separated and refined by column chromatography [Sephadex; LH-20; methanol], 130 mg of crude crystals was obtained. When these crude crystals were recrystallized from methanol-ethanol, 67 mg of the methanesulfonate of the captioned compound (decomposed at 250° C.) (yield 42.2%) was obtained.

IR (KBr) cm$^{-1}$: 3416, 1601, 1460, 1212, 1160, 1042

FAB-MS (m/z): 359 (M$^+$+1)

NMR (DMSO-d$_6$) 500 MHz δ: 2.03 (1H, m), 2.32 (3H, s), 2.54–2.62 (3H, m), 2.87–3.02 (3H, m), 3.10 (1H, d, J=15.8 Hz), 3.30–3.41 (2H, m), 3.61 (1H, m), 3.79 (2H, m), 5.51–5.56 (2H, m), 5.92 (1H, m), 6.54 (1H, dd, J=7.9 Hz, 1.8 Hz), 6.89–6.94 (3H, m), 6.98 (1H, m), 7.04 (1H, t, J=7.9 Hz), 7.18 (1H, d, J=7.9 Hz), 7.33 (1H, d, J=7.9 Hz), 9.26 (1H, s), 9.64 (1H, br), 10.61 (1H, s)

Elementary analyses For C$_{24}$H$_{26}$N$_2$O.CH$_3$SO$_3$H.0.2H$_2$O

|  | C | H | N | S |
|---|---|---|---|---|
| Calculated | 65.53 | 6.69 | 6.11 | 7.00 |
| Found | 65.44 | 6.60 | 6.08 | 7.02 |

Similarly, 2-allyl-4aα-(3-hydroxyphenyl)-7-methyl-1,2,3,4,4a,5,11,11aβ-octahydro-6H-indolo[2,3-g]isoquinoline is produced by using 2-allyl-4aα-(3-methoxyphenyl)-7-methyl-1,2,3,4,4a,5,11,11aβ-octahydro-6H-indolo[2,3-g]isoquinoline instead of 2-allyl-4aα-(3-methoxypheny) -1,2,3,4,4a,5,11,11aβ-octahydro-6H-indolo[2,3-g]isoquinoline, 2-allyl-4aα-(3-hydroxyphenyl)-8-methyl-1,2,3,4,4a,5,11,11aβ-octahydro-6H-indolo[2,3-g]isoquinoline is produced by using 2-allyl-4aα-(3-methoxyphenyl)-8-methyl-1,2,3,4,4a,5,11,11aβ-octahydro-6H-indolo[2,3-g]isoquinoline instead, 2-allyl-4aα-(3-hydroxyphenyl)-9-methyl-1,2,3,4,4a,5,11,11aβ-octahydro-6H-indolo[2,3-g]isoquinoline is produced by using 2-allyl-4aα-(3-methoxyphenyl)-9-methyl-1,2,3,4,4a,5,11,11aβ-octahydro-6H-indolo[2,3-g]isoquinoline instead, 2-allyl-4aα-(hydroxyphenyl)-10-methyl-1,2,3,4,4a,5,11,11aβ-octahydro-6H-indolo[2,3-g]isoquinoline is produced by using 2-allyl-4aα-(3-methoxyphenyl)-10-methyl-1,2,3,4,4a,5,11,11aβ-octahydro-6H-indolo[2,3-g]isoquinoline instead, 2-allyl-4aα-(3-hydroxyphenyl)-7-chloro-1,2,3,4,4a,5,11,11aβ-octahydro-6H-indolo[2,3-g]isoquinoline is produced by using 2-allyl-4aα-(3-methoxyphenyl)-7-chloro-1,2,3,4,4a,5,11,11aβ-octahydro-6H-indolo[2,3g]isoquinoline instead, 2-allyl-4aα-(3-hydroxyphenyl)-8-chloro-1,2,3,4,4a,5,11,11aβ-octahydro-6H-indolo[2,3-g]isoquinoline is produced by using 2-ally-4aα-(3-methoxyphenyl)-8-chloro-1,2,3,4,4a,5,11,11aβ-octahydro-6H-indolo[2,3-g]isoquinoline instead, 2-allyl-4aα-(3-hydroxyphenyl)-9-chloro-1,2,3,4,4a,5,11,11aβ-octahydro-6H-indolo[2,3-g]isoquinoline is produced by using 2-allyl-4aα-(3-methoxyphenyl)-9-chloro-1,2,3,4,4a,5,11,11aβ-octahydro-6H-indolo[2,3-g]isoquinoline instead, 2-allyl-4aα-(3-hydroxyphenyl)-10-chloro-1,2,3,4,4a,5,11,11aβ-octahydro-6H-indolo[2,3-g]isoquinoline is produced by using 2-allyl-4aα-(3-methoxyphenyl)-10-chloro-1,2,3,4,4a,5,11,11aβ-octahydro-6H-indolo[2,3-g]isoquinoline instead, 2-allyl-4aα-(3-hydroxyphenyl)-7-bromo-1,2,3,4,4a,5,11,11aβ-octahydro-6H-indolo[2,3-g]isoquinoline is produced by using 2-allyl-4aα-(3-methoxyphenyl)-7-bromo-1,2,3,4,4a,5,11,11aβ-octahydro-6H-indolo[2,3-g]isoquinoline instead, 2-allyl-4aα-(3-hydroxyphenyl)-8-bromo-1,2,3,4,4a,5,11,11aβ-octahydro-6H-indolo[2,3-g]isoquinoline is produced by using 2-allyl-4aα-(3-methoxyphenyl)-8-bromo-1,2,3,4,4a,5,11,11aβ-octahydro-6H-indolo[2,3-g]isoquinoline instead, 2-allyl-4aα-(3-hydroxyphenyl)-9-bromo-1,2,3,4,4a,5,11,11aβ-octahydro-6H-indolo[2,3-g]isoquinoline is produced by using 2-allyl-4aα-(3-methoxyphenyl)-9bromo-1,2,3,4,4a,5,11,11aβ-octahydro-6H-indolo[2,3-g]isoquinoline instead, 2-allyl-4aα-(3-hydroxyphenyl)-10-bromo-1,2,3,4,4a,5,11,11aβ-octahydro-6H-indolo[2,3-g]isoquinoline is produced by using 2-allyl-4aα-(3-methoxyphenyl)-10-bromo-1,2,3,4,4a,5,11,11aβ-octahydro-6H-indolo[2,3-g]isoquinoline instead, 2-allyl-4aα-(3-hydroxyphenyl)-7-fluoro-1,2,3,4,4a,5,11,11aβ-octahydro-6H-indolo[2,3-g]isoquinoline is produced by using 2-allyl-4aα-(3-methoxyphenyl)-7-fluoro-1,2,3,4,4a,5,11,11aβ-octahydro-6H-indolo[2,3-g]isoquinoline instead, 2-allyl-4aα-(3-hydroxyphenyl)-8-fluoro-1,2,3,4,4a,5,11,11aβ-octahydro-6H-indolo[2,3-g]isoquinoline is produced by using 2-allyl-4aα-(3-methoxyphenyl)-8-fluoro-1,2,3,4,4a,5,11,11aβ-octahydro-6H-indolo[2,3-g]isoquinoline instead, 2-allyl-4aα-(3-hydroxyphenyl)-9-fluoro-1,2,3,4,4a,5,11,11aβ-octahydro-6H-indolo[2,3-g]isoquinoline is produced by using 2-allyl-4aα-(3-methoxyphenyl)-9-fluoro-1,2,3,4,4a,5,11,11aβ-octahydro-6H-indolo[2,3-g]isoquinoline instead, 2-allyl-4aα-(3-hydroxyphenyl)-10-fluoro-1,2,3,4,4a,5,11,11aβ-octahydro-6H-indolo[2,3-g]isoquinoline is produced by using 2-allyl-4aα-(3-methoxyphenyl)-10-fluoro-1,2,3,4,4a,5,11,11aβ-octahydro-6H-indolo[2,3-g]isoquinoline instead, 2-allyl-4aα-(3-hydroxyphenyl)-7-nitro-1,2,3,4,4a,5,11,11aβ-octahydro-6H-indolo[2,3-g]isoquinoline is produced by using 2-allyl-4aα-(3-methoxyphenyl)-7-nitro-1,2,3,4,4a,5,11,11aβ-octahydro-6H-indolo[2,3-g]isoquinoline instead, 2-allyl-4aα-(3-hydroxyphenyl)-8-nitro-1,2,3,4,4a,5,11,11aβ-octahydro-6H-indolo[2,3-g]isoquinoline is produced by using 2-allyl-4aα-(3-methoxyphenyl)-8-nitro-1,2,3,4,4a,5,11,11aβ-octahydro-6H-indolo[2,3-g]isoquinoline instead, 2-allyl-4aα-3-hydroxyphenyl)-9-nitro-1,2,3,4,4a,5,11,11aβ-octahydro-6H-indolo[2,3-g]isoquinoline is produced by using 2-allyl-4aα-(3-methoxyphenyl)-9-nitro-1,2,3,4,4a,5,11,11aβ-octahydro-6H-indolo[2,3-g]isoquinoline instead, 2-allyl-4aα-(3-hydroxyphenyl)-10-nitro-1,2,3,4,4a,5,11,11aβ-octahydro-6H-indolo[2,3-g] isoquinoline is produced by using 2-allyl-4aα-(3-methoxyphenyl)-10-nitro-1,2,3,4,4a,5,11,11aβ-octahydro-6H-indolo[2,3-g]isoquinoline instead, and 2-allyl-4aα-(3-hydroxyphenyl)-1,2,3,4,4a,5,11,11aβ-octahydro-6-methyl-indolo[2,3-g]isoquinoline is produced by using 2-allyl-4aα-(3-methoxyphenyl)-1,2,3,4,4a,5,11,11aβ-octahydro-6-methyl-indolo[2,3-g]isoquinoline instead.

Referential Example 3

2-(2,2,2-Trichloroethoxycarbonyl)-4aα-(3-methoxyphenyl)-6-acetoxy-1,2,3,4,4a,5,6,7,8,8aβ-decahydroisoquinoline 32

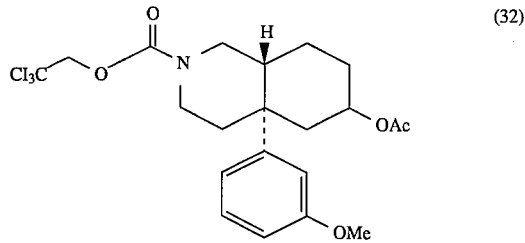

(32)

In an atmosphere of argon, 2.64 g of proton sponge was dissolved in 60 ml of anhydrous 1,2-dichloroethane and the produced solution was cooled to 0° C. and combined with 1.35 ml of 2,2,2-trichloroethyl chloroformate. The resultant mixture and a solution of 2.61 g of 2-methyl-4aα-(3-methoxyphenyl)-6-acetoxy-1,2,3,4,4a,5,6,7,8,8aβ-decahydroisoquinoline in 15 ml of anhydrous 1,2-dichloroethane added dropwise thereto were heated to room temperature and stirred for 30 minutes. The mixture was distilled under a vacuum to expel 1,2-dichloroethane, combined with 60 ml of ethyl acetate, washed with 20 ml of 1N hydrochloric acid and 20 ml of a saturated aqueous saline solution, dried, and concentrated, to afford 4.14 g of an oily substance. When this oily substance was separated and refined by column chromatography [silica gel; cyclohexane/ethyl acetate (4/1)], 950 mg of 6β-acetoxy form and 2.41 g of a mixture of 6α-acetoxy form and 6β-acetoxy form (yield 85.3%) was obtained.

IR (Liquid film method) cm$^{-1}$: 1717, 1433, 1241, 1125, 1033, 716

EI-MS (m/z): 477 (M$^+$) 479, 481

NMR (CDCl$_3$) 500 MHz δ: 1.43–1.49 (2H, m), 1.65 (1H, td, J=13.2 Hz, 4.0 Hz), 1.74 (1H, m), 1.83 (1H, m), 1.96 (3H, s), 2.05 (1H, brd, J=14.3 Hz), 2.13–2.19 (2H, m), 2.47 (1H, m), 2.60 (1H, m), 3.58 (1H, m), 3.81 (3H, s), 3.95 (1H, m), 4.07 (1H, m), 4.39 (1H, m), 4.68–4.78 (2H, m), 6.74 (1H, dd, J=8.1 Hz, 2.2 Hz), 6.99–7.05 (2H, m), 7.26 (1H, t, J=8.1 Hz)

Referential Example 4

2-Cyclopropylcarbonyl-4aα-(3-methoxyphenyl)-6β-acetoxy-1,2,3,4,4a,5,6,7,8,8aβ-decahydroisoquinoline 33

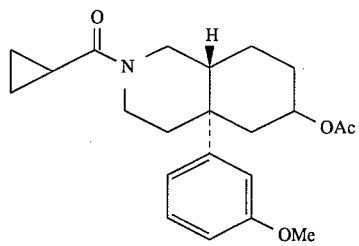
(33)

In an atmosphere of argon, 945 mg of 2-(2,2,2-trichloroethoxycarbonyl)-4aα-(3-methoxyphenyl)-6β-acetoxy-1,2,3,4,4a,5,6,7,8,8aβ-decahydroisoquinoline was dissolved in 20 ml of acetic acid, combined with 1.30 g of zinc dust, and stirred at room temperature for 24 hours. The resultant mixture was filtered to remove zinc, distilled under a vacuum to expel acetic acid, alkalinized by addition of a saturated aqueous solution of sodium hydrogen carbonate, and extracted three times from 50 ml of chloroform. The organic layers consequently separated were combined, washed with a saturated aqueous saline solution, dried, and concentrated to produce 570 mg of a reaction mixture. In an atmosphere of argon, this reaction mixture was dissolved in 20 ml of anhydrous dichloromethane and the produced solution and 0.55 ml of triethylamine and 0.27 ml of cyclopropanecarbonyl chloride added thereto were stirred at room temperature for two hours. When the resultant mixture was washed with 1N hydrochloric acid and water, dried, and concentrated, and 790 mg of an oily substance was obtained. When this oily substance was separated and refined by column chromatography [silica gel; chloroform/ethyl acetate (9/1)], 430 mg of the captioned compound (yield 58.6%) was obtained.

IR (Liquid film method) cm$^{-1}$: 1731, 1634, 1439, 1243, 1031

EI-MS (m/z): 371 (M$^+$)

NMR (CDCl$_3$) 400 MHz δ: 0.69–0.78 (2H, m), 0.92–1.00 (2H, m), 1.39–1.50 (2H, m), 1.63 (1H, m), 1.69–1.82 (3H, m), 1.96 (3H, s), 2.04–2.18 (3H, m), 2.48 (1H, m), 2.55–2.72 (1H, br), 3.40–3.58 (1H, br), 3.81 (3H, s), 4.01–4.43 (3H, m), 6.74 (1H, dd, J=8.3 Hz, 2.0 Hz), 7.01–7.06 (2H, m), 7.26 (1H, t, J=8.1 Hz)

Referential Example 5

2-Cyclopropylmethyl-4aα-(3-methoxyphenyl)-6β-hydroxy-1,2,3,4,4a,5,6,7,8,8aβ-decahydroisoquinoline 34

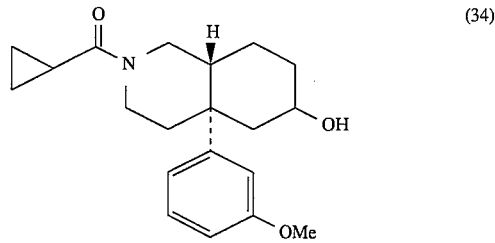
(34)

In an atmosphere of argon, 190 mg of lithium aluminum hydride was suspended in 15 ml of anhydrous THF and cooled to 0° C. The cooled suspension consequently formed and a solution of 430 mg of 2-cyclopropylcarbon-4aα-(3-methoxyphenyl)-6β-acetoxy-1,2,3,4,4a,5, 6,7,8,8aβ-decahydroisoquinoline in 5 ml of anhydrous THF added dropwise thereto were heated to room temperature and stirred for two hours. The resultant mixture was cooled to 0° C. and then combined with ethyl acetate and a saturated aqueous solution of sodium tartrate. The mixture was filtered to remove insolubles and distilled under a vacuum to expel ethyl acetate and produce 360 mg of the captioned compound (yield 98.6%).

IR (Liquid film method) cm$^{-1}$: 3340, 2942, 1607, 1580, 1241, 1075, 1052, 731

EI-MS (m/z): 315 (M$^+$), 314

NMR (CDCl$_3$) 400 MHz δ: 0.04–0.09 (2H, m), 0.44–0.50 (2H, m), 0.83 (1H, m), 1.36–1.42 (2H, m), 1.64–1.86 (4H, m), 1.93–2.28 (6H, m), 2.39 (1H, m), 2.68 (1H, t, J=12.0 Hz), 2.76 (1H, d, J=11.2 Hz), 2.92 (1H, m), 3.31 (1H, m), 3.80 (3H, s), 6.69 (1H, m), 7.01–7.05 (2H, m), 7.21 (1H, t, J=8.0 Hz)

Referential Example 6

2-Cyclopropylmethyl-4aα-(3-methoxyphenyl)-6-oxo-1,2,3,4,4a,5,6,7,8,8aβ-decahydroisoquinoline 35

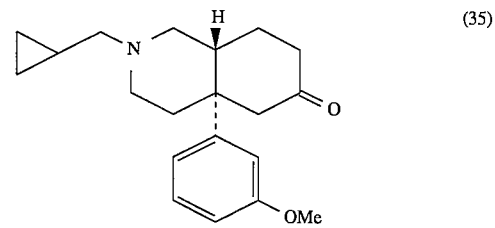
(35)

In an atmosphere of argon, 0.11 ml of oxalyl chloride was dissolved in 5 ml of anhydrous dichloromethane and the produced solution was cooled to −55° C. The cooled solution and a solution of 0.20 ml of DMSO in 0.5 ml of anhydrous dichloromethane added dropwise thereto were stirred at −55° C. for five minutes. The resultant mixture and a solution of 360 mg of 2-cyclopropylmethyl-4aα-(3-methoxyphenyl)-6β-hydroxy-1,2,3,4,4a,5,6,7,8,8aβ-decahydroisoquinoline in 2 ml of anhydrous dichloromethane added dropwise thereto were stirred at −55° C. for 15 minutes. The produced mixture and 1.0 ml of triethylamine added dropwise thereto were heated to room temperature. The resultant reaction solution was combined with 5 ml of water and separated in two layers. The organic layer consequently obtained was washed with a saturated aqueous saline solution, dried, and concentrated, to afford 330 mg of an oily substance. When this oily substance was separated and refined by column chromatography [silica gel; chloroform/methanol/28% aqua ammonia (98/2/0.1)], 290 mg of the captioned compound (yield 81.1%) was obtained.

By the procedure of Referential Examples 4 to 6, from 1.21 g of a mixture of 2-(2,2,2-trichloroethoxycarbonyl)-4aα-(3-methoxyphenyl)-6α-acetoxy-1,2,3,4,4a,5,6,7,8,8aβ-decahydroisoquinoline with 2-(2,2,2-trichloroethoxycarbonyl)-4aα-(3-methoxyphenyl)-6β-acetoxy-1,2,3,4,4a,5,6,7,8,8aβ-decahydroisoquinoline, 480 mg of 2-cyclopropylmethyl-4aα-(3-methoxyphenyl)-6-oxo-1,2,3,4,4a,5,6,7,8,8aβ-decahydroisoquinoline is produced (yield 60.6%).

IR (Liquid film method) cm$^{-1}$: 2942, 1715, 1582, 1245, 1050, 754

EI-MS (m/z): 313 (M$^+$)

NMR (CDCl$_3$) 400 MHz δ: 0.06–0.12 (2H, m), 0.46–0.54 (2H, m), 0.87 (1H, m), 1.94–2.11 (4H, m), 2.24–2.54 (7H, m), 2.68 (1H, t, J=11.7 Hz), 2.84 (1H, m), 2.92 (1H, m), 3.05 (1H, m), 3.78 (3H, s), 6.69 (1H, m), 6.97–7.00 (2H, m), 7.21 (1H, t, J=8.3 Hz)

By the procedure of Referential Examples 4 to 6, 2-allyl-4aα-(3-methoxyphenyl)-6-oxo-1,2,3,4,4a,5,6,7,8,8aβ-decahydroisoquinoline is produced by using acryloyl chloride instead of cyclopropanecarbonyl chloride, 2-benzyl-4aα-(3-methoxyphenyl)-6-oxo-1,2,3,4,4a,5,6,7,8,8aβ-decahydroisoquinoline is produced by using benzoyl chloride instead, and 2-phenethyl-4aα-(3-methoxyphenyl)-6-oxo-1,2,3,4,4a,5,6,7,8,8aβ-decahydroisoquinoline is produced by using phenylacetyl chloride instead.

Example 31

2-Cyclopropylmethyl-4aα-(3-methoxyphenyl)-9-fluoro-1,2,3,4,4a,5,11,11aβ-octahydro-6H-indolo[2,3-g]isoquinoline 36

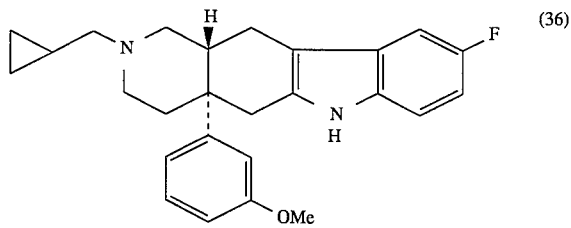

(36)

In an atmosphere of argon, 320 mg of 2-cyclopropylmethyl-4aα-(3-methoxyphenyl)-6-oxo-1,2,3,4,4a,5,6,7,8,8aβ-decahydroisoquinoline and 195 mg of 4-fluorophenyl hydrazine hydrochloride were dissolved in 10 ml of ethanol and the produced solution was heated to 80° C. This solution and 0.65 ml of methanesulfonic acid added thereto were stirred at 80° C. for 15 minutes and then cooled to room temperature. The resultant mixture was distilled under a vacuum to expel ethanol, alkalinized by addition of an aqueous 1N sodium hydroxide solution, and extracted three times from 30 ml of chloroform. The organic layers consequently separated were combined, washed with a saturated aqueous saline solution, dried, and concentrated, to afford 370 mg of a powder. When this powder was separated and refined by column chromatography [silica gel; chloroform/methanol (97/3)], 360 mg of the captioned compound (yield 87.2%) was obtained.

IR (Liquid film method) cm$^{-1}$: 2898, 1607, 1580, 1489, 1460, 1294, 1238, 1044

EI-MS (m/z): 404 (M$^+$), 242, 161

NMR (CDCl$_3$) 400 MHz δ: 0.05–0.14 (2H, m), 0.47–0.56 (2H, m), 0.90 (1, m), 1.95–2.07 (2H, m), 2.22–2.32 (2H, m), 2.39 (1H, m), 2.53–2.64 (2H, m), 2.87–2.99 (4H, m), 3.06 (1H, d, J=16.1 Hz), 3.15 (1H, d, J=8.8 Hz), 3.68 (3H, s), 6.62 (1H, m), 6.80 (1H, td, 9.0 Hz, 2.4 Hz), 7.00–7.11 (5H, m), 7.58 (1H, brs)

Similarly, 2-cyclopropylmethyl-4aα-(3-methoxyphenyl)-1,2,3,4,4a,5,11,11aβ-octahydro-6H-indolo[2,3-g]isoquinoline is produced by using phenyl hydrazine instead of 4-fluorophenylhydrazine, 2-cyclopropylmethyl-4aα-(3-methoxyphenyl)-8-fluoro-1,2,3,4,4a,5,11,11aβ-octahydro-6H-indolo[2,3-g]isoquinoline and 2-cyclopropylmethyl-4aα-(3-methoxyphenyl)-10-fluoro-1,2,3,4,4a,5,11,11aβ-octahydro-6H-indolo[2,3-g]isoquinoline are produced by using 3-fluorophenylhydrazine instead, 2-cyclopropylmethyl-4aα-(3-methoxyphenyl)-7-fluoro-1,2,3,4,4a,5,11,11aβ-octahydro-6H-indolo[2,3-g]isoquinoline is produced by using 2-fluorophenylhydrazine instead, 2-cyclopropylmethyl-4aα-(3-methoxyphenyl)-9-methyl-1,2,3,4,4a,5,11,11aβ-octahydro-6H-indolo[2,3-g]isoquinoline is produced by using 4-methylphenylhydrazine instead, 2-cyclopropylmethyl-4aα-(3-methoxyphenyl)-8-methyl-1,2,3,4,4a,5,11,11aβ-octahydro-6H-indolo[2,3-g]isoquinoline and 2-cyclopropylmethyl-4aα-(3-methoxyphenyl)-10-methyl-1,2,3,4,4a,5,11,11aβ-octahydro-6H-indolo[2,3-g]isoquinoline are produced by using 3-methylphenylhydrazine instead, 2-cyclopropylmethyl-4aα-(3-methoxyphenyl)-7-methyl-1,2,3,4,4a,5,11,11aβ-octahydro-6H-indolo[2,3-g]isoquinoline is produced by using 2-methylphenylhydrazine instead, 2-cyclopropylmethyl-4aα-(3-methoxyphenyl)-9-chloro-1,2,3,4,4a,5,11,11aβ-octahydro-6H-indolo[2,3-g]isoquinoline is produced by using 4-chlorophenylhydrazine instead, 2-cyclopropylmethyl-4aα-(3-methoxyphenyl)-8-chloro-1,2,3,4,4a,5,11,11aβ-octahydro-6H-indolo[2,3-g]isoquinoline and 2-cyclopropylmethyl-4aα-(3-methoxyphenyl)-10-chloro-1,2,3,4,4a,5,11,11aβ-octahydro-6H-indolo[2,3-g]isoquinoline are produced by using 3-chlorophenylhydrazine instead, 2-cyclopropylmethyl-4aα-(3-methoxyphenyl)-7-chloro-1,2,3,4,4a,5,11,11aβ-octahydro-6H-indolo[2,3-g]isoquinoline is produced by using 2-chlorophenylhydrazine instead, 2-cyclopropylmethyl-4aα-(3-methoxyphenyl)-9-bromo-1,2,3,4,4a,5,11,11aβ-octahydro-6H-indolo[2,3-g]isoquinoline is produced by using 4-bromophenylhydrazine instead, 2-cyclopropylmethyl-4aα-(3-methoxyphenyl)-8-bromo-1,2,3,4,4a,5,11,11aβ-octahydro-6H-indolo[2,3-g]isoquinoline and 2-cyclopropylmethyl-4aα-(3-methoxyphenyl)-10-bromo-1,2,3,4,4a,5,11,11aβ-octahydro-6H-indolo[2,3-g]isoquinoline are produced by using 3-bromophenylhydrazine instead, 2-cyclopropylmethyl-4aα-(3-methoxyphenyl)-7-bromo-1,2,3,4,4a,5,11,11aβ-octahydro-6H-indolo[2,3-g]isoquinoline is produced by using 2-bromophenylhydrazine instead, 2-cyclopropylmethyl-4aα-(3-methoxyphenyl)-9-nitro-1,2,3,4,4a,5,11,11aβ-octahydro-6H-indolo[2,3-g]isoquinoline is produced by using 4-nitrophenylhydrazine instead, 2-cyclopropylmethyl-4aα-(3-methoxyphenyl)-8-nitro-1,2,3,4,4a,5,11,11aβ-octahydro-6H-indolo[2,3-g]isoquinoline and 2-cyclopropylmethyl-4aα-(3-methoxyphenyl)-10-nitro-1,2,3,4,4a,5,11,11aβ-octahydro-6H-indolo[2,3-g]isoquinoline are produced by using 3-nitrophenylhydrazine, 2-cyclopropylmethyl-4aα-(3-methoxyphenyl)-7-nitro-1,2,3,4,4a,5,11,11aβ-octahydro-6H-indolo[2,3-g]isoquinoline is produced by using 2-nitrophenylhydrazine instead, and 2-cyclopropylmethyl-4aα-(3-methoxyphenyl)-1,2,3,4,4a,5,11,11aβ-octahydro-6-methyl-indolo[2,3-g]isoquinoline is produced by using 1-methyl-1-phenyl hydrazine instead.

Example 32

2-Cyclopropylmethyl-4aα-(3-hydroxyphenyl)-
9-fluoro-1,2,3,4,4a,5,11,11aβ-octahydro-6H-indolo
[2,3-g]isoquinoline 37

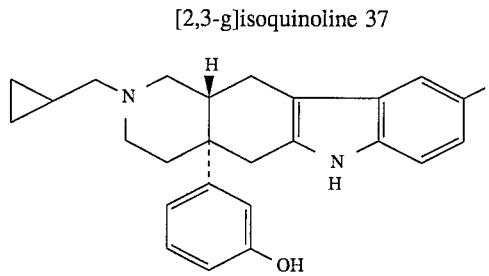

(37)

In an atmosphere of argon, 250 mg of 2-cyclopropylmethyl-4aα-(3-methoxyphenyl)-9-fluoro-1,2,3,4,4a,5,11,11aβ-octahydro-6H-indolo[2,3-g]isoquinoline was dissolved in 6 ml of anhydrous DMF and the produced solution and 350 mg of potassium-t-butoxide and 0.31 ml of n-propane thiol added thereto were stirred at 150° C. for three hours. The resultant mixture was cooled to room temperature, distilled under a vacuum to expel DMF, combined with 10 ml of water, and extracted three times from 30 ml of chloroform/methanol (3/1). The organic layers consequently separated were combined, washed with a saturated aqueous saline solution, dried, and concentrated to afford 220 mg of a powder. This powder was suspended in 2 ml of methanol, converted into a methanesulfonate by addition of 40 μl of methanesulfonic acid, and separated and refined by column chromatography [Sephadex; LH-20; methanol], to produce 199 mg of the methanesulfonate of the captioned compound (decomposed at 245° C.) (yield 66.2%).

IR (KBr) cm$^{-1}$: 3392, 1586, 1477, 1249, 1173, 1049, 790

FAB-MS (m/z): 391 (M$^+$+1)

NMR (DMSO-d$_6$) 500 MHz δ: 0.35–0.41 (2H, m), 0.61–0.65 (2H, m), 1.07 (1H, m), 2.07 (1H, m), 2.31 (3H, s), 2.53–2.67 (3H, m), 2.87–3.06 (5H, m), 3.12 (1H, d, J=16.5 Hz), 3.48 (1H, m), 3.51 (1H, m), 3.72 (1H, m), 6.54 (1H, m), 6.80 (1H, td, J=9.2 Hz, 2.4 Hz), 6.92 (1H, brs), 6.93 (1H, brd, J=8.6 Hz), 7.04 (1H, t, J=7.9 Hz), 7.09 (1H, dd, J=9.8 Hz, 2.4 Hz), 7.17 (1H, dd, J=8.5 Hz, 4.3 Hz), 9.26 (1H, s), 9.40 (1H, brs), 10.73 (1H, s)

Elementary analyses For $C_{25}H_{27}N_2OF \cdot CH_3SO_3H$

|  | C | H | N | F | S |
|---|---|---|---|---|---|
| Calculated | 64.18 | 6.42 | 5.76 | 3.90 | 6.59 |
| Found | 63.91 | 6.61 | 5.91 | 3.91 | 6.57 |

Example 33

2-Cyclopropylcarbonyl-4aα-(3-methoxyphenyl)-
7-chloro-1,2,3,4,4a,5,11,11aβ-octahydro-6H-indolo
[2,3-g]isoquinoline 38

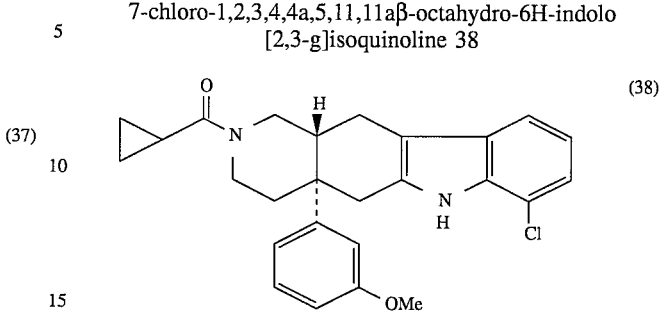

(38)

In an atmosphere of argon, 520 mg of 2-cyclopropylcarbonyl-4aα-(3-methoxyphenyl)-6-oxo-1,2,3,4,4a,5,6,7,8,8aβ-decahydroisoquinoline and 360 mg of 2-chlorophenyl hydrazine sulfate were dissolved in 10 ml of ethanol and the produced solution was heated to 80° C. The resultant mixture and 1.0 ml of methanesulfonic acid added thereto were stirred at 80° C. for 15 minutes and then cooled to room temperature. By separating the precipitated crystals through filtration, 480 mg of the captioned compound (yield 66.1%) was obtained.

IR (KBr) cm$^{-1}$: 3284, 1615, 1578, 1493, 1460, 1257, 1234, 1052, 878, 775

EI-MS (m/z): 434 (M$^+$), 432, 177

NMR (CDCl$_3$) 400 MHz δ: 0.75–0.80 (2H, m), 0.96–1.05 (2H, m), 1.74–1.88 (2H, m), 2.34–2.49 (2H, m), 2.75–2.99 (4H, m), 3.10–3.28 (2H, m), 3.70 (3H, s), 4.04–4.75 (2H, brm), 6.67 (1H, m), 6.97–7.05 (3H, m), 7.08 (1H, brd, J=7.9 Hz), 7.14 (1H, t, J=7.9 Hz), 7.33 (1H, d, J=7.6 Hz), 7.85 (1H, brs)

Similarly, 2-cyclopropylcarbonyl-4aα-(3-methoxyphenyl)-9-chloro-1,2,3,4,4a,5,11,11aβ-octahydro-6H-indolo[2,3-g]isoquinoline is produced by using 4-chlorophenyl hydrazine instead of 2-cyclophenyl hydrazine, and 2-cyclopropylcarbonyl-4aα-(3-methoxyphenyl)-8-chloro-1,2,3,4,4a,5,11,11aβ-octahydro-6H-indolo[2,3-g]isoquinoline and 2-cyclopropylcarbonyl-4aα-(3-methoxyphenyl)-10-chloro-1,2,3,4,4a,5,11,11aβ-octahydro-6H-indolo[2,3-g]isoquinoline are produced by using 3-chlorophenyl hydrazine instead.

Example 34

2-Cyclopropylmethyl-4aα-(3-methoxyphenyl)-7-chloro-1,2,3,4,4a,5,11,11aβ-octahydro-6H-indolo
[2,3-g]isoquinoline 39

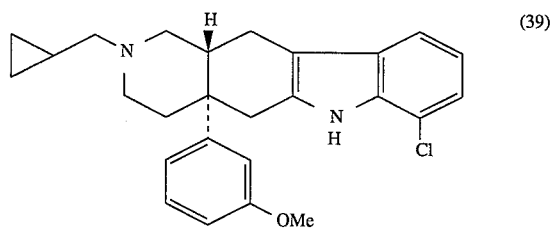

(39)

In an atmosphere of argon, 110 mg of lithium aluminum hydride was suspended in 10 ml of anhydrous THF and the suspension was cooled to 0° C. This suspension and a suspension of 400 mg of 2-cyclopropylcarbonyl-4aα-(3-methoxyphenyl)-7-chloro-1,2,3,4,4a,5,11,11aβ-octahydro-6H-indolo[2,3-g]isoquinoline in 10 ml of anhydrous THF added dropwise thereto were heated to room temperature and stirred for two hours. The resultant mixture was cooled to 0° C. and combined with ethyl acetate and a saturated aqueous solution of potassium sodium tartrate. The produced mixture was filtered to remove insolubles and distilled under a vacuum to expel ethyl acetate and produce 440 mg of an oily substance. When this oily substance was separated and refined by column chromatography [silica gel; chloroform/methanol (98/2)], there were obtained 390 mg of crude crystals. When these crude crystals were recrystallized from ethyl acetate, 256 mg of the captioned compound in a purified form (m.p. 96° to 98° C.) (yield 66.1%) was obtained.

IR (KBr) cm$^{-1}$: 2906, 1607, 1578, 1491, 1460, 1243, 1052, 777

EI-MS (m/z): 420 (M$^+$), 422, 242

NMR (CDCl$_3$) 500 MHz δ: 0.08–0.24 (2H, m), 0.50–0.56 (2H, m), 0.90 (1H, m), 1.99–2.08 (2H, m), 2.24–2.34 (2H, m), 2.41 (1H, m), 2.57–2.67 (2H, m), 2.91–3.03 (4H, m), 3.13 (1H, d, J=15.9 Hz), 3.17 (1H, brd, J=9.2 Hz), 3.69 (3H, s), 6.62 (1H, m), 6.98 (1H, t, J=7.9 Hz), 7.01–7.07 (3H, m), 7.10 (1H, t, J=7.9 Hz), 7.32 (1H, d, J=7.9 Hz), 7.81 (1H, brs)

Similarly, 2-cyclopropylmethyl-4aα-(3-methoxyphenyl)-8-chloro-1,2,3,4,4a,5,11,11aβ-octahydro-6H-indolo[2,3-g]isoquinoline is produced by using 2-cyclopropyl-carbonyl-4aα-(3-methoxyphenyl)-8-chloro-1,2,3,4,4a,5,11,11aβ-octahydro-6H-indolo[2,3-g]isoquinoline instead of 2-cyclopropylcarbonyl-4aα-(3-methoxyphenyl)-7-chloro-1,2,3,4,4a,5,11,11aβ-octahydro-6H-indolo[2,3-g]isoquinoline, 2-cyclopropylmethyl-4aα-(3-methoxyphenyl)-9-chloro-1,2,3,4,4a,5,11,11aβ-octahydro-6H-indolo[2,3-g]isoquinoline is produced by using 2-cyclopropylcarbonyl-4aα-(3-methoxyphenyl)-9-chloro-1,2,3,4,4a,5,11,11aβ-octahydro-6H-indolo[2,3-g]isoquinoline instead, and 2-cyclopropylmethyl-4aα-(3-methoxyphenyl)-10-chloro-1,2,3,4,4a,5,11,11aβ-octahydro-6H-indolo[2,3-g]isoquinoline is produced by using 2-chloropropylcarbonyl-4aα-(3-methoxyphenyl)-10-chloro-1,2,3,4,4a,5,11,11aβ-octahydro-6H-indolo[2,3-g]isoquinoline instead.

Example 35

2-Cyclopropylmethyl-4aα-(3-hydroxyphenyl)-7-chloro-1,2,3,4,4a,5,11,11aβ-octahydro-6H-indolo[2,3-g]isoquinoline 40

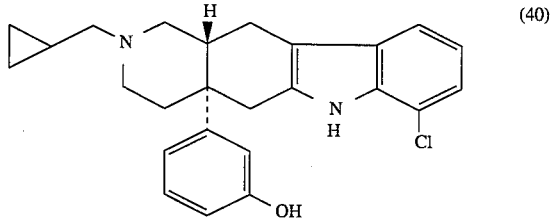

(40)

In an atmosphere of argon, 270 mg of 2-cyclopropylmethyl-4aα-(3-methoxyphenyl)-7-chloro-1,2,3,4,4a,5,11,11aβ-octahydro-6H-indolo[2,3-g]isoquinoline was dissolved in 6 ml of anhydrous DMF and the produced solution and 400 mg of potassium-t-butoxide and 0.36 ml of n-propane thiol added thereto were stirred at 150° C. for 2.5 hours. The resultant mixture was cooled to room temperature, distilled under a vacuum to expel DMF, combined with 5 ml of water, and extracted from 30 ml of chloroform/methanol (3/1). The organic layers consequently separated were combined, washed with a saturated aqueous saline solution, dried, and concentrated to afford 230 mg of a powder. When this powder was suspended in 2 ml of methanol, converted into a methanesulfonate by addition of 40 μl of methanesulfonic acid, and separated and refined by column chromatography [Sephadex; LH-20; methanol], 260 mg of crude crystals were obtained. When the crude crystals were recrystallized from methanol, 149 mg of the methanesulfonate of the captioned compound (decomposed at 260° C.) (yield 46.2%) was obtained.

IR (KBr) cm$^{-1}$: 3320, 1599, 1460, 1201, 1164, 1042, 772

FAB-MS (m/z): 407 (M$^+$+1)

NMR (DMSO-d$_4$) 400 MHz δ: 0.35–0.40 (2H, m), 0.61–0.66 (2H, m), 1.06 (1H, m), 2.06 (1H, m), 2.30 (3H, s), 2.54–2.68 (3H, m), 2.86–3.06 (5H, m), 3.20 (1H, brd, J=16.1 Hz), 3.37 (1H, m), 3.52 (1H, m), 3.73 (1H, m), 6.54 (1H, m), 6.88 (1H, m), 6.92–6.97 (2H, m), 7.02–7.07 (2H, m), 7.33 (1H, d, J=7.8 Hz), 9.27 (1H, s), 9.38 (1H, brs), 10.97 (1H, s)

Elementary analyses For C$_{25}$H$_{27}$N$_2$OCl.CH$_3$SO$_3$H.0H$_2$O

|  | C | H | N | Cl | S |
|---|---|---|---|---|---|
| Calculated | 61.64 | 6.25 | 5.53 | 7.00 | 6.33 |
| Found | 61.46 | 6.25 | 5.56 | 7.14 | 6.26 |

Similarly, 2-cyclopropylmethyl-4aα-(3-hydroxyphenyl)-8-chloro-1,2,3,4,4a,5,11,11aβ-octahydro-6H-indolo[2,3-g]isoquinoline is produced by using 2-cyclopropylmethyl-4aα-(3-methoxyphenyl)-8-chloro-1,2,3,4,4a,5,11,11aβ-octahydro-6H-indolo[2,3-g]isoquinoline instead of 2-cyclopropylmethy-4aα-(3-methoxyphenyl)-7-chloro-1,2,3,4,4a,5,11,11aβ-octahydro-6H-indolo[2,3-g]isoquinoline, 2-cyclopropylmethyl-4aα-(3-hydroxyphenyl)-9-chloro-1,2,3,4,4a,5,11,11aβ-octahydro-6H-indolo[2,3-g]isoquinoline is produced by using 2-cyclopropylmethyl-4aα-(3-methoxyphenyl)-9-chloro-1,2,3,4,4a,5,11,11aβ-octahydro-6H-indolo[2,3-g]isoquinoline instead, and 2-cyclopropylmethy-4aα-(3-hydroxyphenyl)-10-chloro-1,2,3,4,4a,5,11,11aβ-octahydro-6H-indolo[2,3-g]isoquinoline is produced by using 2-cyclopropylmethy-4aα-(3-methoxyphenyl)-10-chloro-1,2,3,4,4a,5,11,11aβ-octahydro-6H-indolo[2,3-g]isoquinoline.

Referential Example 7

Optical resolution of
(±)-2-methyl-4aα-(3-methoxyphenyl)-6-oxo-1,2,3,4,4a,5,11,11aβ-decahydroisoquinoline with
(±)-di-(p-toluoyl)-D-tartaric acid and
(−)-di-(p-toluoyl)-L-tartaric acid 41 42

In methanol, 3.13 g of (±)-2-methyl-4aα-(3-methoxyphenyl)-6-oxo-1,2,3,4,4a,5,11,11aβ-decahydroisoquinoline and 4.68 g of (+)-di-(p-toluoyl)-D-tartaric acid were dissolved. The produced solution was concentrated and crystallized. The resultant salt was dissolved by heating in methanol. In the solution, seeds of (−)-2-methyl-4aα-(3-methoxyphenyl)-6-oxo-1,2,3,4,4a,5,11,11aβ-decahydroisoquinoline. (+)-di-(p-toluoyl)-D-tartrate were left standing at room temperature for a whole day and night. The crystals consequently educed in the solution were separated by filtration and the separated crystals were separated by filtration and the separated crystals were repetitively recrystallized in the same manner as above, to obtain 1.65 g of crystals. These salt crystals were suspended in 15 ml of 1N sodium hydroxide and extracted two times from 25 ml of ethyl acetate. The organic layers consequently separated were washed with a saturated aqueous solution of sodium chloride, dried with anhydrous sodium sulfate, and concentrated, to afford 0.68 g of (−)-2-methyl-4aα-(3-methoxyphenyl)-6-oxo-1,2,3,4,4a,5,11,11aβ-decahydroisoquinoline (yield 43.5%). The crude crystals, on being recrystallized (ethyl acetate/n-hexane), produced 0.45 g of needle crystals (m.p. 91.3° to 91.8° C.).

Then, 4.28 g of the concentrate of the mother liquor produced by the resolution described above was suspended in 40 ml of 1N sodium hydroxide and extracted two times from 50 ml of ethyl acetate. The organic layers consequently separated were washed with a saturated aqueous solution of sodium chloride, dried with anhydrous sodium sulfate, and then concentrated, to afford 2.21 g of (±)-2-methyl-4aα-(3-methoxyphenyl)-6-oxo-1,2,3,4,4a,5,6,7,8,8aβ-decahydroisoquinoline and 3.12 g of (−)-di-(p-toluoyl)-L-tartaric acid. These compounds were dissolved in methanol, concentrated, and then crystallized. The resultant salt was dissolved by heating in methanol. In the solution, seeds of (+)-2-methyl-4aα-(3-methoxyphenyl)-6-oxo-1,2,3,4,4a,5,6,7,8,8aβ-decahydroisoquinoline.(−)-di-(p-toluoyl)-L-tartrate were left standing at room temperature for a whole day and night. The crystals consequently educed in the solution were separated by filtration, to afford 2.16 g of crystals. The salt crystals were suspended in 20 ml of 1N sodium hydroxide and extracted two times from 30 ml of ethyl acetate. The organic layers consequently separated were washed with a saturated aqueous solution of sodium chloride, dried with anhydrous sodium sulfate, and then concentrated, to form 0.89 g of (±)-2-methyl-4aα-(3-methoxyphenyl)-6-oxo-1,2,3,4,4a,5,6,7,8,8aβ-decahydroisoquinoline (yield 56.8%). The crude crystals, on being recrystallized from ethyl acetate/n-hexane, there were produced 0.60 g of needle crystals (m.p. 91.0° to 91.5° C.).

(−)-2-methyl-4aα-(3-methoxyphenyl)-6-oxo-1,2,3,4,4a,5,6,7,8,8aβ-decahydroisoquinoline $[\alpha]_D^{20}=-67°$ (C=2.0, MeOH)

IR (KBr) cm$^{-1}$: 2944, 2908, 2850, 2798, 1709, 1605, 1578

NMR (CDCl$_3$) 500 MHz δ: 1.88–2.00 (3H, m), 2.08 (1H, m), 2.32 (3H, s), 2.31–2.50 (5H, m), 2.60 (1H, m), 2.69 (1H, t, J=11.6 Hz), 2.84 (1H, dd, J=11.6 Hz, J=3.1 Hz), 2.93 (1H, dd, J=14.0 Hz, J=1.2 Hz), 3.78 (3H, s), 6.71 (1H, m), 6.97–7.00 (2H, m), 7.21 (1H, m)

Mass (m/e): 273 (M$^+$)

(+)-2-methyl-4aα-(3-methoxyphenyl)-6-oxo-1,2,3,4,4a,5,6,7,8,8aβ-decahydroisoquinoline $[\alpha]_D^{20}=+66°$ (C=2.0, MeOH)

IR (KBr) cm$^{-1}$: 2946, 2908, 2844, 2798, 1709, 1605, 1578

NMR (CDCl$_3$) 400 MHz δ: 1.88–2.00 (3H, m) 2.07 (1H, m), 2.32 (3H, s), 2.31–2.50 (5H, m), 2.60 (1H, m), 2.69 (1H, t, J=11.7 Hz), 2.84 (1H, m), 2.93 (1H, d, J=14.2 Hz) 3.78 (3H, s), 6.71 (1H, m), 6.97–7.00 (2H, m), 7.21 (1H, m)

Mass (m/e): 273 (M$^+$)

Referential Example 8

(−)-2-(2,2,2-Trichloroethoxycarbonyl)-4aα-(3-methoxyphenyl)-6-oxo-1,2,3,4,4a,5,6,7,8,8aβ-decahydroisoquinoline 43

In an atmosphere of argon, 598 mg of proton sponge was dissolved in 15 ml of anhydrous methylene chloride and 0.433 ml of 2,2,2-trichloroethoxycarbonyl chloride was added dropwise thereto in a stirred state. Then, the resultant mixture was kept cooled with ice and a solution of 507 mg of (−)-2-methyl-4aα-(3-methoxyphenyl)-6-oxo-1,2,3,4,4a,5,6,7,8,8aβ-decahydroisoquinoline in 5 ml of anhydrous methylene chloride was added dropwise thereto meantimes. The produced mixture was returned to room temperature and stirred continuously for two hours. The resultant reaction solution was concentrated, then redissolved in 20 ml of ethyl acetate, washed with 10 ml 1N hydrochloride acid, 10 ml of water, and 10 ml of a saturated aqueous solution of sodium chloride, dried with anhydrous sodium sulfate, and concentrated, to afford 1.41 g of an oily substance. When this oily substance was separated and refined by column chromatography [silica gel; cyclohexane/ethyl acetate (1/1)], 806 mg of the captioned compound (yield 100%) was obtained.

IR (liquid film method) cm$^{-1}$: 2958, 1715, 1607, 1582

NMR (CDCl$_3$) 500 MHz δ: 1.80 (1H, m), 2.03 (1H, m), 2.13 (1H, m), 2.25 (1H, m), 2.31–2.44 (4H, m), 2.85 (1H, m), 2.96 (1H, d, J=14.0 Hz), 3.53 (1H, m), 3.78 (3H, s), 4.03 (1H, m), 4.18 (1H, m), 4.71–4.81 (2H, m), 6.75 (1H, m), 6.95–6.98 (2H, m), 7.25 (1H, m)

Mass (m/e): 433 (M$^+$)

Referential Example 9

(−)-2-Cyclopropylcarbonyl-4aα-(3-methoxyphenyl)-6-oxo-1,2,3,4,4a,5,6,7,8,8aβ-decahydroisoquinoline 44

A solution of 800 mg of (−)-2-(2,2,2-trichloroethoxycarbonyl)-4aα-(3-methoxyphenyl)-6-oxo-1,2,3,4,4a,5,6,7,8,8aβ-decahydroisoquinoline in 20 ml of acetic acid and 1.2 g of zinc powder added thereto were stirred at room temperature for 3.5 hours. The resultant reaction mixture was filtered with a filter cell to remove zinc and washed three times with 20 ml of acetic acid. The washed mixture was concentrated, alkalinized by addition of a saturated aqueous solution of sodium hydrogen carbonate, and extracted three times from 40 ml of chloroform. The organic layers consequently separated were washed with a saturated aqueous solution of sodium chloride, dried with anhydrous sodium sulfate, and concentrated to afford 524 mg of an oily substance.

Subsequently, this oily substance was subjected to azeotropic distillation two times with 10 ml of benzene. In an atmosphere of argon, the resultant azeotropic mixture was dissolved in 18 ml of anhydrous methylene chloride and combined with 0.513 ml of anhydrous triethylamine and the produced mixture and 0.267 ml of cyclopropanecarbonyl chloride added dropwise thereto at room temperature was continuously stirred for four hours. The resultant mixture was deprived of methylene chloride and redissolved in 20 ml of ethyl acetate. The produced solution was washed with 1N HCl and a saturated aqueous solution of sodium chloride, dried with anhydrous sodium sulfate, and concentrated, to afford 641 mg of an oily substance. When this oily substance was separated and refined by column chromatography [silica gel:cyclohexane/ethyl (3/1)], 345 mg of the captioned compound (yield 57.4%) was obtained.

m.p.=149° to 150° C. (recrystallized with n-hexane/ethyl acetate)

$[\alpha]_D^{20}=-107°$ (C=1.0, CHCl$_3$)

IR (KBr) cm$^{-1}$: 2934, 2872, 1715, 1624, 1599

NMR (CDCl$_3$) 400 MHz δ: 0.76–0.79 (2H, m), 0.91–1.00 (2H, m), 1.59 (1H, s), 1.74–1.84 (2H, m), 2.03 (1H, m), 2.16 (1H, d, J=13.7 Hz), 2.25 (1H, m), 2.38–2.42 (3.5H, m), 2.76

(0.5H, m), 2.97 (1H, d, J=14.2 Hz), 3.07 (0.5H, m), 3.27 (0.5H, m), 3.79 (3H, s), 4.01 (0.5H, m), 4.12 (0.5H, m), 4.33 (0.5H, m), 4.59 (0.5H, m), 6.75 (1H, dd, J=8.3 Hz, J=2.4 Hz), 6.95–7.01 (2H, m), 7.25 (1H, m)

Mass (m/e): 327 (M$^+$)

Example 36

(+)-2-Cyclopropylcarbonyl-4aα-(3-methoxyphenyl)-1,2,3,4,4a,5,11,11aβ-octahydro-6H-indolo[2,3-g] isoquinoline 45

In 4 ml of ethanol, 340 mg of (−)-2-cyclopropylcarbonyl-4aα-(3-methoxyphenyl)-6-oxo-1,2,3,4,4a,5,6,7,8,8aβ-decahydroisoquinoline and 0.113 ml of phenyl hydrazine were dissolved. The solution kept refluxed thermally and 0.675 ml of methanesulfonic acid added thereto meanwhile were stirred and further refluxed continuously for 0.5 hour. The resultant reaction mixture was cooled to room temperature, kept cooled with ice, combined with 20 ml of a saturated aqueous solution of sodium hydrogen carbonate, and extracted two times from 30 ml of chloroform. The organic layers consequently separated were combined, washed with a saturated aqueous solution of sodium chloride, dried with anhydrous sodium sulfate, and then concentrated, to afford 507 mg of an oily substance. When this oily substance was separated and refined by column chromatography [silica gel; chloroform], 354 mg of the captioned compound (yield 85.0%) was obtained.

IR (KBr) cm$^{-1}$: 3204, 2902, 1607, 1460

NMR (CDCl$_3$) 500 MHz δ: 0.75–0.78 (2H, m), 0.92–1.00 (2H, m), 1.58 (1H, s), 1.75–1.90 (2H, m), 2.37–2.48 (2H, m), 2.89 (1H, d, J=15.9 Hz), 2.95–3.02 (2H, m), 3.13 (1H, d, J=15.9 Hz), 3.19 (1H, m), 3.68 (3H, s), 4.08 (0.5H, d, J=13.4 Hz), 4.22 (0.5H, d, J=9.2 Hz), 4.44 (0.5H, d, J=13.4 Hz), 4.69 (0.5H, d, J=9.2 Hz), 6.65 (1H, m), 7.00–7.14 (5H, m), 7.22 (1H, m), 7.44 (1H, d, J=7.3 Hz), 7.60 (0.5H, s), 7.67 (0.5H, s)

Mass (m/e): 400 (M$^+$)

Example 37

(+)-2-Cyclopropylmethyl-4aα-(3-methoxyphenyl)-1,2,3,4,4a,5,11,11aβ-octahydro-6H-indolo[2,3-g] isoquinoline 46

In an atmosphere of argon, 100 mg of lithium aluminum hydride was suspended in 8 ml of anhydrous THF. To the produced suspension, a solution of 345 mg of (+)-2-cyclopropylmethyl-4aα-(3-methoxyphenyl)-1,2,3,4,4a,5,11,11aβ-octahydro-6H-indolo[2,3-g]isoquinoline in 17 ml of anhydrous THF was added dropwise as kept cooled with ice. Then, the resultant mixture was stirred at room temperature for two hours. To the resultant reaction mixture, ethyl acetate and a saturated aqueous solution of potassium sodium tartrate were alternately added dropwise and quenched. The mixture was filtered with a filtration cell to remove insolubles and washed three times with 20 ml of ethyl acetate. The mother liquors consequently separated were combined and concentrated, to obtain 318 mg of a powder. When this powder was separated and refined by column chromatography [silica gel; chloroform/methanel (19/1)], 295 mg of the captioned compound (yield 88.7%) was obtained.

m.p.=194.2° to 194.6° C. (recrystallized from ethyl acetate/ethanol)

[α]$_D^{20}$=+151° (C=1.0, CHCl$_3$)

IR (KBr) cm$^{-1}$: 2932, 2838, 1607, 1580, 1454

NMR (CDCl$_3$) 400 MHz δ: 0.08–0.12 (2H, m), 0.48–0.56 (2H, m), 0.89 (1H, m), 1.99–2.08 (2H, m), 2.22–2.33 (2H, m), 2.40 (1H, m), 2.58–2.64 (2H, m), 2.88–3.00 (4H, m), 3.07 (1H, d, J=16.1 Hz), 3.16 (1H, d, J=6.8 Hz), 3.67 (3H, s), 6.60 (1H, m), 7.02–7.10 (5H, m), 7.20 (1H, m), 7.44 (1H, m), 7.59 (1H, s)

Mass (m/e): 386 (M$^+$)

Example 38

(+)-2-Cyclopropylmethyl-4aα-(3-hydroxyphenyl)-1,2,3,4,4a,5,11,11aβ-octahydro-6H-indolo[2,3-g] isoquinoline 47

In an atmosphere of argon, 285 mg of (+)-2-cyclopropylmethyl -4aα-(3-methoxyphenyl)-1,2,3,4,4a,5,11,11aβ-octahydro-6H-indolo[2,3-g]isoquinoline and 497 mg of potassium-t-butoxide were dissolved in 7 ml of anhydrous DMF and the produced solution was combined with 0.415 ml of 1-propane thiol. The resultant mixture was stirred at 140° C. for 3.5 hours and then cooled to room temperature. The mixture was distilled under a vacuum to expel DMF, combined with 20 ml of a saturated aqueous solution of sodium hydrogen carbonate, and extracted three times from 40 ml of a mixed solvent of chloroform: methanol (3:1). The organic layers consequently separated were combined, washed with a saturated aqueous solution of sodium chloride, dried with anhydrous magnesium sulfate, and then concentrated, to afford 337 mg of a powder. When this powder was suspended in 2 ml of methanol, converted into a methanesulfonate by addition of methanesulfonic acid, and then separated by column chromatography (Sephadex, LH-20; methanol), 208 mg of the methanesulfonate of the captioned compound (yield 60.3%), d.p.=240° C. minimum (recrystallized from methanol) was obtained.

[α]$_D^{20}$=+45° (C=0.19, DMF)

IR (KBr) cm$^{-1}$: 3402, 2718, 1599, 1444

NMR (DMSO) 500 MHz δ: 0.37–0.38 (2H, m), 0.63–0.67 (2H, m), 1.06 (1H, m), 2.08 (1H, m), 2.31 (3H, s), 2.55–2.64 (2H, m), 2.88–2.94 (2H, m), 2.97–3.07 (3H, m), 3.09 (1H, d, J=11.0 Hz), 3.33–3.46 (2H, m), 3.52 (1H, d, J=12.8 Hz), 3.74 (1H, d, J=11.0 Hz), 6.53 (1H, dd, J=7.9 Hz, J=1.8 Hz), 6.90–6.99 (4H, m), 7.04 (1H, t, J=7.9 Hz), 7.19 (1H, d, J=7.9 Hz), 7.34 (1H, d, J=7.3 Hz), 9.25 (1H, s), 9.39 (1H, brs), 10.61 (1H, s)

Mass (FAB): 373 (M$^+$+1)

Elementary analyses For C$_{25}$H$_{28}$N$_2$O·CH$_3$SO$_3$H

|  | C | H | N | S |
| --- | --- | --- | --- | --- |
| Calculated | 66.64 | 6.88 | 5.98 | 6.84 |
| Found | 66.45 | 6.96 | 5.90 | 6.80 |

Referential Example 10

(+)-2-(2,2,2-Trichloroethoxycarbonyl-4aα-(3-methoxyphenyl)-6-oxo-1,2,3,4,4a,5,11,11aβ-octahydro-6H-indolo[2,3-g]isoquinoline 48

In an atmosphere of argon, 601 mg of proton sponge was dissolved in 15 ml of anhydrous methylene chloride and 0.435 ml of 2,2,2-trichloroethoxycarbonyl chloride was added dropwise to the produced solution as kept in a stirred state. The resultant mixture was kept cooled with ice and a solution of 509 mg of (+)-2-methyl-4aα-(3-methoxyphenyl)-6-oxo-1,2,3,4,4a,5,6,7,8,8aβ-decahydroisoquinoline in 5 ml of anhydrous methylene chloride was added dropwise thereto. Then, the produced mixture was returned to room temperature and stirred continuously for 1.5 hours. The reaction solution consequently formed was concentrated, redissolved in 20 ml of ethyl acetate, washed with 5 ml of 1N hydrochloric acid, 5 ml of water, and 10 ml of a saturated aqueous solution of sodium chloride, dried with anhydrous sodium sulfate, and then concentrated, to afford 1.09 g of an oily substance. When this oily substance was separated and refined by column chromatography [silica gel; cyclohexane/ ethyl acetate (1/1)], 810 mg of the captioned compound (yield 100%) was obtained.

IR (liquid film method) cm$^{-1}$: 2990, 1713, 1607, 1582

NMR (CDCl$_3$) 400 MHz δ: 1.80 (1H, m), 2.03 (1H, m), 2.13 (1H, m), 2.25 (1H, m), 2.31–2.44 (4H, m), 2.85 (1H, m), 2.96 (1H, d, J=14.2 Hz), 3.53 (1H, m), 3.78 (3H, s), 4.02 (1H, m), 4.18 (1H, m), 4.71–4.81 (2H, m), 6.75 (1H, m), 6.95–6.98 (2H, m), 7.25 (1H, m)

Mass (m/e): 433 (M$^+$)

Referential example 11

(+)-2-Cyclopropylcarbonyl-4aα-(3-methoxyphenyl)-6-oxo-1,2,3,4,4a,5,6,7,8,8aβ-decahydroisoquinoline 49

A solution of 800 mg of (+)-2-(2,2,2-trichloroethoxycarbonyl)-4aα-(3-methoxyphenyl)-6-oxo-1,2,3,4,4a,5,6,7,8,8aβ-decahydroisoquinoline in 20 ml of acetic acid and 1.2 g of zinc powder added thereto were stirred at room temperature for four hours. Then, the resultant reaction mixture was filtered with a filter cell to remove zinc and washed three times with 20 ml of acetic acid. The washed residue of filtration was concentrated, then alkalinized by addition of a saturated aqueous solution of sodium hydrogen carbonate, and extracted three times from 40 ml of chloroform. The organic layers consequently separated were washed with a saturated aqueous solution of sodium chloride, dried with anhydrous sodium sulfate, and then concentrated, to afford 520 mg of an oily substance.

Subsequently, this oily substance was subjected two times to azeotropic distillation with 10 ml of benzene. In an atmosphere of argon, the resultant azeotropic mixture was dissolved in 18 ml of anhydrous methylene chloride, combined with 0.513 ml of anhydrous triethylamine. At room temperature, the resultant mixture and 0.267 ml of cyclopropanecarbonyl chloride added dropwise thereto were stirred continuously for four hours. Then, the mixture was deprived of methylene chloride and the residue was redissolved in 20 ml of ethyl acetate. The produced solution was washed with 1N HCl and a saturated aqueous solution of sodium chloride, dried with anhydrous sodium sulfate, and concentrated, to afford 427 mg of an oily substance. When this oily substance was separated and refined by column chromatography [silica gel; cyclohexane/ethyl acetate (3/1)], 292 mg of the captioned compound (yield 48.6%) was obtained.

m.p.=150° to 151° C. (recrystallized from ethyl acetate)

$[α]_D^{20}$=+110° (C=1.0, CHCl$_3$)

IR (KBr) cm$^{-1}$: 2934, 2872, 1715, 1624, 1599

NMR (CDCl$_3$) 400 MHz δ: 0.76–0.79 (2H, m), 0.91–1.00 (2H, m), 1.59 (1H, s), 1.74–1.84 (2H, m), 2.03 (1H, m), 2.16 (1H, d, J=13.7 Hz), 2.25 (1H, m), 2.38–2.42 (3.5 H, m), 2.76 (0.5H, m), 2.97 (1H, d, J=14.2 Hz), 3.07 (0.5H, m), 3.27 (0.5H, m), 3.79 (3H, s), 4.01 (0.5H, m), 4.12 (0.5H, m), 4.33 (0.5H, m), 4.59 (0.5H, m), 6.75 (1H, dd, J=8.3 Hz, J=2.4 Hz), 6.95–7.01 (2H, m), 7.25 (1H, m)

Mass (m/e): 327 (M$^+$)

Example 39

(−)-2-Cyclopropylcarbonyl-4aα-(3-methoxyphenyl)-1,2,3,4,4a,5,11,11aβ-octahydro-6H-indolo[2,3-g]isoquinoline 50

In 2 ml of ethanol, 145 mg of (+)-2-cyclopropylcarbonyl-4aα-(3-methoxyphenyl)-6-oxo-1,2,3,4,4a,5,6,7,8,8aβ-decahydroisoquinoline and 0.048 ml of phenyl hydrazine were dissolved. The produced solution kept refluxed thermally and 0.288 ml of methanesulfonic acid added thereto meanwhile were stirred and further refluxed for 0.5 hour continuously. The resultant reaction mixture was cooled to room temperature, combined with 15 ml of a saturated aqueous solution of sodium hydrogen carbonate as kept cooled with ice, and extracted two times from 30 ml of chloroform. The organic layers consequently separated were combined, washed with a saturated aqueous solution of sodium chloride, dried with anhydrous sodium sulfate, and then concentrated, to afford 194 mg of an oily substance. When this oily substance was separated and refined by column chromatography [silica gel; chloroform], 160 mg of the captioned compound (yield 90.3%) was obtained.

IR (KBr) cm$^{-1}$: 3204, 2902, 1607, 1460

NMR (CDCl$_3$) 400 MHz δ: 0.75–0.78 (2H, m), 0.92–1.00 (2H, m), 1.58 (1H, s), 1.75–1.90 (2H, m), 2.37–2.48 (2H, m), 2.88–3.02 (3H, m), 3.12–3.30 (2H, m), 3.68 (3H, s), 4.08–4.69 (2H, m), 6.65 (1H, m), 7.00–7.14 (5H, m), 7.22 (1H, m), 7.44 (1H, m), 7.63 (1H, brs)

Mass (m/e): 400 (M$^+$)

Example 40

(−)-2-Cyclopropylmethyl-4aα-(3-methoxyphenyl)-1,2,3,4,4a,5,11,11aβ-octahydro-6H-indolo[2,3-g]isoquinoline 51

In an atmosphere of argon, 44 mg of lithium aluminum hydride was suspended in 3 ml of anhydrous THF and a solution of 150 mg of (−)-2-cyclopropylcarbonyl-4aα-(3-methoxyphenyl)-1,2,3,4,4a,5,11,11aβ-octahydro-6H-indolo[2,3-g]isoquinoline in 7 ml of anhydrous THF was added dropwise to the suspension kept cooled with ice. The resultant mixture was stirred at room temperature for one hour. The resultant reaction mixture was kept cooled with ice and ethyl acetate and a saturated aqueous solution of potassium sodium tartrate were alternately added dropwise thereto meanwhile and the produced mixture was quenched. The mixture was filtered with a filtration cell to remove insolubles and the residue of the filtration was washed three times with 20 ml of ethyl acetate. The mother liquids consequently separated were combined and concentrated, to afford 141 mg of a powder. When this powder was separated and refined by column chromatography [silica gel; chloroform/methanol (9/1)], 132 mg of the captioned compound (yield 91.2%) was obtained.

m.p.=195.0° to 195.3° C. (recrystallized from ethyl acetate)

$[α]_D^{20}$=−137° (C=1.0, CHCl$_3$)

IR(KBr)cm$^{-1}$: 2930, 2838, 1607, 1578, 1454

NMR (CDCl₃) 400 MHz δ: 0.08–0.12 (2H, m), 0.48–0.56 (2H, m), 0.89 (1H, m), 1.99–2.08 (2H, m), 2.24–2.35 (2H, m), 2.40 (1H, m), 2.58–2.66 (2H, m), 2.89–3.00 (4H, m), 3.07 (1H, d, J=15.6 Hz), 3.17 (1H, d, J=7.8 Hz), 3.67 (3H, s), 6.60 (1H, m), 7.02–7.10 (5H, m), 7.20 (1H, m), 7.44 (1H, m), 7.59 (1H, s)

Mass (m/e): 386 (M⁺)

Example 41

(−)-2-Cyclopropylmethyl-4aα-(3-hydroxyphenyl)-1,2,3,4,4a,5,11,11aβ-octahydro-6H-indolo[2,3-g]isoquinoline 52

In an atmosphere of argon, 127 mg of (−)-2-cyclopropylmethyl-4aα-(3-methoxyphenyl)-1,2,3,4,4a,5,11,11aβ-octahydro-6H-indolo[2,3-g]isoquinoline and 221 mg of potassium-t-butoxide were dissolved in 3 ml of anhydrous DMF and 0.185 ml of 1-propane thiol was added to the produced solution. The mixture was stirred at 140° C. for three hours and then cooled to room temperature. This mixture was distilled under a vacuum to expel DMF, combined with 10 ml of a saturated aqueous solution of sodium hydrogen carbonate, and extracted three times from 20 ml of a mixed solvent of chloroform: methanol (3:1). The organic layers consequently separated were combined, washed with a saturated aqueous solution of sodium chloride, dried with anhydrous magnesium sulfate, and then concentrated, to afford 150 mg of a powder. When this powder was suspended in 1 ml of methanol, converted into a methane-sulfonate by addition of methanesulfonic acid, and then separated and refined by column chromatography [Sephadex, LH-20; methanol], 54 mg of the methanesulfonate of the optioned compound (yield 35.1%) was obtained.

d.p.=240° C. minimum (recrystallized from methanol)

$[α]_D^{20}$=−48° (C=0.21, DMF)

IR (KBr) cm⁻¹: 3404, 2710, 1601, 1444

NMR (DMSO) 500 MHz δ: 0.37–0.38 (2H, m), 0.63–0.66 (2H, m), 1.06 (1H, m), 2.08 (1H, m), 2.31 (3H, s), 2.55–2.64 (2H, m), 2.88–2.94 (2H, m), 2.97–3.07 (3H, m), 3.12 (1H, d, J=16.5 Hz), 3.33–3.46 (2H, m), 3.51 (1H, d, J=11.0 Hz), 3.73 (1H, d, J=11.6 Hz), 6.53 (1H, d, J=7.9 Hz), 6.90–6.99 (4H, m), 7.03 (1H, t, J=7.9 Hz), 7.19 (1H, d, J=7.9 Hz), 7.34 (1H, d, J=7.3 Hz), 9.24 (1H, s), 9.38 (1H, brs), 10.61 (1H, s)

Mass (FAB): 373 (M⁺+1)

Elementary analyses For $C_{25}H_{28}N_2O·CH_3SO_3H·0.6H_2O$

|  | C | H | N | S |
|---|---|---|---|---|
| Calculated | 65.14 | 6.98 | 5.84 | 6.69 |
| Found | 65.22 | 6.83 | 5.75 | 6.67 |

The (+) forms and (−) forms of the compounds described hereinabove can be produced by following the pertinent procedures of Referential Examples 7, 8, 9, 10, and 11 and Examples 36, 37, 38, 39, 40, and 41.

Example 42

2-Methyl-4aα-(3-methoxyphenyl)-11aβ-hydroxy-1,2,3,4,4a,5,11,11a-octahydro-6H-indolo[2,3-g]isoquinoline 53

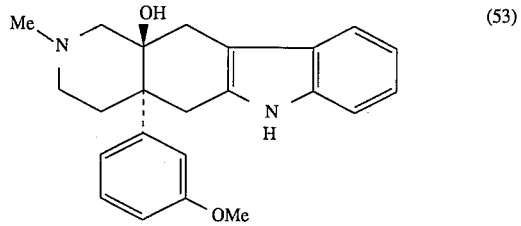

(53)

In 3 ml of ethanol, 102 mg (0.35 mmol) of 2-methyl-4aα-(3-methoxyphenyl)-6-oxo-8aβ-hydroxy-1,2,3,4,4a,5,6,7,8,8a-decahydroisoquinoline was dissolved. To the produced solution was added 38.2 μl (0.39 mmol) of phenyl hydrazine. The mixture was heated to 80° C. and allowed to react with 228 μl (3.5 mmol) of methanesulfonic acid at the same temperature for two hours. The reaction mixture was left cooling to room temperature, then poured in 20 ml of a saturated aqueous solution of sodium hydrogen carbonate, and extracted two times from 15 ml of chloroform. The extract was washed with 10 ml of a saturated aqueous saline solution, dried, concentrated, and refined by silica gel column chromatography [7734, 8 g; chloroform to chloroform/ammonia-saturated chloroform (3/1)], to afford the captioned compound (114%, inclusive of the solvent).

IR (KBr) cm⁻¹: 3304, 2918, 1605, 1580, 1464, 1236, 1040, 785, 741

NMR (CDCl₃) 500 MHz δ: 2.20–2.30 (2H, m), 2.33 (3H, s), 2.40 (1H, dt, J=12.8, 4.3 Hz), 2.66 (2H, s), 2.70–2.75 (1H, m), 2.79 (1H, d, J=15.9 Hz), 2.92 (1H, d, J=15.3 Hz), 3.22 (1H, t, J=15.9 Hz), 3.64 (3H, s), 6.63 (1H, dt, J=6.7, 1.8 Hz), 7.04–7.20 (5H, m), 7.20 (1H, dd, J=6.7, 1.8 Hz), 7.44 (1H, d, J=6.7 Hz), 7.62 (1H, brs)

Mass (EI): 362 (M⁺)

Similarly, 2-methyl-4aα-(3-methoxyphenyl)-9-methyl-11aβ-hydroxy-1,2,3,4,4a,5,11,11a-octahydro-6H-indolo[2,3-g]isoquinoline, 2-methyl-4aα-(3-methoxyphenyl)-8-methyl-11aβ-hydroxy-1,2,3,4,4a,5,11,11a-octahydro-6H-indolo[2,3-g]isoquinoline, 2-methyl-4aα-(3-methoxyphenyl)-10-methyl-11aβ-hydroxy-1,2,3,4,4a,5,11,11a-octahydro-6H-indolo[2,3-g]isoquinoline, 2-methyl-4aα-(3-methoxyphenyl)-7-methyl-11aβ-hydroxy-1,2,3,4,4a,5,11,11a-octahydro-6H-indolo[2,3-]isoquinoline, 2-methyl-4aα-(3-methoxyphenyl)-9-chloro-11aβ-hydroxy-1,2,3,4,4a,5,11,11a-octahydro-6H-indolo[2,3-g]isoquinoline, 2-methyl-4aα-(3-methoxyphenyl)-8-chloro-11aβ-hydroxy-1,2,3,4,4a,5,11,11a-octahydro-6H-indolo[2,3-g]isoquinoline, 2-methyl-4aα-(3-methoxyphenyl)-10-chloro-11aβ-hydroxy-1,2,3,4,4a,5,11,11a-octahydro-6H-indolo[2,3-g]isoquinoline, 2-methyl-4aα-(3-methoxyphenyl)-7-chloro-11aβ-hydroxy-1,2,3,4,4a,5,11,11a-octahydro-6H-indolo[2,3-g]isoquinoline, 2-methyl-4aα-(3-methoxyphenyl)-9-fluoro-11aβ-hydroxy-1,2,3,4,4a,5,11,11a-octahydro-6H-indolo[2,3-g]isoquinoline, 2-methyl-4aα-(3-methoxyphenyl)-8-fluoro-11aβ-hydroxy-1,2,3,4,4a,5,11,11a-octahydro-6H-indolo[2,3-g]isoquinoline, 2-methyl-4aα-(3-methoxyphenyl)-10-fluoro-11aβ-hydroxy-1,2,3,4,4a,5,11,11a-octahydro-6H-indolo[2,3-g]isoquinoline, 2-methyl-4aα-(3-methoxyphenyl)-7-fluoro-11aβ-hydroxy-1,2,3,4,4a,5,11,11a-octahydro-6H-indolo[2,3-g]isoquinoline, 2-methyl-4aα-(3-methoxyphenyl)-9-bromo- 11aβ-hydroxy-1,2,3,4,4a,5,11,11a-octahydro-6H-indolo[2,3-g]isoquinoline, 2-methyl-4aα-(3-methoxyphenyl)-8-bromo-11aβ-hydroxy-1,2,3,4,4a,5,11,11a-octahydro-6H-indolo[2,3-g]isoquinoline, 2-methyl-4aα-(3-methoxyphenyl)-10-bromo-11aβ-hydroxy-1,2,3,4,4a,5,11,11a-octahydro-6H-indolo[2,3-g]isoquinoline, 2-methyl-4aα-(3-methoxyphenyl)-7-bromo-11aβ-hydroxy-1,2,3,4,4a,5,11,11a-octahydro-6H-indolo[2,3-g]isoquinoline, 2-methyl-4aα-(3-methoxyphenyl)-9-nitro-11aβ-hydroxy-1,2,3,4,4a,5,11,11a-octahydro-6H-indolo[2,3-g]isoquinoline, 2-methyl-4aα-(3-methoxyphenyl)-8-nitro-11aβ-hydroxy-1,2,3,4,4a,5,11,11a-octahydro-6H-indolo[2,3-g]isoquinoline, 2-methyl-4aα-(3-methoxyphenyl)-10-nitro-11aβ-hydroxy-1,2,3,4,4a,5,11,11a-octahydro-6H-indolo[2,3-g]isoquinoline, 2-methyl-4aα-(3-methoxyphenyl)-7-nitro-11aβ-hydroxy-1,2,3,4,4a,5,11,11a-octahydro-6H-indolo[2,3-g]isoquinoline, and 2-methyl-4aα-(3-methoxyphenyl)-11aβ-hydroxy-1,2,3,4,4a,5,11,11a-octahydro-6-methyl-indro(2,3-g)isoquinoline are produced by using p-tollyl hydrazine, m-tollyl hydrazine, o-tollyl hydrazine, 4-chlorophenyl hydrazine, 3-chlorophenyl hydrazine, 2-chlorophenyl hydrazine, 4-fluorophenyl hydrazine, 3-fluorophenyl hydrazine, 2-fluorophenyl hydrazine, 4-bromophenyl hydrazine, 3-bromophenyl hydrazine, 2-bromophenyl hydrazine, 4-nitrophenyl hydrazine, 3-nitrophenyl hydrazine, 2-nitrophenyl hydrazine and phenylmethyl hydrazine respectively, instead of phenyl hydrazine.

Example 43

2-Methyl-4aα-(3-hydroxyphenyl)-11aβ-hydroxy-1,2,3,4,4a,5,11,11a-octahydro-6H-indolo[2,3-q]isoquinoline 54

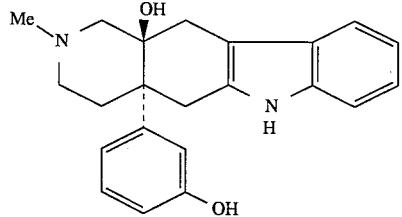
(54)

The 2-methyl-4aα-(3-methoxyphenyl)-11aβ-hydroxy-1,2,3,4,4a,5,11,11a-octahydro-6H-indolo[2,3-g]isoquinoline obtained as described above was dissolved in 5 ml of anhydrous DMF and caused to react with 0.25 ml (2.8 mmol) of propane thiol and 220 ml (2.0 mmol) of potassium-t-butoxide at 150° C. for three hours. The reaction mixture was distilled under a vacuum to expel the solvent, combined with 10 ml of a saturated aqueous solution of sodium hydrogen carbonate, and extracted two times from 10 ml of ethanol/chloroform (3/1). The extract was washed with a saturated aqueous saline solution, dried, concentrated, and refined by silica gel column chromatography (7734, 10 g; chloroform-ammonia-saturated chloroform-5% methanol/ammonia-saturated chloroform), to afford 55.6 mg of the captioned compound (45% in two steps). This compound was dissolved in methanol and, by addition of 10.9 μl of methanesulfonic acid, isolated in the form of a salt.

m.p.=189° to 192° C. (methanesulfonate, discolored to brown at 172° C.)

IR (KBr) cm$^{-1}$: 3408, 2926, 1584, 1454, 1323, 1236, 1048, 897, 741

Mass (EI): 348 (M$^+$)

Elementary analyses For $C_{22}H_{24}N_2O_2$ $CH_3SO_3H$ $H_2O$

|  | C | H | N | S |
|---|---|---|---|---|
| Calculated | 59.72 | 6.54 | 6.05 | 6.93 |
| Found | 59.58 | 6.72 | 5.96 | 7.01 |

Similarly, 2-methyl-4aα-(3-hydroxyphenyl)-9-methyl-11aβ-hydroxy-1,2,3,4,4a,5,11,11a-octahydro-6H-indolo[2,3-g]isoquinoline, 2-methyl-4aα-(3-hydroxyphenyl)-8-methyl-11aβ-hydroxy-1,2,3,4,4a,5,11,11a-octahydro-6H-indolo[2,3-g]isoquinoline, 2-methyl-4aα-(3-hydroxyphenyl)-10-methyl-11aβ-hydroxy-1,2,3,4,4a,5,11,11a-octahydro-6H-indolo[2,3-g]isoquinoline, 2-methyl-4aα-(3-hydroxyphenyl)-7-methyl-11aβ-hydroxy-1,2,3,4,4a,5,11,11a-octahydro-6H-indolo[2,3-g]isoquinoline, 2-methyl-4aα-(3-hydroxyphenyl)-9-chloro-11aβ-hydroxy-1,2,3,4,4a,5,11,11a-octahydro-6H-indolo[2,3-g]isoquinoline, 2-methyl-4aα-(3-hydroxyphenyl)-8-chloro-11aβ-hydroxy-1,2,3,4,4a,5,11,11a-octahydro-6H-indolo[2,3-g]isoquinoline, 2-methyl-4aα-(3-hydroxyphenyl)-10-chloro-11aβ-hydroxy-1,2,3,4,4a,5,11,11a-octahydro-6H-indolo[2,3-g]isoquinoline, 2-methyl-4aα-(3-hydroxyphenyl)-7-chloro-11aβ-hydroxy-1,2,3,4,4a,5,11,11a-octahydro-6H-indolo[2,3-g]isoquinoline, 2-methyl-4aα-(3-hydroxyphenyl)-9-fluoro-11aβ-hydroxy-1,2,3,4,4a,5,11,11a-octahydro-6H-indolo[2,3-g]isoquinoline, 2-methyl-4aα-(3-hydroxyphenyl)-8-fluoro-11aβ-hydroxy-1,2,3,4,4a,5,11,11a-octahydro-6H-indolo[2,3-g]isoquinoline, 2-methyl-4aα-(3-hydroxyphenyl)-10-fluoro-11aβ-hydroxy-1,2,3,4,4a,5,11,11a-octahydro-6H-indolo[2,3-g]isoquinoline, 2-methyl-4aα-(3-hydroxyphenyl)-7-fluoro-11aβ-hydroxy-1,2,3,4,4a,5,11,11a-octahydro-6H-indolo[2,3-g]isoquinoline, 2-methyl-4aα-(3-hydroxyphenyl)-9-bromo-11aβ-hydroxy-1,2,3,4,4a,5,11,11a-octahydro-6H-indolo[2,3-g]isoquinoline, 2-methyl-4aα-(3-hydroxyphenyl)-8-bromo-11aβ-hydroxy-1,2,3,4,4a,5,11,11a-octahydro-6H-indolo[2,3-g]isoquinoline, 2-methyl-4aα-(3-hydroxyphenyl)-10-bromo-11aβ-hydroxy-1,2,3,4,4a,5,11,11a-octahydro-6H-indolo[2,3-g]isoquinoline, 2-methyl-4aα-(3-hydroxyphenyl)-7-bromo-11aβ-hydroxy-1,2,3,4,4a,5,11,11a-octahydro-6H-indolo[2,3-g]isoquinoline, 2-methyl-4aα-(3-hydroxyphenyl)-9-nitro-11aβ-hydroxy-1,2,3,4,4a,5,11,11a-octahydro-6H-indolo[2,3-g]isoquinoline, 2-methyl-4aα-(3-hydroxyphenyl)-8-nitro-11aβ-hydroxy-1,2,3,4,4a,5,11,11a-octahydro-6H-indolo[2,3-g]isoquinoline, 2-methyl-4aα-(3-hydroxyphenyl)-10-nitro-11aβ-hydroxy-1,2,3,4,4a,5,11,11a-octahydro-6H-indolo[2,3-g]isoquinoline, 2-methyl-4aα-3-hydroxyphenyl)-7-nitro-11aβ-hydroxy-1,2,3,4,4a,5,11,11a-octahydro-6H-indolo[2,3-g]isoquinoline, and 2-methyl-4aα-(3-hydroxyphenyl)-11aβ-hydroxy-1,2,3,4,4a,5,11,11a-octahydro-6H-indolo[2,3-g]isoquinoline are produced by using 2-methyl-4aα-(3-methoxyphenyl)-9-methyl-11aβ-hydroxy-1,2,3,4,4a,5,11,11a-octahydro-6H-indolo[2,3-g]isoquinoline, 2-methyl-4aα-(3-methoxyphenyl)-8-methyl-11aβ-hydroxy-1,2,3,4,4a,5,11,11a-octahydro-6H-indolo[2,3-g]isoquinoline, 2-methyl-4aα-(3-methoxyphenyl)-10-methyl-11aβ-hydroxy-1,2,3,4,4a,5,11,11a-octahydro-6H-indolo[2,3-g]isoquinoline, 2-methyl-4aα-(3-methoxyphenyl)-7-methyl-11aβ-hydroxy-1,2,3,4,4a,5,11,11a-octahydro-6H-indolo[2,3-g]isoquinoline, 2-methyl-4aα-(3-methoxyphenyl)-9-chloro-11aβ-hydroxy-1,2,3,4,4a,5,11,11a-octahydro-6H-indolo[2,3-g]isoquinoline, 2-methyl-4aα-(3-methoxyphenyl)-8-chloro-11aβ-hydroxy-1,2,3,4,4a,5,11,11a-octahydro-6H-indolo[2,3-g]isoquinoline, 2-methyl-4aα-(3-methoxyphenyl)-10-chloro-11aβ-hydroxy-1,2,3,4,4a,5,11,11a-octahydro-6H-indolo[2, 3-g]isoquinoline, 2-methyl-4aα-(3-methoxyphenyl)-7-chloro-11aβ-hydroxy-1,2,3,4,4a,5,11,11a-octahydro-6H-indolo[2,3-g]isoquinoline, 2-methyl-4aα-(3-methoxyphenyl)-9-fluoro-11aβ-hydroxy-1,2,3,4,4a,5,11,11a-octahydro-6H-indolo[2,3-g]isoquinoline, 2-methyl-4aα-(3-methoxyphenyl)-8-fluoro-11aβ-hydroxy-1,2,3,4,4a,5,11,11a-octahydro-6H-indolo[2,3-g]isoquinoline, 2-methyl-4aα-(3-methoxyphenyl)-10-fluoro-11aβ-hydroxy-1,2,3,4,4a,5,11,11a-octahydro-6H-indolo[2,3-g]isoquinoline, 2-methyl-4aα-(3-methoxyphenyl)-7-fluoro-11aβ-hydroxy-1,2,3,4,4a,5,11,11a-octahydro-6H-indolo[2,3-g]isoquinoline, 2-methyl-4aα-(3-methoxyphenyl)-9-bromo-11aβ-hydroxy-1,2,3,4,4a,5,11,11a-octahydro-6H-indolo[2,3-g]isoquinoline, 2-methyl-4aα-(3-methoxyphenyl)-8-bromo-11aβ-hydroxy-1,2,3,4,4a,5,11,11a-octahydro-6H-indolo[2,3-g]isoquinoline, 2-methyl-4aα-(3-methoxyphenyl)-10-bromo-11aβ-hydroxy-1,2,3,4,4a,5,11,11a-octahydro-6H-indolo[2,3-g]isoquinoline, 2-methyl-4aα-(3-methoxyphenyl)-7-bromo-11aβ-hydroxy-1,2,3,4,4a,5,11,11a-octahydro-6H-indolo[2,3-g]isoquinoline, 2-methyl-4aα-(3-methoxyphenyl)-9-nitro-11aβ-hydroxy-1,2,3,4,4a,5,11,11a-octahydro-6H-indolo[2,3-g]isoquinoline, 2-methyl-4aα-(3-methoxyphenyl)-8-nitro-11aβ-hydroxy-1,2,3,4,4a,5,11,11a-octahydro-6H-indolo[2,3-g]isoquinoline, 2-methyl-4aα-(3-methoxyphenyl)-10-nitro-11aβ-hydroxy-1,2,3,4,4a,5,11,11a-octahydro-6H-indolo[2,3-g]isoquinoline, 2-methyl-4aα-(3-methoxyphenyl)-7-nitro-11aβ-hydroxy-1,2,3,4,4a,5,11,11a-octahydro-6H-indolo[2,3-g]isoquinoline, and 2-methyl-4aα-(3-methoxyphenyl)-11aβ-hydroxy-1,2,3,4,4a,5,11,11a-octahydro-6-methyl-indolo[2,3-g]isoquinoline respectively instead of 2-methyl-4aα-(3-methoxyphenyl)-11aβ-hydroxy-1,2,3,4,4a,5,11,11a-octahydro-6H-indolo[2,3-g]isoquinoline.

Example 44

2-Cyclopropylmethyl-4aα-(3-methoxyphenyl)-11aβ-hydroxy-1,2,3,4,4a,5,11,11a-octahydro-6H-indolo[2,3-g]isoquinoline 55

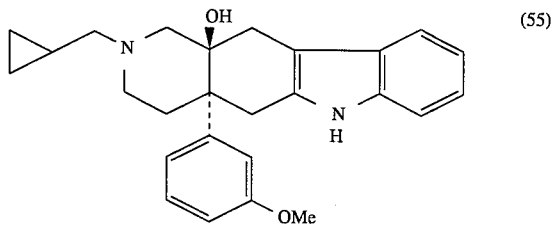

(55)

In 3 ml of ethanol, 102 mg (0.31 mmol) of 2-cyclopropylmethyl-4aα-(3-methoxyphenyl)-6-oxo-8aβ-hydroxy-1,2,3,4,4a,5,6,7,8,8a-decahydroisoquinoline was dissolved and the produced solution was combined with 34 μl (0.34 mmol) of phenyl hydrazine. The resultant mixture was heated to 80° C. and then caused to react with 202 μl (3.1 mmol) of methanesulfonic acid at the same temperature for three hours. The reaction mixture was left cooling to room temperature, poured into 12 ml of a saturated aqueous solution of sodium hydrogen carbonate, and extracted two times from 10 ml of chloroform. The extract was washed with 10 ml of a saturated aqueous saline solution, dried, then concentrated, and refined by silica gel column chromatography (9385, 10 g; chloroform—2% methanol/chloroform—5% methanol/chloroform), to obtain 96.6 mg of the captioned compound (yield 77%).

IR (liquid film method) cm$^{-1}$: 3302, 2914, 1605, 1580, 1456, 1236, 1040, 874, 741

NMR (CDCl$_3$, 500 MHz) δ: 0.04–0.10 (2H, m), 0.45–0.53 (2H, m), 0.72–0.84 (1H, m), 2.18–2.26 (2H, m), 2.36 (1H, s), 2.36 (1H, dt, J=12.4, 4.0 Hz), 2.57–2.66 (2H, m), 2.64 (2H, s), 2.68–2.73 (1H, m) 2.81 (1H, d, J=15.8 Hz), 2.90 (1H, d, J=15.4 Hz), 3.20 (1H, t, J=15.8 Hz), 3.65 (3H, s), 6.62 (1H, dt, J=6.7, 1.8 Hz), 7.00–7.07 (5H, m), 7.21 (1H, dd, J=6.7, 1.8 Hz), 7.44 (1H, d, J=6.7 Hz), 7.48 (1H, brs)

Mass (EI): 402 (M$^+$)

Similarly, 2-benzyl-4aα-(3-methoxyphenyl)-11aβ-hydroxy-1,2,3,4,4a,5,11,11a-octahydro-6H-indolo[2,3-g]isoquinoline, 2-(2-phenylethyl)-4aα-(3-methoxyphenyl)-11aβ-hydroxy-1,2,3,4,4a,5,11,11a-octahydro-6H-indolo[2,3-g]isoquinoline, and 2-allyl-4aα-(3-methoxyphenyl)-11aβ-hydroxy-1,2,3,4,4a,5,11,11a-octahydro-6H-indolo[2,3-g]isoquinoline are produced by using 2-benzyl-4aα-(3-methoxyphenyl)-6-oxo-8aβ-hydroxy-1,2,3,4,5,6,7,8,8a-decahydroisoquinoline, 2-(2-phenylethyl)-4aα-(3-methoxyphenyl)-6-oxo-8aβ-hydroxy-1,2,3,4,5,6,7,8,8a-decahydroisoquinoline, and 2-allyl-4aα-(3-methoxyphenyl)-6-oxo-8aβ-hydroxy-1,2,3,4,5,6,7,8,8a-decahydroisoquinoline respectively instead of 2-cyclopropylmethyl-4aα-(3-methoxyphenyl)-6-oxo-8aβ-hydroxy-1,2,3,4,5,6,7,8,8a-decahydroisoquinoline.

Similarly, 2-cyclopropylmethyl-4aα-(3-methoxyphenyl)-9-methyl-11aβ-hydroxy-1,2,3,4,4a,5,11,11a-octahydro-6H-indolo[2,3-g]isoquinoline, 2-benzyl-4aα-(3-methoxyphenyl)-9-methyl-11aβ-hydroxy-1,2,3,4,4a,5,11,11a-octahydro-6H-indolo[2,3-g]isoquinoline, 2-(2-phenylethyl)-4aα-(3-methoxyphenyl)-9-methyl-11aβ-hydroxy-1,2,3,4,4a,5,11,11a-octahydro-6H-indolo[2,3-g]isoquinoline, and 2-allyl-4aα-(3-methoxyphenyl)-9-methyl-11aβ-hydroxy-1,2,3,4,4a,5,11,11a-octahydro-6H-indolo[2,3-g]isoquinoline are produced by using o-tollyl hydrazine instead of phenyl hydrazine and respectively using 2-cyclopropylmethyl-4aα-(3-methoxyphenyl)-6-oxo-8aβ-hydroxy-1,2,3,4,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-(2-phenylethyl)-4aα-(3-methoxyphenyl)-6-oxo-8aβ-hydroxy-1,2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Similarly, 2-cyclopropylmethyl-4aα-(3-methoxyphenyl)-8-methyl-11aβ-hydroxy-1,2,3,4,4a,5,11,11a-octahydro-6H-indolo[2,3-g]isoquinoline, 2-cyclopropylmethyl-4aα-(3-methoxyphenyl)-10-methyl-11aβ-hydroxy-1,2,3,4,4a,5,11,11a-octahydro-6H-indolo[2,3-g]isoquinoline, 2-benzyl-4aα-(3-methoxyphenyl)-8-methyl-11aβ-hydroxy-1,2,3,4,4a,5,11,11a-octahydro-6H-indolo[2,3-g]isoquinoline, 2-benzyl-4aα-(3-methoxyphenyl)-10-methyl-11aβ-hydroxy-1,2,3,4,4a,5,11,11a-octahydro-6H-indolo[2,3-g]isoquinoline, 2-(2-phenylethyl)-4aα-(3-methoxyphenyl)-8-methyl-11aβ-hydroxy-1,2,3,4,4a,5,11,11a-octahydro-6H-indolo[2,3-g]isoquinoline, 2-(2-phenylethyl)-4aα-(3-methoxyphenyl)-10-methyl-11aβ-hydroxy-1,2,3,4,4a,5,11,11a-octahydro-6H-indolo[2,3-g]isoquinoline, 2-allyl-4aα-(3-methoxyphenyl)-8-methyl-11aβ-hydroxy-1,2,3,4,4a,5,11,11a-octahydro-6H-indolo[2,3-g]isoquinoline, and 2-allyl-4aα-(3-methoxyphenyl)-10-methyl-11aβ-hydroxy-1,2,3,4,4a,5,11,11a-octahydro-6H-indolo[2,3-g]isoquinoline are produced by using m-tollyl hydrazine instead of phenyl hydrazine and respectively using 2-cyclopropylmethyl-4aα-(3-methoxyphenyl)-6-oxo-8aβ-hydroxy-1,2,3,4,4a,5,6,7,8,8a-decahydroisoquinoline, 2-benzyl-4aα-(3- methoxyphenyl)-6-oxo-8aβ-hydroxy-1,2,3,4,4a,5,6,7,8,8a-decahydroisoquinoline, 2-(2-phenylethyl)-4aα-(3-methoxyphenyl)-6-oxo-8aβ-hydroxy-1,2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Similarly, 2-cyclopropylmethy-4aα-(3-methoxyphenyl)-7-methyl-11aβ-hydroxy-1,2,3,4,4a,5,11,11a-octahydro-6H-indolo[2,3-g]isoquinoline, 2-benzyl-4aα-(3-methoxyphenyl)-7-methyl-11aβ-hydroxy-1,2,3,4,4a,5,11,11a-octahydro-6H-indolo[2,3-g]isoquinoline, 2-(2-phenylethyl)-4aα-(3-methoxyphenyl)-7-methyl-11aβ-hydroxy-1,2,3,4,4a,5,11,11a-octahydro-6H-indolo[2,3-g]isoquinoline, and 2-allyl-4aα-(3-methoxyphenyl)-7-methyl-11aβ-hydroxy-1,2,3,4,4a,5,11,11a-octahydro-6H-indolo[2,3-g]isoquinoline are produced by using o-tollyl hydrazine instead of phenylhydrazine and respectively using 2-cyclopropylmethyl-4aα-(3-methoxyphenyl)-6-oxo-8aβ-hydroxy-1,2,3,4,4a,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-(2-phenylethyl)-4aα-(3-methoxyphenyl)-6-oxo-8aβ-hydroxy-1,2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Similarly, 2-cyclopropylmethyl-4aα-(3-methoxyphenyl)-9-chloro-11aβ-hydroxy-1,2,3,4,4a,5,11,11a-octahydro-6H-indolo[2,3-g]isoquinoline, 2-benzyl-4aα-(3-methoxyphenyl)-9-chloro-11aβ-hydroxy-1,2,3,4,4a,5,11,11a-octahydro-6H-indolo[2,3-g]isoquinoline, 2-(2-phenylethyl)-4aα-(3-methoxyphenyl)-9-chloro-11aβ-hydroxy-1,2,3,4,4a,5,11,11a-octahydro-6H-indolo[2,3-g]isoquinoline, and 2-allyl-4aα-(3-methoxyphenyl)-9-chloro-11aβ-hydroxy-1,2,3,4,4a,5,11,11a-octahydro-6H-indolo[2,3-g]isoquinoline are produced by using 4-chlorophenylhydrazine instead of phenyl hydrazine and respectively using 2-cyclopropylmethyl-4aα-(3-methoxyphenyl)-6-oxo-8aβ-hydroxy-1,2,3,4,4a,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-(2-phenylethyl)-4aα-(3-methoxyphenyl)-6-oxo-8aβ-hydroxy-1,2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Similarly, 2-cyclopropylmethyl-4aα-(3-methoxyphenyl)-8-chloro-11aβ-hydroxy-1,2,3,4,4a,5,11,11a-octahydro-6H-indolo[2,3-g]isoquinoline, 2-cyclopropylmethyl-4aα-(3-methoxyphenyl)-10-chloro-11aβ-hydroxy-1,2,3,4,4a,5,11,11a-octahydro-6H-indolo[2,3-g]isoquinoline, 2-benzyl-4aα-(3-methoxyphenyl)-8-chloro-11aβ-hydroxy-1,2,3,4,4a,5,11,11a-octahydro-6H-indolo[2,3-g]isoquinoline, 2-benzyl-4aα-(3-methoxyphenyl)-10-chloro-11aβ-hydroxy-1,2,3,4,4a,5,11,11a-octahydro-6H-indolo[2,3-g]isoquinoline, 2-(2-phenylethyl)-4aα-(3-methoxyphenyl)-8-chloro-11aβ-hydroxy-1,2,3,4,4a,5,11,11a-octahydro-6H-indolo[2,3-g]isoquinoline, 2-(2-phenylethyl)-4aα-(3-methoxyphenyl)-10-chloro-11aβ-hydroxy-1,2,3,4,4a,5,11,11a-octahydro-6H-indolo[2,3-g]isoquinoline, 2-allyl-4aα-(3-methoxyphenyl)-8-chloro-11aβ-hydroxy-1,2,3,4,4a,5,11,11a-octahydro-6H-indolo[2,3-g]isoquinoline, and 2-allyl-4aα-(3-methoxyphenyl)-10-chloro-11aβ-hydroxy-1,2,3,4,4a,5,11,11a-octahydro-6H-indolo[2,3-g]isoquinoline are produced by using 3-chlorophenyl hydrazine instead of phenyl hydrazine and respectively using 2-cyclopropylmethyl-4aα-(3-methoxyphenyl)-6-oxo-8aβ-hydroxy-1,2,3,4,4a,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-(2-phenylethyl)-4aα-(3-methoxyphenyl)-6-oxo-8aβ-hydroxy-1,2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Similarly, 2-cyclopropylmethyl-4aα-(3-methoxyphenyl)-7-chloro-11aβ-hydroxy-1,2,3,4,4a,5,11,11a-octahydro-6H-indolo[2,3-g]isoquinoline, 2-benzyl-4aα-(3-methoxyphenyl)-7-chloro-11aβ-hydroxy-1,2,3,4,4a,5,11,11a-octahydro-6H-indolo[2,3-g]isoquinoline, 2-(2-phenylethyl)-4aα-(3-methoxyphenyl)-7-chloro-11aβ-hydroxy-1,2,3,4,4a,5,11,11a-octahydro-6H-indolo[2,3-g]isoquinoline, and 2-allyl-4aα-(3-methoxyphenyl)-7-chloro-11aβ-hydroxy-1,2,3,4,4a,5,11,11a-octahydro-6H-indolo[2,3-g]isoquinoline are produced by using 2-chlorophenylhydrazine instead of phenyl hydrazine and respectively using 2-cyclopropylmethyl-4aα-(3-methoxyphenyl)-6-oxo-8aβ-hydroxy-1,2,3,4,4a,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-(2-phenylethyl)-4aα-(3-methoxyphenyl)-6-oxo-8aβ-hydroxy-1,2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Similarly, 2-cyclopropylmethyl-4aα-(3-methoxyphenyl)-9-fluoro-11aβ-hydroxy-1,2,3,4,4a,5,11,11a-octahydro-6H-indolo[2,3-g]isoquinoline, 2-benzyl-4aα-(3-methoxyphenyl)-9-fluoro-11aβ-hydroxy-1,2,3,4,4a,5,11,11a-octahydro-6H-indolo[2,3-g]isoquinoline, 2-(2-phenylethyl)-4aα-(3-methoxyphenyl)-9-fluoro-11aβ-hydroxy-1,2,3,4,4a,5,11,11a-octahydro-6H-indolo[2,3-g]isoquinoline, and 2-allyl-4aα-(3-methoxyphenyl)-9-fluoro-11aβ-hydroxy-1,2,3,4,4a,5,11,11a-octahydro-6H-indolo[2,3-g]isoquinoline are produced by using 4-fluorophenylhydrazine instead of phenyl hydrazine and respectively using 2-cyclopropylmethyl-4aα-(3-methoxyphenyl)-6-oxo-8aβ-hydroxy-1,2,3,4,4a,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-(2-phenylethyl)-4aα-(3-methoxyphenyl)-6-oxo-8aβ-hydroxy-1,2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Similarly, 2-cyclopropylmethyl-4aα-(3-methoxyphenyl)-8-fluoro-11aβ-hydroxy-1,2,3,4,4a,5,11,11a-octahydro-6H-indolo[2,3-g]isoquinoline, 2-cyclopropylmethyl-4aα-(3-methoxyphenyl)-10-fluoro-11aβ-hydroxy-1,2,3,4,4a,5,11,11a-octahydro-6H-indolo[2,3-g]isoquinoline, 2-benzyl-4aα-(3-methoxyphenyl)-8-fluoro-11aβ-hydroxy-1,2,3,4,4a,5,11,11a-octahydro-6H-indolo[2,3-g]isoquinoline, 2-benzyl-4aα-(3-methoxyphenyl)-10-fluoro-11aβ-hydroxy-1,2,3,4,4a,5,11,11a-octahydro-6H-indolo[2,3-g]isoquinoline, 2-(2-phenylethyl)-4aα-(3-methoxyphenyl)-8-fluoro-11aβ-hydroxy-1,2,3,4,4a,5,11,11a-octahydro-6H-indolo[2,3-g]isoquinoline, 2-(2-phenylethyl)-4aα-(3-methoxyphenyl)-20-fluoro-11aβ-hydroxy-1,2,3,4,1a,5,11,11a-octahydro-6H-indolo[2,3-g]isoquinoline, 2-allyl-4aα-(3-methoxyphenyl)-8-fluoro-11aβ-hydroxy-1,2,3,4,4a,5,11,11a-octahydro-6H-indolo[2,3-g]isoquinoline, and 2-allyl-4aα-(3-methoxyphenyl)-10-fluoro-11aβ-hydroxy-1,2,3,4,4a,5,11,11a-octahydro-6H-indolo[2,3-g]isoquinoline are produced by using 3-fluorophenylhydrazine instead of phenyl hydrazine and respectively using 2-cyclopropylmethyl-4aα-(3-methoxyphenyl)-6-oxo-8aβ-hydroxy-1,2,3,4,4a,5,6,7,8,8a-decahydroisoquinoline, 2-benzyl-4aα-(3- methoxyphenyl)-6-oxo-8aβ-hydroxy-1,2,3,4,4a,5,6,7,8,8a-decahydroisoquinoline, 2-(2-phenylethyl)-4aα-(3-methoxyphenyl)-6-oxo-8aβ-hydroxy-1,2,3,4,4a,5,6,7,8,8a-decahydroisoquinoline, and 2-allyl-4aα-(3-methyoxyphenyl)-6-oxo-8aβ-hydroxy-1,2,3,4,4a,5,6,7,8,8a-decahydroisoquinoline.

Similarly, 2cyclopropylmethyl-4aα-(3-methoxyphenyl)-7-fluoro-11aβ-hydroxy-1,2,3,4,4a,5,11,11a-octahydro-6H-indolo[2,3-g]isoquinoline, 2-benzyl-4aα-(3-methoxyphenyl)-7fluoro-11aβ-hydroxy-1,2,3,4,4a,5,11,11a-octahydro-6H-indolo[2,3-g]isoquinoline, 2-(2-phenylethyl)-4aα-(3-methoxyphenyl)-7-fluoro-11aβ-hydroxy-1,2,3,4,4a,5,11,11a-octahydro-6H-indolo[2,3-g]isoquinoline, and 2-allyl-4aα-(3-methoxyphenyl)-7-fluoro-11aβ-hydroxy-1,2,3,4,4a,5,11,11a-octahydro-6H-indolo[2,3-g]isoquinoline, are produced by using 2-fluorophenyl hydrazine instead of phenyl hydrazine and respectively using 2-cyclopropylmethy-4aα-(3-methoxypheny)-6-oxo-8aβ-hydroxy-1,2,3,4,4a,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-(2-phenylethyl)-4aα-(3-methoxyphenyl)-6-oxo-8aβ-hydroxy-1,2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Similarly, 2-cyclopropylmethyl-4aα-(3-methoxyphenyl)-9-bromo-11aβ-hydroxy-1,2,3,4,4a,5,11,11a-octahydro-6H-indolo[2,3-g]isoquinoline, 2-benzyl-4aα-(3-methoxyphenyl)-9-bromo-11aβ-hydroxy-1,2,3,4,4a,5,11,11a-octahydro-6H-indolo[2,3-g]isoquinoline, 2-(2-phenylethyl)-4aα-(3-methoxyphenyl)-9-bromo-11aβ-hydroxy-1,2,3,4,4a,5,11,11a-octahydro-6H-indolo[2,3-g]isoquinoline, and 2-allyl-4aα-(3-methoxyphenyl)-9-bromo-11aβ-hydroxy-1,2,3,4,4a,5,11,11a-octahydro-6H-indolo[2,3-g]isoquinoline are produced by using 4-bromophenylhydrazine instead of phenylhydrazine and respectively using 2-cyclopropylmethyl-4aα-(3-methoxyphenyl)-6-oxo-8aβ-hydroxy-1,2,3,4,4a,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-(2-phenylethyl)-4aα-(3-methoxyphenyl)-6-oxo-8aβ-hydroxy-1,2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Similarly, 2-cyclopropylmethyl-4aα-(3-methoxyphenyl)-8-bromo-11aβ-hydroxy-1,2,3,4,4a,5,11,11a-octahydro-6H-indolo[2,3-g]isoquinoline, 2-cyclopropylmethyl-4aα-(3-methoxyphenyl)-10-bromo-11aβ-hydroxy-1,2,3,4,4a,5,11,11a-octahydro-6H-indolo[2,3-g]isoquinoline, 2-benzyl-4aα-(3-methoxyphenyl)-8-bromo-11aβ-hydroxy-1,2,3,4,4a,5,11,11a-octahydro-6H-indolo[2,3-g]isoquinoline, 2-benzyl-4aα-(3-methoxyphenyl)-10-bromo-11aβ-hydroxy-1,2,3,4,4a,5,11,11a-octahydro-6H-indolo[2,3-g]isoquinoline, 2-(2-phenylethyl)-4aα-(3-methoxyphenyl)-8-bromo-11aβ-hydroxy-1,2,3,4,4a,5,11,11a-octahydro-6H-indolo[2,3-g]isoquinoline, 2-(2-phenylethyl)-4aα-(3-methoxyphenyl)-10-bromo-11aβ-hydroxy-1,2,3,4,4a,5,11,11a-octahydro-6H-indolo[2,3-g]isoquinoline, 2-allyl-4aα-(3-methoxyphenyl)-8-bromo-11aβ-hydroxy-1,2,3,4,4a,5,11,11a-octahydro-6H-indolo[2,3-g]isoquinoline, and 2-allyl-4aα-(3-methoxyphenyl)-10-bromo-11aβ-hydroxy-1,2,3,4,4a,5,11,11a-octahydro-6H-indolo[2,3-g]isoquinoline are produced by using 3-bromophenylhydrazine instead of phenylhydrazine and respectively using 2-cyclopropylmethyl-4aα-(3-methoxyphenyl)-6-oxo-8aβ-hydroxy-1,2,3,4,4a,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-(2-phenylethyl)-4aα-(3-methoxyphenyl)-6-oxo-8aβ-hydroxy-1,2,3,4,4a,5,6,7,8,8-a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Similarly, 2-cyclopropylmethyl-4aα-(3-methoxyphenyl)-7-bromo-11aβ-hydroxy-1,2,3,4,4a,5,11,11a-octahydro-6H-indolo[2,3-g]isoquinoline, 2-benzyl-4aα-(3-methoxyphenyl)-7-bromo-11aβ-hydroxy-1,2,3,4,4a,5,11,11a-octahydro-6H-indolo[2,3-g]isoquinoline, 2-(2-phenylethyl)-4aα-(3-methoxyphenyl)-7-bromo-11aβ-hydroxy-1,2,3,4,4a,5,11,11a-octahydro-6H-indolo[2,3-g]isoquinoline, and 1-allyl-4aα-(3-methoxyphenyl)-7-bromo-11aβ-hydroxy-1,2,3,4,4a,5,11,11a-octahydro-6H-indolo[2,3-g]isoquinoline are produced by using 2-bromophenyl hydrazine instead of phenyl hydrazine and respectively using 2-cyclopropylmethyl-4aα-(3-methoxyphenyl)-6-oxo-8aβ-hydroxy-1,2,3,4,4a,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-(2-phenylethyl)-4aα-(3-methoxypheny)-6-oxo-8aβ-hydroxy-1,2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Similarly, 2-cyclopropylmethyl-4aα-(3-methoxyphenyl)-9-nitro-11aβ-hydroxy-1,2,3,4,4a, 5,11,11a-octahydro-6H-indolo[2,3-g]isoquinoline, 2-benzyl-4aα-(3-methoxyphenyl)-9-nitro-11aβ-hydroxy-1,2,3,4,4a,5,11,11a-octahydro-6H-indolo[2,3-g]isoquinoline, 2-(2-phenylethyl)-4aα-(3-methoxyphenyl)-9-nitro-11aβ-hydroxy-1,2,3,4,4a,5,11,11a-octahydro-6H-indolo[2,3-g]isoquinoline, and 2-allyl-4aα-(3-methoxyphenyl)-9-nitro-11aβ-hydroxy-1,2,3,4,4a,5,11,11a-octahydro-6H-indolo[2,3-g]isoquinoline are produced by using 4-nitrophenylhydrazine instead of phenylhydrazine and respectively using 2-cyclopropylmethyl-4aα-(3-methoxyphenyl)-6-oxo-8aβ-hydroxy-1,2,3,4,4a,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-(2-phenylethyl)-4aα-(3-methoxyphenyl)-6-oxo-8aβ-hydroxy-1,2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Similarly, 2-cyclopropylmethyl-4aα-(3-methoxyphenyl)-8-nitro-11aβ-hydroxy-1,2,3,4,4a,5,11,11a-octahydro-6H-indolo[2,3-g]isoquinoline, 2-cyclopropylmethyl-4aα-(3-methoxyphenyl)-10-nitro-11aβ-hydroxy-1,2,3,4,4a,5,11,11a-octahydro-6H-indolo[2,3-g]isoquinoline, 2-benzyl-4aα-(3-methoxyphenyl)-8-nitro-11aβ-hydroxy-1,2,3,4,4a,5,11,11a-octahydro-6H-indolo[2,3-g]isoquinoline, 2-methyl-4aα-(3-methoxyphenyl)-10-nitro-11aβ-hydroxy-1,2,3,4,4a,5,11,11a-octahydro-6H-indolo[2,3-g]isoquinoline, 2-(2-phenylethyl)-4aα-(3-methoxyphenyl)-8-nitro-11aβ-hydroxy-1,2,3,4,4a,5,11,11a-octahydro-6H-indolo[2,3-g] isoquinoline, 2-(2-phenylethyl)-4aα-(3-methoxyphenyl)-10-nitro-11aβ-hydroxy-1,2,3,4,4a,5,11,11a-octahydro-6H-indolo[2,3-g]isoquinoline, 2-allyl-4aα-(3-methoxyphenyl)-8-nitro-11aβ-hydroxy-1,2,3,4,4a,5,11,11a-octahydro-6H-indolo[2,3-g]isoquinoline, and 2-allyl-4aα-(3-methoxyphenyl)-10-nitro-11aβ-hydroxy-1,2,3,4,4a,5,11,11a-octahydro-6H-indolo[2,3-g]isoquinoline are produced by using 3-nitrophenylhydrazine instead of phenylhydrazine and respectively using 2-cyclopropylmethyl-4aα-(3-methoxyphenyl)-6-oxo-8aβ-hydroxy-1,2,3,4,4a,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-(2-phenylethyl)-4aα-(3- methoxyphenyl)-6-oxo-8aβ-hydroxy-1,2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Similarly, 2-cyclopropylmethyl-4aα-(3-methoxyphenyl)-7-nitro-11aβ-hydroxy-1,2,3,4,4a,5,11,11a-octahydro-6H-indolo[2,3-g]isoquinoline, 2-benzyl-4aα-(3-methoxyphenyl)-7-nitro-11aβ-hydroxy-1,2,3,4,4a,5,11,11a-octahydro-6H-indolo[2,3-g]isoquinoline, 2-(2-phenylethyl)-4aα-(3-methoxyphenyl)-7-nitro-11aβ-hydroxy-1,2,3,4,4a,5,11,11a-octahydro-6H-indolo[2,3-g]isoquinoline, and 2-allyl-4aα-(3-methoxyphenyl)-7-nitro-11aβ-hydroxy-1,2,3,4,4a,5,11,11a-octahydro-6H-indolo[2,3-g]isoquinoline are produced by using 2-nitrophenylhydrazine instead of phenylhydrazine and respectively using 2-cyclopropylmethyl-4aα-(3-methoxyphenyl)-6-oxo-8aβ-hydroxy-1,2,3,4,4a,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-(2-phenylethyl)-4aα-(3-methoxyphenyl)-6-oxo-8aβ-hydroxy-1,2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Similarly, 2-cyclopropylmethyl-4-aα-(3-methoxyphenyl)-11aβ-hydroxy-1,2,3,4,4a,5,11,11a-octahydro-6H-indolo[2,3-g]isoquinoline, 2-benzyl-4aα-(3-methoxyphenyl)-11aβ-hydroxy-1,2,3,4,4a,5,11,11a-octahydro-6H-indolo[2,3-g]isoquinoline, 2-(2-phenylethyl)-4aα-(3-methoxyphenyl)-11aβ-hydroxy-1,2,3,4,4a,5,11,11a-octahydro-6H-indolo[2,3-g]isoquinoline, and 2-allyl-4aα-(3-methoxyphenyl)-11aβ-hydroxy-1,2,3,4,4a,5,11,11a-octahydro-6H-indolo[2,3-g]isoquinoline are produced by using phenylmethylhydrazine instead of phenylhydrazine and respectively using 2-cyclopropylmethyl-4aα-(3-methoxyphenyl)-6-oxo-8aβ-hydroxy-1,2,3,4,5,6,7,8,8a-decahydroisoquinoline, 2-benzyl-4aα-(3-methoxyphenyl)-6-oxo-8aβ-hydroxy-1,2,3,4,4a,5,6,7,8,8a-decahydroisoquinoline, 2-(2-phenylethyl)-4aα-(3-methoxyphenyl)-6-oxo-8aβ-hydroxy-1,2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8,8a-decahydroisoquinoline.

Example 45

2-Cyclopropylmethyl-4aα-(3-methoxyphenyl)-11aβ-hydroxy-1,2,3,4,4a,5,11,11a-octahydro-6H-indolo[2,3-g]isoquinoline 56

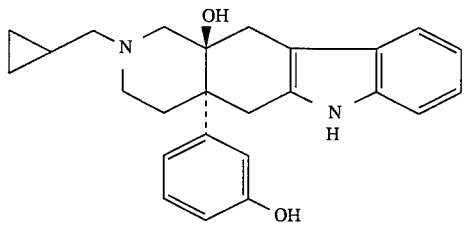

A solution of 70 mg (0.17 mmol) of 2-cyclopropylmethyl-4aα-(3-methoxyphenyl)-11aβ-hydroxy-1,2,3,4,4a,5,11,11a-octahydro-6H-indolo[2,3-g]isoquinoline in 2 ml of anhydrous DMF was caused to react with 0.12 ml (1.3 mmol) of propane thiol and 98 mg (0.87 mmol) of potassium-t-butoxide at 150° C. for three hours. Since the reaction mixture still contained unaltered reactants, it was caused to react further with 0.06 ml (0.7 mmol) of propane thiol and 49 mg (0.44 mmol) of potassium-t-butoxide for two hours and then with 0.12 mol (1.3 mmol) of propane thiol and 98 mg (0.07 mmol) of potassium-t-butoxide for two hours. The resultant reaction mixture was distilled under a vacuum to expel the solvent, combined with 8 ml of a saturated aqueous solution of sodium hydrogen carbonate, and extracted three times from 8 ml of ethanol/chloroform (3/1). The extract was washed with a saturated aqueous saline solution, dried, concentrated, and refined by silica gel column chromatograph (9385, 7 g; chloroform-ammonia-saturated chloroform-5% methanol/ammonia-saturated chloroform), to afford 39.7 mg of the captioned compound (yield 59%). This compound was dissolved in 2 ml of chloroform and 0.2 ml of methanol and isolated as the methanesulfonate by addition of methanesulfonic acid.

m.p.: 153° to 157° C. (methanesulfonate)

Mass (EI): 388 (M$^+$)

Elementary analyses For $C_{25}H_{28}N_2O_2$ $CH_3SO_3H$ $1.5H_2O$

|  | C | H | N | S |
|---|---|---|---|---|
| Calculated | 61.04 | 6.90 | 5.47 | 6.27 |
| Found | 60.95 | 6.73 | 5.34 | 6.31 |

Similarly, 2-benzyl-4aα-(3-hydroxyphenyl)-11aβ-hydroxy-1,2,3,4,4a,5,11,11a-octahydro-6H-indolo[2,3-g]isoquinoline, 2-(2-phenylethyl)-4aα-(3-hydroxyphenyl)-11aβ-hydroxy-1,2,3,4,4a,5,11,11a-octahydro-6H-indolo[2,3-g]isoquinoline, 2-allyl-4aα-(3-hydroxyphenyl)-11aβ-hydroxy-1,2,3,4,4a,5,11,11a-octahydro-6H-indolo[2,3-g]isoquinoline, 2-cyclopropylmethyl-4aα-(3-hydroxyphenyl)-9-methyl-11aβ-hydroxy-1,2,3,4,4a,5,11,11a-octahydro-6H-indolo[2,3-g]isoquinoline, 2-benzyl-4aα-(3-hydroxyphenyl)-9-methyl-11aβ-hydroxy-1,2,3,4,4a,5,11,11a-octahydro-6H-indolo[2,3-g]isoquinoline, 2-(2-phenylethyl)-4aα-(3-hydroxyphenyl)-9-methyl-11aβ-hydroxy-1,2,3,4,4a,5,11,11a-octahydro-6H-indolo[2,3-g]isoquinoline, 2-allyl-4aα-(3-hydroxyphenyl)-9-methyl-11aβ-hydroxy-1,2,3,4,4a,5,11,11a-octahydro-6H-indolo[2,3-g]isoquinoline, 2-cyclopropylmethyl-4aα-(3-hydroxyphenyl)-8-methyl-11aβ-hydroxy-1,2,3,4,4a,5,11a-octahydro-6H-indolo[2,3-g]isoquinoline, 2-cyclopropylmethyl-4aα-(3-hydroxyphenyl)-10-methyl-11aβ-hydroxy-1,2,3,4,4a,5,11,11a-octahydro-6H-indolo[2,3-g]isoquinoline, 2-benzyl-4aα-(3-hydroxyphenyl)-8-methyl-11aβ-hydroxy-1,2,3,4,4a,5,11,11a-octahydro-6H-indolo[2,3-g]isoquinoline, 2-benzyl-4aα-(3-hydroxyphenyl)-10-methyl-11aβ-hydroxy-1,2,3,4,4a,5,11,11a-octahydro-6H-indolo[2,3-g]isoquinoline, 2-(2-phenylethyl)-4aα-(3-hydroxyphenyl)-8-methyl-11aβ-hydroxy-1,2,3,4,4a,5,11,11a-octahydro-6H-indolo[2,3-g]isoquinoline, 2-(2-phenylethyl)-4aα-(3-hydroxyphenyl)-10-methyl-11aβ-hydroxy-1,2,3,4,4a,5,11,11a-octahydro-6H-indolo[2,3-g]isoquinoline, 2-allyl-4aα-(3-hydroxyphenyl)-8-methyl-11aβ-hydroxy-1,2,3,4,4a,5,11,11a-octahydro-6H-indolo[2,3-g]isoquinoline, 2-allyl-4aα-(3-hydroxyphenyl)-10-methyl-11aβ-hydroxy-1,2,3,4,4a,5,11,11a-octahydro-6H-indolo[2,3-g]isoquinoline, 2-cyclopropylmethyl-4aα-(3-hydroxyphenyl)-7-methyl-11aβ-hydroxy-1,2,3,4,4a,5,11,11a-octahydro-6H-indolo[2,3-g]isoquinoline, 2-benzyl-4aα-(3-hydroxyphenyl)-7-methyl-11aβ-hydroxy-1,2,3,4,4a,5,11,11a-octahydro-6H-indolo[2,3-g]isoquinoline, 2-(2-phenylethyl)-4aα-(3-hydroxyphenyl)-7-methyl-11aβ-hydroxy-1,2,3,4,4a,5,11,11a-octahydro-6H-indolo[2,3-g]isoquinoline, 2-allyl-4aα-(3-hydroxyphenyl)-7-methyl-11aβ-hydroxy-1,2,3,4,4a,5,11,11a-octahydro-6H-indolo[2,3-g]isoquinoline, 2-cyclopropylmethyl-4aα-(3-hydroxyphenyl)-9-chloro-11aβ-hydroxy-1,2,3,4,4a,5,11, 11a-octahydro-6H-indolo[2,3-g]isoquinoline, 2-benzyl-4aα-(3-hydroxyphenyl)-9-chloro-11aβ-hydroxy-1,2,3,4,4a,5,11,11a-octahydro-6H-indolo[2,3-g]isoquinoline, 2-(2-phenylethyl)-4aα-(3-hydroxyphenyl)-9-chloro-11aβ-hydroxy-1,2,3,4,4a,5,11,11a-octahydro-6H-indolo[2,3-g]isoquinoline, 2-allyl-4aα-(3-hydroxyphenyl)-9-chloro-11aβ-hydroxy-1,2,3,4,4a,5,11,11a-octahydro-6H-indolo[2,3-g]isoquinoline, 2-cyclopropylmethyl-4aα-(3-hydroxyphenyl)-8-chloro-11aβ-hydroxy-1,2,3,4,4a,5,11,11a-octahydro-6H-indolo[2,3-g]isoquinoline, 2-cyclopropylmethyl-4aα-(3-hydroxyphenyl)-10-chloro-11aβ-hydroxy-1,2,3,4,4a,5,11,11a-octahydro-6H-indolo[2,3-g]isoquinoline, 2-benzyl-4aα-(3-hydroxyphenyl)-8-chloro-11aβ-hydroxy-1,2,3,4,4a,5,11,11a-octahydro-6H-indolo[2,3-g]isoquinoline, 2-benzyl-4aα-(3-hydroxyphenyl)-10-chloro-11aβ-hydroxy-1,2,3,4,4a,5,11,11a-octahydro-6H-indolo[2,3-g]isoquinoline, 2-(2-phenylethyl)-4aα-(3-hydroxyphenyl)-8-chloro-11aβ-hydroxy-1,2,3,4,4a,5,11,11a-octahydro-6H-indolo[2,3-g]isoquinoline, 2-(2-phenylethyl)-4aα-(3-hydroxyphenyl)10-chloro-11aβ-hydroxy-1,2,3,4,4a,5,11,11a-octahydro-6H-indolo[2,3-g]isoquinoline, 2-allyl-4aα-(3-hydroxyphenyl)-8-chloro-11aβ-hydroxy-1,2,3,4,4a,5,11,11a-octahydro-6H-indolo[2,3-g]isoquinoline, 2-allyl-4aα-(3-hydroxyphenyl)-10-chloro-11aβ-hydroxy-1,2,3,4,4a,5,11,11a-octahydro-6H-indolo[2,3-g]isoquinoline, 2-cyclopropylmethyl-4aα-(3-hydroxyphenyl)-7-chloro-11aβ-hydroxy-1,2,3,4,4a,5,11,11a-octahydro-6H-indolo[2,3-g]isoquinoline, 2-benzyl-4aα-(3-hydroxyphenyl)-7-chloro-11aβ-hydroxy-1,2,3,4,4a,5,11,11a-octahydro-6H-indolo[2,3-g]isoquinoline, 2-(2-phenylethyl)-4aα-(3-hydroxyphenyl)-7-chloro-11aβ-hydroxy-1,2,3,4,4a,5,11,11a-octahydro-6H-indolo[2,3-g]isoquinoline, 2-allyl-4aα-(3-hydroxyphenyl)-7-chloro-11aβ-hydroxy-1,2,3,4,4a,5,11,11a-octahydro-6H-indolo[2,3-g]isoquinoline, 2-cyclopropylmethyl-4aα-(3-hydroxyphenyl)-9-fluoro-11aβ-hydroxy-1,2,3,4,4a,5,11,11a-octahydro-6H-indolo[2,3-g]isoquinoline, 2-benzyl-4aα-(3-hydroxyphenyl)-9-fluoro-11aβ-hydroxy-1,2,3,4,4a,5,11,11a-octahydro-6H-indolo[2,3-g]isoquinoline, 2-(2-phenylethyl)-4aα-(3-hydroxyphenyl)-9-fluoro-11aβ-hydroxy-1,2,3,4,4a,5,11,11a-octahydro-6H-indolo[2,3-g]isoquinoline, 2-allyl-4aα-(3-hydroxyphenyl)-9-fluoro-11aβ-hydroxy-1,2,3,4,4a,5,11,11a-octahydro-6H-indolo[2,3-g]isoquinoline, 2-cyclopropylmethyl-4aα-(3-hydroxyphenyl)-8-fluoro-11aβ-hydroxy-1,2,3,4,4a,5,11,11a-octahydro-6H-indolo[2,3-g]isoquinoline, 2-cyclopropylmethyl-4aα-(3-hydroxyphenyl)-10-fluoro-11aβ-hydroxy-1,2,3,4,4a,5,11,11a-octahydro-6H-indolo[2,3-g]isoquinoline, 2-benzyl-4aα-(3-hydroxyphenyl)-8-fluoro-11aβ-hydroxy-1,2,3,4,4a,5,11,11a-octahydro-6H-indolo[2,3-g]isoquinoline, 2-benzyl-4aα-(3-hydroxyphenyl)-10-fluoro-11aβ-hydroxy-1,2,3,4,4a,5,11,11a-octahydro-6H-indolo[2,3-g]isoquinoline, 2-(2-phenylethyl)-4aα-(3-hydroxyphenyl)-8-fluoro-11aβ-hydroxy-1,2,3,4,4a,5,11,11a-octahydro-6H-indolo[2,3-g]isoquinoline, 2(2-phenylethyl)-4aα-(3-hydroxyphenyl)-10-fluoro-11aβ-hydroxy-1,2,3,4,4a,5,11,11a-octahydro-6H-indolo[2,3-g]isoquinoline, 2-allyl-4aα-(3-hydroxyphenyl)-8-fluoro-11aβ-hydroxy-1,2,3,4,4a,5,11,11a-octahydro-6H-indolo[2,3-g]isoquinoline, 2-allyl-4aα-(3-hydroxyphenyl)-10-fluoro-11aβ-hydroxy-1,2,3,4,4a,5,11,11a-octahydro-6H-indolo[2,3-g]isoquinoline, 2-cyclopropylmethyl-4aα-(3-hydroxyphenyl)-7-fluoro-11aβ-hydroxy-1,2,3,4,4a,5,11,11a-octahydro-6H-indolo[2,3-g]isoquinoline, 2-benzyl-4aα-(3-hydroxyphenyl)-7-fluoro-11aβ-hydroxy-1,2,3,4,4a,5,11,11a-octahydro-6H-indolo[2,3-g]isoquinoline, 2-(2-phenylethyl)-4aα-(3-hydroxyphenyl)-7-fluoro-11aβ-hydroxy-1,2,3,4,4a,5,11,11a-octahydro-6H-indolo[2,3-g]isoquinoline, 2-allyl-4aα-(3-hydroxyphenyl)-7-fluoro-11aβ-hydroxy-1,2,3,4,4a,5,11,11a-octahydro-6H-indolo[2,3-g]isoquinoline, 2-cyclopropylmethyl-4aα-(3-hydroxyphenyl)-9-bromo-11aβ-hydroxy-1,2,3,4,4a,5,11,11a-octahydro-6H-indolo[2,3-g]isoquinoline, 2-benzyl-4aα-(3-hydroxyphenyl)-9-bromo-11aβ-hydroxy-1,2,3,4,4a,5,11,11a-octahydro-6H-indolo[2,3-g]isoquinoline, 2-(2-phenylethyl)-4aα-(3-hydroxyphenyl)-9-bromo-11aβ-hydroxy-1,2,3,4,4a,5,11,11a-octahydro-6H-indolo[2,3-g]isoquinoline, 2-allyl-4aα-(3-hydroxyphenyl)-9-bromo-11aβ-hydroxy-1,2,3,4,4a,5,11,11a-octahydro-6H-indolo[2,3-g]isoquinoline, 2-cyclopropylmethyl-4aα-(3-hydroxyphenyl)-8-bromo-11aβ-hydroxy-1,2,3,4,4a,5,11,11a-octahydro-6H-indolo[2,3-g]isoquinoline, 2-cyclopropylmethyl-4aα-(3-hydroxyphenyl)-10-bromo-11aβ-hydroxy-1,2,3,4,4a,5,11,11a-octahydro-6H-indolo[2,3-g]isoquinoline, 2-benzyl-4aα-(3-hydroxyphenyl)-8-bromo-11aβ-hydroxy-1,2,3,4,4a,5,11,11a-octahydro-6H-indolo[2,3-g]isoquinoline, 2-benzyl-4aα-(3-hydroxyphenyl)-10-bromo-11aβ-hydroxy-1,2,3,4,4a,5,11,11a-octahydro-6H-indolo[2,3-g]isoquinoline, 2-(2-phenylethyl)-4aα-(3-hydroxyphenyl)-8-bromo-11aβ-hydroxy-1,2,3,4,4a,5,11,11a-octahydro-6H-indolo[2,3-g]isoquinoline, 2-(2-phenylethyl)-4aα-(3-hydroxyphenyl)-10-bromo-11aβ-hydroxy-1,2,3,4,4a,5,11,11a-octahydro-6H-indolo[2,3-g]isoquinoline, 2-allyl-4aα-(3-hydroxyphenyl)-8-bromo-11aβ-hydroxy-1,2,3,4,4a,5,11,11a-octahydro-6H-indolo[2,3-g]isoquinoline, 2-allyl-4aα-(3-hydroxyphenyl)-10-bromo-11aβ-hydroxy-1,2,3,4,4a,5,11,11a-octahydro-6H-indolo[2,-g]isoquinoline, 2-cyclopropylmethyl-4aα-(3-hydroxyphenyl)-7-bromo-11aβ-hydroxy-1,2,3,4,4a,5,11,11a-octahydro-6H-indolo[2,3-g]isoquinoline, 2-benzyl-4aα-(3-hydroxyphenyl)-7-bromo-11aβ-hydroxy-1,2,3,4,4a,5,11,11a-octahydro-6H-indolo[2,3-g]isoquinoline, 2-(2-phenylethyl)-4aα-(3-hydroxyphenyl)-7-bromo-11aβ-hydroxy-1,2,3,4,4a,5,11,11a-octahydro-6H-indolo[2,3-g]isoquinoline, 2-allyl-4aα-(3-hydroxyphenyl)-7-bromo-11aβ-hydroxy-1,2,3,4,4a,5,11,11a-octahydro-6H-indolo[2,3-g]isoquinoline, 2-cyclopropylmethyl-4aα-(3-hydroxyphenyl)-9-nitro-11aβ-hydroxy-1,2,3,4,4a,5,11,11a-octahydro-6H-indolo[2,3-g]isoquinoline, 2-benzyl-4aα-(3-hydroxyphenyl)-9-nitro-11aβ-hydroxy-1,2,3,4,4a,5,11,11a-octahydro-6H-indolo[2,3-g]isoquinoline, 2-(2-phenylethyl)-4aα-(3-hydroxyphenyl)-9-nitro-11aβ-hydroxy-1,2,3,4,4a,5,11,11a-octahydro-6H-indolo[2,3-g]isoquinoline, 2-allyl-4aα-(3-hydroxyphenyl)-9-nitro-11aβ-hydroxy-1,2,3,4,4a,5,11,11a-octahydro-6H-indolo[2,3-g]isoquinoline, 2-cyclopropylmethyl-4aα-(3-hydroxyphenyl)-8-nitro-11aβ-hydroxy-1,2,3,4,4a,5,11,11a-octahydro-6H-indolo[2,3-g]isoquinoline, 2-cyclopropylmethyl-4aα-(3-hydroxyphenyl)-10-nitro-11aβ-hydroxy-1,2,3,4,4a,5,11,11a-octahydro-6H-indolo[2,3-g]isoquinoline, 2-benzyl-4aα-(3-hydroxyphenyl)-8-nitro-11aβ-hydroxy-1,2,3,4,4a,5,11,11a-octahydro-6H-indolo[2,3-g]isoquinoline, 2-benzyl-4aα-(3-hydroxyphenyl)-10-nitro-11aβ-hydroxy-1,2,3,4,4a,5,11,11a-octahydro-6H-indolo[2,3-g]isoquinoline, 2-(2-phenylethyl)-4aα-(3-hydroxyphenyl)-8-nitro-11aβ-hydroxy-1,2,3,4,4a,5,11,11a-octahydro-6H-indolo[2,3-g]isoquinoline, 2-(2-phenylethyl)-4aα-(3-hydroxyphenyl)-10-nitro-11aβ-hydroxy-1,2,3,4,4a,5,11,11a-octahydro-6H-indolo[2,3-g]isoquinoline, 2-allyl-4aα-(3-hydroxyphenyl)-8-nitro-11aβ-hydroxy-1,2,3,4,4a,5,11,11a-6H-indolo[2,3-g]isoquinoline, 2-allyl-4aα-(3-hydroxyphenyl)-10-nitro-11aβ-hydroxy-1,2,3,4,4a,5,11,11a-octahydro-6H-indolo[2,3-g]isoquinoline, 2-cyclopropylmethyl-4aα-(3-hydroxyphenyl)-7-nitro-11aβ-hydroxy-1,2,3,4,4a,5,11,11a-octahydro-6H- indolo[2,3-g]isoquinoline, 2-benzyl-4aα-(3-hydroxyphenyl)-7-nitro-11aβ-hydroxy-1,2,3,4,4a,5,11,11a-octahydro-6H-indolo[2,3-g]isoquinoline, 2-(2-phenylethyl)-4aα-(3-hydroxyphenyl)-7-nitro-11aβ-hydroxy-1,2,3,4,4a,5,11,11a-octahydro-6H-indolo[2,3-g]isoquinoline, 2-allyl-4aα-(3-hydroxyphenyl)-7-nitro-11aβ-hydroxy-1,2,3,4,4a,5,11,11a-octahydro-6H-indolo[2,3-g]isoquinoline, 2-cyclopropylmethyl-4aα-(3-hydroxyphenyl)-11aβ-hydroxy-1,2,3,4,4a,5,11,11a-octahydro-6-methyl-indolo[2,3-g]isoquinoline, 2-benzyl-4aα-(3-hydroxyphenyl)-11aβ-hydroxy-1,2,3,4,4a,5,11,11a-octahydro-6-methyl-indolo[2,3-g]isoquinoline, 2(2-phenylethyl)-4aα-(3-hydroxyphenyl)-4aα-(3-hydroxyphenyl)-11aβ-hydroxy-1,2,3,4,4a,5,11,11a-octahydro-6-methyl-indolo[2,3-g]isoquinoline, and 2-allyl-4aα-(3-hydroxyphenyl)-11aβ-hydroxy-1,2,3,4,4a,5,11,11a-octahydro-6-methyl-indolo[2,3-g]isoquinoline are produced by respectively using 2-benzyl-4aα-(3-methoxyphenyl)-11aβ-hydroxy-1,2,3,4,4a,5,11,11a-octahydro-6H-indolo[2,3-g]isoquinoline, 2-(2-phenylethyl)-4aα-(3-methoxyphenyl)-11aβ-hydroxy-1,2,3,4,4a,5,11,11a-octahydro-6H-indolo[2,3-g]isoquinoline, 2-allyl-4aα-(3-methoxyphenyl)-11aβ-hydroxy-1,2,3,4,4a,5,11,11a-octahydro-6H-indolo[2,3-g]isoquinoline, 2-cyclopropylmethyl-4aα-(3-methoxyphenyl)-9-methyl-11aβ-hydroxy-1,2,3,4,4a,5,11,11a-octahydro-6H-indolo[2,3-g]isoquinoline, 2-benzyl-4aα-(3-methoxyphenyl)-9-methyl-11aβ-hydroxy-1,2,3,4,4a,5,11,11-a-octahydro-6H-indolo[2,3-g]isoquinoline, 2(2-phenylethyl)-4aα-(3-methoxyphenyl)-9-methyl-11aβ-hydroxy-1,2,3,4,4a,5,11,11a-octahydro-6H-indolo[2,3-g]isoquinoline, 2-allyl-4aα-(3-methoxyphenyl-9-methyl-11aβ-hydroxy-1,2,3,4,4a,5,11,11a-octahydro-6H-indolo[2,3-g]isoquinoline, 2-cyclopropylmethyl-4aα-(3-methoxyphenyl)-8-methyl-11aβ-hydroxy-1,2,3,4,4a,5,11,11a-octahydro-6H-indolo[2,3-g]isoquinoline, 2-cyclopropylmethyl-4aα-(3-methoxyphenyl)-8-methyl-11aβ-hydroxy-1,2,3,4,4a,5,11,11a-octahydro-6H-indolo[2,3-g]isoquinoline, 2-cyclopropylmethyl-4aα-(3-methoxyphenyl)-10-methyl-11aβ-hydroxy-1,2,3,4,4a,-octahydro-6H-indolo[2,3-g]isoquinoline, 2-benzyl-4aα-(3-methoxyphenyl)-8-methyl-11aβ-hydroxy-1,2,3,4,4a,5,11,11a-octahydro-6H-indolo[2,3-g]isoquinoline, 2-benzyl-4aα-(3-methoxyphenyl)-10-methyl-11aβ-hydroxy-1,2,3,4,4a,5,11,11a-octahydro-6H-indolo[2,3-g]isoquinoline, 2-(2-phenylethyl)-4aα-(3-methoxyphenyl)-8-methyl-11aβ-hydroxy-1,2,3,4,4a,5,11,11a-octahydro-6H-indolo[2,3-g]isoquinoline, 2-(2-phenylethyl)-4aα-(3-methoxyphenyl)-10-methyl-11aβ-hydroxy-1,2,3,4,4a,5,11,11a-octahydro-6H-indolo[2,3-g]isoquinoline, 2-allyl-4aα-(3-methoxyphenyl)-8-methyl-11aβ-hydroxy-1,2,3,4,4a,5,11,11a-octahydro-6H-indolo[2,3-g]isoquinoline, 2-allyl-4aα-(3-methoxyphenyl)-10-methyl-11aβ-hydroxy-1,2,3,4,4a,5,11,11a-octahydro-6H-indolo[2,3-g]isoquinoline, 2-cyclopropylmethyl-4aα-(3-methoxyphenyl)-7-methyl-11aβ-hydroxy-1,2,3,4,4a,5,11,11a-octahydro-6H-indolo[2,3-g]isoquinoline, 2-benzyl-4aα-(3-methoxyphenyl)-7-methyl-11aβ-hydroxy-1,2,3,4,4a,5,11,11a-octahydro-6H-indolo[2,3-g]isoquinoline, 2-(2-phenylethyl)-4aα-(3-methoxyphenyl)-7-methyl-11aβ-hydroxy-1,2,3,4,4a,5,11,11a-octahydro-6H-indolo[2,3-g]isoquinoline, 2-allyl-4aα(3-methoxyphenyl)-7-methyl-11aβ-hydroxy-1,2,3,4,4a,5,11,11a-octahydro-6H-indolo[2,3-g]isoquinoline, 2-cyclopropylmethyl-4aα-(3-methoxyphenyl)-9-chloro-11aβ-hydroxy-1,2,3,4,4a,5,11,11a-octahydro-6H-indolo[2,3-g]isoquinoline, 2-benzyl-4aα-(3-methoxyphenyl)-9-chloro-11aβ-hydroxy-1,2,3,4,4a,5,11,11a-octahydro-6H-indolo[2,-g]isoquinoline, 2-(2-phenylethyl)-4aα-(3-methoxyphenyl)-9-chloro-11aβ-hydroxy-1,2,3,4,4a,5,11,11a-octahydro-6H-indolo[2,3-g]isoquinoline, 2-allyl-4aα-(3-methoxyphenyl)-9-chloro-11aβ-hydroxy-1,2,3,4,4a,5,11,11a-octahydro-6H-indolo[2,3-g]isoquinoline, 2-cyclopropylmethyl-4aα-(3-methoxyphenyl)-8-chloro-11aβ-hydroxy-1,2,3,4,4a,5,11,11a-octahydro-6H-indolo[2,3-g]isoquinoline, 2-cyclopropylmethyl-4aα-(3-methoxyphenyl)-10-chloro-11aβ-hydroxy-1,2,3,4,4a,5,11,11a-octahydro-6H-indolo[2,3-g]isoquinoline, 2-benzyl-4aα-(3-methoxyphenyl)-8-chloro-11aβ-hydroxy-1,2,3,4,4a,5,11,11a-ocotahydro-6H-indolo[2,3-g]isoquinoline, 2-benzyl-4aα-(3-methoxyphenyl)-10-chloro-11aβ-hydroxy-1,2,3,4,4a,5,11,11a-octahydro-6H-indolo[2,3-g]isoquinoline, 2-(2-phenylethyl)-4aα-(3-methoxyphenyl)-8-chloro-11aβ-1,2,3,4,4a,5,11,11a-octahydro-6H-indolo[2,3-g]isoquinoline, 2-(2-phenylethyl)-4aα-(3-methoxyphenyl)-10-chloro-11aβ-hydroxy-1,2,3,4,4a,5,11,11a-octahydro-6H-indolo[2,3-g]isoquinoline, 2-allyl-4aα-(3-methoxyphenyl)-8-chloro-11aβ-hydroxy-1,2,3,4,4a,5,11,11a-octahydro-6H-indolo[2,3-g]isoquinoline, 2-allyl-4aα-(3-methoxyphenyl)-10-chloro-11aβ-hydroxy-1,2,3,4,4a,5,11,11a-octahydro-6H-indolo[2,3-g]isoquinoline, 2-cyclopropylmethyl-4aα-(3-methoxyphenyl)-7-chloro-11aβ-hydroxy-1,2,3,4,4a,5,11,11a-octahydro-6H-indolo[2,3-g]isoquinoline, 2-benzyl-4aα-(3-methoxyphenyl)-7-chloro-11aβ-hydroxy-1,2,3,4,4a,5,11,11a-octahydro-6H-indolo[2,3-g]isoquinoline, 2-(2-phenylethyl)-4aα-(3-methoxyphenyl)-7-chloro-11aβ-hydroxy-1,2,3,4,4a,5,11,11a-octahydro-6H-indolo[2,3-g]isoquinoline, 2-allyl-4aα-(3-methoxyphenyl)-7-chloro-11aβ-hydroxy-1,2,3,4,4a,5,11,11a-octahydro-6H-indolo[2,3-g]isoquinoline, 2-cyclopropylmethyl-4aα-(3-methoxyphenyl)-9-fluoro-11aβ-hydroxy-1,2,3,4,4a,5,11,11a-octahydro-6H-indolo[2,3-g]isoquinoline, 2-benzyl-4aα-(3-methoxyphenyl)-9-fluoro-11aβ-hydroxy-1,2,3,4,4a,5,11,11a-octahydro-6H-indolo[2,3-g]isoquinoline, 2-(2-phenylethyl)-4aα-(3-methoxyphenyl)-9-fluoro-11aβ-hydroxy-1,2,3,4,4a,5,11,11a-octahydro-6H-indolo[2,3-g]isoquinoline, 2-allyl-4aα-(3-methoxyphenyl)-9-fluoro-11aβ-hydroxy-1,2,3,4,4a,5,11,11a-octahydro-6H-indolo[2,3-g]isoquinoline, 2-cyclopropylmethyl-4aα-(3-methoxyphenyl)-8-fluoro-11aβ-hydroxy-1,2,3,4,4a,5,11,11a-octahydro-6H-indolo[2,3-g]isoquinoline, 2-cyclopropylmethyl-4aα-(3-methoxyphenyl)-10-fluoro-11aβ-hydroxy-1,2,3,4,4a,5,11,11a-octahydro-6H-indolo[2,3-g]isoquinoline, 2-benzyl-4aα-(3-methoxyphenyl)-8-fluoro-11aβ-hydroxy-1,2,3,4,4a,5,11,11a-octahydro-6H-indolo[2,3-g]isoquinoline, 2-benzyl-4aα(3-methoxyphenyl)-10-fluoro-11aβ-hydroxy-1,2,3,4,4a,5,11,11a-octahydro-6H-indolo[2,3-g]isoquinoline, 2-(2-phenylethyl)-4aα-(3-methoxyphenyl)-8-fluoro-11aβ-hydroxy-1,2,3,4,4a,5,11,11a-octahydro-6H-indolo[2,3-g]isoquinoline, 2-(2-phenylethyl)-4aα-(3-methoxyphenyl)-10-fluoro-11aβ-hydroxy-1,2,3,4,4a,5,11,11a-octahydro-6H-indolo[2,3-g]isoquinoline, 2-allyl-4aα-(3-methoxyphenyl)-8-fluoro-11aβ-hydroxy-1,2,3,4,4a,5,11,11a-octahydro-6H-indolo[2,3-g]isoquinoline, 2-allyl-4aα-(3-methoxyphenyl)-10-fluoro-11aβ-hydroxy-1,2,3,4,4a,5,11,11a-octahydro-6H-indolo[2,3-g]isoquinoline, 2-cyclopropylmethyl-4aα-(3-methoxyphenyl)-7fluoro-11aβ-hydroxy-1,2,3,4,4a,5,11,11a-octahydro-6H-indolo[2,3-g]isoquinoline, 2-benzyl-4aα-(3-methoxyphenyl)-7-fluoro-11aβ-hydroxy-1,2,3,4,4a,5,11,11a-octahydro-6H-indolo[2,3-g]isoquinoline, 2-(2-phenylethyl)-4aα-(3-methoxyphenyl)-7-fluoro-11aβ-hydroxy-1,2,3,4,4a,5,11,11a-octahydro-6H-indolo[2,3-g]isoquinoline, 2-allyl-4aα-(3-methoxyphenyl)-7-fluoro-11aβ-hydroxy-1,2,3,4,4a,5,11,11a-octahydro-6H-indolo[2,3-g]isoquinoline, 2-cyclopropylmethyl-4aα-(3-methoxyphenyl)-9-bromo-11aβ-hydroxy-1,2,3,4,4a,5,11, 11a-octahydro-6H-indolo[2,3-g]isoquinoline, 2-benzyl-4aα-(3-methoxyphenyl)-9-bromo-11aβ-hydroxy-1,2,3,4,4a,5,11,11a-octahydro-6H-indolo[2,3-g]isoquinoline, 2-(2-phenylethyl)-4aα-(3-methoxyphenyl)-9-bromo-11aβ-hydroxy-1,2,3,4,4a,5,11,11a-octhydro-6H-indolo[2,3-g]isoquinoline, 2-allyl-4aα-(3-methoxyphenyl)-9-bromo-11aβ-hydroxy-1,2,3,4,4a,5,11,11a-octahydro-6H-indolo[2,3-g]isoquinoline, 2-cyclopropylmethyl-4aα-(3-methoxyphenyl)-8-bromo-11aβ-hydroxy-1,2,3,4,4a,5,11,11a-octahydro-6H-indolo[2,3-g]isoquinoline, 2-cyclopropylmethyl-4aα-(3-methoxyphenyl)-10-bromo-11aβ-hydroxy-1,2,3,4,4a,5,11,11a-octahydro-6H-indolo[2,3-g]isoquinoline, 2-benzyl-4aα-(3-methoxyphenyl)-8-bromo-11aβ-hydroxy-1,2,3,4,4a,5,11,11a-octahydro-6H-indolo[2,3-g]isoquinoline, 2-benzyl-4aα-(3-methoxyphenyl)-10-bromo-11aβ-hydroxy-1,2,3,4,4a,5,11,11a-octahydro-6H-indolo[2,3-g]isoquinoline, 2-(2-phenylethyl)-4aα-(3-methoxyphenyl)-bromo-11aβ-hydroxy-1,2,3,4,4a,5,11,11a-octahydro-6H-indolo[2,3-g]isoquinoline, 2-(2-phenylethyl)-4aα-(3-methoxyphenyl)-10-bromo-11aβ-hydroxy-1,2,3,4,4a,5,11,11a-octahydro-6H-indolo[2,3-g]isoquinoline, 2-allyl-4aα-(3-methoxyphenyl)-8-bromo-11aβ-hydroxy-1,2,3,4,4a,5,11,11a-octahydro-6H-indolo[2,3-g]isoquinoline, 2-allyl-4aα-(3-methoxyphenyl)-10-bromo-11aβ-hydroxy-1,2,3,4,4a,5,11,11a-octahydro-6H-indolo[2,3-g]isoquinoline, 2-cyclopropylmethyl-4aα-(3-methoxyphenyl)-7-bromo-11aβ-hydroxy-1,2,3,4,4a,5,11,11a-octahydro-6H-indolo[2,3-g]isoquinoline, 2-benzyl-4aα-(3-methoxyphenyl)-7-bromo-11aβ-hydroxy-1,2,3,4,4a,5,11,11a-octahydro-6H-indolo[2,3-g]isoquinoline, 2-(2-phenylethyl)-4aα-(3-methoxyphenyl)-7-bromo-11aβ-hydroxy-1,2,3,4,4a,5,11,11a-octahydro-6H-indolo[2,3-g]isoquinoline, 2-allyl-4aα-(3-methoxyphenyl)-7-bromo-11aβ-hydroxy-1,2,3,4,4a,5,11,11a-octahydro-6H-indolo[2,3-g]isoquinoline, 2-cyclopropylmethyl-4aα-(3-methoxyphenyl)-9-nitro-11aβ-hydroxy-1,2,3,4,4a,5,11,11a-octahydro-6H-indolo[2,3-g]isoquinoline, 2-benzyl-4aα-(3-methoxyphenyl)-9-nitro-11aβ-hydroxy-1,2,3,4,4a,5,11,11a-octahydro-6H-indolo[2,3-g]isoquinoline, 2-(2-phenylethyl)-4aα-(3-methoxyphenyl)-9-nitro-11aβ-hydroxy-1,2,3,4,4a,5,11,11a-octahydro-6H-indolo[2,3-g]isoquinoline, 2-allyl-4aα-(3-methoxyphenyl)-9-nitro-11aβ-hydroxy-1,2,3,4,4a,5,11,11a-octahydro-6H-indolo[2,3-g]isoquinoline, 2-cyclopropylmethyl-4aα-(3-methoxyphenyl)-8-nitro-11aβ-hydroxy-1,2,3,4,4a,5,11,11a-octahydro-6H-indolo[2,3-g]isoquinoline, 2-cyclopropylmethyl-4aα-(3-methoxyphenyl)-10-nitro-11aβ-hydroxy-1,2,3,4,4a,5,11,11a-octahydro-6H-indolo[2,3-g]isoquinoline, 2-benzyl-4aα-(3-methoxyphenyl)-8-nitro-11aβ-hydroxy-1,2,3,4,4a,5,11,11a-octahydro-6H-indolo[2,3-g]isoquinoline, 2-benzyl-4aα-(3-methoxyphenyl)-10-nitro-11aβ-hydroxy-1,2,3,4,4a,5,11,11a-octahydro-6H-indolo[2,3-g]isoquinoline, 2-(2-phenylethyl)-4aα-(3-methoxyphenyl)-8-nitro-11aβ-hydroxy-1,2,3,4,4a,5,11,11a-octahydro-6H-indolo[2,3-g]isoquinoline, 2-(2-phenylethyl)-4aα-(3-methoxyphenyl)-10-nitro-11aβ-hydroxy-1,2,3,4,4a,5,11,11a-octahydro-6H-indolo[2,3-g]isoquinoline, 2-allyl-4aα-(3-methoxyphenyl)-8-nitro-11aβ-hydroxy-1,2,3,4,4a,5,11,11a-octahydro-6H-indolo[2,3-g]isoquinoline, 2-allyl-4aα-(3-methoxyphenyl)-10-nitro-11aβ-hydroxy-1,2,3,4,4a,5,11,11a-octahydro-6H-indolo[2,3-g]isoquinoline, 2-cyclopropylmethyl-4aα-(3-methoxyphenyl)-7-nitro-11aβ-hydroxy-1,2,3,4,4a,5,11,11a-octahydro-6H-indolo[2,3-g]isoquinoline, 2-benzyl-4aα-(3-methoxyphenyl)-7-nitro-11aβ-hydroxy-1,2,3,4,4a,5,11,11a-octahydro-6H-indolo[2,3-g]isoquinoline, 2-(2-phenylethyl)-4aα-(3-methoxyphenyl)-7-nitro-11aβ-hydroxy-1,2,3,4,4a,5,11,11a-octahydro-6H-indolo[2,3-g]isoquinoline, 2-(2-phenylethyl)-4aα-(3-methoxyphenyl)-7-nitro-11aβ-hydroxy-1,2,3,4,4a,5,11,11a-octahydro-6H-indolo[2,3-g]isoquinoline, 2-allyl-4aα-(3-methoxyphenyl)-7-nitro-11aβ-hydroxy-1,2,3,4,4a,5,11,11a-octahydro-6H-indolo[2,3-g]isoquinoline, 2-cyclopropylmethyl-4aα-(3-methoxyphenyl)-11aβ-hydroxy-1,2,3,4,4a,5,11,11a-octahydro-6H-indolo[2,3-g]isoquinoline, 2-benzyl-4aα-(3-methoxyphenyl)-11aβ-hydroxy-1,2,3,4,4a,5,11,11a-octahydro-6H-indolo[2,3-g]isoquinoline, 2-(2-phenylethyl)-4aα-(3-methoxyphenyl)-11aβ-hydroxy-1,2,3,4,4a,5,11,11a-octahydro-6H-indolo[2,3-g]isoquinoline, and 2-allyl-4aα-(3-methoxyphenyl)-11aβ-hydroxy-1,2,3,4,4a,5,11,11a-octahydro-6H-indolo[2,3-g]isoquinoline instead of 2-cyclopropylmethyl-4aα-(3-methoxyphenyl)-11aβ-hydroxy-1,2,3,4,4a,5,11,11a-octahydro-6H-indolo[2,3-g]isoquinoline.

Referential Example 12

2-(2,2,2-Trichloroethoxycarbonyl)-4a-(3-methoxyphenyl)-6-acetoxy-2,3,4,4a,5,6,7,8-octahydroisoquinoline 57

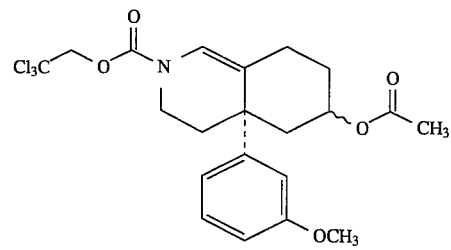

(57)

In an atmosphere of argon, 19.5 g of 2-methyl-4aα-(3-methoxyphenyl)-6-acetoxy-2,3,4,4a,5,6,7,8-octahydroisoquinoline was dissolved in 100 ml of 1,2-dichloroethane and 6.6 g of proton sponge was added to the produced solution. At 0° C., 12.8 ml of 2,2,2-trichloroethylchloroformate was added dropwise to the resultant mixture. The suspension consequently obtained was heated to room temperature and stirred for 15 hours. The resultant reaction mixture was distilled under a vacuum to expel the solvent, combined with 400 ml of ether, and washed two times with 150 ml of 1N hydrochloric acid, then with 100 ml of a saturated aqueous saline solution, dried, and refined by silica gel column chromatography cyclohexane/ethyl acetate=10:1–5:1), to afford 21.2 g of the captioned compound (6-position acetoxy mixture) (yield 72%).

Partially separated 6-position acetoxy isomers were subjected to spectral analysis.

Highly polar component (6-αacetoxy form)

IR (liquid film method) cm$^{-1}$:3024, 1717, 1415, 1255, 1216, 758

NMR (CDCl$_3$, 400 MHz) α:1.31 (3H, d, J=4.8 Hz), 1.57–1.65 (2H, m), 1.75–1.86 (2H, m), 1.98–2.06 (1H, m), 2.14–2.23 (1H, m) 2.63–2.74 (1H, m), 2.77–2.88 (1H, m), 3.08 (1H, d, J=15.1 Hz), 3.80 (3H, s), 3.82–3.89 (1H, m), 4.67–4.85 (2H, m), 4.98 (1H, s), 6.70 (1H, dd, J=6.3, 2.0 Hz), 6.80 (1H, dd, J=2.5, 1.9 Hz), 6.85 (1H, d, J=7.8 Hz), 7.01 (1H, d, J=7.8 Hz), 7.22 (1H, t, J=7.8 Hz)

Mass (EI): 475 (M$^{+1}$)

High-resolving mass spectrum: For C$_{21}$H$_{24}$O$_5$NC$_{13}$ Calculated 475.0720 Found 475.0716

Lowly polar component (6β acetoxy form)

IR (liquid film method) cm$^{-1}$: 2954, 1725, 1410, 1251, 1141, 1046, 754

NMR (CDCl$_3$, 400 MHz) δ: 1.39–1.53 (2H, m), 1.83–2.09 (3H, m), 2.02 (3H, s), 2.25–2.30 (2H, m), 2.83–3.07 (2H, m), 3.82 (3H, s), 3.85–3.95 (1H, m), 4.54–4.61 (1H, m), 4.70–4.88 (2H, m), 6.77 (1H, dd, J=7.8, 2.4 Hz), 6.91–6.95 (2H, m), 6.98 (1H, d, J=9.3 Hz), 7.27 (1H, t, J=7.8 Hz)

Mass (EI): 475 (M$^+$)

High-resolving mass spectrum: For $C_{21}H_{23}O_5NC_{12}$ Calculated 475.0720 Found 475.0718

Example 46

2-(2,2,2-Trichloroethoxycarbonyl)-4aα-(3-methoxyphenyl)-6-acetoxy-8aβ-hydroxy-1,1,2,3,4,4a,5,6,7,8,8a-decahydroisoquinoline 58

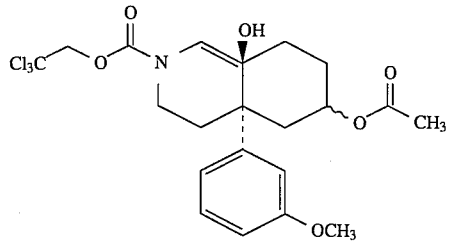
(58)

In an atmosphere of argon, 16.5 g of 2-(2,2,2-trichloroethoxycarbonyl)-4a-(3-methoxyphenyl)-6-acetoxy-2,3,4,4a,5,6,7,8-octahydroisoquinoline was dissolved in 200 ml of methylene chloride and the produced solution was cooled to 0° C. The cooled solution was caused to react with 8.6 g of m-chlorobenzoic acid for 1.5 hours. The reaction solution consequently obtained was distilled to expel the solvent. The solid distillate was used in its unmodified form for the following reaction.

The crude product was dissolved in 150 ml of acetic acid and cooled to 0° C. and sodium borohydride was added piecemeal to the cooled solution. The resultant reaction mixture was heated to room temperature and left reacting for 15 minutes. The reaction solution was distilled under a vacuum to expel the acetic acid, combined with 300 ml of a saturated aqueous solution of sodium hydrogen carbonate, and extracted three times from 200 ml of ethyl acetate. The extract was dried with sodium sulfate, distilled under a vacuum to expel the solvent, and refined by silica gel column chromatograph (chloroform), to produce 10.8 g of the captioned compound (6-position acetoxy mixture) (yield 63%). The partially separatedless polar component was subjected to spectral analysis.

IR (liquid film method) cm$^{-1}$: 3462, 2958, 1715, 1605, 1582, 1437, 1249, 1033, 758

NMR (CDCl$_3$, 90 MHz) δ: 1.55–1.65 (2H, m), 1.65–1.85 (2H, m), 1.92 (3H, s), 1.97–2.18 (2H, m), 2.20–2.57 (3H, m), 3.50 (1H, t, J=7.8 Hz), 3.79 (3H, s), 3.80–3.95 (2H, m), 4.78 (2H, d, J=6.5 Hz), 5.10–5.30 (1H, m), 6.68–6.84 (2H, m), 6.92–7.25 (2H, m)

Mass (EI): 493 (M$^+$).

Example 47

2-Methyl-4aα-(3-methoxyphenyl)-6,8aβ-dihydroxy-1,2,3,4,4a,5,6,7,8,8a-decahydroisoquinoline 59

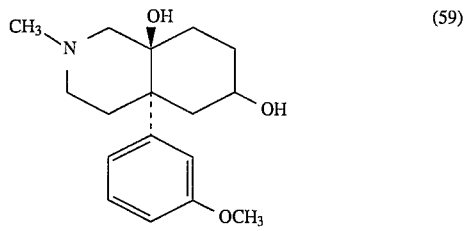
(59)

In an atmosphere of argon, 1.5 g of 2-(2,2,2-trichloroethoxycarbonyl)-4aα-(3-methoxyphenyl)-6-acetoxy-8aβ-hydroxy-1,2,3,4,4a,5,6,7,8,8a-decahydroisoquinoline was dissolved in 20 ml of anhydrous THF and 0.35 g of lithium aluminum hydride was added to the produced solution. The resultant mixture was left reacting at room temperature for 30 minutes and then cooled to 0° C. The reaction mixture, after assuming a solidified state in consequence of gradual dropwise addition of a saturated aqueous solution of Rochelle salt, was thoroughly stirred with 20 ml of chloroform and then filtered through a bed of celite. The residue was thoroughly washed with chloroform. The filtrate and the washings were combined and concentrated under a vacuum. The concentrate was refined by silica gel column chromatography (chloroform-ammonia-saturated chloroform-5% methanol/ammonia-saturated chloroform), to produce 0.63 g of the captioned compound (71%, 6-hydroxy mixture).

IR (KBr) cm$^{-1}$: 3412, 1599, 1493, 1236, 1071, 893, 795, 723, 540

Mass (EI): 291 (M$^+$).

Example 48

2-Methyl-4aα-(3-methoxyphenyl)-6-oxo-8aβ-hydroxy-1,2,3,4,4a,5,6,7,8,8a-decahydroisoquinoline 60

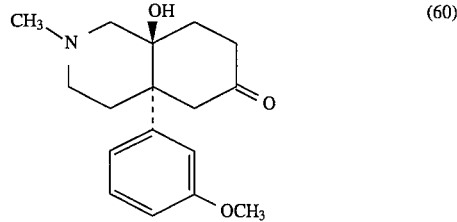
(60)

In an atmosphere of argon, 0.19 ml of oxalyl chloride was dissolved in 12 ml of anhydrous methylene chloride and the produced solution was cooled to −55° C. The cooled solution and 1.5 ml of a solution of DMSO in methylene chloride gradually added cropwise thereto were stirred at the same temperature for two minutes. The produced mixture and a solution of 0.5 g of 2-methyl-4aα-(3-methoxyphenyl)-6,8aβ-dihydroxy-1,2,3,4,4a,5,6,7,8,8a-decahydroisoquinoline in 2 ml of methylene chloride added dropwise thereto and 2 ml of methylene chloride as a cleaning liquid similarly added thereto were stirred at −55° C. for 30 minutes. The resultant mixture and 1.2 ml of triethylamine added thereto were heated to room temperature. The produced reaction mixture was subjected to phase separation by the addition of 20 ml of distilled water. The aqueous phase consequently separated was further extracted two times from 12 ml of methylene chloride. The organic layers were combined, washed with 10 ml of a saturated aqueous saline solution, dried, and then concentrated. When the concentrate was refined by silica gel column chromatography (chloroform —2% methanol/chloroform—5% methanol/chloroform), 0.45 g of the captioned compound (yield 91%) was obtained. This compound, on being recrystallized from n-hexane-ethyl acetate, produced 0.38 g of a pure product of the compound (m.p. 96° to 97° C.) (yield 77%).

IR (Kbr) $cm^{-1}$: 3406, 2944, 1711, 1605, 1578, 1452, 1257, 1114, 1038, 895, 774, 708

NMR (CDCl$_3$, 400 MHz) δ: 1.85–1.93 (2H, m), 2.15–2.32 (3H, m), 2.33 (3H, s), 2.55 (2H, t, J=11.0 Hz), 2.62–2.66 (1H, m), 2.77 (1H, d, J=11.0 Hz), 2.79–2.86 (1H, m), 3.13 (1H, d, J=14.6 Hz), 3.78 (3H, s), 6.72 (1H, dd, J=7.4, 3.0 Hz), 6.96–6.97 (2H, m), 7.21 (1H, t, J=8.5 Hz)

Mass (EI): 289 (M$^+$).

Example 49

4aα-(3-methoxyphenyl)-6-acetone-8aβ-hydroxy-1,2,3,4,4a,5,6,7,8,8a-decahydroisoquinoline 61

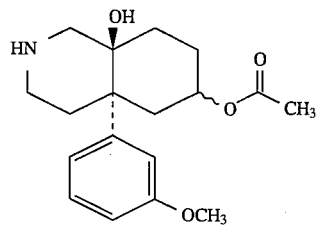
(61)

In an atmosphere of argon, 2.04 g of 2-(2,2,-trichloroethoxycarbonyl)-4aα-(3-methoxyphenyl)-6-acetoxy-8aβ-hydroxy-1,2,3,4,4a,5,6,7,8,8a-decahydroisoquinoline was dissolved in 50 ml of acetic acid and the produced solution was combined with 2.70 g of zinc dust. The resultant suspension was stirred at room temperature for four hours and passed through celite to remove impurities originating in zinc. The impurities were thoroughly washed with acetic acid. The washing and the filtrate were combined and distilled under a vacuum to expel acetic acid. The distillate was combined with 50 ml of a saturated aqueous solution of sodium hydrogen carbonate, extracted three times from 50 ml of chloroform, and washed with 50 ml of a saturated aqueous saline solution. The washed extract was dried, concentrated, and refined by silica gel column chromatography (chloroform—5% methanol/ammonia-saturated chloroform), to afford 0.95 g of the captioned compound (6-position acetoxy mixture) (yield 72%).

IR (liquid film method) $cm^{-1}$: 3360, 2936, 1712, 1607, 1582, 1455, 1248, 1053, 888, 713

Mass (EI): 319 (M$^+$).

Example 50

2-Cyclopropylcarbonyl-4aα-(3-methoxyphenyl)-6-acetoxy-8aβ-hydroxy-1,2,3,4,4a,5,6,7,8,8a-decahydroisoquinoline 62

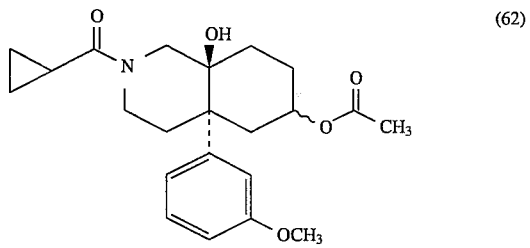
(62)

In an atmosphere of argon, 0.68 g of 4aα-(3-methoxyphenyl)-6-acetoxy-8aβ-hydroxy-1,2,3,4,4a,5,6,7,8,8a-decahydroisoquinoline was dissolved in 15 ml of anhydrous 1,2-dichloroethane and the produced solution was combined with 0.46 g of proton sponge and 0.29 ml of cyclopropanecarbonyl chloride. The resultant mixture was distilled under a vacuum to expel the solvent, combined with 20 ml of ether, and washed with 20 ml of 1N hydroxhloric acid and 10 ml of a saturated aqueous saline solution. The washed distillate was dried and concentrated to afford the captioned compound in an oily state (crude yield 91%), which was used in its unmodified form in the following reaction.

IR (liquid film method) $cm^{-1}$: 3430, 2944, 1702, 1605, 1582, 1453, 1240, 1029, 750

MASS (EI): 387 (M$^+$).

Similarly, 2-benzoyl-4aα-(3-methoxyphenyl)-6-acetoxy-8aβ-hydroxy-1,2,3,4,4a,5,6,7,8,8a-decahydroisoquinoline, 2-phenylacetyl-4aα-(3-methoxyphenyl)-6-acetoxy-8aβ-hydroxy-1,2,3,4,4a,5,6,7,8,8a-decahydroisoquinoline, and 2-acryloyl-4aα-(3-methoxyphenyl)-6-acetoxy-8aβ-hydroxy-1,2,3,4,4a,5,6,7,8,8a-decahydroisoquinoline are produced by using benzoyl chloride, phenylacetyl chloride, and acryloyl chloride respectively instead of cyclopropanecarbonyl chloride.

Example 51

2-Cyclopropylmethyl-4aα-(3-methoxyphenyl)-6,8aβ-dihydroxy-1,2,3,4,4a,5,6,7,8,8a-decahydroisoquinoline 63

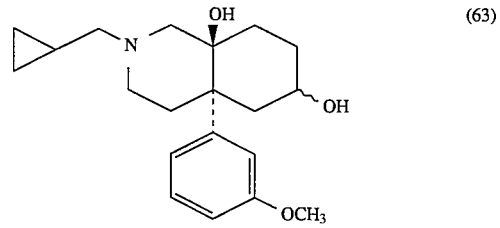
(63)

In an atmosphere of argon, the 2-cyclopropylcarbonyl-4aα-(3-methoxyphenyl)-6-acetoxy-8aβ-hydroxy-1,2,3,4,4a,5,6,7,8,8a-decahydroisoquinoline obtained in Example 50 was dissolved in 20 ml of anhydrous THF and the produced solution was combined with 0.24 g of lithium aluminum hydroxide, left reacting at 0° C. for two hours and at room temperature for one hour, and combined slowly with 5 ml of a saturated aqueous solution of a Rochelle salt. The resultant reaction mixture was combined with 50 ml of chloro-form, filtered through a bed of sellaite, washed with chloroform, and concentrated, to afford the captioned compound in an oily state (crude yield 85%), which was put to the following reaction in its unmodified form.

IR (liquid film method) cm$^{-1}$: 3425, 2940, 1607, 1582, 1444, 1292, 1091, 880, 753

MASS (EI): 331 (M$^+$).

Similarly, 2-benzyl-4aα-(3-methoxyphenyl)-6,8aβ-dihydroxy-1,2,3,4,4a,5,6,7,8,8a-decahydroisoquinoline, 2-phenethyl-4aα-(3-methoxyphenyl)-6,8aβ-dihydroxy-1,2,3,4,4a, 5,6,7,8,8a-decahydroisoquinoline, and 2-allyl-4aα-(3-methoxyphenyl)-6-,8aβ-dihydroxy-1,2,3,4,4a,5,6,7,8,8a-decahydroisoquinoline are produced by using 2-benzoyl-4aα-(3-methoxyphenyl)-6-acetoxy-8aβ-hydroxy-1,2,3,4,4a, 5,6,7,8,8a-decahydroisoquinoline, 2-phenylacetyl-4aα-(3-methoxyphenyl)-6-acetoxy-8aβ-hydroxy-1,2,3,4,4a,5,6,7,8, 8a-decahydroisoquinoline, and 2-acryloyl-4aα-(3-methoxyphenyl)-6-acetoxy-8aβ-hydroxy-1,2,3,4,4a,5,6,7,8, 8a-decahydroisoquinoline respectively instead of 2-cyclopropylcarbonyl-4aα-(3-methoxyphenyl)-6-acetoxy-8aβ-hydroxy-1,2,3,4a,5,6,7,8,8a-decahydroisoquinoline.

Example 52

2-Cyclopropylmethyl-4aα-(3-methoxyphenyl)-6-oxo-8aβ-hydroxy-1,2,3,4,4a,5,6,7,8,8a-decahydroisoquinoline 64

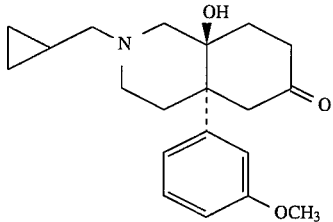

(64)

In an atmosphere of argon, 0.15 ml of oxalyl chloride in 10 ml of anhydrous methylene chloride and the produced solution was cooled to –55° C. The resultant cooled solution and a solution of 0.24 ml of DMSO in 1 ml of anhydrous methylene chloride added slowly dropwise thereto were left reacting at –55° C. for two minutes. To the resultant reaction mixture, a solution of the 2-cyclopropylmethyl-4aα-(3-methoxyphenyl)-6,8aβ-dihydroxy-1,2,3,4,4a,5,6,7,8,8a-decahydroisoquinoline obtained in Example 51 ml in 2 ml of anhydrous methylene chloride was added and 2 ml of a washing liquid was similarly added. The resultant mixture was left reacting at –55° C. for 30 minutes, combined with 1.09 ml of triethylamine, and heated to room temperature. The mixture was subjected phase separation by addition of 15 ml of distilled water. The aqueous layer consequently separated was further extracted from 10 ml of methylene chloride. The organic layers consequently separated were combined, washed with 10 ml of a saturated aqueous saline solution, dried, concentrated, and refined by silica gel column chromatography (chloroform-2% methanol/chloroform), to afford 0.48 g of the captioned compound (three steps, yield 68%).

IR (liquid film method) cm$^{-1}$: 3404, 2940, 1711, 1605, 1582, 1493, 1429, 1241, 1038, 897, 756

NMR (CDCl$_3$, 400 MHz) δ: 0.11 (2H, d, J=5.9 Hz), 0.50–0.55 (2H, m), 0.81–0.89 (1H, m), 1.86–1.90 (2H, m), 2.25–2.28 (2H, m), 2.32–2.37 (3H, m), 2.39–2.46 (1H, m), 2.53 (1H, d, J=14.3 Hz), 2.75–2.87 (4H, m), 3.14 (1H, d,32 14.3 Hz), 3.77 (3H, s), 6.70–6.72 (1H, m), 6.97–6.98 (2H, m), 7.20 (1H, t, J=8.8 Hz)

Mass (EI) : 329 (M$^+$)

High-resolution mass spectrum: For C$_{21}$H$_{27}$O$_3$N Calculated 329.1991 Found 329.1955

Similarly, 2-benzyl-4aα-(3-methoxyphenyl)-6-oxo-8aβ-hydroxyl-1,2,3,4,4a,5,6,7,8,8a-decahydroisoquinoline, 2-phenethyl-4aα-(3-methoxyphenyl)-6-oxo-8aβ-hydroxy-1, 2,3,4,4a,5,6,7,8,8a-decahydroisoquinoline, and 2-allyl-4aα-(3-methoxyphenyl)-6-oxo-8aβ-hydroxy-1,2,3,4,4a,5,6,7,8, 8a-decahydroisoquinoline are produced by using 2-benzyl-4aα-(3-methoxyphenyl)-6,8aβ-dihydroxy-1,2,3,4,4a,5,6,7, 8,8a-decahydroisoquinoline, 2-phenethyl-4aα-(3-methoxyphenyl)-6,8aβ-dihydroxy-1,2,3,4,4a,5,6,7,8,8a-decahydroisoquinoline, and 2-allyl-4aα-(3-methoxyphenyl)-6,8aα-dihydroxy-1,2,3,4,4a,5,6,7,8,8a-decahydroisoquinoline respectively instead of 2-cyclopropylmethyl-4aα-(3-methoxyphenyl)-6,8aβ-dihydroxy-1,2,3,4,4a,5,6,7,8,8a-decahydroisoquinoline.

Referential Example 13

2-(2,2,2-Trichloroethoxycarbonyl)-4aα-(3-methoxyphenyl)-2,3,4,4a,5,6,7,8-octahydroisoquinoline 65

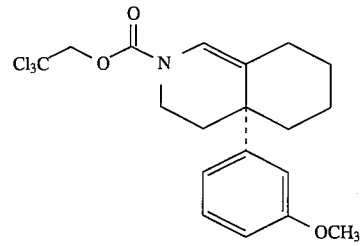

(65)

In an atmosphere of argon, 1.41 g of 2-methyl-4aα-(3-methoxyphenyl)-2,3,4,4a,5,6,7,8-octahydroisoquinoline was dissolved in 15 ml of 1,2-dichloroethane and 0.59 g of proton sponge was added to the produced solution. To the mixture, 1.13 ml of 2,2,2-trichloroethyl chloroformate was added dropwise. The suspension consequently formed was heated to room temperature and then stirred for 24 hours. The resultant reaction mixture was distilled under a vacuum to expel the solvent, combined with 15 ml of ether, washed two times (10 ml, 6 mlxz) of 1N hydrochloric acid, and further washed with 10 ml of a saturated aqueous saline solution, dried, and refined by silica gel column chromatography (cyclohexane/ethyl acetate=5:1), to produce 2.30 g of the captioned compound (yield 100%).

IR (liquid film method) cm$^{-1}$: 2936, 1763, 1717, 1667, 1607, 1582, 1412, 1125, 1054, 820, 706

NMR (CDCl$_3$, 400 MHz) δ: 1.15–1.25 (1H, m), 1.26–1.27 (1H, m), 1.40–1.49 (1H, m), 1.52–1.60 (1H, m), 1.66–1.72 (1H, m), 1.80–1.93 (2H, m), 2.15–2.21 (2H, m), 2.56 (1H, d, J=13.4 Hz), 2.90–3.01 (1H, m), 3.80 (3H, s), 3.83–3.90 (1H, m), 4.79–4.88 (2H, m), 6.75 (1H, dd, J=7.9, 2.5 Hz), 6.87 (1H,s), 6.92(2H, d, J=8.5 Hz), 7.26(1H, t, J=7.9 Hz)

Mass (EI): 417 (M$^+$).

Similarly, 2-(2,2,2-trichloroethoxycarbonyl-4aα-(3-methoxyphenyl)-2,3,4,4a,5,6,7,8-octahydro-2,2-dimethyl-1, 3-dioxolo[4,5-g]isoquinoline is produced by using 2-methyl-4aα-(3-methoxyphenyl)-2,3,4,4a,5,6,7,8-octahydro-2, 2-dimethyl-1,3-dioxolo[4,5-g]isoquinoline instead of 2-methyl-4aα-(3-methoxyphenyl)-2,3,4,4a,5,6,7,8-octahydroisoquinoline.

Example 53

2-(2,2,2-trichloroethoxycarbonyl)-4aα-(3-methoxyphenyl)-8aβ-hydroxy-1,2,3,4,4a,5,6,7,8,8a-decahydroisoquinoline 66

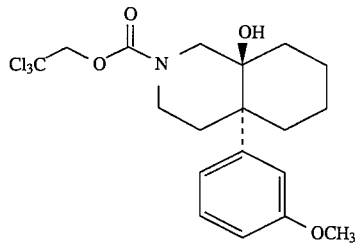
(66)

In an atmosphere of argon, 0.94 g of 2-(2,2,2-trichloroethoxycarbonyl)-4a-(3-methoxyphenyl)-2,3,4,4a,5,6,7,8,8a-octahydroisoquinoline was dissolved in 20 ml of methylene chloride and the produced solution was cooled to 0° C. The cooled solution was caused to react with 0.55 g of m-chloroperbenzoic acid for 15 minutes. The resultant solid product was put in its unmodified form to the following reaction.

The crude product obtained above was dissolved in 20 ml of acetic acid and cooled to 0° C. and sodium borohydride was added piecemeal to the cooled product. The resultant mixture was heated to room temperature and left reacting for five minutes. The resultant reaction mixture was distilled under a vacuum to expel acetic acid, combined with 20 ml of a saturated aqueous solution of sodium hydrogen carbonate, and extracted two times from 20 ml of ethyl acetate. The organic layers consequently separated were combined and washed with 15 ml of a saturated aqueous saline solution. The extract was dried with sodium sulfate, distilled under a vacuum to expel the solvent, and refined by silica gel column chromatography (chloroform), to produce 0.73 g of the captioned compound (yield 74%).

IR (liquid film method) cm$^{-1}$: 3460, 2934, 1705 1607, 1582, 1444, 1245, 1127, 994, 882, 758

NMR (CDCl$_3$ 400 MHz) δ: 0.90–1.01 (1H, m), 1.33–1.40 (1H, m), 1.52–1.60 (2H, m), 1.67–1.76 (2H, m), 1.80–1.90 (1H, m), 2.05–2.12 (1H, m), 2.20–2.40 (2H, m), 2.48–2.63 (1H, m), 3.81 (3H, m), 3.86–4.00 (3H, m), 4.73 (2H, s), 6.73 (1H, dd, J=8.6, 2.5 Hz), 7.03 (2H, s), 7.06 (1H, d, J=7.9 Hz), 7.24 (1H, t, J=7.9 Hz)

Mass (EI): 435 (M$^+$).

Similarly, 2-(2,2,2-trichloroethoxycarbonyl)-4aα-(3-methoxyphenyl)-8aβ-hydroxy-1,2,4,4a,5,6,7,8,8a-decahydro-2,2-dimethyl-1,3-dioxolo[4,5-g]isoquinoline is produced by using 2-(2,2,2-trichloroethoxycarbonyl)-4a-(3-methoxyphenyl)-2,3,4,4a,5,6,7,8,-octahydro-2,2-dimethyl-1,3-dioxolo[4,5-g]isoquinoline instead of 2-(2,2,2-trichloroethoxycarbonyl)-4aα-(3-methoxyphenyl)-2,3,4,4a,5,6,7,8-octahydroisoquinoline.

Example 54

4aα-(3-Methoxyphenyl)-8aβ-hydroxy-1,2,3,4,4a,5,6,7,8,8a-decahydroisoquinoline 67

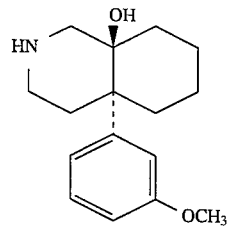
(67)

A solution of 330 mg of 2-(2,2,2-trichloroethoxycarbonyl)-4aα-(3-methoxyphenyl)-8aβ-hydroxy-1,2,3,4,4a,5,6,7,8,8a-decahydroisoquinoline was dissolved in 12 ml of an aqueous 90% acetic acid solution and the produced solution was caused to react with 0.37 g of zinc at a room temperature for 3 hours and then at 50° C. for 15 minutes. The resultant solution was distilled under a vacuum to expel acetic acid, combined with 15 ml of a saturated aqueous solution of sodium hydrogen carbonate and 15 ml of chloroform, and filtered through a bed of celite. The filtrate was subjected to phase separation and extracted two times from 10 ml of chloroform. The organic layers consequently separated were combined, washed with 15 ml of a saturated aqueous saline solution, dried, concentrated, and refined by silica gel column chromatography (chloroform-5% methanol/chloroform), to afford 164 mg of the captioned compound (yield 83%).

IR (liquid film method) cm$^{-1}$: 3358, 2938, 1607, 1582, 1452, 1249, 1054, 886, 712

NMR (CDCl$_3$, 400 MHz) δ: 0.87–0.98 (1H, m), 1.31–1.37 (1H, m), 1.48–1.55 (2H, m), 1.63–1.71 (2H, m), 1.80–1.92 (1H, m), 2.10–2.19 (2H, m), 2.27 (1H, dt, J=13.4, 5.5 Hz), 2.35 (1H, dt, J=12.8, 1.8 Hz), 2.54 (1H, d, J=11.0 Hz), 2.64 (1H, d, J=11.6 Hz), 3.59 (1H, d, J=11.0 Hz), 3.81 (3H, s), 6.69 (1H, dd, J=7.9, 2.4 Hz), 7.06–7.09 (2H, m), 7.21 (1H, t, J=7.9 Hz)

Mass (EI): 261 (M$^+$).

Similarly, 4aα-(3-methoxyphenyl)-8aβ-hydroxy-1,2,3,4,4a,5,6,7,8,8a-decahydro-2,2-dimethyl-1,3-dioxolo[4,5-g]isoquinoline by using 2-(2,2,2-trichloroethoxycarbonyl)-4aα-(3-methoxyphenyl)-8aβ-hydroxy-1,2,3,4,4a,5,6,7,8,8a-decahydro-2,2-dimethyl-1,3-dioxolo[4,5-g]isoquinoline instead of 2-(2,2,2-trichloroethoxycarbonyl)-4aα-(3-methoxyphenyl)-8aβ-hydroxy-1,2,3,4,4a,5,6,7,8,8a-decahydroisoquinoline.

Example 55

2-Cyclopropylcarbonyl-4aα-(3-methoxyphenyl)-8aβ-hydroxy-1,2,3,4,4a,5,6,7,8,8a-decahydroisoquinoline 68

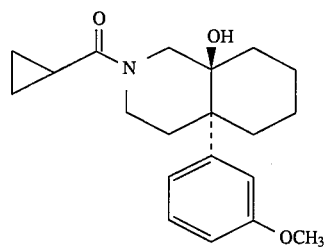
(68)

A solution of 164 mg of 4aα-(3-methoxyphenyl)-8aβ-hydroxy-1,2,3,4,4a, 5,6,7,8,8a-decahydroisoquinoline in 5 ml of anhydrous 1,2-dichloroethane was combined with 134 mg of proton sponge.

The produced mixture was caused to react with 0.14 ml of cyclopropyl carbonyl chloride at room temperature for 30 minutes. The resultant reaction solution was distilled under a vacuum to expel the solvent, combined with 15 ml of ether, and washed two times with 10 ml of 1N hydrochloric acid and further with 10 ml of a saturated aqueous saline solution. The washed distillate was dried and distilled under a vacuum to expel the solvent. The crude product was subjected to azeotropic distillation with chloroform-toluene. The azeotropic mixture consequently obtained (0.20 g and 97% in yield) was used in the following reaction.

IR (liquid film method) cm$^{-1}$: 3426, 2940, 1700, 1605, 1456, 1245, 1031, 886, 756

Mass (EI): 329 (M$^+$).

Similarly, 2-cyclopropylcarbonyl-4aα-(3-methoxyphenyl)-8aβ-hydroxy-1,2,3,4,4a,5,6,7,8,8a-decahydro-2,2-dimethyl-1,3-dioxolo[4,5-g]isoquinoline is produced by using 4aα-(3-methoxyphenyl)-8aβ-hydroxy-1,2,3,4,4a,5,6,7,8,8a-decahydro-2,2-dimethyl-1,3-dioxolo[4,5-g]isoquinoline instead of 4aα-(3-methoxyphenyl)-8aβ-hydroxy-1,2,3,4,4a,5,6,7,8,8a-decahydroisoquinoline.

Example 56

2-Cyclopropylmethyl-4aα-(3-methoxyphenyl)-8aβ-hydroxy-1,2,3,4,4a,5,6,7,8,8a-decahydroisoquinoline 69

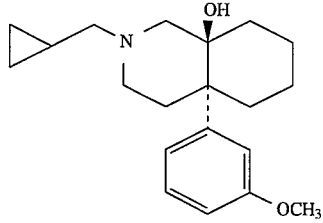

(69)

In 5 ml of anhydrous THF, 0.19 g of 2-cyclopropylcarbonyl-4aα-(3-methoxyphenyl)-8aβ-hydroxy-1,2,3,4,4a,5,6,7,8,8a-decahydroisoquinoline obtained in a crude form in Example 112 was dissolved. The produced solution was cooled to 0° C. and caused to react with lithium aluminum hydride at 0° C. for 15 minutes and then at room temperature for one hour. The resultant reaction solution, after being solidified in consequence of gradual addition of 0.5 ml of a saturated aqueous solution of Rochelle salt, was suspended in chloroform. The suspension was filtered through a bed of celite. The filtrate was distilled under a vacuum to expel the solvent and refined by silica gel column chromatography (chloroform-ammonia-saturated chloroform), to afford 0.14 g of the captioned compound (yield 77%).

IR (liquid film method) cm$^{-1}$: 3426, 2938, 1607, 1582, 1456, 1290, 1093, 1052, 1031, 884, 756

NMR (CDCl$_3$, 400 MHz) δ: 0.02–0.08 (2H, m), 0.42–0.51 (2H, m), 0.75–0.83 (1H, m), 0.83–0.96 (1H, m), 1.30–1.38 (1H, m), 1.48–1.58 (2H, m), 1.58–1.92 (5H, m), 2.10–2.32 (2H, m), 2.60–2.68 (2H, m), 2.97 (1H, d J=10.8 Hz), 3.81 (3H, s), 6.69 (1H, dd, J=8.3 Hz, 1.9 Hz), 7.04–7.08 (2H, m), 7.20 (1H, t, J=8.3 Hz)

Mass (EI): 315 (M$^+$)

Similarly, 2-cyclopropylmethyl-4aα-(3-methoxyphenyl)-8aβ-hydroxy-1,2,3,4,4aβ-5,6,7,8,8aβ-decahydro-2,2-dimethyl-1,3-dioxolo[4,5-g]isoquinoline is produced by using 2-cyclopropylcarbonyl-4aα-(3-methoxyphenyl)-8aβ-hydroxy-1,2,3,4,4a,5,6,7,8,8a-decahydro-2,2-dimethyl-1,3-dioxolo[4,5-g]isoquinoline instead of 2-cyclopropylcarbonyl-4aα(3-methoxyphenyl)-8aβ-hydroxy-1,2,3,4,4a,5,6,7,8,8a-decahydroisoquinoline.

Example 57

The pharmacological activities of compounds of this invention are shown below.

In the test for bonding, the homogenate of the brain of a guinea pig was diluted with Tris buffer in a ratio calculated to give to the produced solution a protein content of 0.7 mg per prot/tube was used as incorporated in the reaction solution. With regard to ligands for binding assay, 3H-DAGO (μ), DPDPE (δ), and EKC (κ) were used for hot samples and naloxone (μ), DADLE (δ), and naloxone (κ) for cold samples.

The test of the compounds of this invention for agonist and antagonist activities was carried out in according to the method proposed by Takemori et al. (Takemori, A, E. et al.: Eur. J. Pharmacal., 1982, 85, 163) using Guinea Pig Ileal Longitudinal Muscle Mouse Vas Deferens (MVD).

Table 1 show the pharmacological activities of main compounds. These compounds are antagonists exhibiting very high selectivity for the δ-receptor of opioid. Particularly, the 2-cyclopropylmethyl-4aα-(3-hydroxyphenyl)-1,2,3,4,4a,5,11,11aβ-octahydro-6H-indolo[2,3-g]isoquinoline 19 (Ki value=3.50) exhibits selectivity twice as high (μ/δ: 100=NTI, 205=19) as nartol indole (NTI, a substance which is held to possess the highest selectivity for the δ-receptor in all currently known substances. This compound avoids affecting the inhibition of contraction of the ileum of a guinea pig, shows a Ke value of 4.80 to DPDPE, a peptide which is highly selective for the δ-receptor in the Mouse Vas Deferens, and selectively attenuate the inhibition of contraction by DPDPE. This fact safely supports a conclusion that the indole compounds represented by the compound 19 constitute themselves antagonists selectively effective on the δ-receptor.

TABLE 1

| | | | | | | | | | | | | | | |
|---|---|---|---|---|---|---|---|---|---|---|---|---|---|---|
| | | MVD | | | | | | | | | GPI | | | |
| | | Antagonism to | | | | Bonding assay | | | | | | Naloxone | nor-BNI | |
| com-pound | IC$_{50}$ (nM) | DPDPE at 100 nM | | | Ki value | | | Ki ratio | | IC$_{50}$ (nM) | | | | |
| | | DR | Ke | pA2 | μ | δ | κ | μ/δ | μ/δ | κ/μ | | DR | DR | Ke | pA2 |
| 2 | 68600 | 8.14 | 140 | 6.86 | 1650 | 193 | 5970< | 8.55 | 30.9< | 3.62< | 65100 | 1.12 | 1.25 | 301 | 6.65 |

TABLE 1-continued

Pharmacological activity of indole derivatives

| | MVD | | | | | | | | | GPI | | | | |
|---|---|---|---|---|---|---|---|---|---|---|---|---|---|---|
| | | Antagonism to DPDPE at 100 nM | | | Bonding assay | | | | | | Nalox-one | nor-BN1 | | |
| com-pound | IC$_{50}$ (nM) | DR | Ke | pA2 | Ki value | | | Ki ratio | | IC$_{50}$ (nM) | DR | DR | Ke | pA2 |
| | | | | | μ | δ | κ | μ/δ | μ/δ κ/μ | | | | | |
| 19 | + 7940 28900 + 5640 | (20 nM)– 5.17 (50 nM)– 9.62 | 4.80 5.80 | 8.30 8.22 | (1230– 2340) 716 (4.10– 1320) | (138– 280) 3.50 (2.78– 4.23) | 951 (784– 1120) | 205 | 272 1.33 | (46500– 91100) 34600 (25800– 46400) | (0.78– 1.60) 0.93 (0.74– 1.17) | (0.69– 2.45) 0.95 (0.75– 1.21) | | |
| 4 | 46100 + 6780 | 3.37 | 422 | 6.37 | 6420 (4830– 11200) | 1240 (938– 1660) | 11600< | 5.18 | 9.35< 1.81< | 28000 (20000– 39100) | 0.62 (0.41– 1.03) | 1.17 (0.75– 1.21) | | |
| 6 | 23600 + 3460 | 5.16 | 240 | 6.62 | 7090< | 1100 (724– 1680) | 27400< | 6.45< | 24.9< 3.86< | 7900 (7060– 8840) | 0.86 (0.69– 1.07) | 1.23 (1.08– 1.41) | 77.0 | 7.16 |
| 8 | 25900 + 4520 | 15.0 | 71.4 | 7.15 | 4590 (4110– 5260) | 59.0 (48.6– 71.6) | 6750< | 77.8 | 114< 1.47< | 23000 (19800– 26700) | 0.80 (0.62– 1.02) | 1.04 (0.81– 1.33) | | |
| 10 | 21900 + 2180 | | | | N.D. | 1390 | K.D. | — | — — | 14300 (11900– 17200) | 0.92 (0.66– 1.23) | 1.31 (0.99– 1.67) | 64.5 | 7.19 |
| 12 | (25000) | 8.27 | 138 | 6.86 | 1230 (350– 1940) | 120 65.1– 209) | 380 (367– 527) | 10.3 | 3.17 0.31 | 38700 (33000– 45400) | 0.61 (0.51– 0.71) | 0.70 (0.58– 0.84) | | |
| 14 | 32300 + 2180 | 2.60 | 625 | 6.20 | N.D. | 201 (138– 200) | 3090 | — | 15.4 — | 28100 (20900– 37600) | 1.02 (0.83– 1.25) | 1.27 (0.98– 1.68) | 74.1 | 7.13 |
| 25 | | | | | 1530 (1300– 1780) | 2.77 (1.25– 6.15) | 144 (66.1– 365) | 552 | 52.0 0.09 | 14500 (13400– 15600) | 0.55 (0.40– 0.72) | 0.77 (0.66– 0.90) | | |
| 29 | | (20 nM)– 6.22 (50 nM)– 34.1 | 3.83 1.51 | 8.41 8.82 | 1180 (889– 1600) | 1.91 (1.37– 2.63) | 370 (164– 1080) | 618 | 194 0.31 | 6640 (5080– 8630) | 2.50 (0.84– 6.64) | 2.06 (1.25– 3.23) | 18.9 | 7.72 |
| 31 | | 4.84 | 13.0 | 7.89 | (27000) (2.07– 4.32) | 2.97 | 2240 (886– 9170) | 9090< | 754 0.09 | 20500 (17100– 24600) | 0.93 (0.72– 1.20) | 0.98 (0.74– 1.28) | | |
| 37 | | 8.93 | 6.31 | 8.20 | 1550 (1030– 2550) | 6.94 (3.32– 22.5) | 342 (140– 1140) | 223 | 49.3 0.22 | 10500 (8200– 13500) | 1.19 (0.90– 1.59) | 1.26 (0.73– 2.25) | | |
| 40 | | (20 nM)– 3.02 (50 nM)– 18.5 | 9.90 2.86 | 8.00 8.54 | 1650 (1420– 1900) | 8.31 (3.92– 15.1) | 936 (770– 1100) | 199 | 113 0.57 | 11700 (8070– 16900) | 2.17 (1.00– 4.24) | 2.05 (1.37– 2.97) | 19.0 | 7.72 |
| 47 | | (20 nM)– 4.44 (50 nM)– 30.5 | 5.81 1.69 | 8.24 8.77 | 1170 (619– 2860) | 0.37 (0.20– 0.61) | 388 (252– 617) | 3160 | 1050 0.33 | 64500 (26800– 155000) | 1.06 (0.67– 1.77) | 1.29 (0.85– 2.12) | | |
| 52 | | 7.33 | 158 | 6.80 | (81100) | 135 (97.0– 173) | 2280 (785– 23200) | 601 | 16.9 0.03 | 16400 (13500– 20000) | 1.06 (0.88– 1.29) | 1.03 (0.85– 1.26) | | |
| 54 | 10200 + 1710 | (20 nM)– 14.3 (50 nM)– 22.4 | 8.13 11.3 | 8.24 8.77 | 1430 (597– 53300) | 2.75 +0.47 | 662 (359– 1940) | 520 | 241 0.46 | 5961 (4430– 8021) | 1.30 (0.68– 2.72) | 3.30 (1.95– 6.78) | 8.70 | 8.06 |
| 56 | | | | | 723 (510– 1050) | 1.71 (1.15– 2.46) | 1550 (964– 2970) | 423 | 906 2.14 | | | | | |

Now, the immunosuppressive activity of the compound 19 which is representative of the compounds of the present invention will be shown. Activity in inhibiting proliferation of mouse T cells by Con-A stimulation
(Method of test)

A monocellular suspension was prepared by sterilely removing the spleen from a mouse and passing the spleen through a mesh. This suspension was adjusted to a concentration of $5 \times 10^6$ cells/ml and dispensed by the unit of 100 μl in all the individual wells of a 96-well plate. The plate sown with the spleen cells, after having the wells thereof severally fed with ConA as a mitogen (of a concentration of 1 μg/ml) in a fixed ratio of 50 μl/well and with the compound 19 of a concentration varying ratio (0.1, 0.5, 0.75, 1.0, 2.5, 5.0, 7.5, 10, 12.5, 15, 17.5 and 20 μg/ml) in a fixed ratio of 50 μl/well, was kept in a $CO_2$ incubator to have the cells incubated at 37° C. for 48 hours. Eight hours before completion of the incubation, [$^3$H]thymidine was added to the contents of the wells in a fixed ratio of 2 μCi/10 μl/well. Eight hours after this addition, the cells in the wells were collected on filter papers with the aid of a cell harvester. The cells on the filter papers were dried, then combined with a toluene type scintillator, and counted for the radioactivity of the [³H] thymidine occluded in the cells by means of a scintillation counter.

The ratio of suppression of T cell proliferation was calculated in accordance with the following formula:

Rate of suppression=(Radioactivity in the absence of compound–Radioactivity after addition of compound)/ (Radioactivity in the absence of compound–Radioactivity in the absence of ConA)

The rate of suppression of T cell proliferation obtained of the compound 19 and NTI for comparison are shown in Table 2.

TABLE 2

| Concentration of compound | Ratio of suppression of T cell proliferation, % (n = 3) | |
|---|---|---|
| (μg/ml) | 19 | NTI |
| 0.1 | 6 | 0 |
| 0.5 | 0 | 0 |
| 0.75 | 18 | 0 |
| 1.0 | 1 | 0 |
| 2.5 | 33 | 0 |
| 5.0 | 94 | 15 |
| 7.5 | 100 | 35 |
| 10.0 | 100 | 62 |
| 12.5 | 100 | 85 |
| 15.0 | 100 | 98 |
| 17.5 | 100 | 100 |
| 20.0 | 100 | 100 |

It is noted from the results that the compound 19 exhibited a clearly strong activity in immunosuppression as elucidated by the comparison between the $IC_{50}$ value 3 μg/ml of the compound 19 and the $IC_{50}$ value 8.6 μg/ml of NTI.

Other indole derivatives exhibited activities in inhibiting T cell proliferation equal to or higher than the activity of the compound 19 as shown in Table 3.

TABLE 3

| Activity of indole-skeletoned compound in inhibiting T cell hyperplasia | |
|---|---|
| Compound | $IC_{50}$ (μg/ml) |
| 19 | 2.7 |
| 25 | 3.0 |
| 29 | 0.9 |
| 31 | 2.6 |
| 37 | 1.9 |
| 40 | 2.6 |
| 47 | 3.8 |
| 52 | 3.5 |
| 56 | 14.0 |

Economic Utility of the Invention

This invention not only contributes to the study of opioid by permitting very easy and inexpensive supply of δ-opioid receptor antagonists of high selectivity but also offers useful immunity inhibitors.

We claim:

1. A method for the production of an isoquinoline derivative represented by the general formula (101):

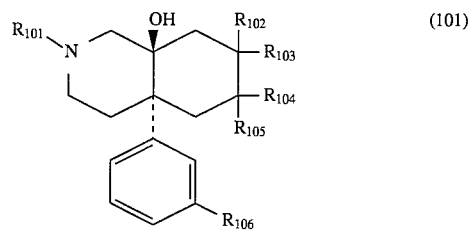

wherein $R_{101}$ stands for a hydrogen atom, an alkyl group having 1 to 5 carbon atoms, a cycloalkylalkyl group having 4 to 7 carbon atoms, a cycloalkenylalkyl group having 6 to 8 carbon atoms, an aralkyl group having 7 to 14 carbon atoms, a transalkenyl group having 4 to 5 carbon atoms, an allyl group, furanyl-2-alkyl, thienyl-2-alkyl, $R_{107}OCO$ (wherein $R_{107}$ stands for 2,2,2-trichloroethyl or benzyl), or $R_{108}CO$ (wherein $R_{108}$ stands for an alkyl group having 1 to 5 carbon atoms, a cycloalkyl group having 3 to 6 carbon atoms, a cycloalkenyl group having 5 to 7 carbon atoms, phenyl, an aralkyl group having 7 to 13 carbon atoms, a trans-alkenyl group having 4 to 5 carbon atoms, vinyl, 2-furanyl or 2-ethienyl), $R_{102}$, $R_{103}$, $R_{104}$ and $R_{105}$ independently stand for a hydrogen atom, a hydroxy group, an alkanoyloxy group having 1 to 5 carbon atoms, or an alkoxy group having 1 to 5 carbon atoms, provided that $R_{102}$ and $R_{103}$ jointly or $R_{104}$ and $R_{105}$ jointly may form an oxo group or $R_{103}$ and $R_{104}$ jointly may form a 1,3-dioxolan ring, $R_{106}$ a hydrogen atom, a hydroxy group, an alkoxy group having 1 to 5 carbon atoms, or an alkanoyloxy group having 1 to 5 carbon atoms, provided that said general formula (101) embraces a (+) form, a (−) form, and a (±) form or a pharmacologically acceptable salt thereof, characterized by proceeding through a step of oxidizing with an oxidizing agent and followed by reducing, the carbamate form of an enamine represented by the general formula (103):

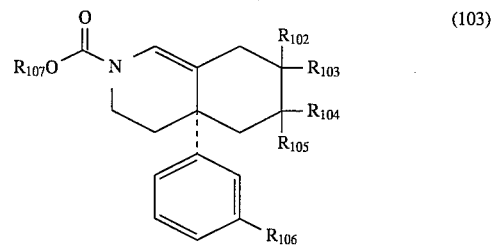

wherein $R_{102}$, $R_{103}$, $R_{104}$, $R_{105}$, $R_{106}$, and $R_{107}$ have the same meanings as defined above, thereby forming an oxide represented by the general formula (101a):

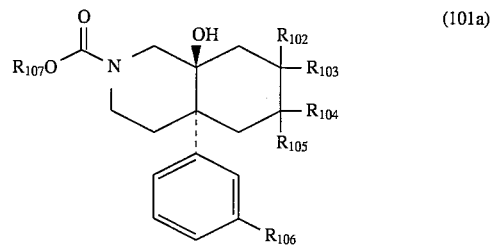

wherein $R_{102}$, $R_{103}$, $R_{104}$, $R_{105}$, $R_{106}$, and $R_{107}$ have the same meanings as defined above, provided that said general formula (101a) embraces a (+) form, a (−) form, and a (±) form.

2. A method for producing an isoquinoline derivative represented by the general formula (101a):

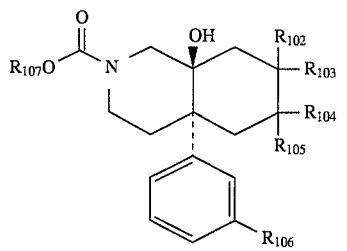

wherein $R_{102}$, $R_{103}$, $R_{104}$, and $R_{105}$ independently stand for a hydrogen atom, hydroxy, alkanoyloxy having 1 to 5 carbon atoms, or alkoxy having 1 to 5 carbon atoms, provided that $R_{102}$ and $R_{103}$ jointly or $R_{103}$ and $R_{104}$ jointly may form an oxo group or $R_{103}$ and $R_{104}$ may jointly form a 1,3-dioxolane ring, $R_{106}$ stands for a hydrogen atom, hydroxy, alkoxy having 1 to 5 carbon atoms, or alkanoyloxy having 1 to 5 carbon atoms, or a pharmacologically acceptable salt thereof and $R_{107}$ stands for 2,2,2-trichloroethyl or benzyl, provided that formula (101a) embraces a (+) form, a (−) form and a ± form comprising:

epoxidizing a carbonate represented by the formula (103):

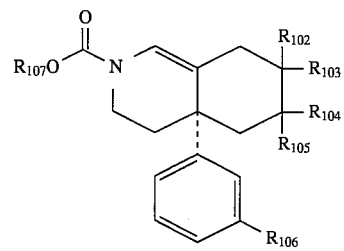

wherein $R_{102}$, $R_{103}$, $R_{104}$, $R_{105}$, $R_{106}$ and $R_{107}$ have the same meanings as defined above;

to form an epoxy compound represented by the formula (104):

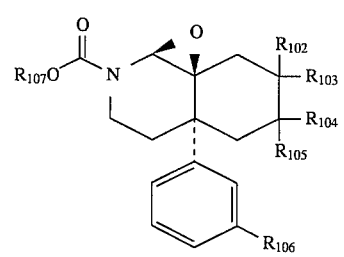

wherein $R_{102}$, $R_{103}$, $R_{104}$, $R_{105}$, $R_{106}$ and $R_{107}$ have the same meanings as defined above; and reducing the epoxy compound to obtain an isoquinoline represented by the formula (101)a.

* * * * *